United States Patent
Rikihisa

(10) Patent No.: US 10,393,741 B2
(45) Date of Patent: Aug. 27, 2019

(54) **COMPOSITIONS AND METHODS FOR THE DETECTION OF *ANAPLASMA PLATYS***

(71) Applicant: Ohio State Innovation Foundation, Columbus, OH (US)

(72) Inventor: Yasuko Rikihisa, Worthington, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 440 days.

(21) Appl. No.: 14/993,678

(22) Filed: Jan. 12, 2016

(65) Prior Publication Data

US 2016/0153988 A1 Jun. 2, 2016

Related U.S. Application Data

(63) Continuation of application No. 14/008,344, filed as application No. PCT/US2012/031580 on Mar. 30, 2012, now abandoned.

(60) Provisional application No. 61/470,209, filed on Mar. 31, 2011.

(51) Int. Cl.
| | |
|---|---|
| A61K 39/395 | (2006.01) |
| A61K 38/00 | (2006.01) |
| G01N 33/53 | (2006.01) |
| G01N 33/567 | (2006.01) |
| G01N 33/554 | (2006.01) |
| G01N 33/569 | (2006.01) |
| C07K 16/12 | (2006.01) |
| C12Q 1/6893 | (2018.01) |
| C12Q 1/689 | (2018.01) |
| C07K 14/29 | (2006.01) |

(52) U.S. Cl.
CPC ........ *G01N 33/56911* (2013.01); *C07K 14/29* (2013.01); *C07K 16/1246* (2013.01); *C12Q 1/689* (2013.01); *C12Q 1/6893* (2013.01); *A61K 39/395* (2013.01); *C12Q 2600/16* (2013.01); *G01N 2333/29* (2013.01); *G01N 2469/20* (2013.01)

(58) Field of Classification Search
CPC ........ A61K 39/395; A61K 38/00; C07K 5/14; C12Q 1/6895; G01N 33/56911
See application file for complete search history.

(56) References Cited

U.S. PATENT DOCUMENTS

| | | | |
|---|---|---|---|
| 4,478,914 A | 10/1984 | Giese | |
| 5,401,656 A | 3/1995 | Dawson et al. | |
| 5,413,931 A | 5/1995 | Dawson et al. | |
| 5,789,176 A | 8/1998 | Dawson et al. | |
| 5,869,335 A | 12/1999 | Munderloh et al. | |
| 6,025,338 A | 12/2000 | Barbet et al. | |
| 6,207,169 B1 | 3/2001 | Reed et al. | |
| 6,231,869 B1 | 5/2001 | Reed | |
| 6,251,872 B1 | 6/2001 | Barbet | |
| 6,306,394 B1 | 10/2001 | Murphy et al. | |
| 6,392,023 B1 | 5/2002 | Walker | |
| 6,432,649 B1 | 8/2002 | Stich et al. | |
| 6,436,399 B1 | 8/2002 | Rikihisa et al. | |
| 6,544,517 B1 | 4/2003 | Rikihisa et al. | |
| 6,893,640 B2 | 5/2005 | Rikihisa et al. | |
| 6,923,963 B2 | 8/2005 | Rikihisa et al. | |
| 7,063,846 B2 | 6/2006 | Rikihisa et al. | |
| 7,183,060 B2 | 2/2007 | O'Connor | |
| 7,332,171 B2 | 2/2008 | Walker et al. | |
| 7,507,789 B2 * | 3/2009 | Beall | C07K 14/195 435/7.22 |
| 8,784,828 B2 | 7/2014 | Rikihisa | |
| 9,359,407 B2 | 6/2016 | Rikihisa | |
| 2003/0099639 A1 * | 5/2003 | Rikihisa | C07K 14/195 424/139.1 |
| 2004/0265333 A1 | 12/2004 | Rikihisa et al. | |
| 2008/0248497 A1 * | 10/2008 | Beall | C07K 14/195 435/7.22 |
| 2009/0155825 A1 * | 6/2009 | Beall | C07K 14/195 435/7.92 |
| 2011/0182925 A1 | 7/2011 | Krah, III et al. | |
| 2014/0341943 A1 | 11/2014 | Rikihisa et al. | |

FOREIGN PATENT DOCUMENTS

| | | |
|---|---|---|
| WO | 1998/014584 | 4/1998 |
| WO | 1998/016554 | 4/1998 |
| WO | 1998/049312 | 11/1998 |
| WO | 1999/013720 | 3/1999 |

(Continued)

OTHER PUBLICATIONS

Aguero-Rosenfeld, M.E., et al., "Serology of Culture-Confirmed Cases of Human Granulocytic Ehrlichiosis," J Clin Microbiol, vol. 38, 2000, pp. 635-638.
Alberti, A., et al., "Equine and Canine *Anaplasma phagocytophilum* Strains Isolated on the Island of Sardinia (Italy) Are Phylogenetically Related to Pathogenic Strains from the United States," Appl Environ Microbiol, vol. 71, 2005, pp. 6418-6422.
Anderson, B.E., et al., "*Ehrlichia ewingii* sp. nov., the Etiologic Agent of Canine Granulocytic Ehrlichiosis," Int J Syst Bacteriol, vol. 42, 1992, pp. 299-302.

(Continued)

*Primary Examiner* — Gary B Nickol
*Assistant Examiner* — Lakia J Jackson-Tongue
(74) *Attorney, Agent, or Firm* — Meunier Carlin & Curfman LLC

(57) ABSTRACT

Described herein are improved diagnostic tools for veterinary and human use which can be used for serodiagnosing *A. platys* in mammals, particularly in members of the Canidae family and in humans. The diagnostic tools are a group of outer membrane proteins of *A. platys* and variants thereof, referred to hereinafter as the "OMP

(56) References Cited

FOREIGN PATENT DOCUMENTS

| WO | 1999/052370 | 10/1999 |
|---|---|---|
| WO | 2000/032745 | 6/2000 |
| WO | 2001/058466 | 8/2001 |
| WO | 2001/080897 | 11/2001 |
| WO | 2008/112007 | 9/2008 |
| WO | 2008/137881 | 11/2008 |
| WO | 2010/126993 | 11/2010 |
| WO | 2014/089061 | 6/2014 |

OTHER PUBLICATIONS

Bagos, P.G., et al., "PRED-TMBB: a web server for predicting the topology of β-barrel outer membrane proteins," Nucleic Acids Res, vol. 32, 2004, pp. W400-W404.
Barbet, A.F., et al., "Antigenic Variation of *Anaplasma marginale* by Expression of MSP2 Mosaics," Infect Immun, vol. 68, No. 11, 2000, pp. 6133-6138.
Barbet, A.F., et al., "Antigenic variation of *Anaplasma marginale*: Major Surface Protein 2 Diversity during Cyclic Transmission between Ticks and Cattle," Infect Immun, vol. 69, No. 5, 2001, pp. 3057-3066.
Barbet, A.F., et al., "Expression of Multiple Outer Membrane Protein Sequence Variants from a Single Genomic Locus of *Anaplasma phagocytophilum*," Infect Immun, vol. 71, No. 4, 2003, pp. 1706-1718.
Barbet, A.F., et al., "Identification of functional promoters in the msp2 expression loci of *Anaplasma marginale* and *Anaplasma phagocytophilum*," Gene, vol. 353, 2005, pp. 89-97.
Barbet, A.F., et al., "Structure of the Expression Site Reveals Global Diversity in MSP2 (P44) Variants in *Anaplasma phagocytophilum*," Infect and Immun, vol. 74, No. 11, 2006, pp. 6429-6437.
Brayton, K.A., et al., "Antigenic variation of *Anaplasma marginale* msp2 occurs by combinatorial gene conversion," Mol Microbiol, vol. 43, No. 5, 2002, pp. 1151-1159.
Brayton, K.A., et al., "Complete genome sequencing of *Anaplasma marginale* reveals that the surface is skewed to two superfamilies of outer membrane proteins," Proc Natl Acad Sci U.S.A., vol. 102, 2005, pp. 844-849.
Brown, G.K., et al., "Detection of *Ehrlichia platys* in dogs in Australia," Aust Vet J, vol. 79, 2001, pp. 554-558.
Cardoso, L., et al., "Molecular detection of *Anaplasma platys* and *Ehrlichia canis* in dogs from the North of Portugal," Vet J., vol. 183, Issue 2, Feb. 2010, pp. 232-233.
Carver, T.J., et al., "ACT: the Artemis comparison tool," Bioinformatics, vol. 21, No. 16, 2005, pp. 3422-3423.
Chang, W.L., et al., "Specific Amplification of *Ehrlichia platys* DNA from Blood Specimens by Two-Step PCR," J Clin Microbiol, vol. 34, No. 12, 1996, pp. 3142-3146.
Dumler, J.S., et al., "Reorganization of genera in the families Rickettsiaceae and Anaplasmataceae in the order Rickettsiales: unification of some species of *Ehrlichia* with *Anaplasma*, *Cowdria* with *Ehrlichia* and *Ehrlichia* with *Neorickettsia*, descriptions of six new species combinations and designation of *Ehrlichia equi* and 'HE agent' as subjective synonyms of *Ehrlichia phagocytophila*," Int J Syst Evol Microbiol, vol. 51, 2001, pp. 2145-2165.
Dumler, J.S., et al., "Serologic Cross-Reactions among *Ehrlichia equi*, *Ehrlichia phagocytophila*, and Human Granulocytic Ehrlichia," J Clin Microbiol, vol. 33, No. 5, 1995, pp. 1098-1103.
Eid, G., et al., "Expression of Major Surface Protein 2 Antigenic Variants during Acute *Anaplasma marginale* Rickettsemia," Infect and Immun, vol. 64, No. 3, 1996, pp. 836-841.
EMBL Accession No. AY040556, Anaplasma central clone 337 major surface protein-2 gene, complete cds. 1203 bps sequence, Feb. 5, 2002, retrieved from the internet at http://www.ebi.ac.uk/Tools/dbfetch/dbfetch?db=embl&id=AY040556&f . . . on Sep. 10, 2012, pp. 2-3.
Felek, S., et al., "Sequence Analysis of p44 Homologs Expressed by *Anaplasma phagocytophilum* in Infected Ticks Feeding on Naïve Hosts and in Mice Infected by Tick Attachment," Infect and Immun, vol. 72, No. 2, 2004, pp. 659-666.
Ferreira, R.F., et al., "*Anaplasma platys* Diagnosis in Dogs: Comparison Between Morphological and Molecular Tests," Intern J Appl Res Vet Med, vol. 5, 2007, p. 7.
French, D.M., et al., "Expression of *Anaplasma marginale* Major Surface Protein 2 Variants during Persistent Cyclic Rickettsemia," Infect Immun, vol. 66, No. 3, 1998, pp. 1200-1207.
French, T.W., et al., "Serologic diagnosis of infectious cyclic thrombocytopenia in dogs using an indirect fluorescent antibody test," Am J Vet Res, vol. 44, 1983, pp. 2407-2411.
Ganta, R.R., et al., "Differential Clearance and Immune Responses to Tick Cell-Derived versus Macrophage Culture-Derived *Ehrlichia chaffeensis* in Mice," Infect Immun, vol. 75, No. 1, 2007, pp. 135-145.
Greig, B., et al., "Geographic, Clinical, Serologic, and Molecular Evidence of Granulocytic Ehrlichiosis, a Likely Zoonotic Disease, in Minnesota and Wisconsin dogs," J Clin Microbiol, vol. 34, No. 1, 1996, pp. 44-48.
Harvey, J.W., et al., "Cyclic thrombocytopenia induced by a Rickettsia-like agent in dogs," J Infect Dis, vol. 137, 1978, pp. 182-188.
Hotopp, J.C., et al., "Comparative Genomics of Emerging Human Ehrlichiosis Agents," PLoS Genet 2: e21, vol. 2, Issue 2, 2006, pp. 0210-0223.
Hua, P., et al., "Canine Ehrlichiosis Caused Simultaneously by *Ehrlichia canis* and *Ehrlichia platys*," Microbiol Immunol, vol. 44, No. 9, 2000, pp. 737-739.
Huang, H., et al., "Porin Activity of *Anaplasma phagocytophilum* Outer Membrane Fraction and Purified P44," J Bacteriol, vol. 189, No. 5, 2007, pp. 1998-2006.
Huang, H., et al., "Prevalence and Molecular Analysis of *Anaplasma platys* from Dogs in Lara, Venezuela," Brazilian J. Microbiol, vol. 36, 2005, pp. 211-216.
Ijdo, J.W., et al., "Serodiagnosis of Human Granulocytic Ehrlichiosis by a Recombinant HGE-44-Based Enzyme-Linked Immunosorbent Assay," J Clin Microbiol, vol. 37, No. 11, 1999, pp. 3540-3544.
Inokuma, H., et al., "Demonstration of *Anaplasma* (*Ehrlichia*) *platys* inclusions in peripheral blood platelets of a dog in Japan," Vet Parasitol, vol. 110, 2002, pp. 145-152.
Inokuma, H., et al., "Detection of *Ehrlichia platys* DNA in Brown Dog Ticks (*Rhipicephalus sanguineus*) in Okinawa Island, Japan," J Clin Microbiol, vol. 38, No. 11, 2000, pp. 4219-4221.
Inokuma, H., et al., "Determination of the Nucleotide Sequences of Heat Shock Operon groESL and the Citrate Synthase Gene (gltA) of *Anaplasma* (*Ehrlichia*) *platys* for Phylogenetic and Diagnostic Studies," Clin Diagn Lab Immunol, vol. 9, No. 5, 2002, pp. 1132-1136.
Jeanteur, D., et al., "The bacterial porin superfamily: sequence alignment and structure prediction," Mol Microbiol, vol. 5, No. 9, Sep. 1991, pp. 2153-2164.
Kim, H.Y., et al., "Characterization of monoclonal antibodies to the 44-kilodalton major outer membrane protein of the human granulocytic ehrlichiosis agent," J Clin Microbiol, vol. 36, 1998, pp. 3278-3284.
Kumagai, Y., et al., "Expression and Porin Activity of P28 and OMP-1F during Intracellular *Ehrlichia chaffeensis* Development," J Bacteriol, vol. 190, No. 10, 2008, pp. 3597-3605.
Lin, Q., et al., "Analysis of Involvement of the RecF Pathway in p44 Recombination in *Anaplasma phagocytophilum* and in *Escherichia coli* by Using a Plasmid Carrying the p44 Expression and p44 Donor Loci," Infect Immun, vol. 74, No. 4, 2006, pp. 2052-2062.
Lin, Q., et al., "Analysis of Sequences and Loci of p44 Homologs Expressed by *Anaplasma phagocytophila* in Acutely Infected Patients," J Clin Microbial, vol. 40, No. 8, 2002, pp. 2981-2988.
Lin, Q., et al., "Establishment of Cloned *Anaplasma phagocytophilum* and Analysis of p44 Gene Conversion within an Infected Horse and Infected SCID Mice," Infect Immun, vol. 73, No. 8, 2005, pp. 5106-5114.
Lin, Q., et al., "Mechanisms of Variable p44 Expression by *Anaplasma phagocytophilum*," Infect Immun, vol. 71, No. 10, 2003, pp. 5650-5661.

(56) References Cited

OTHER PUBLICATIONS

Mathew, J.S., et al., "Characterization of a new isolate of *Ehrlichia platys* (Order Rickettsiales) using electron microscopy and polymerase chain reaction," Vet Parasitol, vol. 68, 1997, pp. 1-10.

Mylonakis, M.E., et al., Chronic canine ehrlichiosis (*Ehrlichia canis*): a retrospective study of 19 natural cases, J Am Anim Hosp Assoc, vol. 40, 2004, pp. 174-184.

Nelson, C.M., et al., "Whole genome transcription profiling of *Anaplasma phagocytophilum* in human and tick host cells by tiling array analysis," BMC Genomics, vol. 9, 2008, p. 364.

Ohashi, N., et al., "Cloning and Characterization of Multigenes Encoding the Immunodominant 30-Kilodalton Major Outer Membrane Proteins of Ehrlichia canis and Application of the Recombinant Protein for Serodiagnosis," J Clin Microbiol, vol. 36, No. 9, 1998, pp. 2671-2680.

Ohashi, N., et al., "Immunodominant Major Outer Membrane Proteins of *Ehrlichia chaffeensis* Are Encoded by a Polymorphic Multigene Family," Infect and Immun, vol. 66, No. 1, 1998, pp. 132-139.

Palmer, G.H., et al., "Nothing is permanent but change—antigenic variation in persistent bacterial pathogens," Cell Microbiol, vol. 11, No. 12, 2009, pp. 1697-1705.

Palmer, G.H., et al., "Insights into mechanisms of bacterial antigenic variation derived from the complete genome sequence of *Anaplasma marginale*," Ann NY Acad Sci, vol. 1078, 2006, pp. 15-25.

Park, J., et al., "Major Surface Protein 2 of *Anaplasma phagocytophilum* Facilitates Adherences to Granulocytes," Infect Immun, vol. 71, No. 7, 2003, pp. 4018-4025.

Poitout, F.M., et al, "Genetic Variants of *Anaplasma phagocytophilum* Infecting Dogs in Western Washington State," J Clin Microbiol, vol. 43, No. 2, 2005, pp. 796-801.

Pusterla, N., et al., "Granulocytic Ehrlichiosis in Two Dogs in Switzerland," J Clin Microbiol, vol. 35, No. 9, 1997, pp. 2307-2309.

Roux, K.H., et al., "One-step optimization using touchdown and stepdown PCR," Methods Mol Biol, vol. 67, 1997, pp. 39-45.

Rurangirwa, F.R., et al., "Restriction of major surface protein 2 (MSP2) variants during tick transmission of the ehrlichia *Anaplasma marginale*," Proc Natl Acad Sci U.S.A., vol. 96, Mar. 1999, pp. 3171-3176.

Sainz, A., et al., "*Ehrlichia platys* Infection and disease in dogs in Spain," J Vet Diagn Invest, vol. 11, 1999, pp. 382-384.

Sanogo, Y.O., et al., "First evidence of *Anaplasma platys* in *Rhipicephalus sanguineus* (Acari: Ixodida) collected from dogs in Africa," Onderstepoort J Vet Res, vol. 70, 2003, pp. 205-212.

Simpson, R.M., et al., "Evaluation of *Rhipicephalus sanguineus* as a potential biologic vector of *Ehrlichia platys*," Am J Vet Res, vol. 52, 1991, pp. 1537-1541.

Singu, V., et al., "*Ehrlichia chaffeensis* Expresses Macrophage- and Tick Cell-Specific 28-Kilodalton Outer Membrane Proteins," Infect Immun, vol. 73, No. 1, 2005, pp. 79-87.

Sparagano, O.A., et al., "Molecular detection of *Anaplasma platys* in dogs using polymerase chain reaction and reverse line blot hybridization," J Vet Diagn Invest, vol. 15, 2003, pp. 527-534.

Suksawat, J., et al., "Coinfection with Three *Ehrlichia* Species in Dogs from Thailand and Venezuela with Emphasis on Consideration of 16S Ribosomal DNA Secondary Structure," J Clin Microbiol, vol. 39, No. 1, 2001, pp. 90-93.

Tajima, T., et al, "Comparison of Two Recombinant Major Outer Membrane Proteins of the Human Granulocytic Ehrlichiosis Agent for Use in an Enzyme-Linked Immunosorbent Assay," Clin Diagn Lab Immunol, vol. 7, No. 4, 2000, pp. 652-657.

Unver, A., et al., "Analysis of 16S rRNA gene sequences of *Ehrlichia canis, Anaplasma platys*, and *Wolbachia* species from canine blood in Japan," Ann NY Acad Sci, vol. 990, 2003, pp. 692-698.

Unver, A., et al., "Western and Dot Blotting Analyses of *Ehrlichia chaffeensis* Indirect Fluorescent-Antibody Assay-Positive and-Negative Human Sera by Using Native and Recombinant *E. chaffeensis* and *E. canis* Antigens," J Clin Microbiol, vol. 37, No. 12, 1999, pp. 3888-3895.

Van Vliet, A., et al., "Molecular Cloning, Sequence Analysis, and Expression of the Gene Encoding the Immunodominant 32-Kilodalton Protein of *Cowdria ruminantium*," Infect Immun, vol. 62, No. 4, 1994, pp. 1451-1456.

Wang, X., et al., "*Anaplasma phagocytophilum* p44 mRNA Expression Is Differentially Regulated in Mammalian and Tick Host Cells: Involvement of the DNA Binding Protein ApxR," J Bacteriol, vol. 189, No. 23, 2007, pp. 8651-8659.

Wang, X., et al., "Rapid Sequential Changeover of Expressed p44 Genes during the Acute Phase of *Anaplasma phagocytophilum* Infection in Horses," Infect and Immun, vol. 72, No. 12, 2004, pp. 6852-6859.

Yu, X., et al., "Characterization of the complete transcriptionally active *Ehrlichia chaffeensis* 28 kDa outer membrane protein multigene family," Gene, vol. 248, 2000, pp. 59-68.

Yu, X., et al., "Phylogenetic relationships of *Anaplasma marginale* and 'Ehrlichia platys' to other *Ehrlichia* species determined by GroEL amino acid sequences," Int J Syst Evol Microbiol, vol. 51, 2001, pp. 1143-1146.

Zhang, C., et al., "Identification of 19 Polymorphic Major Outer Membrane Protein Genes and Their Immunogenic Peptides in *Ehrlichia ewingii* for Use in a Serodiagnostic Assay," Clin Vaccine Immunol, vol. 15, No. 3, 2008, pp. 402-411.

Zhi, N., et al., "Cloning and Expression of the 44-Kilodalton Major Outer Membrane Protein Gene of the Human Granulocytic Ehrlichiosis Agent and Application of the Recombinant Protein to Serodiagnosis," J Clin Microbiol, vol. 36, No. 6, 1998, pp. 1666-1673.

Zhi, N., et al., "Multiple p44 genes encoding major outer membrane proteins are expressed in the human granulocytic ehrlichiosis agent," J Biol Chem, vol. 274, 1999, pp. 17828-178236.

Zhi, N., et al., "Transcript Heterogeneity of the p44 Multigene Family in a Human Granulocytic Ehrlichiosis Agent Transmitted by Ticks," Infect Immun, vol. 70, No. 3, 2002, pp. 1175-1184.

International Search Report, dated Sep. 24, 2012, received in connection with corresponding International Application No. PCT/US2012/031580.

International Preliminary Report on Patentability and Written Opinion, dated Oct. 1, 2013, received in connection with corresponding International Application No. PCT/US2012/031580.

Adelman, J.P., et al., "In Vitro Deletional Mutagenesis for Bacterial Production of the 20,000-Dalton Form of Human Pituitary Growth Hormone," DNA, vol. 2, 1983, pp. 183-193.

Aguero-Rosenfeld, M.E., et al., "Human Granulocytic Ehrlichiosis: A Case Series from a Medical Center in New York State," Annals of Internal Medicine, vol. 125, Issue 11, 1996, pp. 904-908.

Aguirre, D.H., et al., "Transmission of *Anaplasma marginale* with Adult Boophilus Microplus ticks Fed as Nymphs on Calves with Different Levels of Rickettsaemia," Parasite, vol. 1, 1994, pp. 405-407.

Alleman, A.R., et al., "*Anaplasma marginale* Major Surface Protein 3 Is Encoded by a Polymorphic Multigene Family," Infection and Immunity, vol. 65, No. 1, 1997, pp. 156-163.

Altschul, S.F., et al., "Basic Local Alignment Search Tool," J. Mol. Biol., vol. 215, 1990, pp. 403-410.

Anderson, B.E., et al., "*Amblyomma Americanum*: A Potential Vector of Human Ehrlichiosis," Am. J. Trop. Med. Hyg, vol. 49, No. 2, 1993, pp. 239-244.

Anderson, B.E., et al., "*Ehrlichia chaffeensis*, a New Species Associated with Human Ehrlichiosis," Journal of Clinical Microbiology, vol. 29, No. 12, Dec. 1991, pp. 2838-2842.

Anziani, O.S., et al., "Experimental transmission of a granulocytic form of the tribe Ehrlichieae by *Dermacentor variabilis* and *Amblyomma americanum* to dogs," Am. J. Vet. Res., vol. 51, No. 6, 1990, pp. 929-931.

Asanovich, K.M., et al., "Antigenic Diversity of Granulocytic *Ehrlichia* isolates from Humans in Wisconsin and New York and a Horse in California," J. Infect Dis., vol. 176, 1997, pp. 1029-1034.

Bakken, J.S., et al., "Clinical and Laboratory Characteristics of Human Granulocytic Ehrlichiosis," Journal of the American Medical Association, vol. 275, No. 3, 1996, pp. 199-205.

(56) References Cited

OTHER PUBLICATIONS

Bakken, J.S., et al., "Serological Evidence of Human Granulocytic Ehrlichiosis in Norway," Eur. J. Clin. Microbiol. Infect. Dis., vol. 15, No. 10, 1996, pp. 829-832.
Barbet, A.F., "Recent developments in the molecular biology of anaplasmosis," Veterinary Parasitology, vol. 57, 1995, pp. 43-49.
Barbour, A.G., "Antigenic Variation of a Relapsing Fever *Borrelia* species," Annu. Rev. Microbiol., vol. 44, 1990, pp. 155-171.
Bollon, A.P., "DNA Transformation Efficiency of Various Bacterial and Yeast Host-Vector Systems," Journal of Clinical Hematology and Oncology, vol. 10, Nos. 2 and 3, Apr.-Jul. 1980, pp. 39-48.
Breitschwerdt, E.B., et al., "Doxycycline Hyclate Treatment of Experimental Canine Ehrlichiosis Followed by Challenge Inoculation with Two *Ehrlichia canis* Strains," Antimicrobial Agents and Chemotherapy, vol. 42, No. 2, Feb. 1998, pp. 362-368.
Breitschwerdt, E.B., et al., "Sequential Evaluation of Dogs Naturally Infected with *Ehrlichia canis, Ehrlichia chaffeensis, Ehrlichia equi, Ehrlichia ewingii*, or *Bartonella vinsonii*," Journal of Clinical Microbiology, vol. 36, No. 9, Sep. 1998, pp. 2645-2651.
Bremer, W.G., et al., "Transstadial and intrastadial experimental transmission of *Ehrlichia canis* by male *Rhipicephalus sanguineus*," Veterinary Parasitology, vol. 131, 2005, pp. 95-105.
Broach, J.R., "The Yeast Plasmid 2µ Circle," Cell, vol. 28, Feb. 1982, pp. 203-204.
Brouqui, P., et al., "Antigenic characterization of ehrlichiae: protein immunoblotting of Ehrlichia canis, Ehrlichia sennetsu, and Ehrlichia risticii," Journal of Clinical Microbiology, vol. 30, No. 5, 1992, pp. 1062-1066.
Brouqui, P., et al., "Serologic Diagnosis of Human Monocytic Ehrlichiosis by Immunoblot Analysis," Clinical and Diagnostic Laboratory Immunology, vol. 1, No. 6, 1994, pp. 645-649.
Buck, G.A., et al., "Design Strategies and Performance of Custom DNA Sequencing Primers," Biotechniques, vol. 27, No. 3, Sep. 1999, pp. 528-536.
Buller, R.S., et al., "*Ehrlichia ewingii*, a Newly Recognized Agent of Human Ehrlichiosis," The New England Journal of Medicine, vol. 341, No. 3, Jul. 15, 1999, pp. 148-155.
Chaichanasiriwithaya, W., et al., "Antigenic, Morphologic, and Molecular Characterization of new *Ehrlichia resiticii* Isolates," Journal of Clinical Microbiology, vol. 38, No. 12, 1994, pp. 3026-3033.
Chen, S.M., et al., "Analysis and Ultrastructure Localization of *Ehrlichia chaffeensis* Proteins with Monoclonal Antibodies," Am J Trop Med Hyg, vol. 54, No. 4, 1996, pp. 405-412.
Chen, S.M., et al., "Antigenic Diversity Among Strains of *Ehrlichia chaffeensis*," Proceedings of the International Symposium of Rickettsiae and Rickettsial Diseases, Slovak Academy of Sciences, Sep. 1-6, 1996, pp. 329-334.
Chen, S.M., et al., Genetic and Antigenic Diversity of *Ehrlichia chaffeensis*: Comparative Analysis of a Novel Human Strain from Oklahoma and Previously Isolated Strains, J. Infect. Dis., vol. 175, Apr. 1997, pp. 856-863.
Chen, S.M., et al., "Identification of a Granulocytotropic *Ehrlichia* Species as the Etiologic Agent of Human Disease," Journal of Clinical Microbiology, vol. 32, No. 3, 1994, pp. 589-595.
Chen, S.M., et al., "Identification of the Antigenic Constituents of *Ehrlichia chaffeensis*," Am. J. Trop. Med. Hyg., vol. 50, No. 1, 1994, pp. 52-58.
Chen, S.M., et al., "Western Immunoblotting Analysis of the Antibody Responses of Patients with Human Monocytotropic Ehrlichiosis to Different Strains of *Ehrlichia chaffeensis* and *Ehrlichia canis*," Clinical and Diagnostic Laboratory Immunology, vol. 4, No. 6, Nov. 1997, pp. 731-735.
Coughlin, R.T., et al., "Transmission, Isolation, and Cultivation of Granulocytic *Ehrlichia* Resulting from Infection of Dogs by Adult *Ixodes scapularis* Collected from Eastern United States," Abstract 52 in Abstracts of 21$^{st}$ Semi-annual meeting of the American Society for Rickettsiology and Rickettsial diseases, Albany, NY, 1996, one page.
Crea, R., et al., "Chemical synthesis of genes for human insulin," Proc. Natl. Acad. Sci. USA, vol. 75, No. 12, 1978, pp. 5765-5769.
Crocquet-Valdes, P.A., et al., "Analysis of Ehrlichial p28 Gene Expression in a Murine Model of Persistent Infection," Ann. N.Y. Acad. Sci., vol. 1063, 2005, pp. 420-424.
Dawson, J.E., et al., "Ehrlichia-like 16S rDNA Sequence from Wild White-Tailed Deer (*Odocoileus virginianus*)," J. Parasitol., vol. 82, No. 1, 1996, pp. 52-58.
Dawson, J.E., et al., "Isolation and Characterization of an *Ehrlichia* sp. from a Patient Diagnosed with Human Ehrlichiosis," Journal of Clinical Microbiology, vol. 29, No. 12, Dec. 1991, pp. 2741-2745.
Dawson, J.E., et al., "Polymerase chain reaction evidence of *Ehrlichia chaffeensis*, an etiologic agent of human ehrlichiosis, in dogs from southeast Virginia," Am. J. Vet. Res., vol. 57, No. 8, 1996, pp. 1175-1179.
Dawson, J.E., et al., "Serologic Diagnosis of Human Ehrlichiosis Using Two *Ehrlichia canis* Isolates," Journal of Infectious Diseases, vol. 163, 1991, pp. 564-567.
Dawson, J.E., et al., "The Interface Between Research and the Diagnoses of an Emerging Tick-borne Disease, Human Ehrlichiosis Due to *Ehrlichia chaffeensis*," Archives of Journal of Medicine, vol. 156, No. 2, 1996, pp. 137-142.
Dhingra, A., et al., "ASAP: Amplification, sequencing & annotation of plastomes," BMC Genomics, vol. 6, No. 176, 2005, 13 pages.
Dumler, J.S., et al., "Ehrlichioses in Humans: Epidemiology, Clinical Presentation, Diagnosis, and Treatment," Clinical Infectious Diseases, vol. 45, Supp. 1, 2007, pp. S45-S51.
Dumler, J.S., et al., "Human Granulocytic Ehrlichiosis in Wisconsin and Minnesota: A Frequent Infection with the Potential for Persistence," Journal of Infectious Diseases, vol. 173, 1996, pp. 1027-1030.
Dumler, J.S., et al., "Isolation and Characterization of a New Strain of *Ehrlichia chaffeensis* from a Patient with Nearly Fatal Monocytic Ehrlichiosis," Journal of Clinical Microbiology, vol. 33, No. 7, Jul. 1995, pp. 1704-1711.
Edelman, D.C., et al., "Evaluation of an Improved PCR Diagnostic Assay for Human Granulocytic Ehrlichiosis," Molecular Diagnosis, vol. 1, No. 1, 1996, pp. 41-49.
Emini, E.A., et al., "Induction of Hepatitis: A Virus-Neutralizing Antibody by a Virus-Specific Synthetic Peptide," Journal of Virology, vol. 55, No. 3, 1985, pp. 836-839.
Eng, T.R., et al., "Epidemiologic, Clinical, and Laboratory Findings of Human Ehrlichiosis in the United States, 1988," JAMA, vol. 264, 1990, pp. 2251-2258.
Eremeeva, M., et al., "Differentiation among Spotted Fever Group Rickettsiae Species by Analysis of Restriction Fragment Length Polymorphism of PCR-Amplified DNA," Journal of Clinical Microbiology, vol. 32, No. 3, 1994, pp. 803-810.
Ewing, S.A., et al., "A New Strain of *Ehrlichia canis*," Journal of the American Veterinary Medical Association, vol. 159, No. 12, 1971, pp. 1771-1774.
Ewing, S.A., et al., "Dogs Infected with a Human Granulocytotropic *Ehrlichia* spp. (Rickettsiales: Ehrlichieae)," Journal of Medical Entomology, vol. 34, No. 6, 1997, pp. 710-718.
Ewing, S.A., et al., "Experimental Transmission of *Ehrlichia chaffeensis* (Rickettsiales: Ehrlichieae) Among White-Tailed Deer by *Amblyomma americanum* (Acari: Isodidae)," Journal of Medical Entomology, vol. 32, No. 3, May, 1995, pp. 368-374.
Ewing, S.A., et al., "Human Infection with *Ehrlichia canis*," The New England Journal of Medicine, vol. 317, No. 14, Oct. 1, 1987, pp. 899-900.
Felek, S., et al., "Transcriptional Analysis of p30 Major Outer Membrane Protein Genes of *Ehrlichia canis* in Naturally Infected Ticks and Sequence Analysis of p30-10 of *E. Canis* from Diverse Geographic Regions," Journal of Clinical Microbiology, vol. 41, No. 2, Feb. 2003, pp. 886-888.
Frutos, R., et al., "Comparative Genomic Analysis of Three Strains of *Ehrlichia ruminantium* Reveals an Active Process of Genome Size Plasticity," Journal of Bacteriology, vol. 188, No. 7, Apr. 1, 2006, pp. 2533-2542.
GenBank Accession No. AF021338.
GenBank Accession No. AF029322.
GenBank Accession No. AF029323.

(56) References Cited

OTHER PUBLICATIONS

GenBank Accession No. AF037599.
GenBank Accession No. AF059181.
GenBank Accession No. AF062761.
GenBank Accession No. AF068234.
GenBank Accession No. AF077732.
GenBank Accession No. AF077732.1.
GenBank Accession No. AF077733.
GenBank Accession No. AF077733.1.
GenBank Accession No. AF077734.
GenBank Accession No. AF077734.1.
GenBank Accession No. AF077735.
GenBank Accession No. AF077735.1.
GenBank Accession No. AF078553.
GenBank Accession No. AF078554.
GenBank Accession No. AF078555.
GenBank Accession No. AF082744.
GenBank Accession No. AF082744.1.
GenBank Accession No. AF082745.
GenBank Accession No. AF082745.1.
GenBank Accession No. AF082746.
GenBank Accession No. AF082746.1.
GenBank Accession No. AF082747.
GenBank Accession No. AF082747.1.
GenBank Accession No. AF082748.
GenBank Accession No. AF082748.1.
GenBank Accession No. AF082749.
GenBank Accession No. AF082749.1.
GenBank Accession No. AF082750.
GenBank Accession No. AF082750.1.
GenBank Accession No. AF107766.
GenBank Accession No. AF107767.
GenBank Accession No. AF125274.
GenBank Accession No. AF125275.
GenBank Accession No. AF125276.
GenBank Accession No. AF125277.
GenBank Accession No. AF125278.
GenBank Accession No. AF125279.
GenBank Accession No. AF135254.
GenBank Accession No. AF135255.
GenBank Accession No. AF135256.
GenBank Accession No. AF135257.
GenBank Accession No. AF135258.
GenBank Accession No. AF135259.
GenBank Accession No. AF135260.
GenBank Accession No. AF135261.
GenBank Accession No. AF135262.
GenBank Accession No. AF135263.
GenBank Accession No. AF230642.
GenBank Accession No. AF287961.
GenBank Accession No. AF287962.
GenBank Accession No. AF287963.
GenBank Accession No. AF287964.
GenBank Accession No. AF287965.
GenBank Accession No. AF287966.
GenBank Accession No. AF324792.
GenBank Accession No. DQ365879.
GenBank Accession No. DQ902688.
GenBank Accession No. EF116932.
GenBank Accession No. L01987.
GenBank Accession No. U07862.
GenBank Accession No. U36193.
GenBank Accession No. U50830.
GenBank Accession No. U50831.
GenBank Accession No. U50832.
GenBank Accession No. U50833.
GenBank Accession No. U50834.
GenBank Accession No. U50835.
GenBank Accession No. U72291.
GenBank Accession No. X74250.

Gilman, M.Z., et al., "Isolation of sigma-28-specific promoters from *Bacillus subtilis* DNA," Gene, vol. 32, 1984, pp. 11-20.

Gold, L., et al., "Translational Initiation in Prokaryotes," Ann. Rev. Microbiol., vol. 35, 1981, pp. 365-403.

Goldman, E.E., et al., "Granulocytic Ehrlichiosis in Dogs from North Carolina and Virginia," J. Vet. Intern. Med., vol. 12, 1998, pp. 61-70.

Goodman, J.L., et al., Direct Cultivation of the Causative Agent of Human Granulocytic Ehrlichiosis, The New England Journal of Medicine, vol. 334, No. 4, 1996, pp. 209-215.

Grover, D.L., et al., "Detection of *Ehrlichia canis* in *Rhipicephalus sanguineus* with a p30-based PCR Assay," 79th Conference of Research Workers in Animal Diseases, Chicago, Illinois, Nov. 7-9, 1999.

Groves, M.G., "Transmission of *Ehrlichia canis* to Dogs by Ticks (*Rhipicephalus sanguineus*)," Am J Vet Res, vol. 36, No. 7, Jul. 1975, pp. 937-940.

Gusa, A.A., et al., "Identification of a p28 Gene in *Ehrlichia ewingii*: Evaluation of Gene for Use as a Target for a Species-Specific PCR Diagnostic Assay," Journal of Clinical Microbiology, vol. 39, No. 11, 2001, pp. 3871-3876.

Haas, R., et al., "The Repertoire of Silent Pilus Genes in Neisseria gonorrhoeae; Evidence for Gene Conversion," Cell, vol. 44, 1986, pp. 107-115.

Hair, J.A., et al., "Behavioral ecology of *Amblyomma americanum*," Chapter 18, Morphology, Physiology, and Behavioral Biology of Ticks, Ellis Horwood Limited, 1986, 13 pages.

Hamer, D.H., et al., "Regulation In Vivo of a Coned Mammalian Gene: Cadmium Induces the Transcriptio of a Mouse Metallothionein Gene in SV40 Vectors," Journal of Molecular and Applied Genetics, vol. 1, 1982, pp. 273-288.

Hardalo, C.J., et al., "Human Granulocytic Ehrlichiosis in Connecticut: Report of a Fatal Case," Clinical Infectious Diseases, vol. 21, 1995, pp. 910-914.

Harlow, E., "Antibodies: A Laboratory Manual," Cold Spring Harbor Laboratory, 1988, 152 pages.

Heberling, R.L., et al., "Rapid Dot-Immunobinding Assay on Nitrocellulose for Viral Antibodies," Journal of Clinical Microbiology, vol. 23, No. 1, 1986, pp. 109-113.

Hildebrandt, P.K., "Pathology of Canine Ehrlichiosis (Tropical Canine Pancytopenia)," Am. J. Vet. Res., vol. 34, No. 10, Oct. 1973, pp. 1309-1320.

Hodzic, E., et al., "Acquisition and Transmission of the Agent of Human Granulocytic Ehrlichiosis by *Ixodes scapularis* Ticks," Journal of Clinical Microbiology, vol. 36, No. 12, Dec. 1998, pp. 3574-3578.

Holmes, E., "PSMA specific antibodies and their diagnostic and therapeutic use," Exp. Opin. Invest. Drugs, vol. 10, No. 3, 2001, pp. 511-519.

IJdo, J.W., et al., "Cloning of the Gene Encoding the 44-Kilodalton Antigen of the Agent of Human Granulocytic Ehrlichiosis and Characterization of the Humoral Response," Infection and Immunity, vol. 66, No. 7, 998, pp. 3264-3269.

IJdo, J.W., et al., "The Early Humoral Response in Human Granulocytic Ehrlichiosis," The Journal of Infectious Diseases, vol. 176, 1997, pp. 687-692.

Iqbal, Z., et al., "Application of the polymerase chain reaction for the detection of *Ehrlichia canis* in tissues of dogs," Veterinary Microbiology, vol. 42, 1994, pp. 281-287.

Iqbal, Z., et al., "Comparison of PCR with Other Tests for Early Diagnosis of Canine Ehrlichiosis," Journal of Clinical Microbiology, vol. 32, No. 7, Jul. 1994, pp. 1658-1662.

Iqbal, Z., et al., "Reisolation of *Ehrlichia canis* from Blood and Tissues of Dogs after Doxycycline Treatment," Journal of Clinical Microbiology, vol. 32, No. 7, Jul. 1994, pp. 1644-1649.

Jameson, B.A., et al., "The antigenic index: a novel algorithm for predicting antigen determinants," CABIOS, vol. 4, No. 1, 1988, pp. 181-186.

Kawahara, M., et al., "Characterization of Ehrlichial Organisms Isolated from a Wild Mouse," Journal of Clinical Microbiology, vol. 31, No. 1, 1993, pp. 89-96.

(56) References Cited

OTHER PUBLICATIONS

Kelly, P.J., et al., "Serological evidence for antigenic relationships between *Ehrlichia canis* and *Cowdria ruminatium*," Research in Veterinary Science, vol. 56, No. 2, 1994, pp. 170-174.

Kocan, K.M., et al., "Development of *Anaplasma marginale* in male *Dermacentor andersoni* transferred from parasitemic to susceptible cattle," Am J Vet Res, vol. 53, No. 4, Apr. 1992, pp. 499-507.

Kocan, K.M., et al., "Development of *Anaplasma marginale* in salivary glands of male *Dermacentor andersoni*," Am J Vet Res, vol. 54, No. 1, Jan. 1993, pp. 107-112.

Kocan, K.M., et al., "Persistence of *Anaplasma* marginale Rickettsiales: Anaplasmataceae) in Male *Dermacentor* andersoni (Acari: Ixodidae) Transferred Successively from Infected to Susceptible Calves," Journal of Medical Entomology, vol. 29, No. 4, Jul. 1992, pp. 657-668.

Koehler, J.E., et al., "Overexpression and surface localization of the *Chlamydia trachomatis* major outer membrane protein in *Escherichia coli*," Molecular Microbiology, vol. 6, No. 9, 1992, pp. 1087-1094.

Kuehn, N.F., et al., "Clinical and hematologic findings in canine ehrlichiosis," Journal of the American Veterinary Medical Association, vol. 186, No. 4, Feb. 1985, pp. 355-358.

Kyte, J., et al., "A Simple Method for Displaying the Hydropathic Character of a Protein," J. Mol. Biol., vol. 157, 1982, pp. 105-132.

Lederman, S., et al., "A Single Amino Acid Substitution in a Common African Allele of the CD4 Molecule Ablates Binding of the Monoclonal Antibody, OKT4," Molecular Immunology, vol. 28, No. 11, 1991, pp. 1171-1181.

Lewis, G.E., "The Brown Dog Tick *Rhipicephalus sanguineus* and the Dog as Experimental Hosts of *Ehrlichia canis*," Dec. 1977, Am J Vet Res, vol. 38, No. 12, pp. 1953-1955.

Li, C.H., et al., "β-Endorphin omission analogs: Dissociation of immunoreactivity from other biological activities," Proc. Natl. Acad. Sci. USA, vol. 77, No. 6, 1980, pp. 3211-3214.

Lidell, A.M., et al., "Predominance of *Ehrlichia ewingii* in Missouri Dogs," Journal of Clinical Microbiology, vol. 41, No. 10, 2003, pp. 4617-4622.

Liu, A.Y., et al., "Chimeric mouse-human IgG1 antibody that can mediate lysis of cancer cells," Proc. Natl. Acad. Sci. USA, vol. 84, 1987, pp. 3439-3443.

Lockhart, J.M., "Site-Specific Geographic Association Between *Amblyomma americanum* (Acari: Ixodidae) Infestations and *Ehrlichia chaffeensis*-Reactive (Rickettsiales: Ehrlichieae) Antibodies in White-Tailed Deer," J. Med. Entomology, vol. 33, No. 1, 1996, pp. 153-158.

Logan, L.L., et al., "The Development of *Cowdria Ruminantium* in Neutrophils," Ondersopoort Journal of Vet. Research, vol. 54, No. 3, 1987, pp. 197-204.

Madigan, J.E., et al., "Equine Granulocytic Ehrlichiosis in Connecticut Caused by an Agent Resembling the Human Granulocytotropic Ehrlichia," Journal of Clinical Microbiology, vol. 34, No. 2, 1996, pp. 434-435.

Madigan, J.E., "Transmission and Passage in Horses of the Agent of Human Granulocytic Ehrlichiosis," Journal of Infectious Diseases, vol. 172, 1995, pp. 1141-1144.

Maeda, M.D., K., et al., "Human Infection with *Ehrlichia canis*, a Leukocytic Rickettsia," N. Engl. J. Med., vol. 316, 1987, pp. 853-856.

Mahan, S.M., et al., "An immunoblotting diagnostic assay for heartwater based on the immunodominant 32-kilodalton protein of *Cowdria ruminantium* detects false positive in the field sera," Journal of Clinical Microbiology, vol. 31, No. 10, 1993, pp. 2729-2737.

Maniatis, T., "Recombinant DNA Procedures in the Study of Eukaryotic Genes," Cell Biology, vol. 3, 1980, 24 pages.

Mathew, J.S., et al., "Efficacy of a modified polymerase chain reaction assay for detection of *Ehrlichia canis* infection," J Vet Diagn Invest, vol. 12, 2000, pp. 456-459.

Matthewman, L.A., et al., "Reactivity of sera collected from dogs in Mutare, Zimbabwe, to antigens of *Ehrlichia canis* and *Cowdria ruminantium*," The Veterinary Record, vol. 134, No. 19, May 7, 1994, pp. 498-499.

Mavromatis, K., et al., "The Genome of the Obligately Intracellular Bacterium *Ehrlichia canis* Reveals Themes of Complex Membrane Structure and Immune Evasion Strategies," Journal of Bacteriology, vol. 188, No. 11, 2006, pp. 4015-4023.

McBride, J.W., et al., "A conserved, transcriptionally active p28 multigene locus of *Ehrlichia canis*," Gene, vol. 254, 2000, pp. 245-252.

McBride, J.W., et al., "Molecular characterization of a new 28-kilodalton protein gene and a multigene locus encoding five homologous 28-kilodalton immunodominant outer member proteins of *Ehrlichia canis*," Chapter 1, Rickettsiae and Rickettsial Diseases at the Turn of the Third Millennium, 1999, pp. 43-47.

McBride, J.W., et al., "Molecular Cloning of the Gene for a Conserved Major Immunoreactive 28-kilodalton Protein of *Ehrlichia canis*: a Potential Serodiagnostic Antigen," Clinical and Diagnostic Laboratory Immunology, vol. 6, No. 3, 1999, pp. 392-399.

McBride, J.W., et al., "Immunodiagnosis of *Ehrlichia canis* infection with Recombinant Proteins," Journal of Clinical Microbiology, vol. 39, No. 1, Jan. 2001, pp. 315-322.

McDade, J.E., "Ehrlichiosis—A Disease of Animals and Humans," J. Infect Dis., vol. 161, No. 4, 1990, pp. 609-617.

McKnight, S.L., "Functional Relationships between Transcriptional Control Signals of the Thymidine Kinase Gene of Herpes Simplex Virus," Cell, vol. 31, Dec. 1982, pp. 355-365.

Miller, D.W., et al., "An Insect Baculovirus Host-Vector System for High-Level Expression of Foreign Genes," Genetic Engineering, Principles and Methods, vol. 8, 1979, 24 pages.

Murphy, G.L., et al., "A molecular and serologic survey of *Ehrlichia canis, E. chaffeensis*, and *E. ewingii* in dogs and ticks from Oklahoma," Veterinary Parasitology, vol. 79, 1998, pp. 325-339.

Murphy, C.I., et al., "Major Antigenic Proteins of the Agent of Human Granulocytic Ehrlichiosis are Encoded by Members of a Multigene Family," Infection and Immunity, vol. 66, No. 8, 1998, pp. 3711-3718.

Nadelman, R.B., et al., "Simultaneous Human Granulocytic Ehrlichiosis and Lyme Borreliosis," The New England Journal of Medicine, vol. 337, No. 1, 1997, pp. 27-30.

Ndip, L.M., et al., "Ehrlichial infection in Cameroonian canines by *Ehrlichia canis* and *Ehrlichia ewingii*," Veterinary Microbiology, vol. 111, 2005, pp. 59-66.

Neer, T.M., et al., "Consensus Statement on Ehrlichial Disease of Small Animals from the Infectious Disease Study Group of the ACVIM," J. Vet. Intern. Med., vol. 16, 2002, pp. 309-315.

Oberle, S.M., et al., "Derivation of the complete msp4 gene sequence of *Anaplasma marginate* without cloning," Gene, vol. 136, 1993, pp. 291-294.

Ohashi, N., et al., "Analysis of Transcriptionally Active Gene Clusters of Major Outer Membrane Protein Multigene Family in *Ehrlichia canis* and *E. chaffeensis*," Infection and Immunity, vol. 69, No. 4, Apr. 2001, pp. 2083-2091.

Ohashi, N., et al., "Characterization of p30 Multigene Family of *Ehrlichia canis*," Abstract D/B-126, 99th General Meeting of the American Society for Microbiology, Chicago, Illinois, May 30-Jun. 3, 1999, 2 pages.

Ohashi, N., et al., "Immunoprotective 28-kDa outer membrane protein of Ehrlichia chaffeensis is a member of multi-sized protein antigen family," In Abstracts of the 97th General Meeting of the American Society for Microbiology, D-80, May 4, 1997, two pages.

Palmer, G.H., et al., "Immunization of Cattle with a 36-Kilodalton Surface Protein Induces Protection against Homologous and Heterologous *Anaplasma marginale* Challenge," Infection and Immunity, vol. 56, No. 6, 1988, pp. 1526-1531.

Palmer, G.H., et al., "The Immunoprotective *Anaplasma marginale* Major Surface Protein 2 is Encoded by a Polymorphic Multigene Family," Infection and Immunity, vol. 62, No. 9, Sep. 1994, pp. 3808-3816.

(56) References Cited

OTHER PUBLICATIONS

Perez, M., et al., "*Ehrlichia canis*-Like Agent Isolated from a Man in Venezuela: Antigenic and Genetic Characterization," Journal of Clinical Microbiology, Sep. 1996, vol. 34, No. 9, Sep. 1996, pp. 2133-2139.

Philipp, M.T., et al., "A Decline in $C_6$ Antibody Titer Occurs in Successfully Treated Patients with Culture-Confirmed Early Localized or Early Disseminated Lyme Borreliosis," Clinical and Diagnostic Laboratory Immunology, vol. 12, No. 9, Sep. 2005, pp. 1069-1074.

Pollock, R.M., "Determination of Protein-DNA Sequence Specificity by PCR-Assisted Binding-Site Selection," Current Protocols in Molecular Biology, 1996, Supplement 33, 2000, 15 pages.

Pretorius, A-M, et al., "Serological survey for antibodies reactive with *Ehrlichia canis* and *E. chaffeensis* in dogs from the Bloemfontein area, South Africa," Tydskr.S.Afr.vet.Ver., vol. 69, No. 4, 1998, pp. 126-128.

Pusterla, N., et al., "Identification of a Granulocytic *Ehrlichia* Strain Isolated from a Horse in Switzerland and Comparison with Other Rickettsiae of the *Ehrlichia phagocytophila* Genogroup," Journal of Clinical Microbiology, vol. 36, No. 7, 1998, pp. 2035-2037.

Rechav, Y., et al., "Evidence for Attachment Pheromones in the Cayenne Tick (Acari: Ixodidae)," J. Med. Entomol., vol. 34, No. 2, 1997, pp. 234-237.

Reddy, G., et al., "A Family of 28 kDa Variant Surface Antigen Genes of the tribe *Ehrlichiae*: Does it play a role in immune evasion?" Abstract Annual Meeting of ASRRD, Sep. 23, 1997, two pages.

Reddy, G., et al., "Molecular characterization of a 28 kDa Surface Antigen Gene Family of the Tribe Ehrlichiae," Biochemical and Biophysical Research Communications, vol. 247, Jun. 1998, pp. 636-643.

Reddy, G., et al., "Sequence Heterogeneity of the Major Antigenic Protein 1 Genes from *Cowdria ruminantium* Isolates from Different Geographical Areas," Clinical and Diagnostic Laboratory Immunology, vol. 3, No. 4, 1996, pp. 417-422.

Reddy, G.R., et al., "Variability in the 28-kDa Surface Antigen Protein Multigene Locus of Isolates of the Emerging Disease Agent Ehrlichia chaffeensis Suggests that it plays a role in Immune Evasion," Mol. Cell. Biology Research Communications, vol. 1, 1999, pp. 167-175.

Rikihisa, Y., et al., "Analyses of *Ehrlichia canis* and a Canine Granulocytic *Ehrlichia* Infection," Journal of Clinical Microbiology, vol. 30, No. 1, 1992, pp. 143-148.

Rikihisa, Y., et al., "C-Reactive Protein and α1-Acid Glycoprotein Levels in Dogs Infected with *Ehrlichia canis*," Journal of Clinical Microbiology, vol. 32, No. 4, 1994, pp. 912-917.

Rikihisa, Y., "Clinical and biological aspects of infections caused by *Ehrlichia chaffeensis*," Microbes and Infection, vol. 1, 1999, pp. 367-376.

Rikihisa, Y., "Ehrlichiae of Veterinary Importance," In Rickettsiae and rickettsial diseases at the turn of the third millennium, D. Raoult, P. Brouqui, Ed., 1999, pp. 393-404.

Rikihisa, Y., et al., "Ehrlichiosis," Journal of Clinical Microbiology, vol. 22, No. 4, 1995, 15 pages.

Rikihisa, Y., "Rickettsiae and Rickettsial Diseases," In Proceedings of the $5^{th}$ International Symposium on Rickettsiae and Rickettsial Diseases, Bratislava, Slovak Republic, Sep. 1-6, 1996, pp. 272-286.

Rikihisa, Y., et al., "Molecular Characterization of *Aegyptianella pullorum* (Rickettsiales, Anaplasmataceae)," Journal of Clinical Microbiology, vol. 41, No. 11, 2003, pp. 5294-5297.

Rikihisa, Y., "The Tribe Ehrlichieae and Ehrlichial Diseases," Clinical Microbiology Reviews, vol. 4, No. 3, Jul., 1991, pp. 286-308.

Rikihisa, Y., et al., "Ultrastructural and Antigenic Characterization of a Granulocytic Ehrlichiosis Agent Directly Isolated and Stably Cultivated from a Patient in New York State," Journal of Infectious Diseases, vol. 175, 1997, pp. 210-213.

Rikihisa, Y., et al., "Western Immunoblot Analysis of *Ehrlichia chaffeensis*, *E. canis*, or *E. ewingii* Infections in Dogs and Humans," Journal of Clinical Microbiology, vol. 32, No. 9, Sep. 1994, pp. 2107-2112.

Rutherford, K., et al., "Artemis: sequence visualization and annotation," Bioinformatics, vol. 16, No. 10, 2000, pp. 944-945.

Sambrook, J., et al., "Molecular Cloning: A Laboratory Manual," $2^{nd}$ edition, Cold Spring Harbor Laboratory Press, 1989, cover page, contents pp. xi-xxxviii, Chapters 2, 5 and 6, 160 pages.

Scherf, A., et al., "Antigenic variation in malaria: in situ switching, relaxed and mutually exclusive transcription of var genes during intra-erythrocytic development in *Plasmodium falciparum*," The EMBO Journal, vol. 17, No. 18, 1998, pp. 5418-5426.

Seidman, C.E., "Introduction of Plasmid DNA into Cells," Current Protocols in Molecular Biology, Supplement 37, 1997, 37 pages.

Shaw, D.R., et al., "Mouse/Human Chimeric Antibodies to a Tumor-Associated Antigen: Biologic Activity of the Four Human IgG Subclasses," Articles, vol. 80, No. 19, 1988, pp. 1553-1559.

Smith, R.D., et al., "Development of *Ehrlichia canis*, Causative Agent of Canine Ehrlichiosis, in the Tick *Rhipicephalus sanguineus* and Its Differentiation from a Symbiotic Rickettsia," American Journal of Veterinary Research, vol. 37, No. 2, 1976, pp. 119-126.

Sonenshine, D.E., "Biology of Ticks," vol. 1, Oxford University Press, Inc., 1991, 66 pages.

St. Geme, III, J.W., et al., "Characterization of the Genetic Locus Encoding *Haemophilus influenza* Type b Surface Fibrils," Journal of Bacteriology, vol. 178, No. 21, 1996, pp. 6281-6287.

Standaert, S.M., et al., "Primary Isolation of *Ehrlichia chaffeensis* from Patients with Febrile Illnesses: Clinical and Molecular Characteristics," Journal of Infectious Diseases, vol. 181, 2000, pp. 1082-1088.

Stern, A., et al., "Opacity Genes in Neisseria gonorrheae: Control of Phase and Antigenic Variation," Cell, vol. 47, 1986, pp. 61-71.

Stich, et al., "A Polymerase Chain Reaction Assay for *Ehrlichia canis*," $3^{rd}$ International Conference, Ticks and Tick-Borne Pathogens: Into the $21^{st}$ Century, Hotel Academia, High Tatra Mountains, Slovakia, Aug. 30-Sep. 3, 1999, 2 pages.

Stich, R.W., et al., "Detection of *Anaplasma marginate* in *Dermacentor* species ticks with the polymerase chain reaction," Thesis presented to Oklahoma State University, Jul. 1992, 284 pages.

Stich, R.W., et al., "Detection of *Anaplasma marginate* (Rickettsiales: Anaplasmataceae) in Secretagogue-Induced Oral Secretions of Dermacentor *andersoni* (Acari: Ixodidae) with the Polymerase Chain Reaction," Journal of Mededical Entomology, vol. 30, No. 4, 1993, pp. 789-794.

Stich, R.W., et al., "Detection of *Ehrlichia canis* in Canine Carrier Blood and in Individual Experimentally Infected Ticks with a p30-Based PCR Assay," Journal of Clinical Microbiology, vol. 40, No. 2, 2002, pp. 540-546.

Stich, R.W., et al., "Preliminary Development of a Polymerase Chain Reaction Assay for *Anaplasma marginale* in Ticks," Biotechnology Techniques, vol. 5, No. 4, 1991, pp. 269-274.

Stich, R.W., et al., "Transstadial and attempted transovarial transmission of *Anaplasma marginale* by *Dermacentor variabilis*," Am. J. Vet. Res., vol. 50, No. 8, 1989, pp. 1377-1380.

Stiller, D., et al., "Detection of colonies of *Anaplasma marginale* in salivary glands of three *Dermacentor* spp infected as nymphs or adults," Am. J. Vet Res., vol. 50, No. 8, 1989, pp. 1381-1385.

Stiller, D., et al., "Recent developments in elucidating tick vector relationships for anaplasmosis and equine piroplasmosis," Veterinary Parasitology, vol. 57, 1995, pp. 97-108.

Stockham, S.L., et al., "Evaluation of granulocytic ehrlichiosis in dogs of Missouri, including serologic status to *Ehrlichia canis*, *Ehrlichia equi*, and *Borrelia burgdorferi*," Am. J. Vet. Res., vol. 53, No. 1, 1992, pp. 63-68.

Stockham, S.L., et al., "Experimental Transmission of Granulocytic Ehrlichial Organisms in Dogs," Veterinary Clinical Pathology, vol. 19, No. 4, 1990, pp. 99-104.

Storey, J.R., et al., "Molecular Cloning and Sequencing of Three Granulocytic *Ehrlichia* Genes Encoding High-Molecular-Weight Immunoreactive Proteins," Infection and Immunity, vol. 66, No. 4, 1998, pp. 1356-1363.

(56) References Cited

OTHER PUBLICATIONS

Sulsona, C.R., et al., "The map1 Gene of *Cowdria ruminantium* Is a Member of a Multigene Family Containing Both Conserved and Variable Genes," Biochemical and Biophysical Research Communications, vol. 257, 1999, pp. 300-305.
Sumption, K.J., et al., "Human ehrlichiosis in the UK," The Lancet, vol. 364, 1995, pp. 1487-1488.
Telford, III, S.R., et al., "Perpetuation of the agent of human granulocytic ehrlichiosis in a deer tick-rodent cycle," Proc. Natl. Acad. Sci. USA, vol. 93, 1996, pp. 6209-6214.
Uilenberg, G., "Heartwater (*Cowdria ruminatium* Infection): Current Status," Advances in Vet. Sci. and Comparative Med., vol. 27, 1983, pp. 427-480.
Ulmanen, I., et al., "Transcription and translation of foreign genes in Bacillus subtilis by the aid of a secretion vector," Journal of Bacteriology, vol. 162, No. 1, 1985, pp. 176-182.
Unver, et al., "Dot Immunoblot Assay for Canine Ehrlichiosis: Using Recombinant Major Protein Antigen of Ehrlichia Canis," Abstract D-29, 98th General Meeting of the American Society for Microbiology, Atlanta, Georgia, May 17-21, 1998.
Unver, A., et al., "Transcriptional Analysis of p30 Major Outer Membrane Multigene Family of *Ehrlichia canis* in Dogs, Ticks, and Cell Culture at Different Temperatures," Infection and Immunity, vol. 69, No. 10, 2001, pp. 6172-6178.
Urakami, H., et al., "Serodiagnosis of Scrib Typhus with Antigens Immobilized on Nitrocellulose Sheet," Journal of Clinical Microbiology, vol. 27, No. 8, 1989, pp. 1841-1846.
Van Heerden, H., et al., "Characterization of a major outer membrane protein multigene family in *Ehrlichia ruminantium*," Gene, vol. 330, 2004, pp. 159-168.
Vanhamme, L., et al., "Control of Gene Expression in Trypanosomes," Microbiological Reviews, vol. 59, No. 2, 1995, pp. 223-240.
Vieira, J., et al., "Production of Single-Stranded Plasmid DNA," Methods in Enzymology, vol. 153, 1987, pp. 3-11.
Voytek, M.A., et al., "Detection of ammonium-oxidizing bacteria of the beta-subclass of the class Proteobacteria in aquatic samples with the PCR," Applied and Environmental Microbiology, vol. 61, No. 4, 1995, pp. 1444-1450.
Walker, D.H., et al., "Emergence of the Ehrlichioses as Human Health Problems," Emerging Infectious Diseases, vol. 2, No. 1, 1996, pp. 18-29.
Walker, D.H., et al., "Emerging Bacterial Zoonotic and Vector-Borne Diseases: Ecological and Epidemiological Factors," Journal of the American Medical Association, vol. 275, No. 6, 1996, pp. 463-469.
Wen, B., et al., "Comparison of Nested PCR with Immunofluorescent-Antibody Assay for Detection of *Ehrlichia canis* Infection in Dogs Treated with Doxycycline," Journal of Clinical Microbiology, vol. 35, No. 7, 1997, pp. 1852-1855.
Whitlock, J.E., et al., "Prevalence of *Ehrlichia chaffeensis* (Rickettsiales: Rickettsiaceae) in *Amblyomma americanum* (Acari: Ixodidae) from the Georgia Coast and Barrier Islands," Journal of Medical Entomology, vol. 37, No. 2, 2000, pp. 276-280.
Wormser, G.P., et al., "False-positive Lyme disease serology in human granulocytic ehrlichiosis," The Lancet, vol. 347, 1996, pp. 981-982.
Yabsley, M.J., et al. "Ehrlichia *ewingii* Infection in White-Tailed Deer (*Odocoileus virginianus*)," Emerging Infectious Diseases, vol. 8, No. 7, 2002, pp. 668-671.
Yamamoto, S., et al., "Detection of Antibody to *Ehrlichia canis* in Dogs," J. Japanese Med. Assoc., vol. 47, 1994, pp. 765-767.
Yu, X-J, et al., "Characterization of the genus-common outer member proteins in *Ehrlichia*," Rickettsiae and Rickettsial Diseases at the Turn of the Third Millennium, 1999, pp. 103-107.
Yu, X-J, et al., "Genetic Diversity of the 28-Kilodalton Outer Membrane Protein Gene in Human Isolates of *Ehrlichia chaffeensis*," Journal of Clinical Microbiology, vol. 37, No. 4, 1999, pp. 1137-1143.
Yu, X-J, et al., "Sequence and characterization of an *Ehrlichia chaffeensis* gene encoding 314 amino acids highly homologous to the NAD A enzyme," FEMS Microbiol Let, vol. 154, No. 1, 1997, pp. 53-58.
Zaugg, J.L., et al., "Transmission of *Anaplasma marginate* Theiler by males of *Dermacentor andersoni* Stiles fed on an Idaho field-infected, chronic carrier cow," Am. J. Vet Res., vol. 47, No. 10, 1986, pp. 2269-2271.
Zhang, J-R., et al., "Antigenic Variation in Lyme Disease Borreliae by Promiscuous Recombination of VMP-like Sequence Cassettes," Cell, vol. 89, 1997, pp. 275-285.
Zhang, Y., et al., "Binding of Outer Membrane Proteins of *Ehrlichia chaffeensis* to DH82 Cells," Abstract D-79, 97th General Meeting of the American Society for Microbiology, Miami, May 4-8, 1997, one page.
Zhi, N., et al., "Characterization of the Expressed Genes in p44 Multigene Family Encoding Major Antigenic Outer Membrane Proteins of the Human Granulocytic Ehrlichiosis Agent in HL-60 cells," Abstract D/B-124, 99th General Meeting American Society for Microbiology, Chicago, Illinois, May 30-Jun. 3, 1999, one page.
Zhi, N., et al., "Comparison of Major Antigenic Proteins of Six Strains of the Human Granulocytic Ehrlichiosis Agent by Western Immunoblot Analysis," Journal of Clinical Microbiology, vol. 35, No. 10, 1997, pp. 2606-2611.
International Search Report, dated Feb. 25, 1999, in connection with International Application No. PCT/US1998/019600.
International Search Report and Written Opinion, dated Mar. 10, 2014, in connection with International Application No. PCT/US2013/072850.
International Search Report, dated Jan. 19, 2009, in connection with International Application No. PCT/US2008/062714.
International Search Report and Written Opinion, dated Mar. 10, 2014, in connection with related International Application No. PCT/US2013/072850.
Non-final Office Action received in U.S. Appl. No. 15/174,643 dated Mar. 29, 2017, 45 pages.
Notice of Allowance issued in co-pending U.S. Appl. No. 15/17,643, dated Aug. 30, 2017.

* cited by examiner

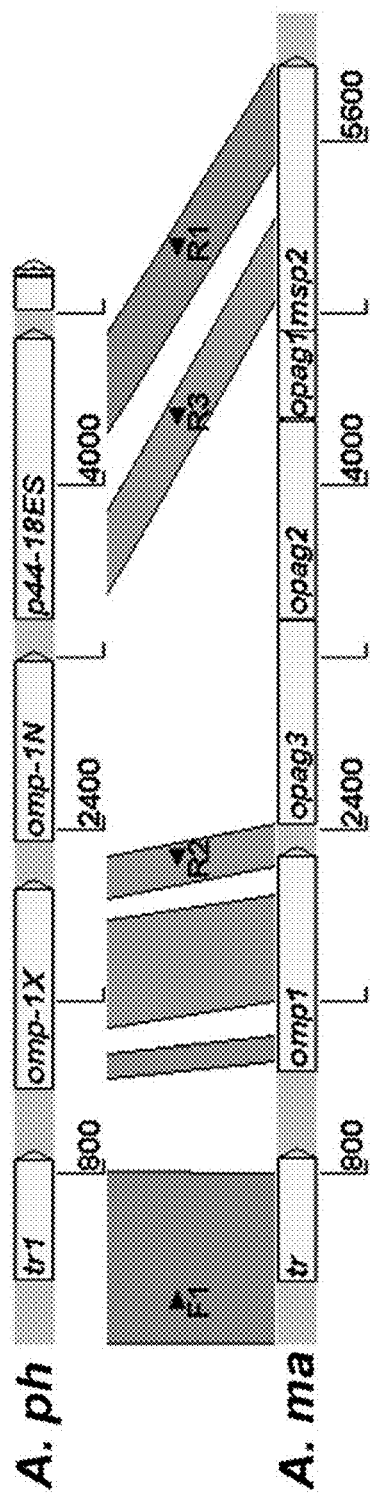
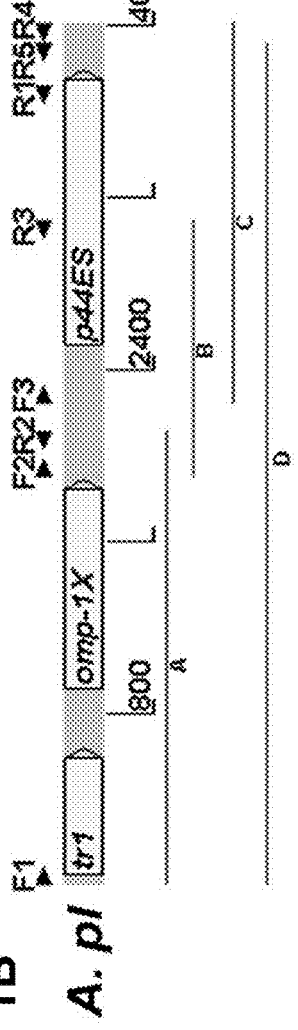
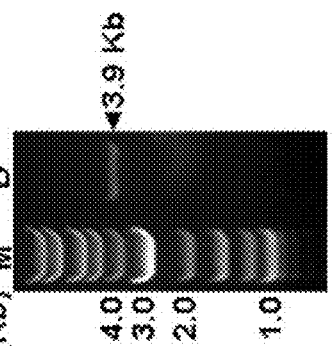
Figure 1A
Figure 1B
Figure 1C

A. platys Omp-1x

A. Platys P44ES

COMPOSITIONS AND METHODS FOR THE DETECTION OF *ANAPLASMA PLATYS*

GOVERNMENT RIGHTS

This invention was made with government support under R01 AI47885 and R01 AI054476 awarded by the National Institutes of Health. The government has certain rights in the invention.

BACKGROUND

*Anaplasma platys* (formerly *Ehrlichia platys*), an obligatory intracellular bacterium, was first described as a *rickettsia*-like agent in the platelets of dogs from Florida with infectious canine cyclic thrombocytopenia (ICCT) in 1978.[25] Authors pointed out morphological and biological similarity of this bacterium to *Ehrlichia canis* in infected dogs and *Anaplasma marginate* in infected cattle, two members of the family Anaplasmataceae,[25] which were well-known at that time. Clinical signs of ICCT are fever, depression, appetite loss, anorexia, and bleeding tendencies.[22] Parasitemia and thrombocytopenia occur in cycles at approximately 10 to 14 day intervals.[22] *Anaplasma platys* responds well to doxycycline, a tetracycline antibiotic, as the primary means of treatment.

Based on indirect fluorescence antibody (IFA) tests using the platelet-rich plasma from a dog experimentally infected with ICCT, minimal serologic cross-reaction was found to occur between *A. platys* and *E. canis*, and the researchers proposed the name "*Ehrlichia platys*" for this bacterium.[22] In 1992, the 16S rRNA gene sequence of *A. platys* was reported.[3] Subsequently, the groEL gene sequence of *A. platys* was disclosed.[29, 67] Phylogenetic analysis of these sequences showed that this is a distinct bacterium closely related to *Anaplasma phagocytophilum* and *Anaplasma marginate*, which led to reclassification of this bacterium into the genus *Anaplasma*.[17] Later it was reported that although *A. platys* does not cross-react with serum antibodies from dogs infected with *E. canis* on IFA tests, the *A. platys* antigen cross-reacts with anti-*Anaplasma phagocytophilum* antibodies.[32]

Seropositive dogs have been found in Florida, Pennsylvania, Texas, Louisiana, Illinois, California, Arkansas, Mississippi, Idaho, and North Carolina. High rates of *A. platys* and *E. canis* dual positive dogs have also been reported throughout these areas.[22] *A. platys* DNA has also been detected in dogs throughout Brazil,[20] Greece,[43] France,[33] Taiwan,[15] Spain,[54] China,[28] Australia,[12] Portugal,[13] the Democratic Republic of Congo,[55] Japan,[61] Thailand,[29] and Venezuela.[59] It is believed that the brown dog tick, *Rhipicephalus sanguineus*, is the biological vector which transfers *A. platys* to potential hosts. In fact, *A. platys* has been detected in brown dog ticks in Okinawa, Japan,[34] Spain,[58] and the Democratic Republic of Congo.[55] However, it has not been experimentally proven that *R. sanguineus* is the biological vector responsible for the transfer of *A. platys*.[56] To date, *A. platys* has never been culture isolated. Consequently this bacterium is poorly understood at the molecular, cellular, or immunologic level, and to date, no antigen has been identified for this bacterium.

In *A. phagocytophilum* and *A. marginate*, surface-exposed immunodominant 44 kDa major outer membrane proteins (P44s/Msp2s) are encoded by the p44 (msp2) polymorphic multigene family.[6, 9, 39, 41, 69-71] In *A. phagocytophilum*, P44 proteins consist of a single central hypervariable region of approximately 94 amino acid residues and an N-terminal and C-terminal conserved regions of approximately 186 and 146 amino acid residues, respectively.[41] A single polymorphic p44/msp2 expression locus (p44/msp2ES) is found in the genome of *A. phagocytophilum*[10] and *A. marginale*,[26] respectively. Both expression loci are found downstream of tr1 genes encoding putative transcriptional factor and homologs of *Ehrlichia chaffeensis* omp-1 genes encoding polymorphic major outer membrane protein (MOMP).[6, 8, 39] At p44/msp2ES, p44s and msp2 donor sequences elsewhere in the genome undergo recombination via RecF pathway to allow variable p44/msp2ES expression under the same promoter.[6, 8, 39, 40] This mechanism is thought to facilitate P44/Msp2 antigenic variation persistent infection and for adaptation to new environments such as transmission between tick and mammalian hosts.[7, 11, 38, 40, 65, 71] Purified native P44 from *A. phagocytophilum* and purified native OMP-1s (P28 and OMP-1F) of *Ehrlichia chaffeensis* have porin activity.[30, 37]

*Anaplasma platys* (Apl) is an obligate intracellular bacteria that infects platelets and causes a cyclic thrombocytopenia in the dog. The observation than a dog can be affected by this *rickettsia*' agent, and the disease is most likely transmitted by the *Rhipicephalus* spp of ticks. *Anaplasma platys* was first reported in the United States in 1978 and has since been reported in Europe, Asia, South America, the Middle East, Australia, and Africa. Because of the common vector, *Anaplasma platys* infection is often found as a coinfection with *Ehrlichia canis*. The ability of the organism to produce clinical disease in the dog appears to vary with geography, suggesting that strain differences may contribute to virulence. *Anaplasma platys* is related to another *Anaplasma* species known to cause clinical disease in the dog, *Anaplasma phagocytophilum* (Aph).

Current diagnostic tests that attempt to distinguish Aph and *Anaplasma platys* have limited specificity. PCR for Aph and *Anaplasma platys* using 16SrRNA has also had problems with specificity. Therefore, assays for specific detection of *Anaplasma platys* are needed in the art. Additionally, serological tests for *Anaplasma platys* are also needed.

BRIEF DESCRIPTION OF THE SEVERAL VIEWS OF THE DRAWINGS

FIG. 1A shows the strategy for *A. platys* p44ES cluster sequencing. *A. phagocytophilum* p44ES and *A. marginate* msp2ES were aligned to design primer F1 (targeting tr1/orf3 upstream highly conserved region) and degenerate primers R1 (targeting p44ES/msp2 C-terminal highly conserved region), R2 (targeting conserved intergenetic region between omp-1X/omp4 and omp-1N/omp3), R3 (targeting p44ES/msp2 N-terminal conserved region) and R4 (based on p44ES/msp2ES downstream conserved valS gene). Primers F2 and F3 were designed based on the sequence results. FIG. 1B shows the final sequence (4,009 bp) was assembled with the SeqMan program from the DNASTAR software suite. Genes are represented as boxes with arrows indicating their orientation. FIG. 1C shows the entire expression locus fragment D (arrow) amplified from the dog 2 blood DNA specimen by primers F1 and R5.

Figure 4:
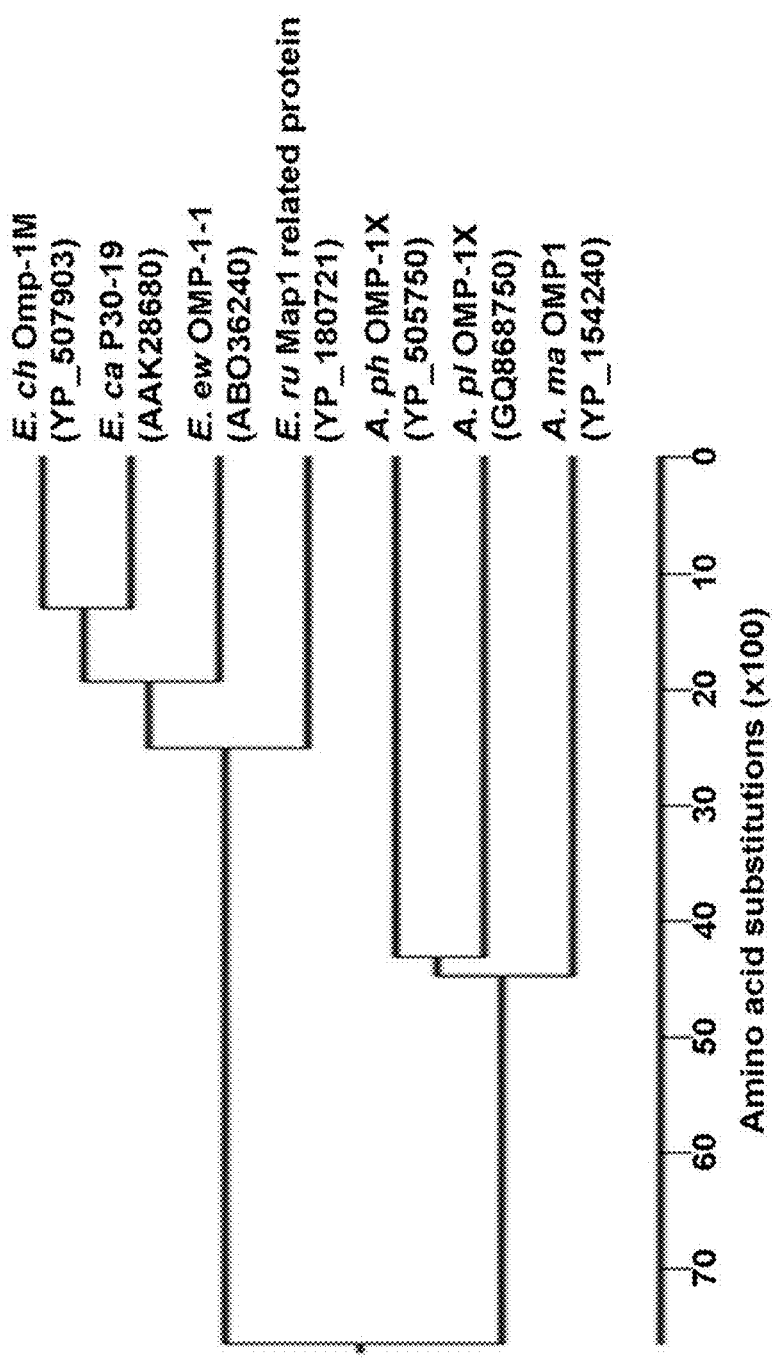

FIG. 4 shows the hylogenetic tree of OMP-1X proteins of *A. platys, A. phagocytophilum, A. marginate, E. canis, E. chaffeensis, E. ewingii, E. ruminantium*. The tree was constructed using DNASTAR MegAlign Clustal W method.

Figure 5:
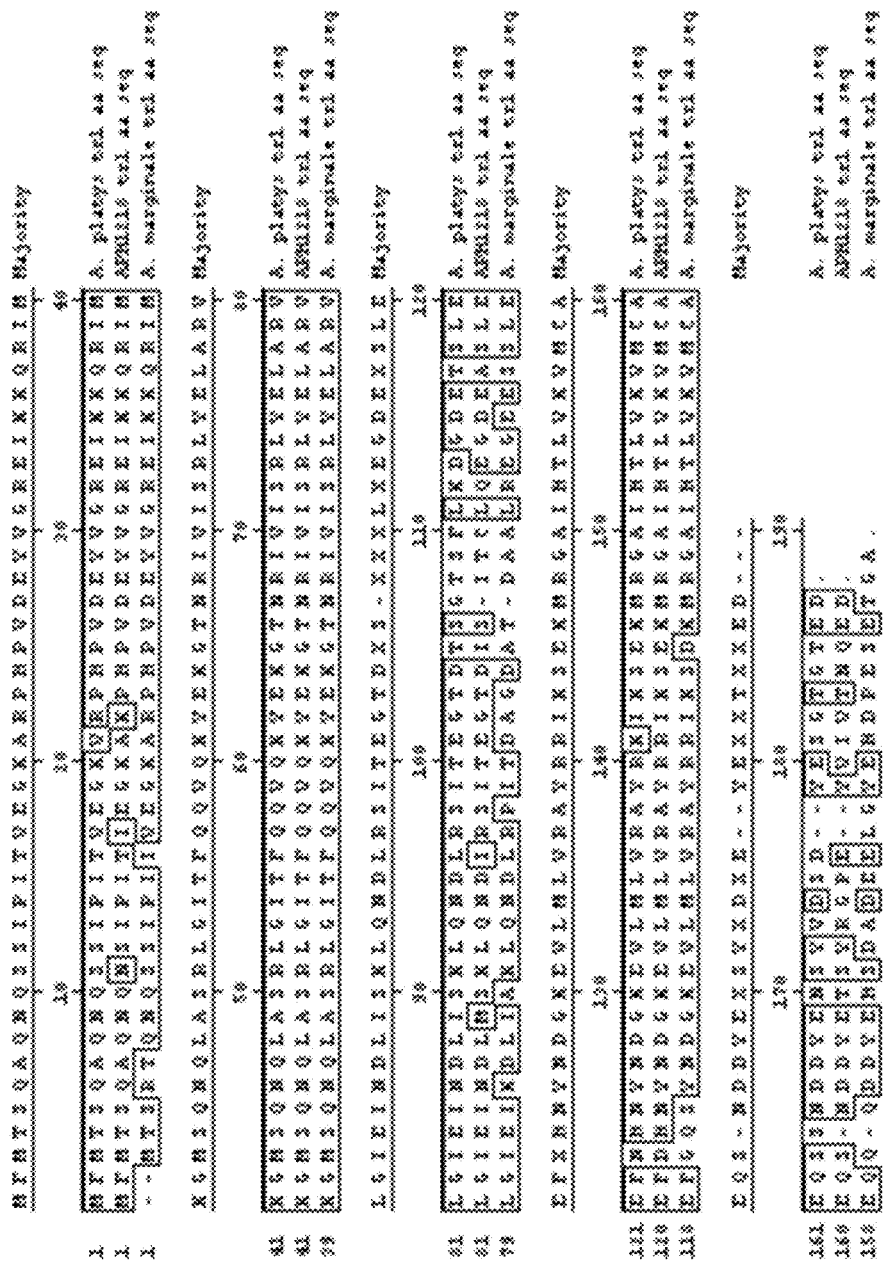

FIG. 5 shows the Tr1 sequence alignment of *A. platys, A. phagocytophilum*, and *A. marginate*. Sequences: Majority equals SEQ ID NO:133; *A. platys* seq equals SEQ ID NO:134; APH1218 equals SEQ ID NO:135; *A. marginale* equals SEQ ID NO:136.

Figure 6A:
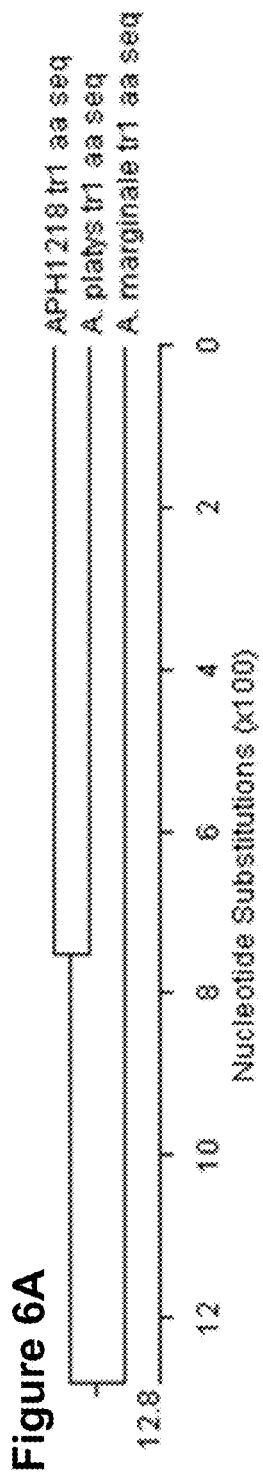

FIG. 6A shows the phylogram of Tr1 proteins of *A. platys, A. phagocytophilum*, and *A. marginate*. The tree was constructed using DNASTAR MegAlign Clustal W method.

Figure 6B:
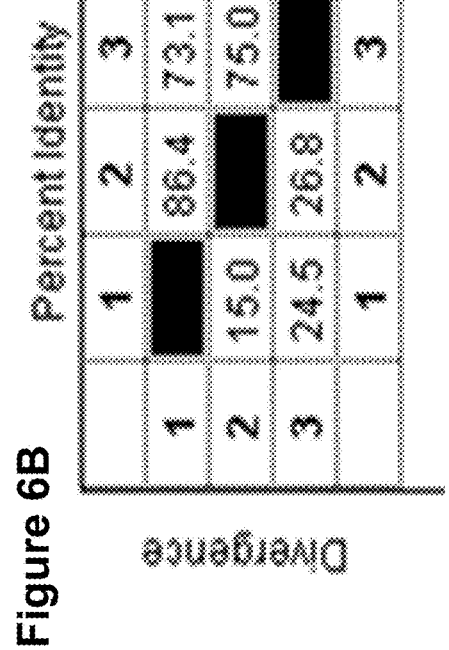

FIG. 6B shows the amino acid sequences identity between *A. platys* Tr1 and *A. phagocytophilum* Tr1 (YP_505749) or *A. marginate* AM1138 (YP_154239) were 86.4% and 73.1%, respectively.

Figure 7:
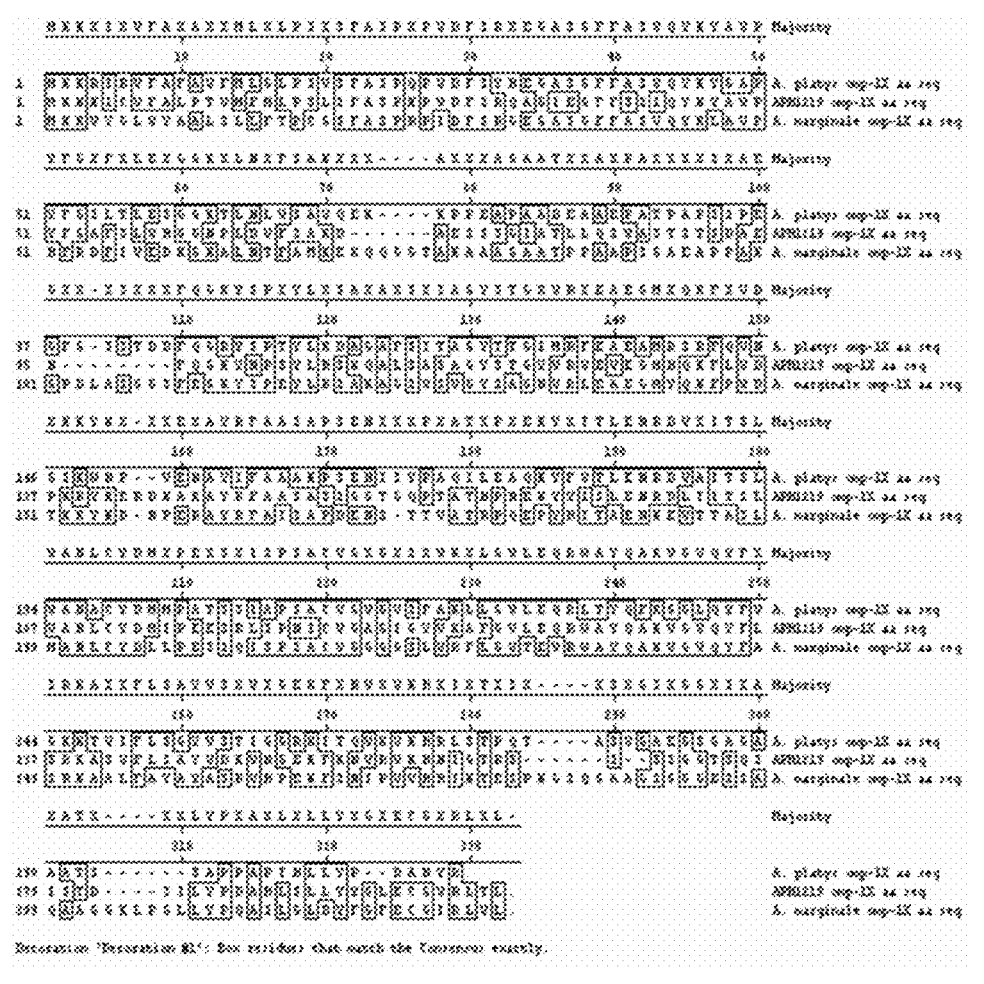

FIG. 7 shows the OMP-1X sequence alignment of *A. platys, A. phagocytophilum*, and *A. marginate*. Sequences: Majority equals SEQ ID NO:137; *A. platys* equals SEQ ID NO:1; APH1219 equals SEQ ID NO:138; *A. marginate* equals SEQ ID NO:139.

Figure 8A:
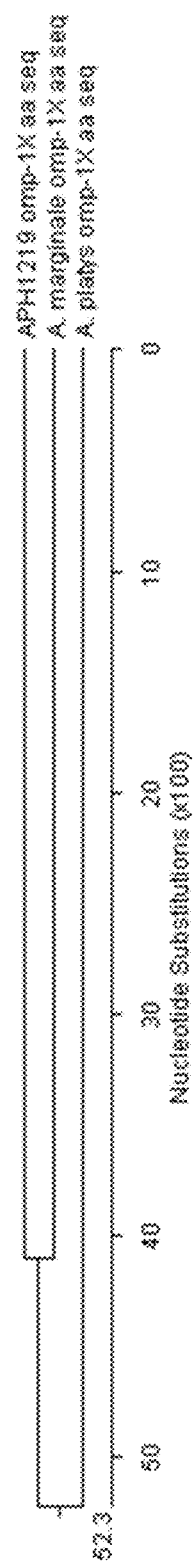
Figure 8B:
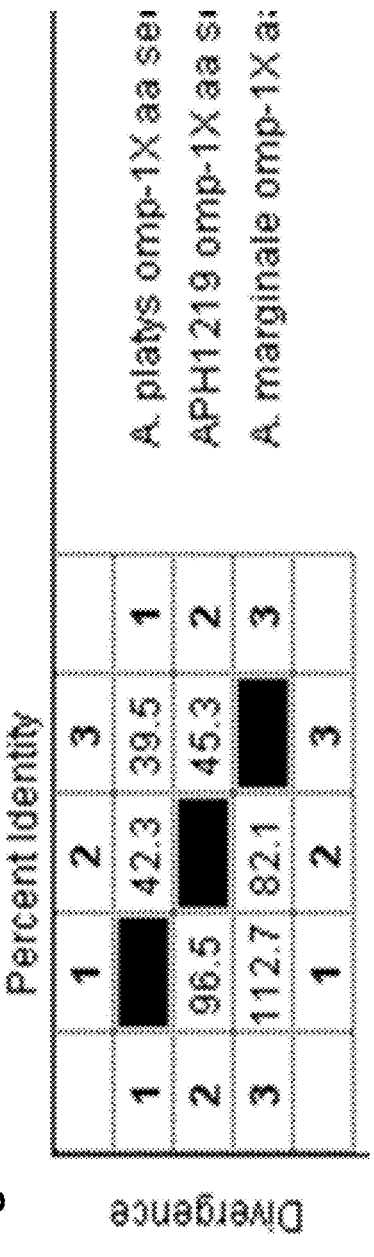

FIG. 8A shows the phylogram of OMP-1X proteins of *A. platys, A. phagocytophilum*, and *A. marginate*. The tree was constructed using DNASTAR MegAlign Clustal W method. FIG. 8B shows the amino acid sequence identities between *A. platys* OMP-1X and *A. phagocytophilum* OMP-1X (YP_505750) or *A. marginate* outer membrane protein 1 (YP_154240) were 42.3% and 39.5%, respectively.

Figure 9:
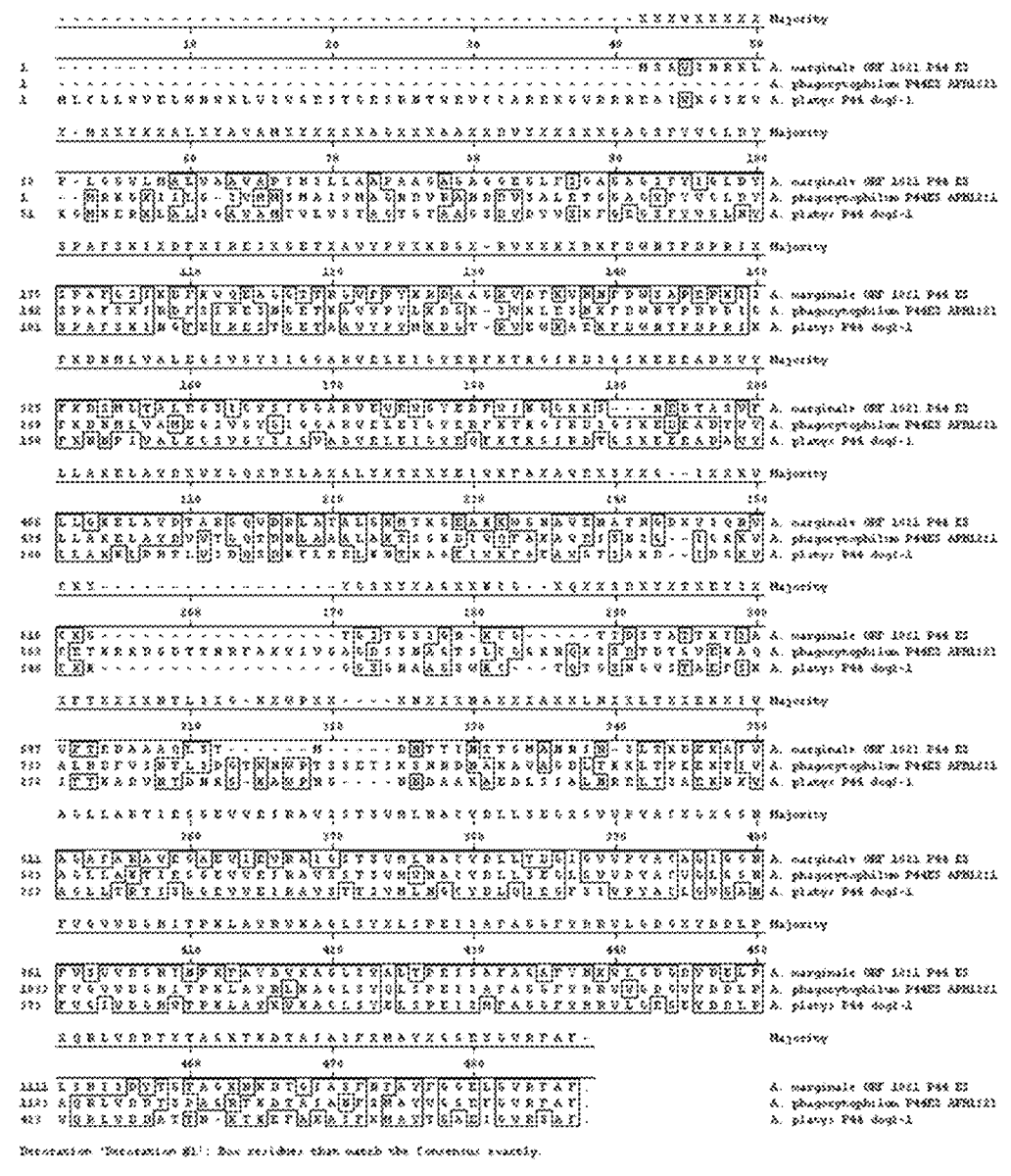

FIG. 9 shows the P44 sequence alignment of *A. platys, A. phagocytophilum*, and *A. marginate*. Sequences: Majority equals SEQ ID NO:140; *A. marginale* equals SEQ ID NO:141; *A. phagocytophilum* equals SEQ ID NO:142; *A. platys* equals SEQ ID NO:143.

Figure 10A:
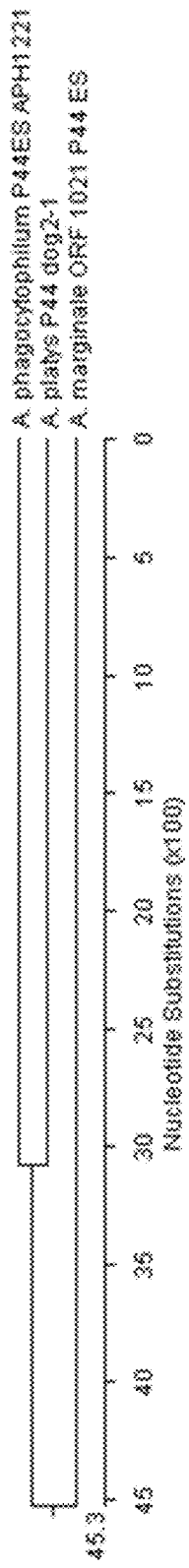
Figure 10B:
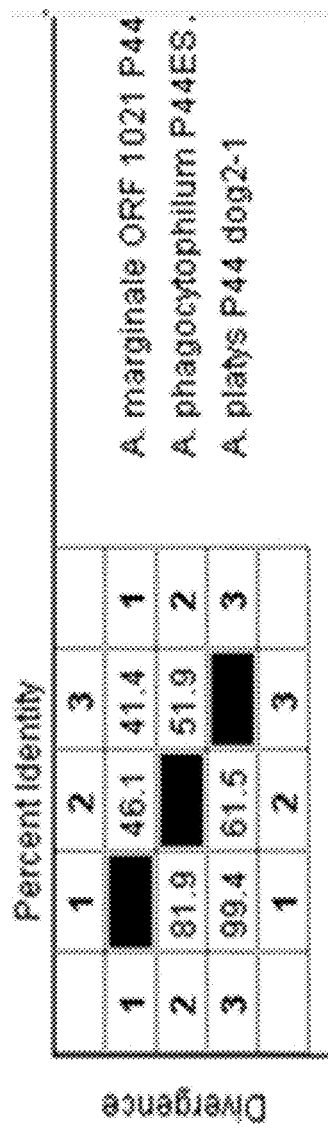

FIG. 10A shows the phylogram of P44 proteins of *A. platys, A. phagocytophilum*, and *A. marginate*. The tree was constructed using DNASTAR MegAlign Clustal W method. FIG. 10B shows the amino acid sequences identity between *A. platys* P44ES and *A. phagocytophilum* P44-18ES (YP_505752) or *A. marginate* msp2 (YP_154245) were 55.0~56.9% and 41.5~42.1%, respectively.

Figure 11:
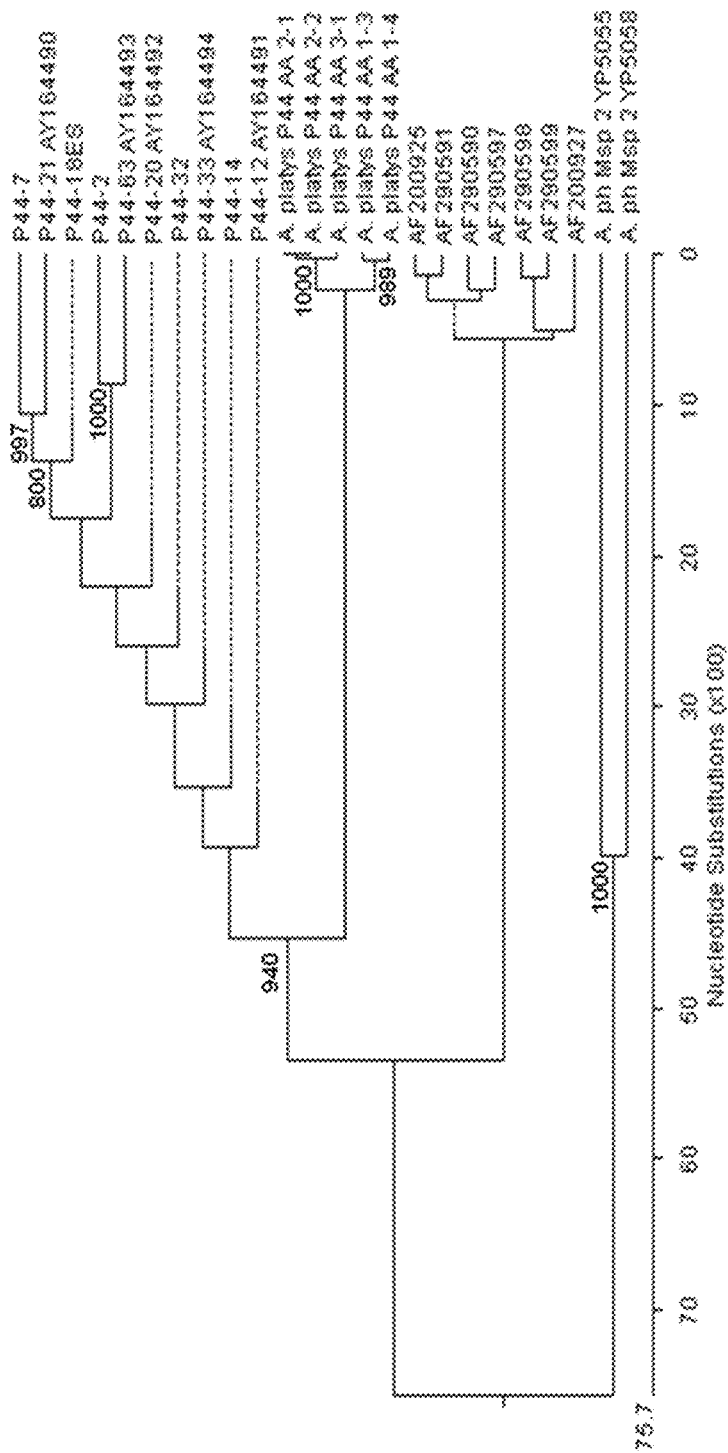
Figure 12:
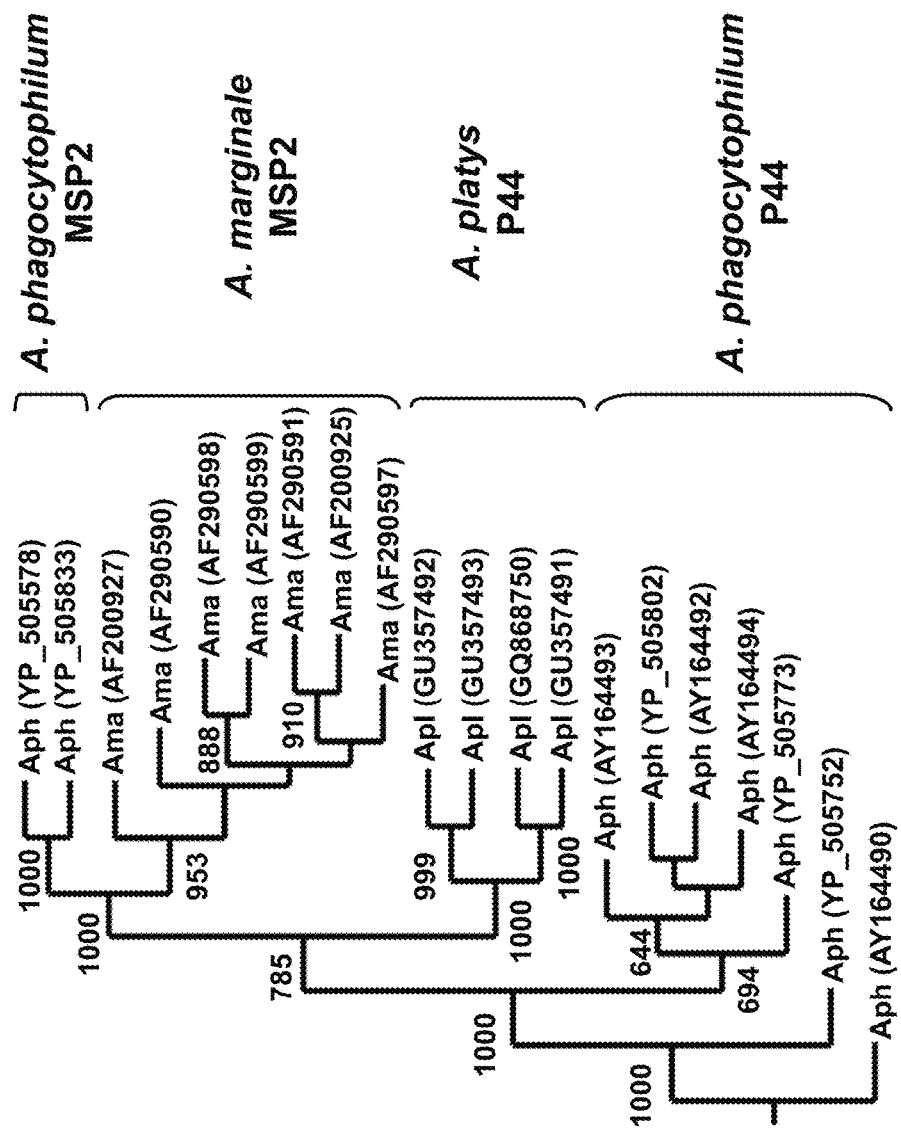

FIGS. 11 and 12 show P44ES/Msp2 proteins of *A. platys, A. phagocytophilum*, and *A. marginate*. A total of 24 P44/Msp2s were segregated into 3 clusters. The tree was constructed using the Neighbor-Joining (NEIGHBOR program from PHYLIP) method based on the alignment generated with Clustal V; 1,000 bootstrap replications were performed. The nodes supported by bootstrap values greater than 60% are labeled.

Figure 13A:
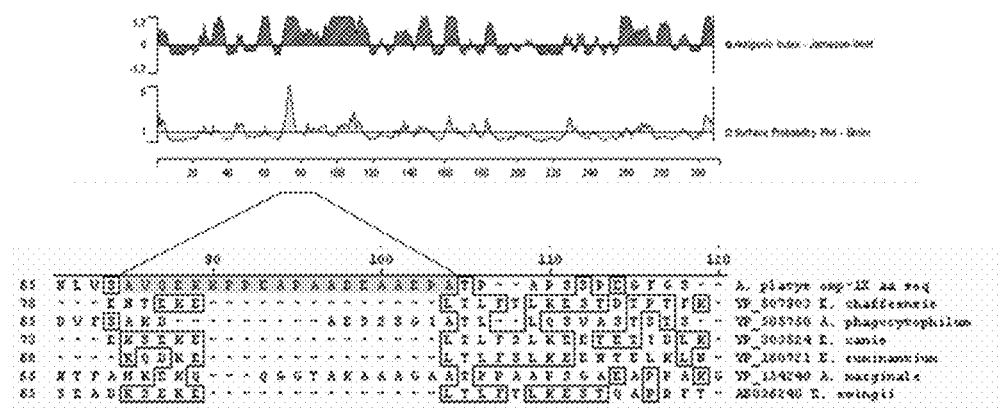
Figure 13B:
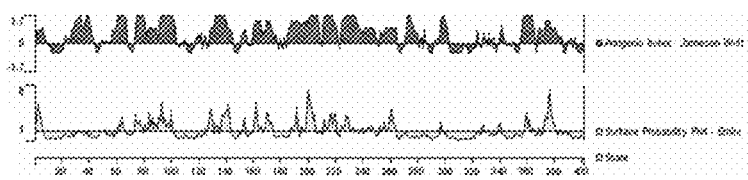
Figure 13B:
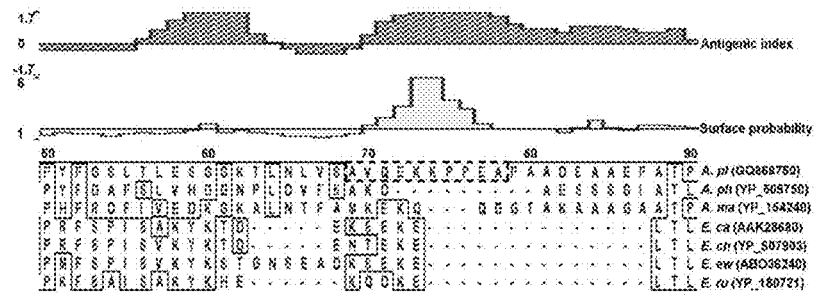

FIGS. 13A and 13B show the sequence alignment was completed using a DNASTAR SeqMan program. Alignment of *A. platys* (*A. pl*) OMP-1X protein (FIG. 13A) and P44DS protein (FIG. 13B) with related proteins from *A. phagocytophilum* (*A. ph*), *A. marginate* (*A. ma*), *E. canis* (*E. ca*), *E. chaffeensis* (*E. ch*), *E. ewingii* (*E. ew*), and *E. ruminantium* (*E. ru*) using the Clustal W method revealed a unique region in *A. platys* (AVQEKKPPEA (SEQ ID NO: 98), box lined by dashed bar). The antigenic index and surface probability profile suggest that this region is both antigenic and surface-exposed. Sequences: *A. platys* omp-1x aa equals SEQ ID NO:144; YP-507903 equals SEQ ID NO:145; YP-505750 equals SEQ ID NO:146; YP-303524 equals SEQ ID NO:147; YP-180721 equals SEQ ID NO:148; YP154240 equals SEQ ID NO:149; AB036240 equals SEQ ID NO:150; *A. pl* (GQ868750) equals SEQ ID NO:151; *A. ph* (YP505750) equals SEQ ID NO:152; *A. ma* (YP154240) equals SEQ ID NO:153; *E. ca* (AAK28680); *E. ch* (YP507903) equals SEQ ID NO:155; *E. ew* (AB036240) equals SEQ ID NO:156; *E. ru* (YP180721) equals SEQ ID NO:157.

Figure 14:
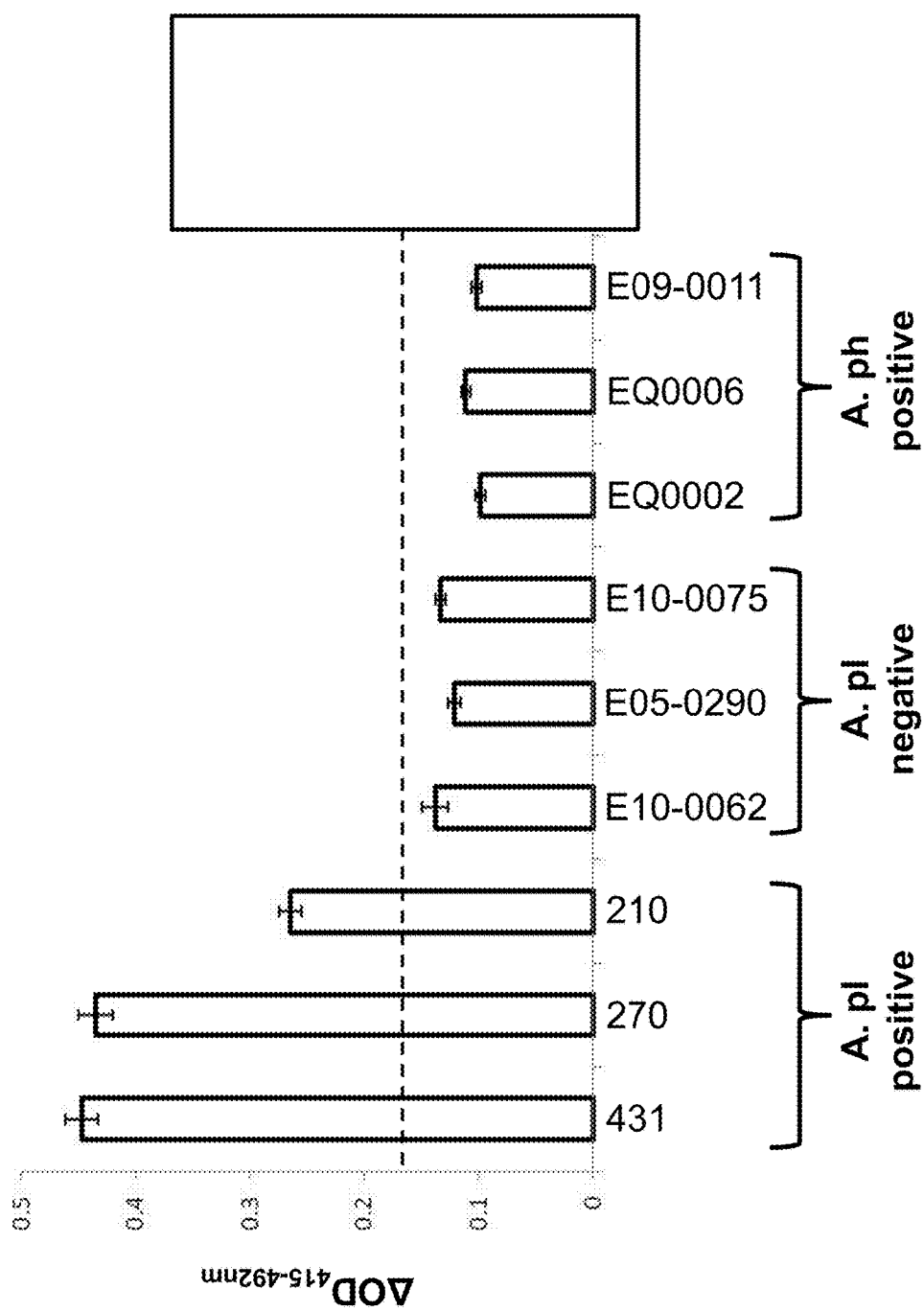

FIG. 14 shows the ELISA analysis of samples from *A. platys* PCR-positive dogs (No. 1-3), *A. platys* PCR-negative dogs (No. 4-6), and *A. phagocytophilum* seropositive horse serum samples (No. 7-9) with the *A. platys* specific peptide. The y axis shows the $OD_{415}$-$OD_{492}$ values. A reaction was considered positive when the plasmas from infected dogs yielded an $OD_{415}$-$OD_{492}$ value greater than the mean $OD_{415}$-$OD_{492}$ value for negative control plasma plus 3 standard deviations (dashed line). Representative data from triplicate assays are shown.

Figure 15:
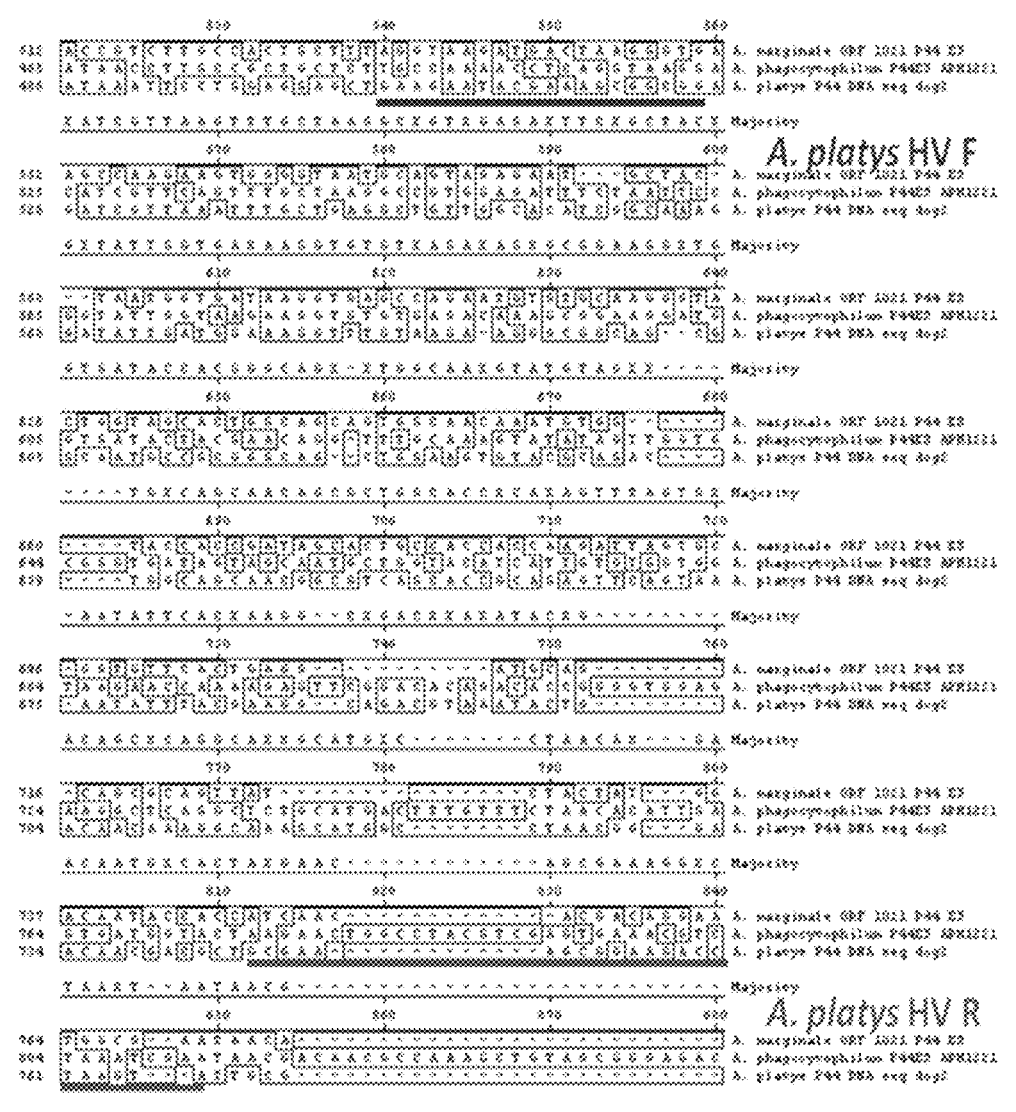

FIG. 15 shows the alignment of *A. platys, A. phagocytophilum*, and *A. marginate* p44/msp2 DNA. *A. platys*-species specific primers useful for species-specific PCR diagnosis are underlined in bold. Sequences: *A. marginale* equals SEQ ID NO:158; *A. phagocytophilum* equals SEQ ID NO:159; *A. platys* equals SEQ ID NO:160; Majority equals SEQ ID NO:161.

Figure 16:
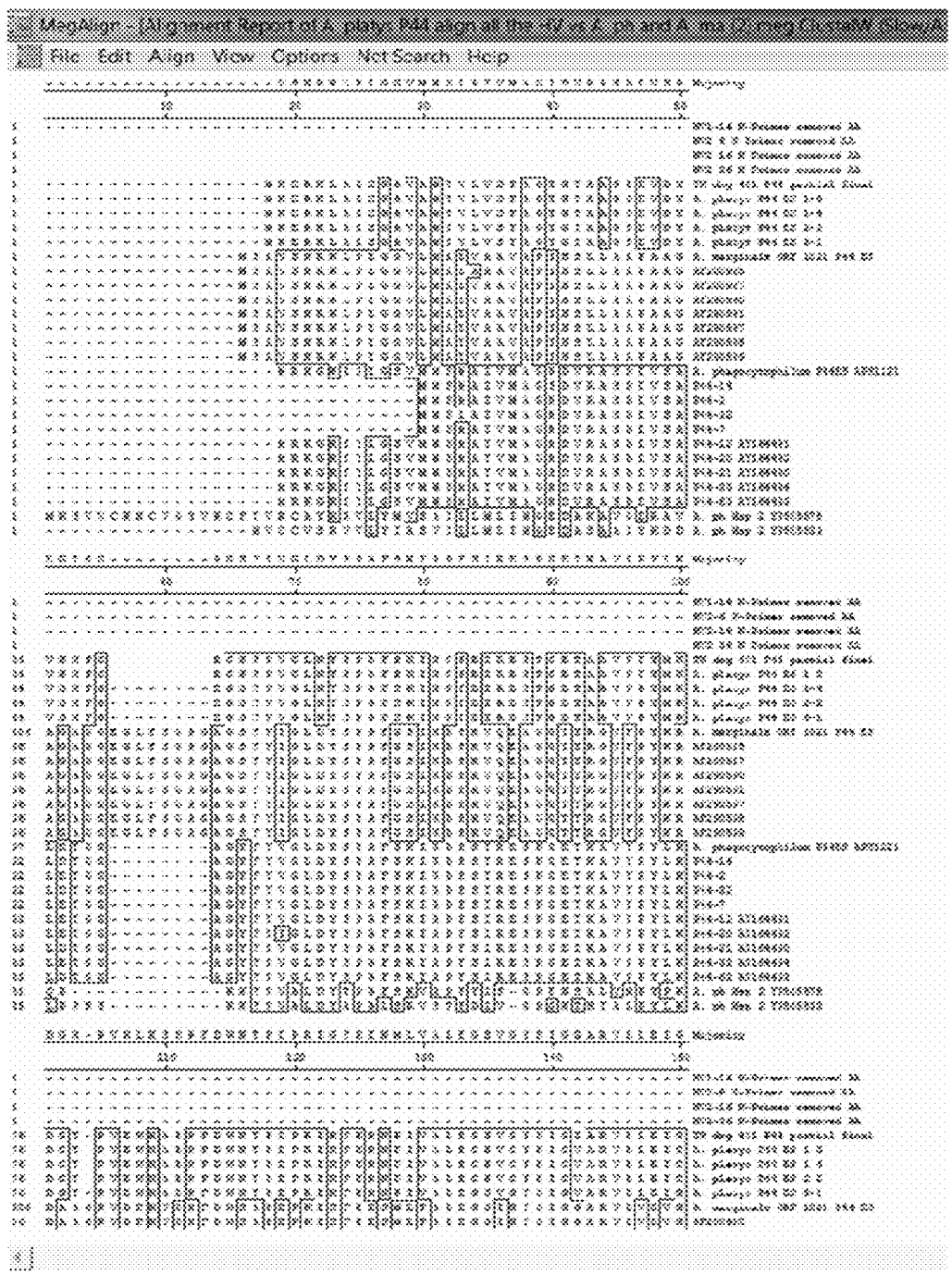
Figure 16:
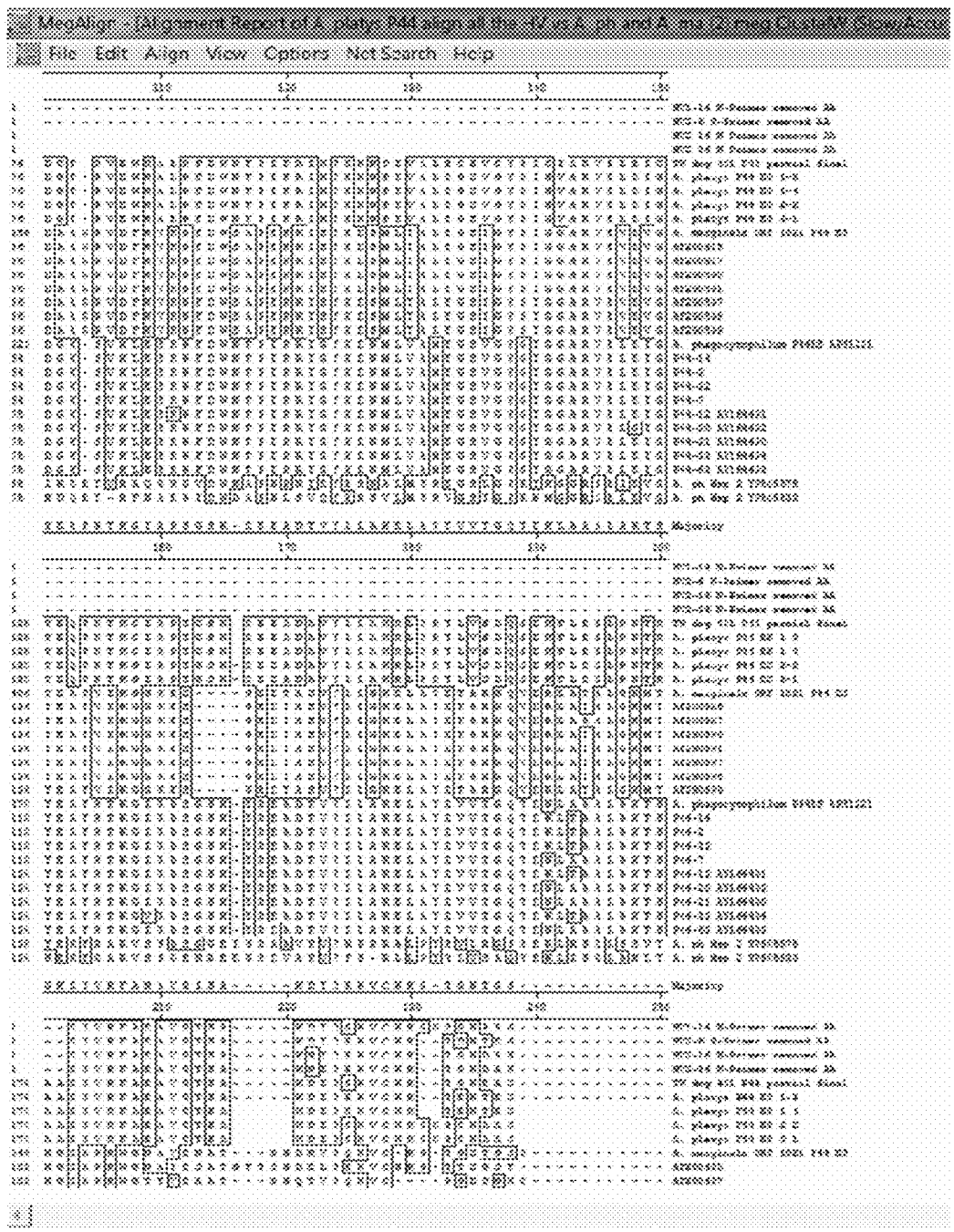
Figure 16:
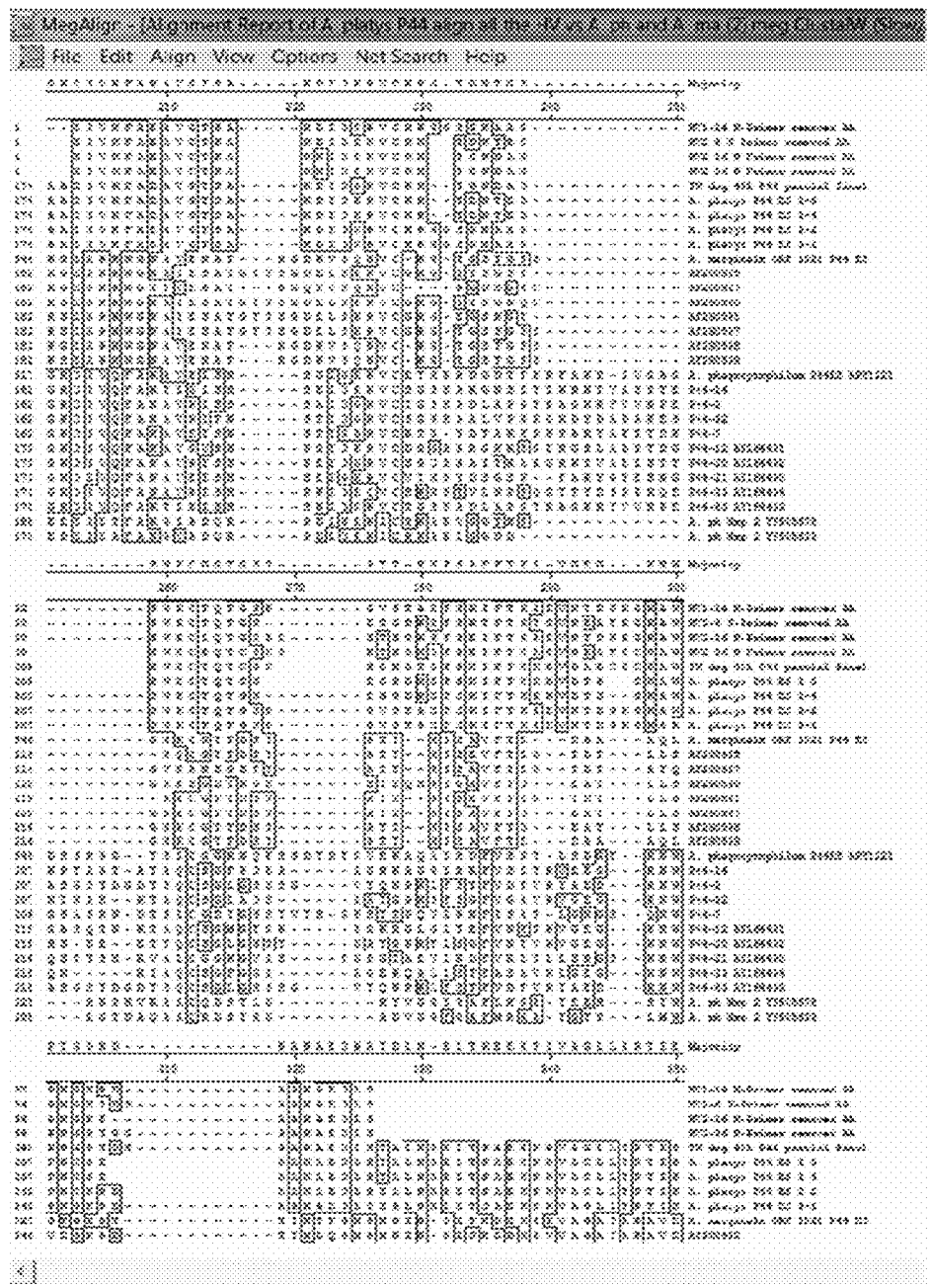
Figure 16:
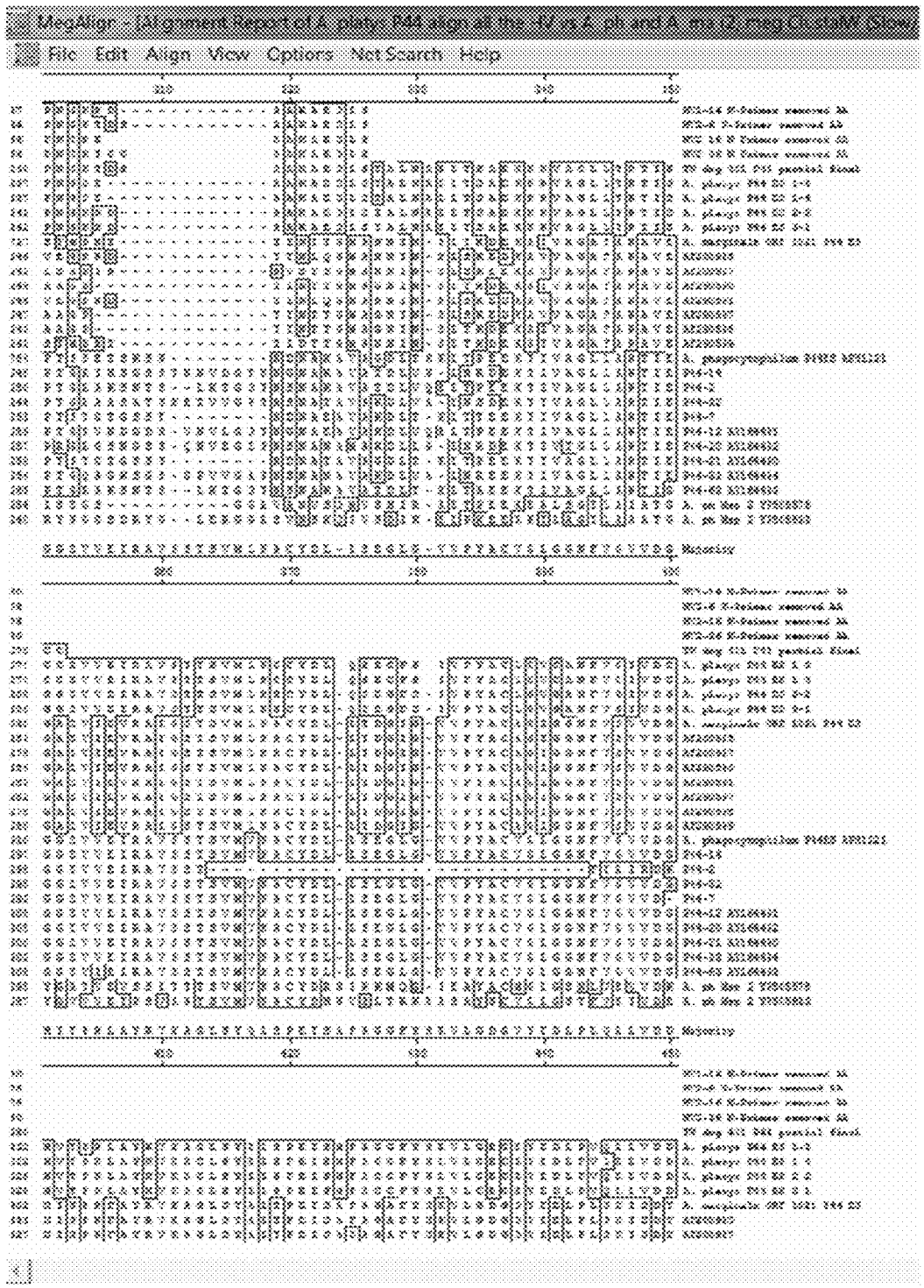

FIG. 16 shows the *A. platys, A. phagocytophilum*, and *A. marginate* amino acid sequence alignment. Sequences: Majority equals SEQ ID NO:162; HV1-14 N Primer sequence removed aa (GU357494) equals SEQ ID NO:163; HV2-6 N Primer sequence removed aa (GU357495) equals SEQ ID NO:164; HV2-16 N Primer sequence removed aa (GU357496) equals SEQ ID NO:165; HV2-36 N Primer sequence removed aa (GU357497) equals SEQ ID NO:166; TW Jury (dog 431) HQ735871 equals SEQ ID NO:167; *A. platys* P44 ES 1-3 equals SEQ ID NO:168; *A. platys* P44 ES 1-4 (GU357491) equals SEQ ID NO:22; *A. platys* P44 ES 2-2 (GU357492) equals SEQ ID NO:23; *A. platys* P44 ES 3-1 (GU357493) equals SEQ ID NO:24; *A. marginale* (YP_154245) equals SEQ ID NO:141; AF200925 equals SEQ ID NO:169; AF200927 equals SEQ ID NO:170; AF290590 equals SEQ ID NO:171; AF290591 equals SEQ ID NO:172; AF290597 equals SEQ ID NO:173; AF290598 equals SEQ ID NO:174; AF290599 equals SEQ ID NO:175; *A. phagocytophilum* equals SEQ ID NO:176; P44-14 equals SEQ ID NO:177; P44-2 equals SEQ ID NO:178; P44-32 equals SEQ ID NO:179; P44-7 equals SEQ ID NO:180; P44-12 (AY164491) equals SEQ ID NO:181; P44-20 (AY164492) equals SEQ ID NO:182; P44-21 (AY164490) equals SEQ ID NO:183; P44-33 (AY164494) equals SEQ ID NO:184; P44-63 (AY164493) equals SEQ ID NO:185; *A. ph*. MSP2 (YP505578) equals SEQ ID NO:186; *A. ph*. MSP2 (YP505833) equals SEQ ID NO:187.

Figure 17:
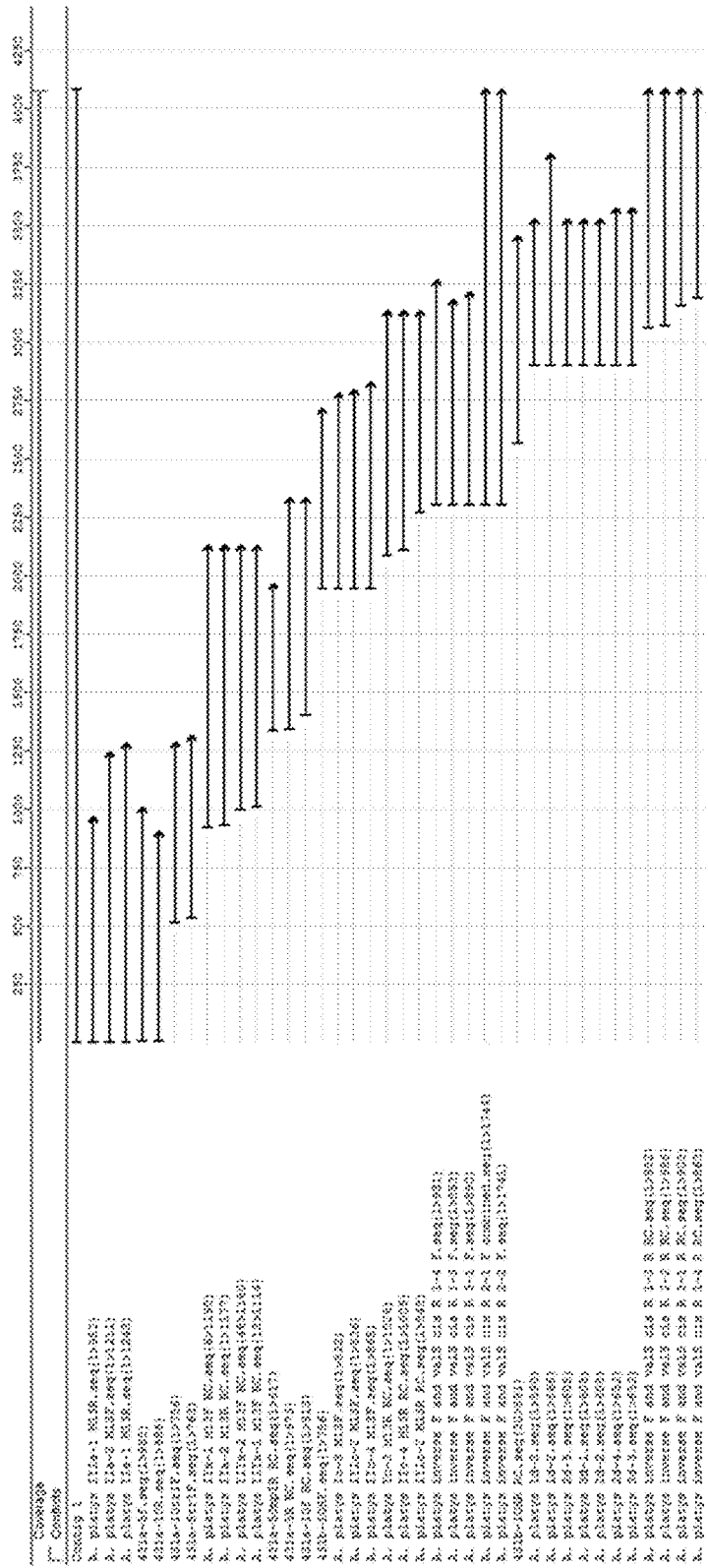

FIG. 17 shows the complete sequence assembly for the *A. platys* expression locus.

Figure 18:
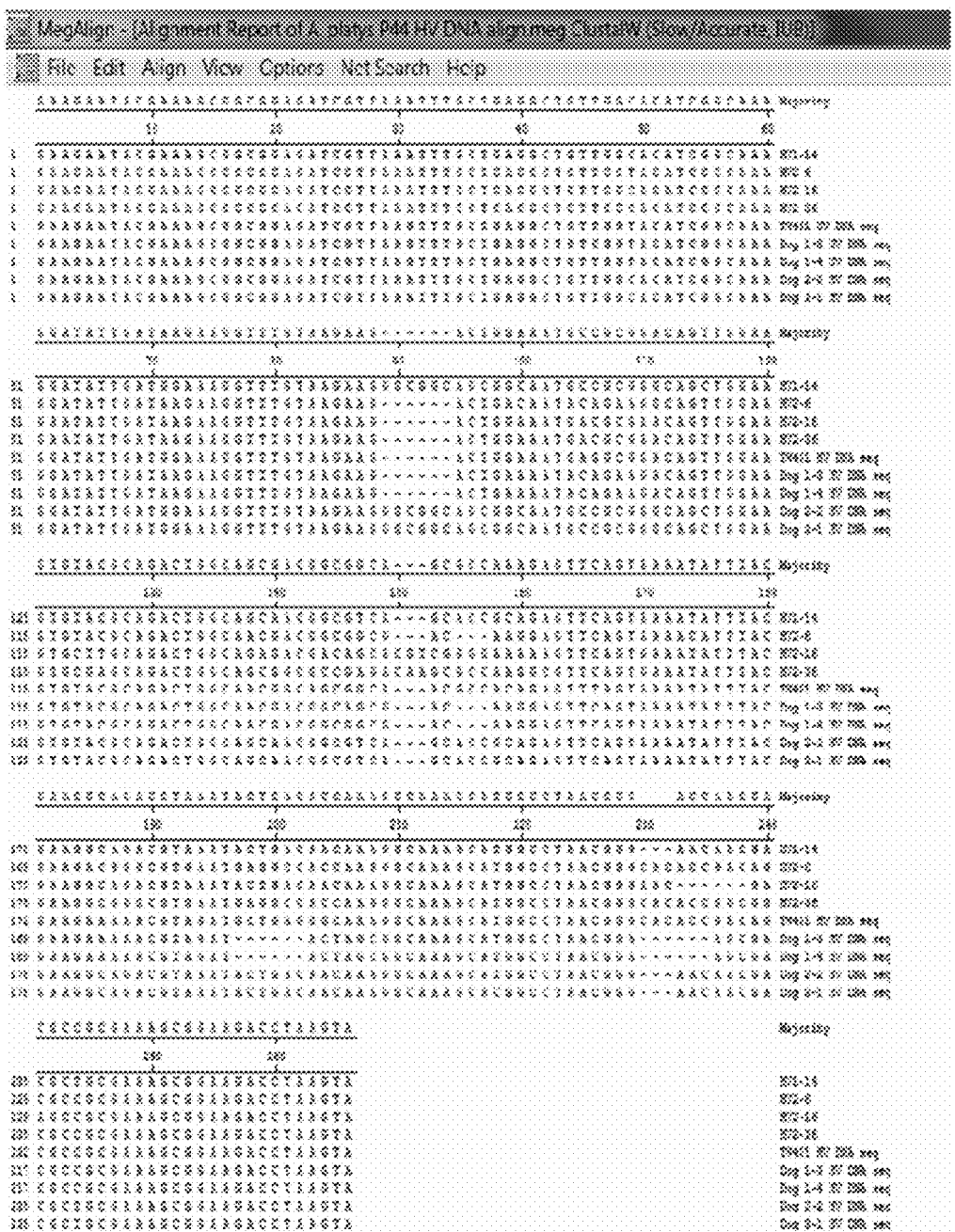
Figure 18:
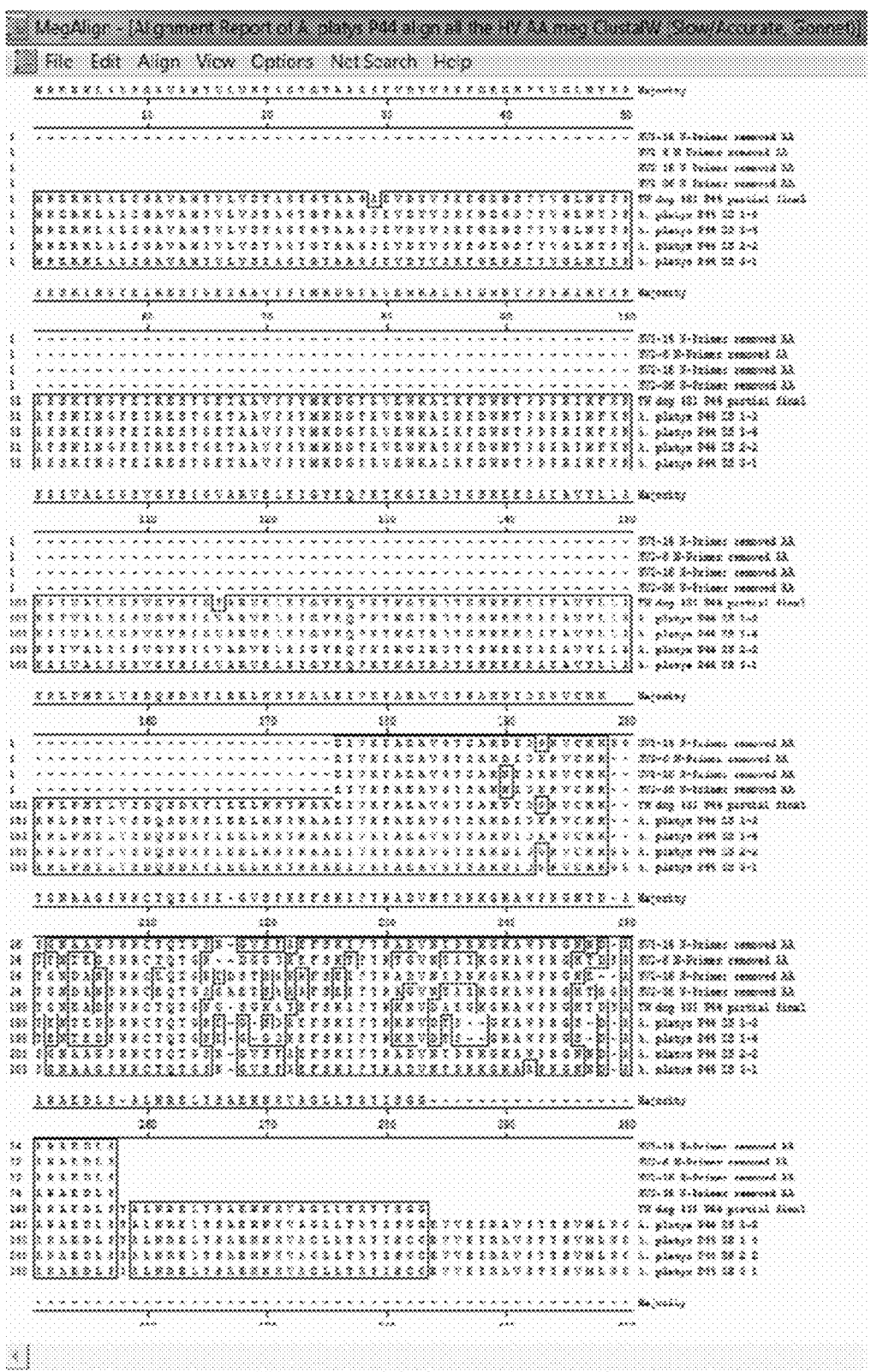

FIG. 18 shows the *A. platys* P44 alignment (DNA and protein). Sequences: Majority equals SEQ ID NO:188; H/1-14 (GU357494) equals SEQ ID NO:34; H/2-6 (GU357495) equals SEQ ID NO:35; H/2-16 (GU357496) equals SEQ ID NO:36; H/2-36 (GU357497) equals SEQ ID NO:37; TW431 HV (HQ735871) equals SEQ ID NO:189; Dog 1-3 (HQ868750) equals SEQ ID NO:190; Dog 1-4 (GU357491) equals SEQ ID NO:191; Dog 2-2 (GU357492) equals SEQ ID NO:192; Dog 3-1 (GU357493) equals SEQ ID NO:193; Majority equal SEQ ID NO:194.

Figure 19:
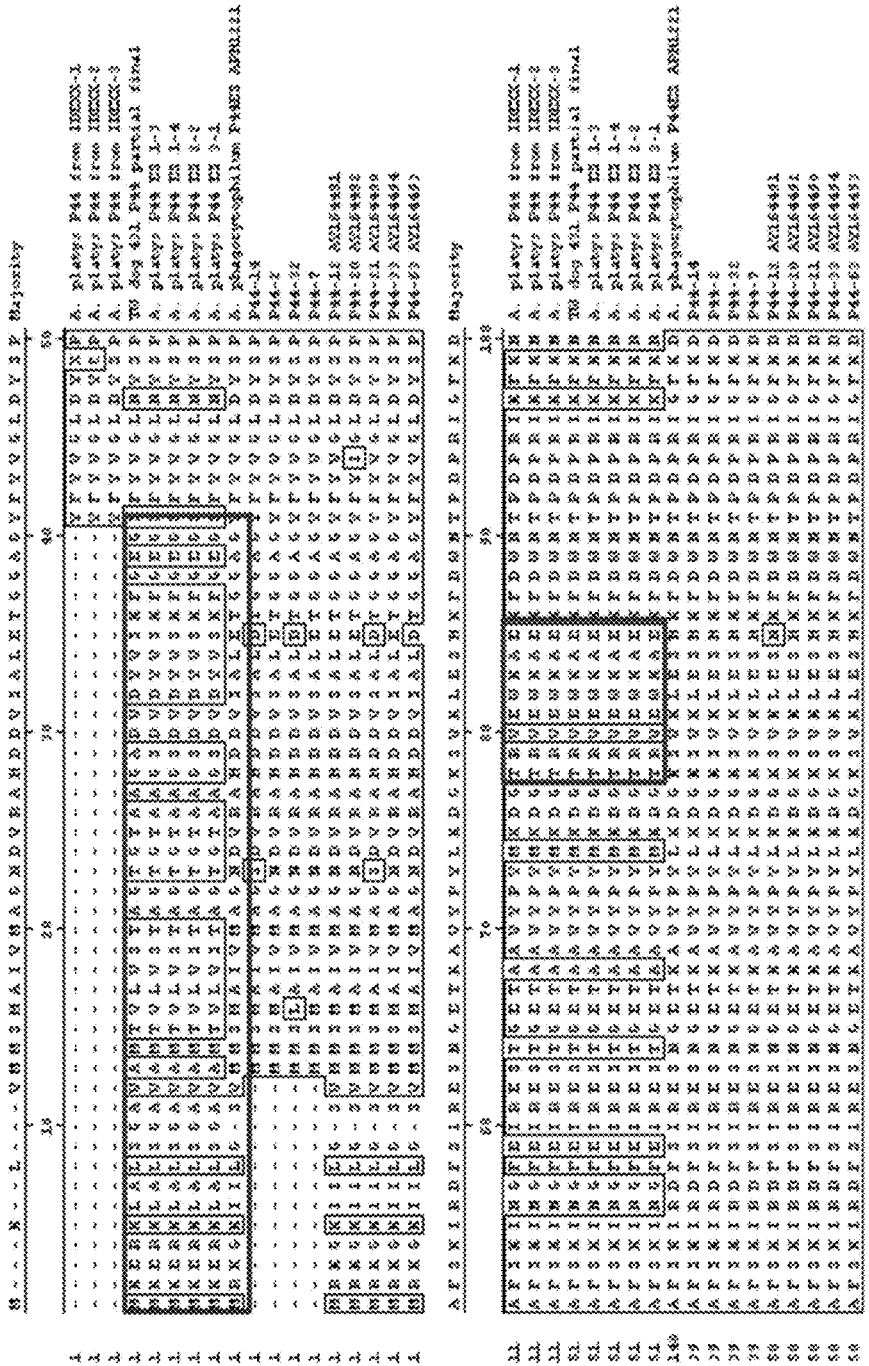
Figure 19:
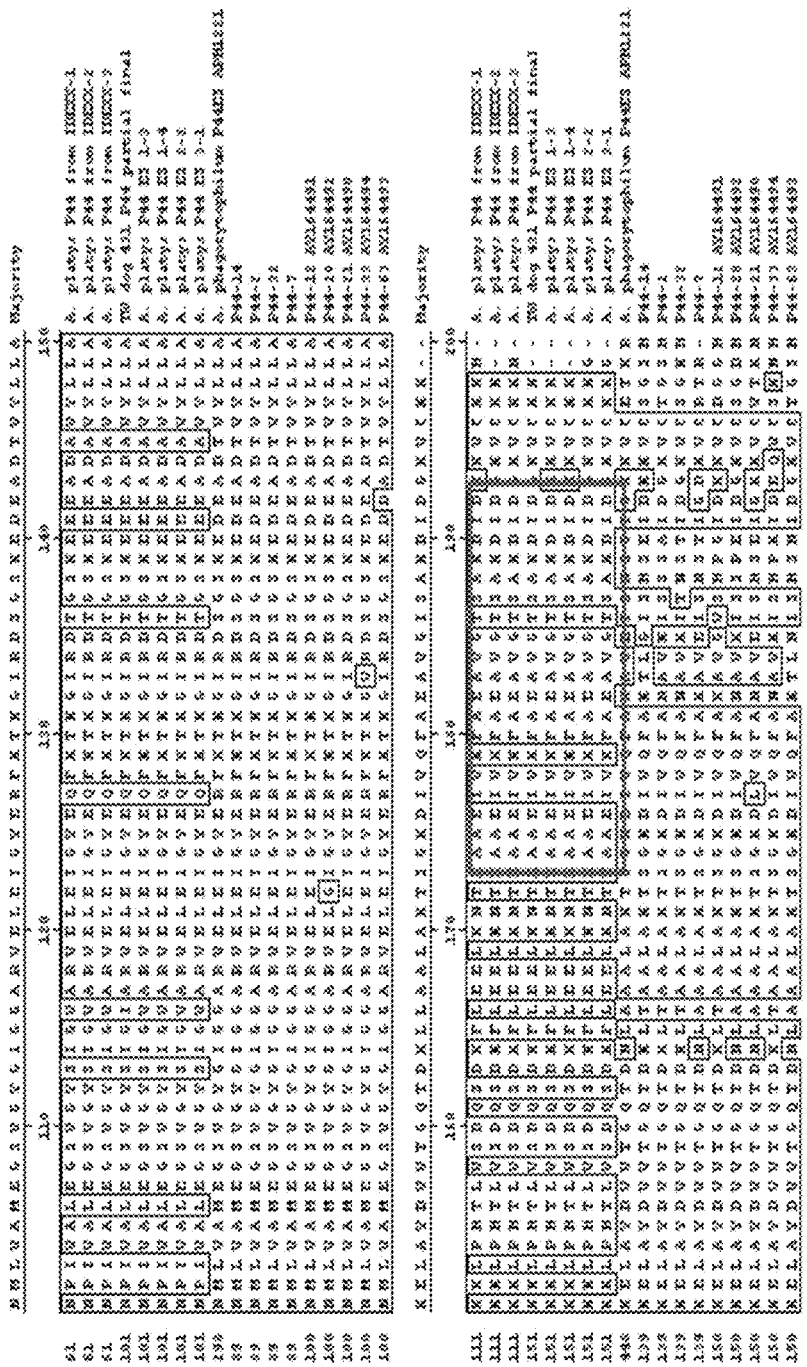
Figure 19:
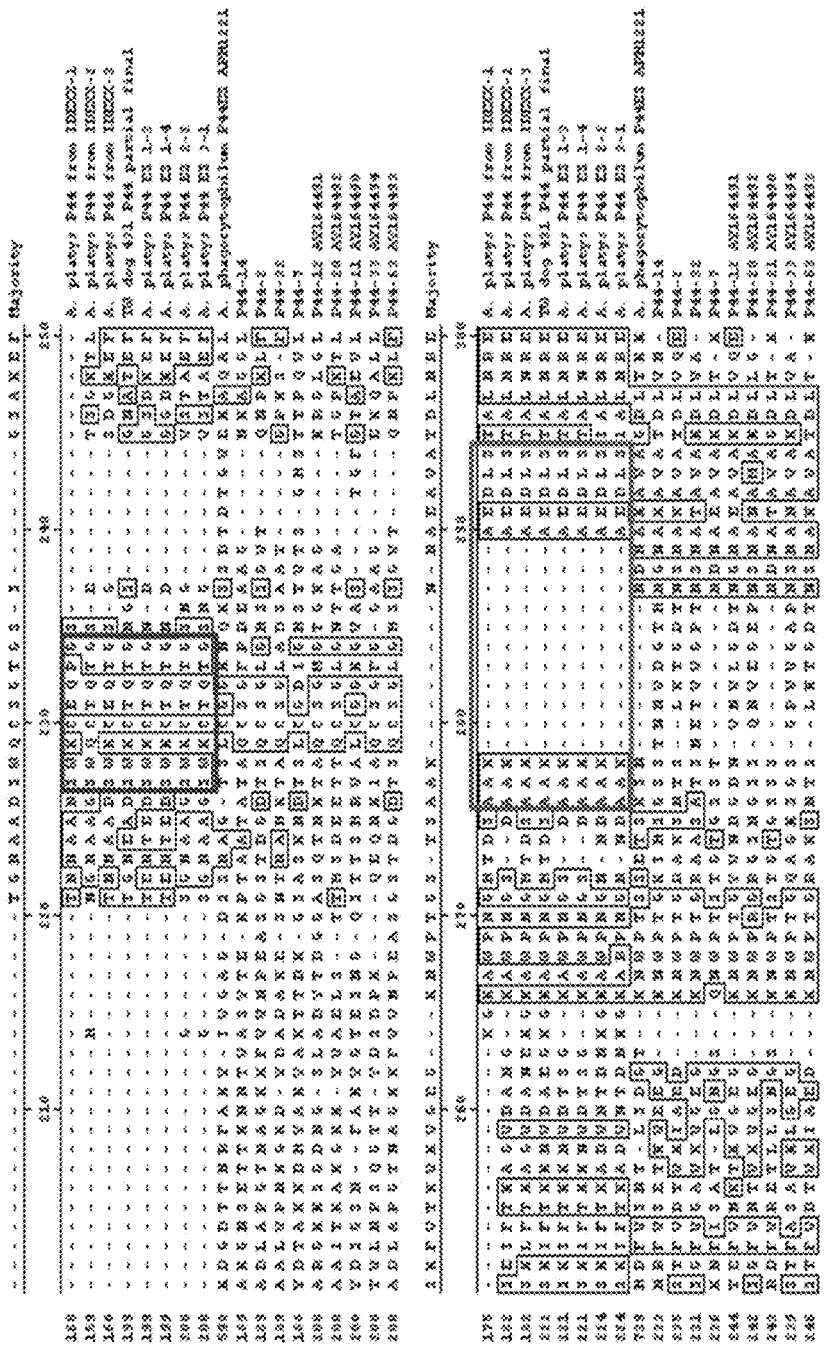
Figure 19:
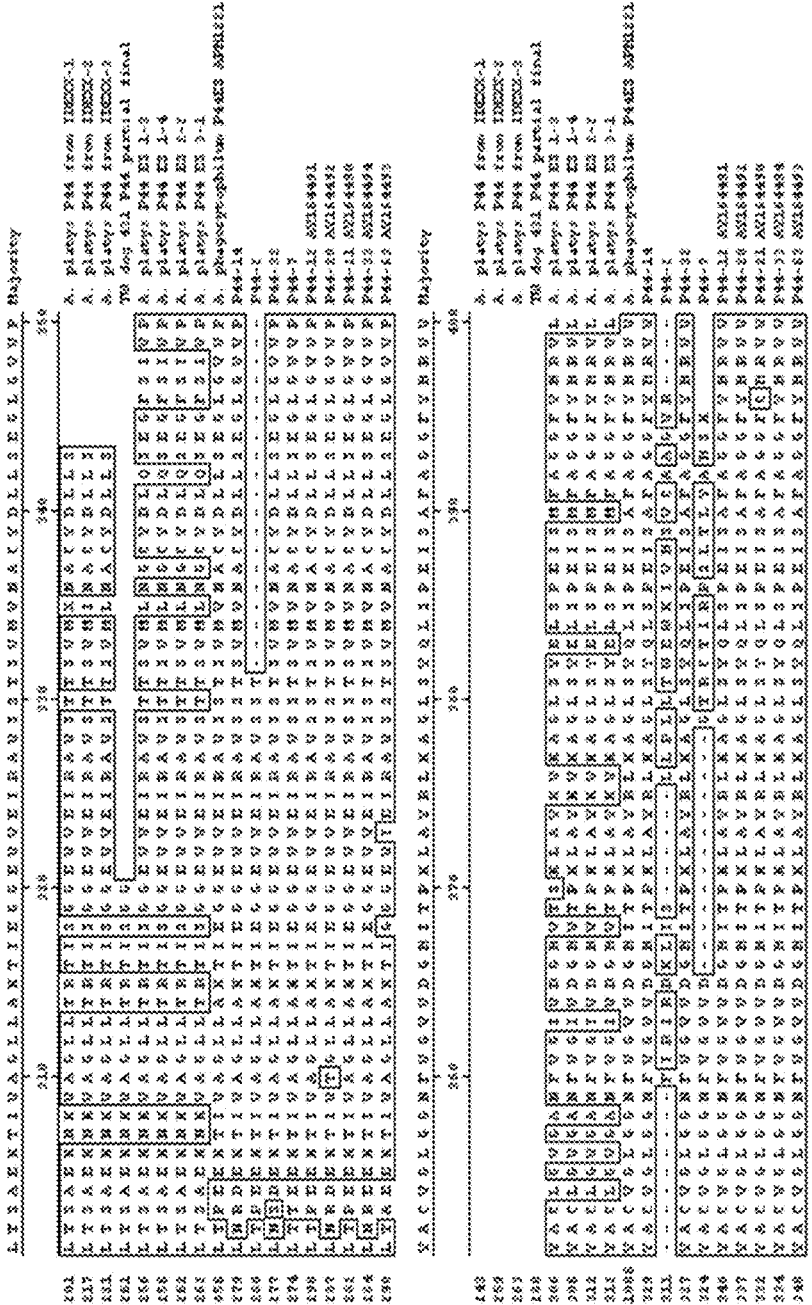
Figure 19:
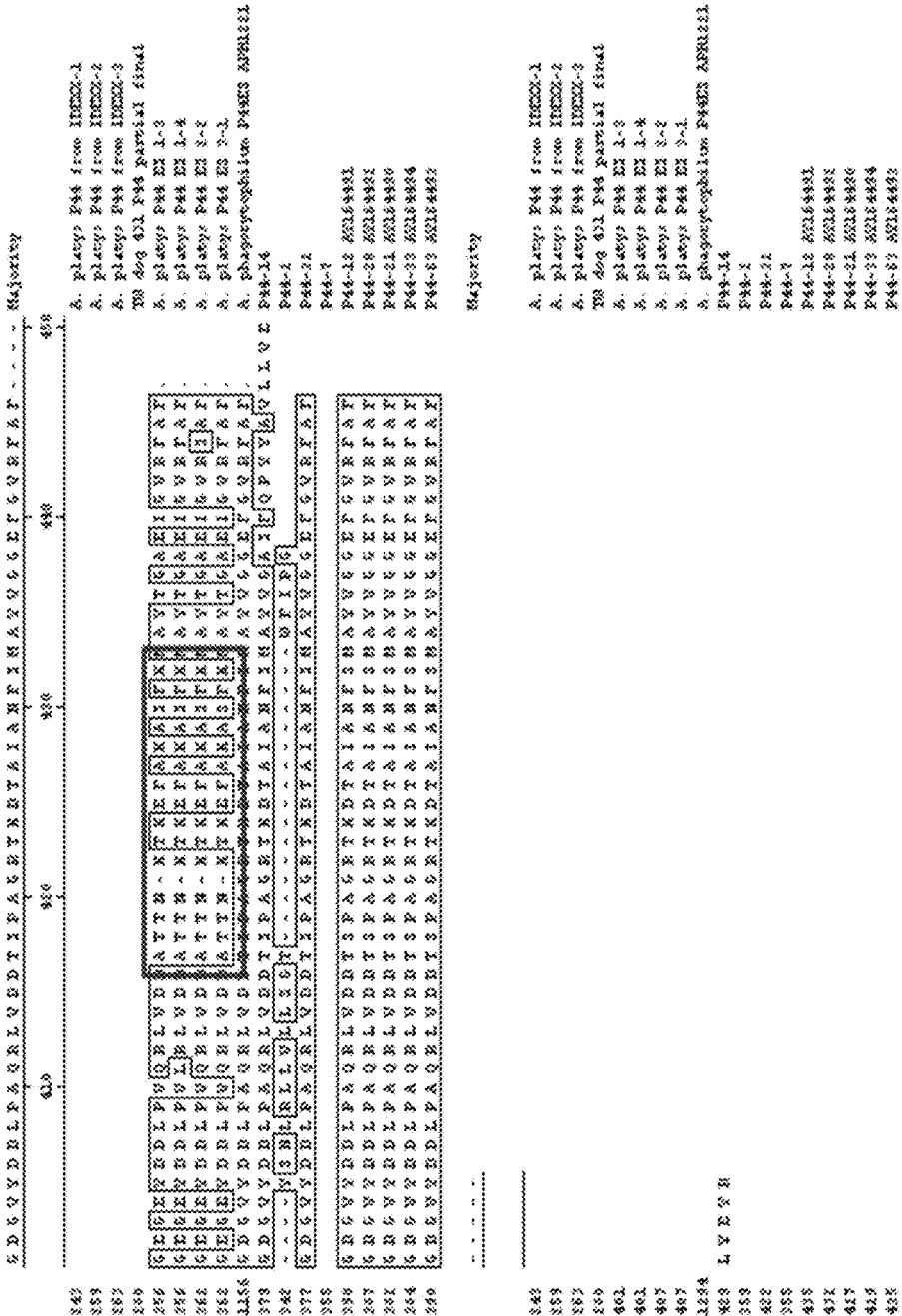

FIG. 19 shows the *A. platys*-specific P44 sequence, distinct from *A. phagocytophilum* and *A. marginate* or IDEXX P44 partial sequences useful for species-specific serodiagnosis. Sequences: Majority equals SEQ ID NO:200; *A. platys* P44 from IDEXX-1 equals SEQ ID NO:201; *A. platys* P44 from IDEXX-2 equals SEQ ID NO:202; *A. platys* P44 from IDEXX-3 equals SEQ ID NO:203; TW dog 431 P44 partial final equals SEQ ID NO:204; *A. platys* P44 ES 1-3 (GQ8687580) equals SEQ ID NO:168; *A. platys* P44 ES 1-4 (GU357491) equals SEQ ID NO:22; *A. platys* P44 ES 2-2 (GU357492) equals SEQ ID NO:23; *A. platys* P44 ES 3-1 (GU357493) equals SEQ ID NO:24; *A. phagocytophilum* P44 ES (YP505662) equals SEQ ID NO:205; *A. phagocytophilum* P44-14 (YP505746.1) equals SEQ ID NO:206; P44-2 (YP505715.1) equals SEQ ID NO:178; P44-32 (YP505802.1) equals SEQ ID NO:179; P44-7 (YP505662.1) equals SEQ ID NO:180; P44-12 (AY164491) equals SEQ ID NO:181; P44-20 (AY164492) equals SEQ ID NO:182; P44-21 (AY164490) equals SEQ ID NO:183; P44-33 (AY164494) equals SEQ ID NO:184; P44-63 (AY164493) equals SEQ ID NO:185.

Figure 20:
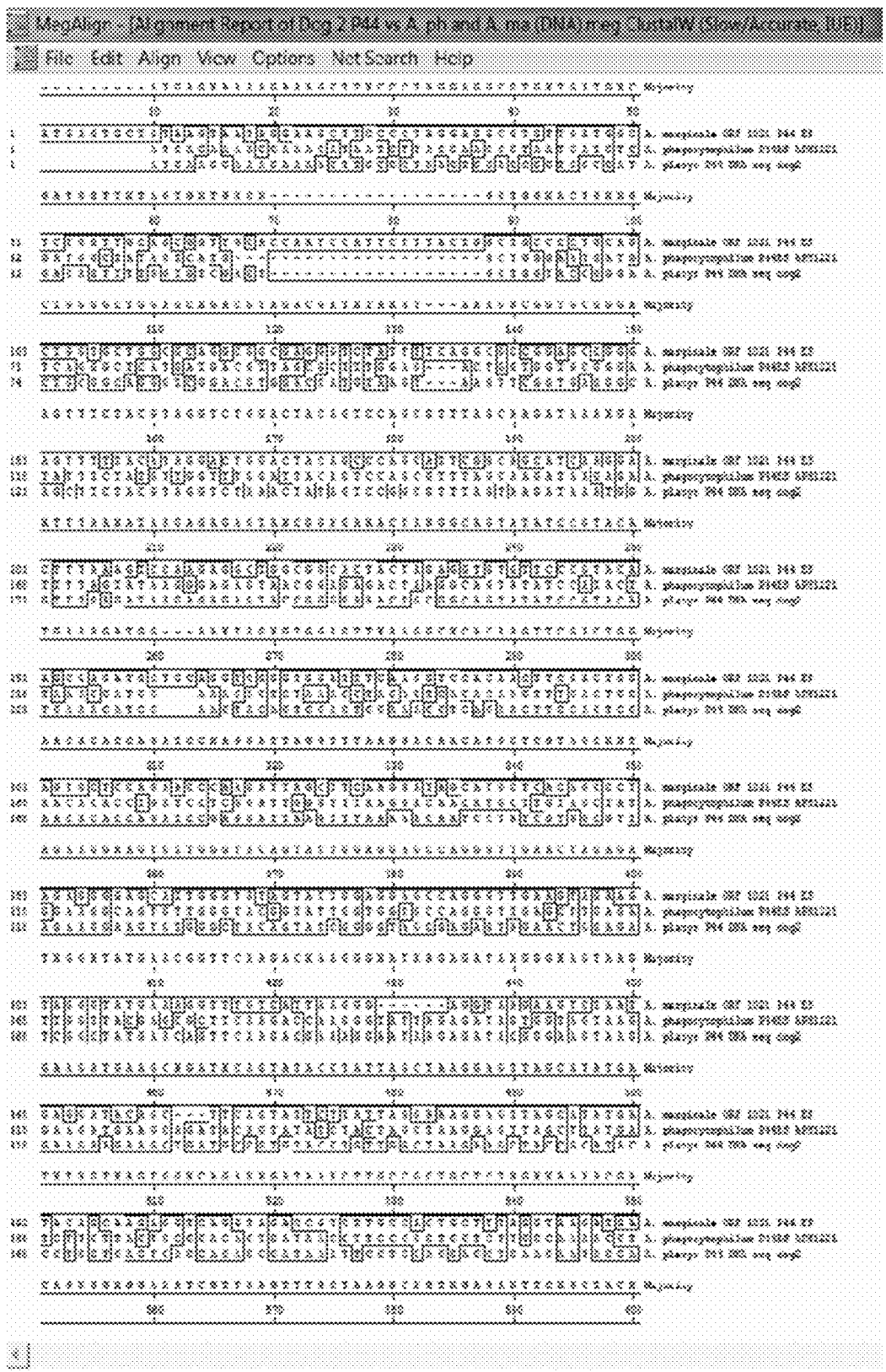
Figure 20:
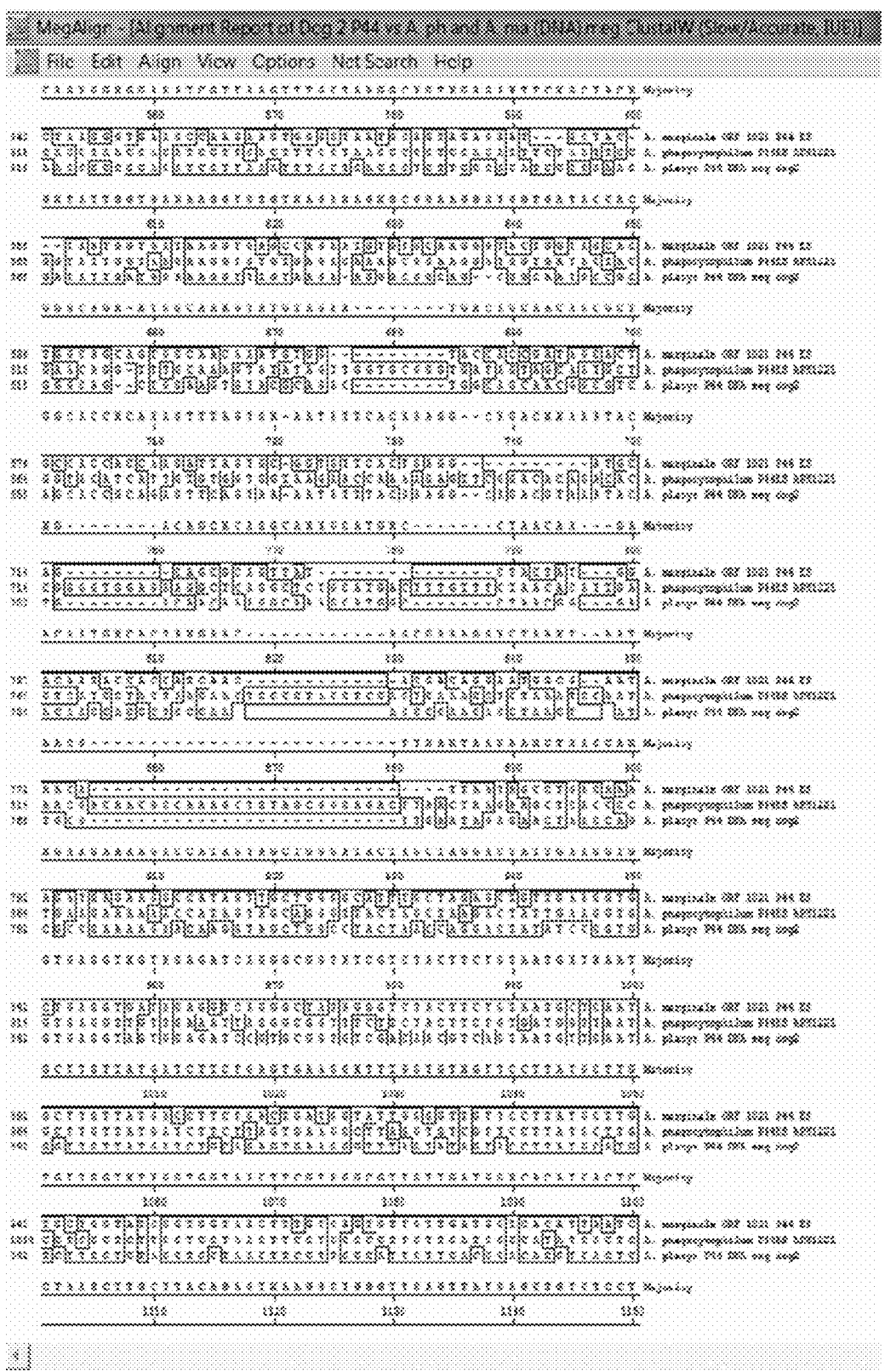
Figure 20:
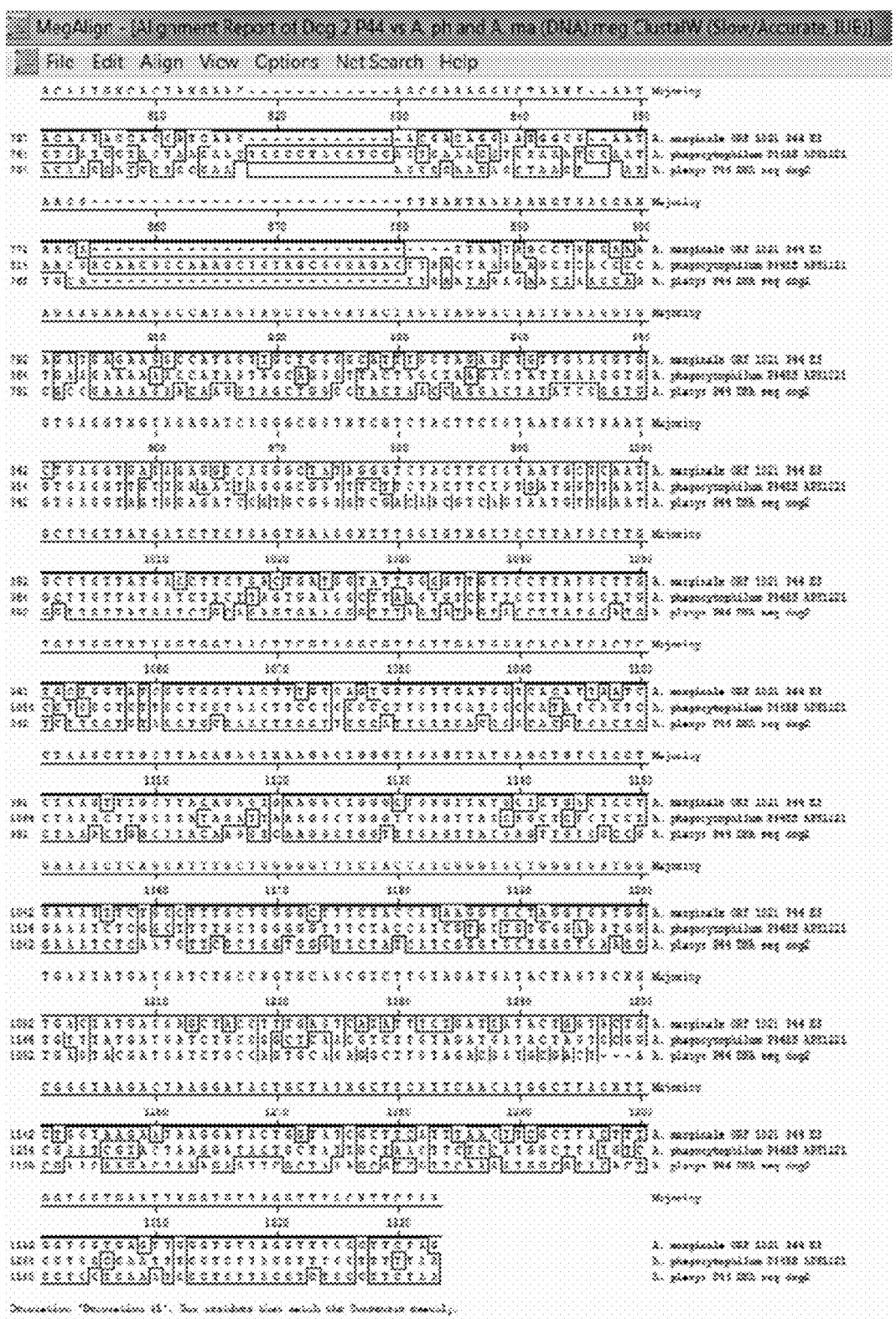

FIG. 20 shows the comparison of the *A. platys*-specific P44 sequence to the sequences of *A. phagocytophilum* and *A. marginate*. Sequences: Majority equals SEQ ID NO:207; *A. marginate* equals SEQ ID NO:208; *A. phagocytophilum* equals SEQ ID NO:209; *A. platys* equals SEQ ID NO:30.

Figure 21:
Figure 21:
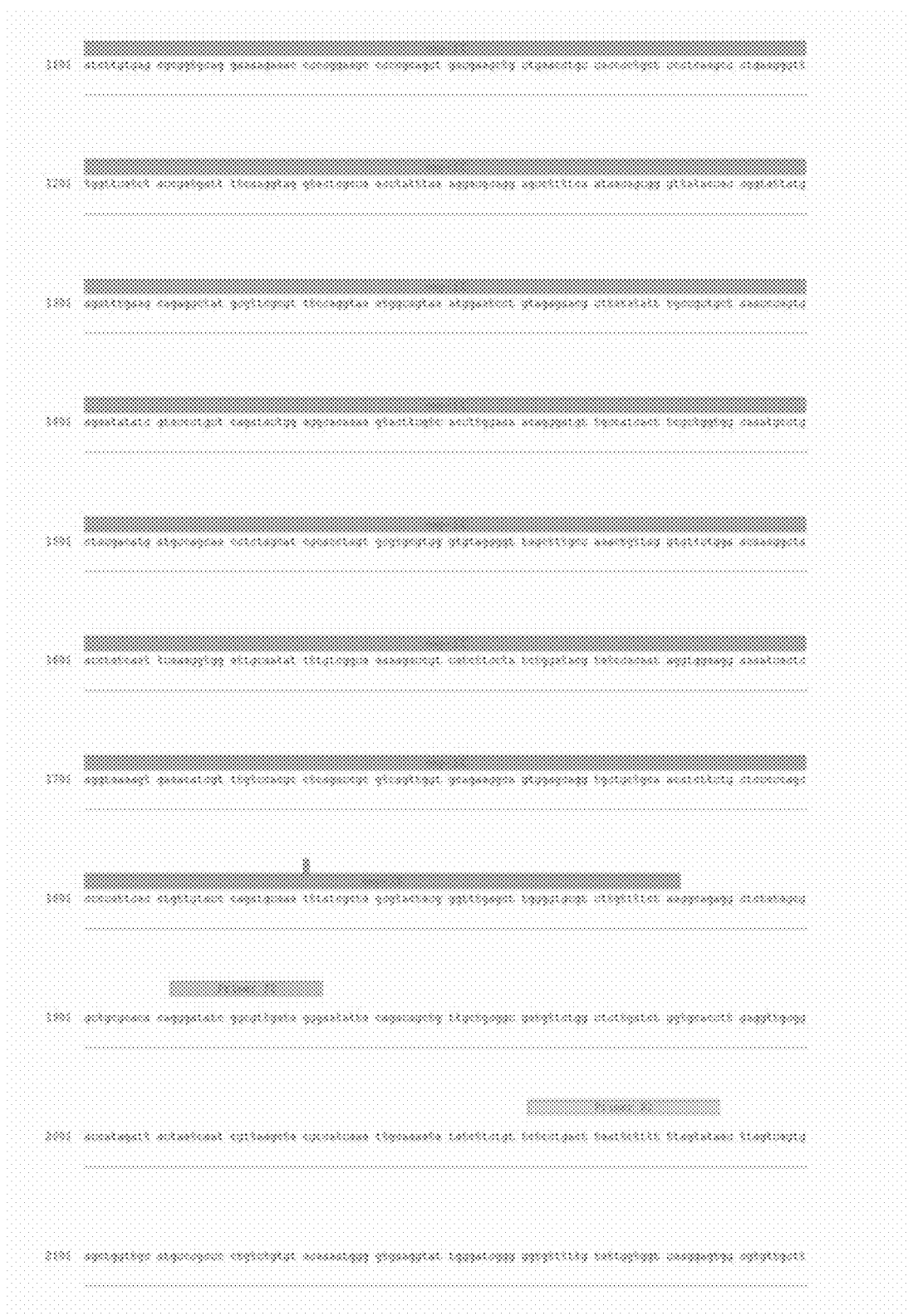
Figure 21:
Figure 21:

FIG. 21 shows the *A. platys*-specific primer regions and sequences from dog 2. Sequences: GQ868750 equals SEQ ID NO:210.

Figure 22:
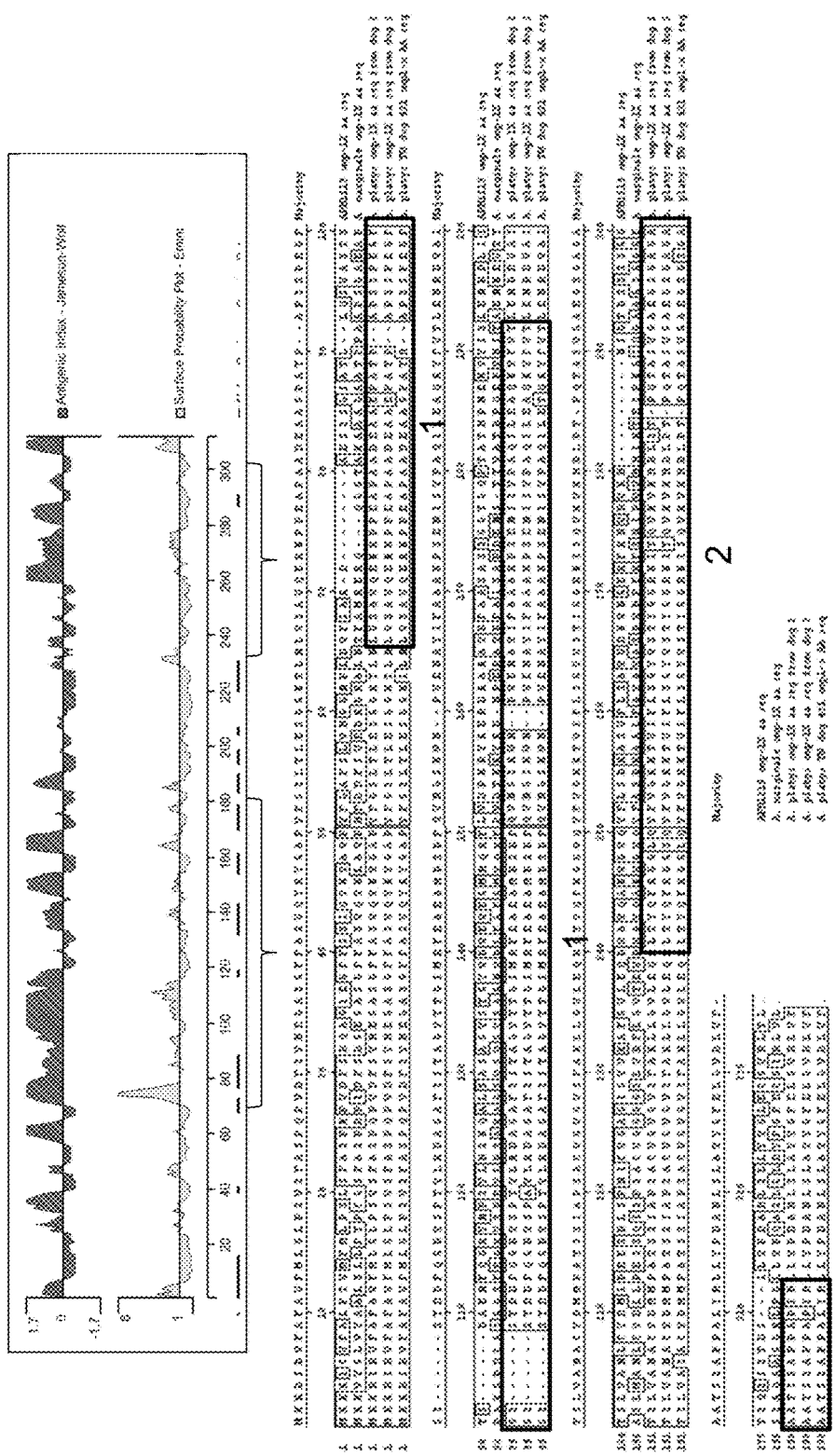

FIG. 22 shows the sequence alignment was completed using a DNASTAR SeqMan program. Alignment of *A. platys* (*A. pl*) OMP-1X protein with related proteins from *A. phagocytophilum* (*A. ph*), *A. marginate* (*A. ma*), *E. canis* (*E. ca*), *E. chaffeensis* (*E. ch*), *E. ewingii* (*E. ew*), and *E. ruminantium* (*E. ru*) using the Clustal W method revealed a unique region in *A. platys* (AVQEKKPPEA (SEQ ID NO: 98). The antigenic index and surface probability profile suggest that this region is both antigenic and surface-exposed, and distinct from those of other species. FIG. 22 also shows the identification of two regions in *A. platys* that are both antigenic and surface-exposed, and distinct from those of other species. These two regions are identified in boxes as "1" and "2". Sequences: Majority equals SEQ ID NO:211; APH1219 omp-1X aa seq equals SEQ ID NO:138; *A. marginate* omp-1X aa seq equals SEQ ID NO:139; *A. platys* dog 2 (HQ868750) equals SEQ ID NO:1; *A. platys* dog 3 (GU357491) equals SEQ ID NO:10; *A. platys* TW dog (HQ738571) equals SEQ ID NO:212.

Figure 23:
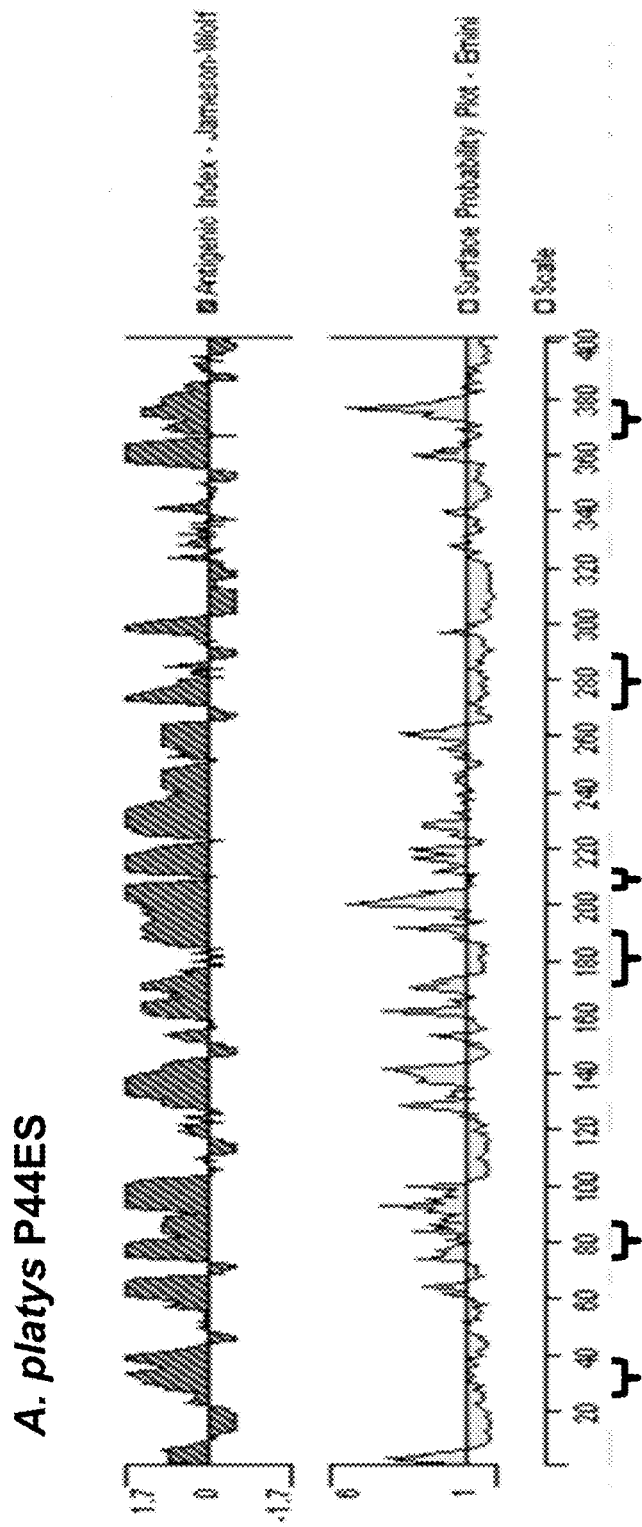
Figure 23:
Figure 23:
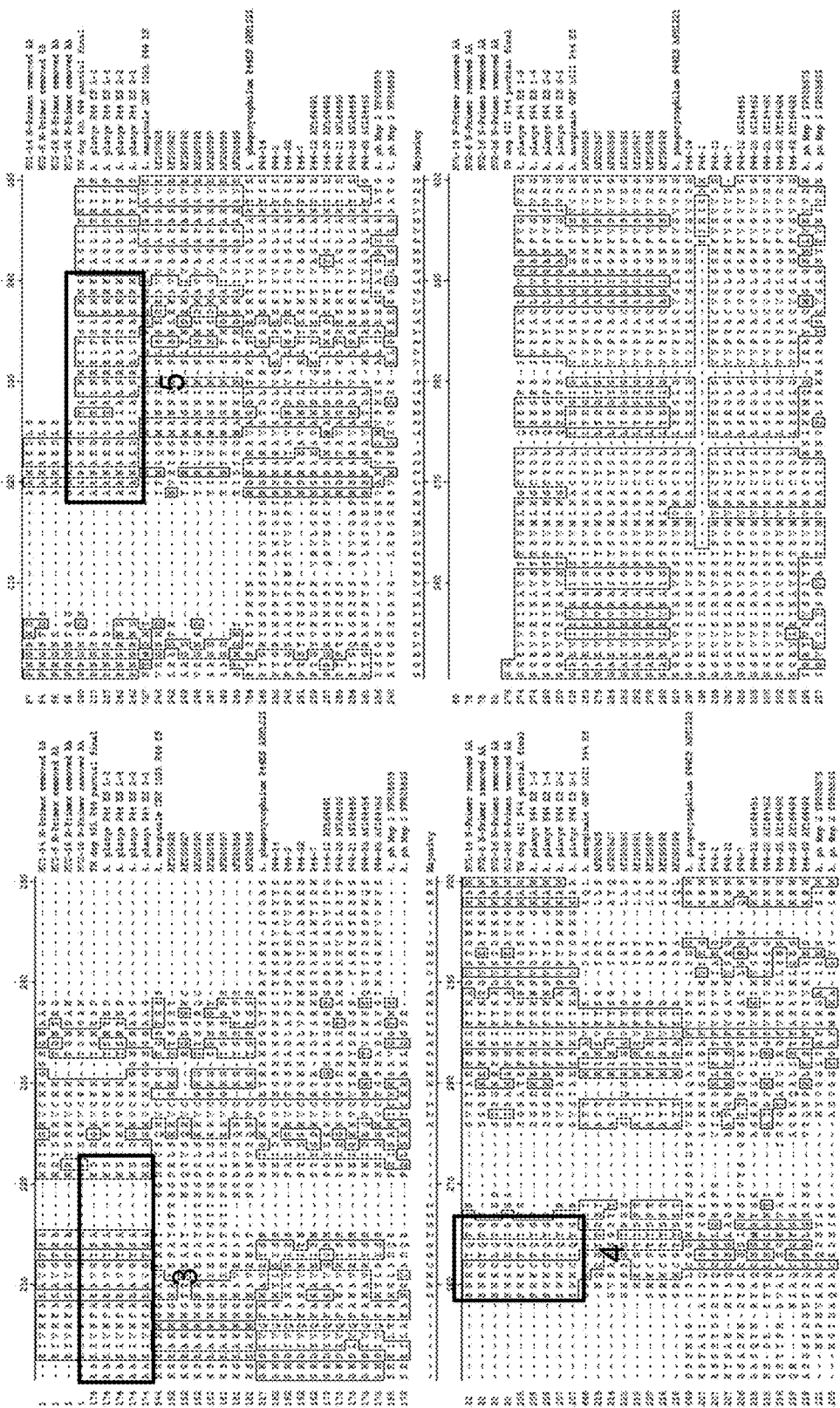

FIG. 23 shows the sequence alignment was completed using a DNASTAR SeqMan program. Alignment of *A. platys* (*A. pl*) p44ES protein with related proteins from *A. phagocytophilum* (*A. ph*), *A. marginate* (*A. ma*), *E. canis* (*E. ca*), *E. chaffeensis* (*E. ch*), *E. ewingii* (*E. ew*), and *E. ruminantium* (*E. ru*) using the Clustal W method revealed regions in *A. platys* wherein the antigenic index and surface probability profile suggest that these regions are both antigenic and surface-exposed, and distinct from other species. These regions are identified in boxes as "1" through "6" as well as in brackets under the antigenic index and surface probability profile. Sequences: HV1-14 N Primer sequence removed aa equals SEQ ID NO:163; HV2-6 N Primer sequence removed aa equals SEQ ID NO:164; HV2-16 N Primer sequence removed aa equals SEQ ID NO:165; HV2-36 N Primer sequence removed aa equals SEQ ID NO:166; TW Jury (dog 431) (HQ735871) equals SEQ ID NO:167; *A. platys* P44 ES 1-3 equals SEQ ID NO:168; *A. platys* P44 ES 1-4 equals SEQ ID NO:22; *A. platys* P44 ES 2-2 equals SEQ ID NO:23; *A. platys* P44 ES 3-1 equals SEQ ID NO:24; *A. marginale* ORF 1021 equals SEQ ID NO:141; AF200925 equals SEQ ID NO:169; AF200927 equals SEQ ID NO:170; AF290590 equals SEQ ID NO:171; AF290591 equals SEQ ID NO:172; AF290597 equals SEQ ID NO:173; AF290598 equals SEQ ID NO:174; AF290599 equals SEQ ID NO:175; *A. phagocytophilum* equals SEQ ID NO:205; P44-14 equals SEQ ID NO:206; P44-2 equals SEQ ID NO:178; P44-32 equals SEQ ID NO:179; P44-12 (AY164491) equals SEQ ID NO:181; P44-20 (AY164492) equals SEQ ID NO:182; P44-21 (AY164490) equals SEQ ID NO:183; P44-33 (AY164494) equals SEQ ID NO:184; P44-63 (AY164493) equals SEQ ID NO:185; A ph msp 2 (YP505578) equals SEQ ID NO:186; A ph msp 2 (YP505833) equals SEQ ID NO:187.

DETAILED DESCRIPTION

Described herein are improved diagnostic tools for veterinary and human use which can be used for serodiagnosing *A. platys* in mammals, particularly in members of the Canidae family and in humans. The diagnostic tools are a group of outer membrane proteins of *A. platys* and variants thereof, referred to hereinafter as the "OMP proteins", a group of outer membrane proteins of *A. platys* and variants thereof referred to hereinafter as the "P44 proteins", and antibodies to the OMP proteins and the P44 proteins.

The present invention can be understood more readily by reference to the following detailed description of the invention and the Examples included therein.

All patents, patent applications, and publications cited herein, whether supra or infra, are hereby incorporated by reference in their entireties into this application in order to more fully describe the state of the art as known to those skilled therein as of the date of the invention described and claimed herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Definitions

Unless otherwise defined, all technical and scientific terms used herein have the same meaning as commonly understood by one of ordinary skill in the art to which this disclosure belongs. The terminology used in the description of the embodiments herein is for describing particular embodiments only and is not intended to be limiting of the embodiments disclosed. As used in the description, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in this disclosure are to be understood as being modified in all instances by the term "about." Accordingly, unless indicated to the contrary, the numerical parameters set forth in this disclosure are approximations that may vary depending upon the desired properties sought to be obtained by the present disclosure. At the very least, and not as an attempt to limit the application of the doctrine of equivalents to the scope of any claims, each numerical parameter should be construed in light of the number of significant digits and ordinary rounding approaches.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values described herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data are provided in a number of different formats, and that these data, represent endpoints, starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

The term "subject" means an individual. In one aspect, a subject is a mammal such as a primate, and, more preferably, a human. Non-human primates include marmosets, monkeys, chimpanzees, gorillas, orangutans, and gibbons, to name a few. The term "subject" also includes domesticated animals, such as cats, dogs, etc., livestock (for example, cattle (cows), horses, pigs, sheep, goats, etc.), laboratory animals (for example, ferret, chinchilla, mouse, rabbit, rat, gerbil, guinea pig, etc.) and avian species (for example, chickens, turkeys, ducks, pheasants, pigeons, doves, parrots, cockatoos, geese, etc.). Subjects can also include, but are not limited to fish (for example, zebrafish, goldfish, tilapia, salmon, and trout), amphibians and reptiles. As used herein, a "subject" is the same as a "patient," and the terms can be used interchangeably.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. The terms "polypeptide," "peptide," and "protein" can be used interchangeably.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, "isolated polypeptide" or "purified polypeptide" is meant to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length proteins and/or polypeptides.

As used herein, "peptidomimetic" means a mimetic of a function of a protein which includes some alteration of the normal peptide chemistry. Peptidomimetics typically are short sequences of amino acids that in biological properties, mimic the function(s) of a particular protein. Peptide analogs enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural L- or D-amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "isolated nucleic acid" or "purified nucleic acid" is meant to mean DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "modulate" is meant to mean to alter, by increasing or decreasing.

As used herein, "effective amount" of a compound is meant to mean a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

As used herein, "prevent" is meant to mean minimize the chance that a subject who has an increased susceptibility for developing *A. platys* infection will develop *A. platys* infection.

As used herein, "specifically binds" is meant that an antibody recognizes and physically interacts with its cognate antigen (for example, the disclosed *A. platys* peptides) and does not significantly recognize and interact with other antigens; such an antibody may be a polyclonal antibody or a monoclonal antibody, which are generated by techniques that are well known in the art.

As used herein, "probe," "primer," or oligonucleotide is meant to mean a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for nucleic acids capable of encoding the disclosed *A. platys* peptides (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid capable of encoding the disclosed *A. platys* peptides to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, and electrophoretic mobility shift assay (EMSA).

As used herein, "specifically hybridizes" is meant to mean that a probe, primer, or oligonucleotide recognizes and physically interacts (that is, base-pairs) with a substantially complementary nucleic acid (for example, a nucleic acid capable of encoding the disclosed *A. platys* peptides) under high stringency conditions, and does not substantially base pair with other nucleic acids.

As used herein, "high stringency conditions" is meant to mean conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

In addition, where features or aspects of the inventions are described in terms of Markush groups or other grouping of alternatives, those skilled in the art will recognize that the invention is also thereby described in terms of any individual member or subgroup of members of the Markush group or other group.

Compositions

Described herein are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Also disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein.

Described herein are compositions and methods for the detection of *Anaplasma platys* in a sample obtained from an animal, particularly a member of the Canidae family. One embodiment of the invention provides a PCR-based method for the amplification of minute amounts of *A. platys* DNA isolated from canines. For example, and not to be limiting, amplification of DNA can be carried out with a high fidelity Taq polymerase.

Polynucleotides

Described herein are isolated or purified nucleotides. For example, disclosed herein are *Anaplasma platys* nucleotides. The disclosed *Anaplasma platys* nucleotides can be used in one or more of the methods disclosed herein.

As used herein, "*Anaplasma platys* nucleotides" or "*Anaplasma* platy polynucleotides" refers to the P44 or the OMP-1X nucleotide sequences as well as combinations or fragments thereof described herein. For example, *Anaplasma platys* nucleotides include, but are not limited to, the P44 nucleotide sequences provided in the Figures as well as the sequences provided in SEQ ID NOs: 30-38, SEQ ID NOs: 46-51, combinations thereof as well as fragments thereof. Such sequences can also be referred to as *Anaplasma platys* P44 nucleotides or *Anaplasma platys* P44 polynucleotides. Additional examples of *Anaplasma platys* P44 nucleotides include, but are not limited to Genebank Accession Nos: GQ868750, GU357491, GU357492, GU357493, GU357494, GU357495, GU357496, GU357497, and HQ738571.

Also disclosed herein are regions of the *Anaplasma platys* P44 and OMP-1X peptides that have been identified as being highly antigenic as identified through the Jameson-Wolf method as well through a surface probability plot analysis. These regions are herein referred to as a "Box" regions. For example, six regions of the *Anaplasma platys* P44 protein sequence have been identified in FIGS. 19 and 23. These six regions, from the N-terminal to the C-terminal regions are herein referred to as "P44 Box 1", "P44 Box 2", "P44 Box 3", "P44 Box 4", "P44 Box 5", and "P44 Box 6", respectively. In addition, two regions of the *Anaplasma platys* OMP-1X protein sequence have been identified in FIG. 22. These two regions, from the N-terminal to the C-terminal regions are herein referred to as "OMP-1X Box 1" and "OMP-1X Box 2", respectively.

Disclosed herein are isolated or purified polynucleotides that consist of or comprise the nucleotide sequence of "P44 Box 1". P44 Box 1 includes, but is not limited to, SEQ ID NO: 46. Also disclosed herein are isolated or purified polynucleotides that consist of or comprise a polynucleotide sequence capable of hybridizing to or amplifying the sequence of "P44 Box 1". For example, P44 Box 1 primers can include, but are not limited to: SEQ ID NOs: 52 and 53.

Disclosed herein are isolated or purified polynucleotides that consist of or comprise the nucleotide sequence of "P44 Box 2". P44 Box 2 includes, but is not limited to, SEQ ID NO: 47. Also disclosed herein are isolated or purified polynucleotides that consist of or comprise a polynucleotide sequence capable of hybridizing to or amplifying the sequence of "P44 Box 2". For example, P44 Box 1 primers can include, but are not limited to: SEQ ID NOs: 54 and 55.

Disclosed herein are isolated or purified polynucleotides that consist of or comprise the nucleotide sequence of "P44 Box 3". P44 Box 3 includes, but is not limited to, SEQ ID NO: 48. Also disclosed herein are isolated or purified polynucleotides that consist of or comprise a polynucleotide sequence capable of hybridizing to or amplifying the sequence of "P44 Box 3". For example, P44 Box 1 primers can include, but are not limited to: SEQ ID NOs: 56 and 57.

Disclosed herein are isolated or purified polynucleotides that consist of or comprise the nucleotide sequence of "P44 Box 4". P44 Box 4 includes, but is not limited to, SEQ ID NO: 49. Also disclosed herein are isolated or purified polynucleotides that consist of or comprise a polynucleotide sequence capable of hybridizing to or amplifying the sequence of "P44 Box 4". For example, P44 Box 1 primers can include, but are not limited to: SEQ ID NOs: 58 and 59.

Disclosed herein are isolated or purified polynucleotides that consist of or comprise the nucleotide sequence of "P44 Box 5". P44 Box 5 includes, but is not limited to, SEQ ID NO: 50. Also disclosed herein are isolated or purified polynucleotides that consist of or comprise a polynucleotide sequence capable of hybridizing to or amplifying the sequence of "P44 Box 5". For example, P44 Box 1 primers can include, but are not limited to: SEQ ID NOs: 60 and 61.

Disclosed herein are isolated or purified polynucleotides that consist of or comprise the nucleotide sequence of "P44 Box 6". P44 Box 6 includes, but is not limited to, SEQ ID NO: 51. Also disclosed herein are isolated or purified polynucleotides that consist of or comprise a polynucleotide sequence capable of hybridizing to or amplifying the sequence of "P44 Box 6". For example, P44 Box 1 primers can include, but are not limited to: SEQ ID NOs: 62 and 63.

Also disclosed are primers that can be used to amplify one or more *Anaplasma platys* P44 nucleotides. Examples include, but are not limited to SEQ ID NOs: 82-91.

*Anaplasma platys* nucleotides include, but are not limited to, the OMP-1X nucleotide sequences provided in the Figures as well as the sequences provided in SEQ ID NOs: 11-17, combinations thereof as well as fragments thereof. Such sequences can also be referred to as *Anaplasma platys* OMP-1X nucleotides or *Anaplasma platys* OMP-1X polynucleotides. Other examples of *Anaplasma platys* OMP-1X nucleotides include, but are not limited to the sequences provided in GenBank Accession Nos: GQ868750, HQ738571, GU357491.

Disclosed herein are isolated or purified polynucleotides that consist of or comprise the nucleotide sequence of "OMP-1X Box 1". OMP-1X Box 1 includes, but is not limited to, SEQ ID NO: 14. Also disclosed herein are isolated or purified polynucleotides that consist of or comprise a polynucleotide sequence capable of hybridizing to or amplifying the sequence of "OMP-1X Box 1".

Disclosed herein are isolated or purified polynucleotides that consist of or comprise the nucleotide sequence of "OMP-1X Box 2". OMP-1X Box 2 includes, but is not limited to, SEQ ID NO: 15. Also disclosed herein are isolated or purified polynucleotides that consist of or comprise a polynucleotide sequence capable of hybridizing to or amplifying the sequence of "OMP-1X Box 2".

The polynucleotides described herein can contain less than an entire microbial genome and can be RNA, DNA, or combinations thereof. Polynucleotides described herein can be isolated. An isolated polynucleotide is a naturally-occurring polynucleotide that is not immediately contiguous with one or both of the 5' and 3' flanking genomic sequences that it is naturally associated with. Isolated polynucleotides can also include non-naturally occurring nucleic acid molecules. In some aspects, polynucleotides can also comprise fragments that encode immunogenic polypeptides.

In some aspects, polynucleotides described herein can be probes or primers, for example, PCR primers, to detect the presence of *A. platys* polynucleotides in a biological sample. Probes are molecules capable of interacting with a target nucleic acid, typically in a sequence specific manner, for example, through hybridization. Primers are a subset of probes that can support an enzymatic manipulation and that can hybridize with a target nucleic acid sequence. A primer can be made from any combination of nucleotides or nucleotide derivatives or analogs available in the art that do not interfere with the manipulation of peptides, enzymes, or proteins. In one aspect, the primers disclosed herein can comprise any of the isolated polynucleotides described herein. For example, and not to be limiting, the isolated polynucleotide can be SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 18, SEQ ID NO: 19, SEQ ID NO: 20, or SEQ ID NO: 99.

The hybridization of nucleic acids is well understood in the art and hence need not be discussed herein. Typically a primer can be made from any combination of nucleotides, nucleotide derivatives, and analogs available in the art. The ability of such probes and primers to specifically hybridize to *A. platys* polynucleotide sequences can enable the primer to be used for the detection of the presence of complementary sequences. In some embodiments, polynucleotide primers and probes of the invention described herein can hybridize to complementary sequences in a sample, including saliva, blood, plasma, serum, cerebrospinal fluid, and tissue. In some embodiments, the polynucleotides from the sample can be subjected to gel electrophoresis, size separation techniques, immobilization without size separation, and labeling. Suitable labels and methods for labeling primers are known in the art and include radioactive labels, biotin labels, fluorescent labels, bioluminescent labels, and enzyme labels.

When referring to a nucleotide sequence "N" represents any of the four common nucleotides (e.g., A, C, G, or T), "M" represents either an A or C nucleotide, "S" will be defined to mean C or G, and "Y" will be defined henceforth as C or T. For example, SEQ ID NO: 85 (GCAAAC-CTAACACCMAAYTCMCCACC) includes an "M" at positions 15 and 22. As such, position 15 or 22 of SEQ ID NO: 85 can be an A or C nucleotide. In addition, SEQ ID NO: 85 includes a "Y" at position 19. As such, position 9 of SEQ ID NO: 85 can be a C or T.

Primers

Disclosed herein are P44 primer sets comprising F1 through F3 and R1 through R5. Each p44 primer set comprises a first primer, i.e., forward, and a second primer, i.e., reverse, both of which can be about 10 to about 35 nucleotides in length or a primer of alternant length (e.g., 10-15, 10-20, 10-25, 10-30, 15-20, 15-25, 15-30, 15-35, 20-25, 20-30, 20-35, 25-30, 25-35, 30-35). The first primer comprises a sequence that is complementary to a consecutive sequence of at least 10 nucleotides in length, within the following sequences: ATTATGTATGATTTATCCTAAGT-TATCTGAG (SEQ ID NO: 82), GGGATATCGGCGTTGA-TAGGG (SEQ ID NO: 83), and GGTTTGTGTTGCTGGT-GATTGGAGG (SEQ ID NO: 84). The second primer comprises a sequence which is complementary to the inverse complement of a consecutive sequence of at least 10 nucleotides in length, within the following sequences: GCAAAC-CTAACACCMAAYTCMCCACC (SEQ ID NO: 85), TATACTAAAAAAGAATTAAGTCAAGAG (SEQ ID NO: 86), ATGGTAGAAASCCCCAGCAAA (SEQ ID NO: 87), CACGTNTTTAGTTACTGCCA (SEQ ID NO: 88), and GTACTAGTCAGCGCCACTAACATCAA (SEQ ID NO: 89). As used herein, "N" represents any of the four common nucleotides (e.g., A, C, G, or T), "M" represents either an A or C nucleotide, "S" will be defined to mean C or G, and "Y" will be defined henceforth as C or T. Such primers can be useful for detecting the presence of *A. platys* in members of the Anaplasmataceae family. HVF and HVR (Table 1) are the *A. platys*-specific primers (FIG. 16). Using the nested PCR (genus-specific primer Pair F3 and R1 during the first PCR and species-specific primer pair HVF and HVR in second PCR) sensitive and *A. platys*-specific PCR can be performed. Such primers can also useful for detecting the presence of *A. platys* DNA in samples obtained from ticks or other invertebrate carriers that feed on the vertebrate hosts.

Also disclosed herein are primers that can be used to synthesize one or more of the *A. platys* polypeptides described herein. For example, disclosed herein are primers that can be used to produce an *A. platys* polypeptide comprising a sequence that is capable of encoding a multimeric *A. platys* polypeptide wherein the intervening sequence present in the full *A. platys* P44 or OMP-1X nucleotide or peptide sequence are removed. For example, disclosed herein are primers that can be used to add a restriction site into a nucleic acid sequence described herein through inverse PCR. The nucleotide can then be digested and self-ligated to remove a specific intervening sequence. For example, SEQ ID NO: 66 (OMP-1X box 1 and box 2 Forward primer: AACATATGAATCTTGTGAGCGCGG) can be used to introduce an NdeI site in combination with SEQ ID NO: 67 (OMP-1X box 1 and box 2 Reverse primer: GGGGATCCGGCTGGGGGAGCAGAAG) which can introduce a BamHI site.

Also disclosed are primers that can be used to remove an intervening sequence between OMP-1X Box 1 and Box 2. For example, the primer pair of SEQ ID NO: 68 can be used in combination with SEQ ID NO: 69.

Also disclosed are primers that can be used to remove an intervening sequence between P44 Box 1 and Box 2. For example, the primer pair of SEQ ID NO: 70 can be used in combination with SEQ ID NO: 71.

Also disclosed are primers that can be used to remove the intervening sequence of P44 Box 1 and Box 2. For example, the primer pair of SEQ ID NO: 72 can be used in combination with SEQ ID NO: 73.

Also disclosed are primers that can be used to remove the intervening sequence of P44 Box 3 and Box 4. For example, the primer pair of SEQ ID NO: 74 can be used in combination with SEQ ID NO: 75 or SEQ ID NO: 76 can be used in combination with SEQ ID NO: 77

Also disclosed are primers that can be used to remove the intervening sequence of P44 Box 5 and Box 6. For example, the primer pair of SEQ ID NO: 78 can be used in combination with SEQ ID NO: 79 or SEQ ID NO: 80 can be used in combination with SEQ ID NO: 81

Also disclosed are methods for detecting *A. platys* provides a p44 primer set comprising a first primer sequence which can be complementary to a sequence of the *A. platys* p44 gene sense strand and a second primer which can be complementary to the sequence of the *A. platys* p44 gene antisense strand, amplifying the DNA in the sample using a polymerase chain reaction (PCR) and the p44 primer set, and determining the length which corresponds to the sequence or length of that portion to which the first p44 primer and the second p44 primer bind is indicative of the presence of *A. platys* in the DNA sample.

Also disclosed herein are aspects related to primers in the p44 primer set. The first p44 and the second p44 primers can be from about 10 to about 35 nucleotides in length or a primer of alternant length (e.g., 10-15, 10-20, 10-25, 10-30, 15-20, 15-25, 15-30, 15-35, 20-25, 20-30, 20-35, 25-30, 25-35, 30-35). The first p44 primer, comprises a sequence which is substantially identical to the complement of a consecutive sequence of at least 10 nucleotides in length, within the following sequence: GAAGAATACGAAAGCGGCGG (SEQ ID NO: 90). In some embodiments, the primer can be capable of hybridizing to a target sequence.

The second primer comprises a sequence which can be complementary to the inverse complement of a consecutive sequence of at least 10 nucleotides in length, within the following sequence: TACTTAGGTCTTCCGCTTTCGC (SEQ ID NO: 91).

HVF and HVR (Table 1 and FIG. 16) can be useful for detecting the presence of *A. platys* in samples obtained from vertebrate animals such as humans or dogs, or from the invertebrate vectors such as brown ticks, which can transmit this pathogen from one vertebrate animal to another.

Also disclosed herein are compositions and methods for detecting the presence of *A. platys* in samples obtained from a vertebrate or invertebrate animal. The method comprises amplifying the DNA contained within the sample using a primer set comprising primers which comprise sequences that can be complementary to select regions of the p44 gene of *A. platys* and a polymerase chain reaction (PCR) to provide a pool of PCR products, and then assaying the pool for the presence or absence of a PCR product whose length or sequence indicates that PCR product corresponds to the region of the p44 gene that is flanked by the nucleotide sequences which are complementary to the first and second members of the p44 primer set. The tools are the members of the p44 primer sets. Multiple *A. platys* p44 gene sequences are set forth in GenBank under accession No. GQ868750 and GU357491, respectively. Additional p44ES and p44 sequences were set forth in GenBank under accession No. GU357492, GU357493, GU357494, GU357495, GU357496 and GU357497.

In some embodiments, the primers in the p44 primer set can be based upon select sequences in the p44 gene of *A. platys*. The p44 gene encodes a major outer membrane protein of *A. platys*. The sequences of the first and second primers in the p44 primer set are distinct from sequences found in the closely related p44 gene homologs in *A. phagocytophilum* or *A. marginate*. The first primer in the p44 primer set can be an oligonucleotide of various lengths, including but not limited to 10-15, 10-20, 10-25, 10-30, 15-20, 15-25, 15-30, 15-35, 20-25, 20-30, 20-35, 25-30, 25-35, 30-35, and 10 to 35 nucleotides in length. In some embodiments, the first primer can be at least 10 nucleotides in length. The second p44 primer in the *A. platys* primer set can be an oligonucleotide of 10-15, 10-20, 10-25, 10-30, 15-20, 15-25, 15-30, 15-35, 20-25, 20-30, 20-35, 25-30, 25-35, 30-35, or 10 to 35 nucleotides in length. In one embodiment, the second p44 primer can be at least about 10 nucleotides in length. The first p44 primer can comprise a sequence which is substantially identical to the complement of consecutive sequence located between nucleotide positions 540-559 of the sense strand of the open reading frame sequence of the p44 gene of *A. platys*.

As used herein the term "substantially identical" means that the sequence is at least 90% identical, at least 95% identical, or 100% identical to a particular reference sequence (nucleotides 540-559 or 812-849) within FIG. 22.

The second p44 primer, comprises a sequence which is substantially identical to and the inverse of a consecutive sequence located between nucleotides 812-849 of the sense strand of the p44 gene of *A. platys*. The sequence of the second p44 primer is substantially identical to the complement of the inverse complement of a consecutive sequence contained within FIG. 22. In some embodiments, the primers can be capable of hybridizing to target sequences.

In specific embodiments, the first and second primers in the p44 primer set can comprise the sequences shown in Table 1. The first and second primers can also comprise sequences which are shorter by one to ten nucleotides than the sequences shown in Table 1 below. The first and second primers of the *A. platys* primer set can also comprise a sequence which is longer than the sequences shown in Table 1 below. Such sequences can have one to ten additional nucleotides attached to the 5' end of the above-listed sequences. The additional nucleotides can be selected from the group consisting of adenine, cytosine, guanine, thymine, adenylic acid, guanylic acid, and combinations thereof.

In another embodiment, the sequence of the nine first and second p44 primer sets shown in Table 1 can be based upon a comparison of the open-reading frame sequences of nine *A. platys* isolates. Such primer sets can specifically amplify the target sequence of multiple *A. platys* isolates, but not *A. phagocytophilum* or *A. marginate* isolates. The primers shown in Table 1 are both species-universal (e.g., F1, F2, F3, R1, R2, R3, R4, and R5) and species-specific (e.g., HVF and HVR) for *A. platys*.

Disclosed herein are isolated polynucleotides encoding an outer membrane protein of *Anaplasma platys*, or a fragment thereof. In one aspect, the outer membrane protein can be P44 or OMP-1X protein. In a further aspect, disclosed herein are isolated polynucleotides comprising any of the sequences described herein, or a fragment thereof. For example, and not to be limiting, the polynucleotide sequence can be SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 46, SEQ ID NO: 47, SEQ ID NO: 48, SEQ ID NO: 49, SEQ ID NO: 50, SEQ ID NO: 51, SEQ ID NO: 11, SEQ ID NO: 12, SEQ ID NO: 13, SEQ ID NO: 14, SEQ ID NO: 15, SEQ ID NO: 16, SEQ ID NO: 17, or a fragment thereof. In yet a further aspect, the isolated polynucleotide sequence can be a polynucleotide capable of encoding any peptide sequence described herein or a fragment thereof. For example and not to be limiting, the polynucleotide sequence can be a polynucleotide capable of encoding SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 93, SEQ ID NO: 94, SEQ ID NO: 95, SEQ ID NO: 96, SEQ ID NO: 97, or a fragment thereof. By way of further example, the polynucleotide sequences disclosed herein can also be polynucleotides capable of encoding the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, a combination or a fragment thereof. In still a further aspect, disclosed herein are isolated polynucleotides that encode the peptide sequences described herein. For example, and not to be limiting, the polynucleotide sequence can encode P44 Box 1, P44, Box 2, P44 Box 3, P44 Box 4, P44 Box 5, P44 Box 6, OMP-1X Box 1, OMP-1X Box 2, OMP-1X Box 1 and OMP-1X Box 2, SEQ ID NO: 2, SEQ ID NO: 6, SEQ ID NO: 3, SEQ ID NO: 7, SEQ ID NO: 4, SEQ ID NO: 8, or a fragment thereof. By way of further example, the polynucleotide sequences disclosed herein can also be polynucleotides that can encode the amino acid sequence comprising the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof.

Also disclosed herein are isolated polynucleotides that encode variants of the proteins described herein. In one aspect, disclosed herein are isolated polynucleotides that can encode a variant of an outer membrane protein of *Anaplasma platys*, or a fragment thereof. For example, and not to be limiting, the outer membrane protein can be P44 or OMP-1X protein. In a further aspect, the polynucleotide can encode a variant that can have at least 95% identity to, for example, and not to be limiting, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof. In a further aspect, the variant can be immunoreactive with at least one antibody that binds to P44 protein, P44 Box 1, P44 Box 2, P44 Box 3, P44 Box 4, P44 Box 5, P44 Box 6, OMP-1X protein, OMP-1X Box 1, OMP-1X Box 2, OMP-1X Box 1 and OMP-1X Box 2, or a fragment thereof.

Disclosed herein are polynucleotides that contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The polynucleotides described herein can encode one or more of the polypeptides described elsewhere herein. For example, disclosed herein are polynucleotides capable of encoding the peptides described herein, for example: an *Anaplasma platys* P44 or OMP-1X protein; a variant of the *Anaplasma platys* P44 or OMP-1X protein; or an antigenic fragment of the *Anaplasma platys* P44 or OMP-1X protein, or fragments thereof. Polynucleotides can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

The polynucleotides disclosed herein can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides can also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide.

The polynucleotides disclosed herein can also comprise fragments that encode immunogenic polypeptides. The polynucleotides disclosed herein can encode full-length polypeptides, polypeptide fragments, and variant or fusion polypeptides.

The polynucleotides disclosed herein can be degenerate nucleotide sequences encoding one or more of the polypeptides disclosed herein, as well as homologous nucleotide sequences that are at least about 80, 85, 90, 95, 96, 97, 98, 99% or 100% identical to the polynucleotide sequences disclosed herein and the complements thereof are also disclosed herein. Percent sequence identity can be calculated as described elsewhere herein. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of *Anaplasma platys* polynucleotides that encode biologically functional *Anaplasma platys* polypeptides also are *Anaplasma platys* polynucleotides.

The polynucleotides described herein can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

The polynucleotides disclosed herein can be used, for example, as probes or primers, for example, PCR primers, to detect the presence of *Anaplasma platys* polynucleotides in a test sample, such as a biological sample. Probes are molecules capable of interacting with a target nucleic acid, typically in a sequence specific manner, for example, through hybridization. Primers are a subset of probes that can support an enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation.

The hybridization of nucleic acids is well understood in the art and discussed herein. Typically a probe can be made from any combination of nucleotides or nucleotide derivatives or analogs available in the art. The ability of such probes and primers to specifically hybridize to *Anaplasma platys* P44 or *Anaplasma platys* OMP-1x polynucleotide sequences will enable them to be of use in detecting the presence of complementary sequences in a given test sample. Polynucleotide probes and primers can hybridize to complementary sequences in a test sample such as a biological sample, including, but not limited to, saliva, sputum, blood, plasma, serum, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of *Anaplasma platys* or an *Anaplasma platys* polynucleotide sequence in the sample.

Polypeptides

Described herein are isolated or purified polypeptides. For example, disclosed herein are isolated or purified *Anaplasma platys* polypeptides. The disclosed isolated or purified *Anaplasma platys* polypeptides can be used in one or more of the methods disclosed herein.

A polypeptide can be a polymer of three or more amino acids covalently linked by amide bonds. A polypeptide can be post-translationally modified. A purified polypeptide can be a polypeptide preparation that is substantially free of cellular material, other peptides and polypeptides, chemical precursors, synthetic chemicals, or combinations thereof.

As used herein, "*Anaplasma platys* peptides" or "*Anaplasma* platy proteins" refers to the P44 or the OMP-1X peptide sequences as well as combinations or fragments thereof described herein. For example, *Anaplasma platys* peptides include, but are not limited to, the P44 amino acid sequences provided in the Figures as well as the sequences provided in SEQ ID NOs: 21-29, SEQ ID NOs: 39-45, SEQ ID NOs: 92-98, combinations thereof as well as fragments thereof. Such sequences can also be referred to as *Anaplasma platys* P44 peptides or *Anaplasma platys* P44 proteins. Other examples of *Anaplasma platys* P44 peptides include, but are not limited to the sequences provided in GenBank Accession Nos: GQ868750, GU357491, GU357492, GU357493, HQ738571, GU357494, GU357495, GU357496, and GU357497.

*Anaplasma platys* peptides also include, but are not limited to, the OMP-1X amino acid sequences provided in the Figures as well as the sequences provided in SEQ ID NOs: 1-11, combinations thereof as well as fragments thereof. Such sequences can also be referred to as *Anaplasma platys* OMP-1X proteins. Other examples of *Anaplasma platys* OMP-1X peptides include, but are not limited to the sequences provided in GenBank Accession Nos: GQ868750, HQ738571, and GU357491.

Also disclosed herein are regions of the *Anaplasma platys* P44 and OMP-1X peptides that have been identified as being highly antigenic as identified through the Jameson-Wolf method as well through a surface probability plot analysis. These regions are herein referred to as a "Box" regions. For example, six regions of the *Anaplasma platys* P44 protein sequence have been identified in FIGS. 19 and 23. These six regions, from the N-terminal to the C-terminal regions are herein referred to as "P44 Box 1", "P44 Box 2", "P44 Box 3", "P44 Box 4", "P44 Box 5", and "P44 Box 6", respectively. In addition, two regions of the *Anaplasma platys* OMP-1X protein sequence have been identified in FIG. 22. These two regions, from the N-terminal to the C-terminal regions are herein referred to as "OMP-1X Box 1" and "OMP-1X Box 2", respectively.

Disclosed herein are isolated or purified polypeptides that consist of or comprise the amino acid sequence of "P44 Box 1". P44 Box 1 includes, but is not limited to, the P44 Box 1 amino acid sequences identified in FIG. 19 or 23, for example the sequence from about position 22 to about position 39 of FIG. 19 or the sequence from about position 40 to about position 64 of FIG. 23. In addition, P44 Box 1 includes, but is not limited to, the amino acid sequences of SEQ ID NO: 39, SEQ ID NO: 92, SEQ ID NOs: 100-103, the amino acid sequences from about position 22 to about position 39 of SEQ ID NOs: 21-24, or the amino acid sequence encoded by SEQ ID NO: 46. Also disclosed herein are isolated or purified polynucleotides that consist of or comprise a polynucleotide sequence capable of encoding the amino acid sequence of "P44 Box 1".

Disclosed herein are isolated or purified polypeptides that consist of or comprise the amino acid sequence of "P44 Box 2". P44 Box 2 includes, but is not limited to, the P44 Box 2 amino acid sequences identified in FIG. 19 or 23, for example the sequence from about position 77 to about position 85 of FIG. 19 or the sequence from about position 102 to about position 111 of FIG. 23. In addition, P44 Box 2 includes, but is not limited to, the amino acid sequences of SEQ ID NO: 40, SEQ ID NO: 93, SEQ ID NOs: 104-107, the amino acid sequences from about position 77 to about position 85 of SEQ ID NOs: 21-24, or the amino acid sequence encoded by SEQ ID NO: 47. Also disclosed herein are isolated or purified polynucleotides that consist of or comprise a polynucleotide sequence capable of encoding the amino acid sequence of "P44 Box 2".

Disclosed herein are isolated or purified polypeptides that consist of or comprise the amino acid sequence of "P44 Box 3". P44 Box 3 includes, but is not limited to, the P44 Box 3 amino acid sequences identified in FIG. 19 or 23, for example the sequence from about position 151 to about position 190 of FIG. 19 or the sequence from about position 178 to about position 222 of FIG. 23. In addition, P44 Box 3 includes, but is not limited to, the amino acid sequences of SEQ ID NO: 41, SEQ ID NO: 94, SEQ ID NOs: 108-111, the amino acid sequences from about position 151 to about position 191 of SEQ ID NOs: 21-24, or the amino acid sequence encoded by SEQ ID NO: 48. Also disclosed herein are isolated or purified polynucleotides that consist of or comprise a polynucleotide sequence capable of encoding the amino acid sequence of "P44 Box 3".

Disclosed herein are isolated or purified polypeptides that consist of or comprise the amino acid sequence of "P44 Box 4". P44 Box 4 includes, but is not limited to, the P44 Box 4 amino acid sequences identified in FIG. 19 or 23, for example the sequence from about position 227 to about position 234 of FIG. 19 or the sequence from about position 259 to about position 266 of FIG. 23. In addition, P44 Box 4 includes, but is not limited to, the amino acid sequences of SEQ ID NO: 42, SEQ ID NO: 95, SEQ ID NOs: 112-115, the amino acid sequences from about position 207 to about position 214 of SEQ ID NOs: 21-24, or the amino acid sequence encoded by SEQ ID NO: 49. Also disclosed herein are isolated or purified polynucleotides that consist of or comprise a polynucleotide sequence capable of encoding the amino acid sequence of "P44 Box 4".

Disclosed herein are isolated or purified polypeptides that consist of or comprise the amino acid sequence of "P44 Box 5". P44 Box 5 includes, but is not limited to, the P44 Box 5 amino acid sequences identified in FIG. 19 or 23, for example the sequence from about position 276 to about position 308 of FIG. 19 or the sequence from about position 319 to about position 340 of FIG. 23. In addition, P44 Box 5 includes, but is not limited to, the amino acid sequences of SEQ ID NO: 43, SEQ ID NO: 96, SEQ ID NOs: 116-119, the amino acid sequences from about position 248 to about position 269 of SEQ ID NOs: 21-24, or the amino acid sequence encoded by SEQ ID NO: 50. Also disclosed herein are isolated or purified polynucleotides that consist of or comprise a polynucleotide sequence capable of encoding the amino acid sequence of "P44 Box 5".

Disclosed herein are isolated or purified polypeptides that consist of or comprise the amino acid sequence of "P44 Box 6". P44 Box 6 includes, but is not limited to, the P44 Box 6 amino acid sequences identified in FIG. 19 or 23, for example the sequence from about position 417 to about position 426 of FIG. 19 or the sequence from about position 451 to about position 460 of FIG. 23. In addition, P44 Box 6 includes, but is not limited to, the amino acid sequences of SEQ ID NO: 44, SEQ ID NO: 97, SEQ ID NOs: 120-123, the amino acid sequences from about position 378 to about position 386 of SEQ ID NOs: 21-24, or the amino acid sequence encoded by SEQ ID NO: 51. Also disclosed herein are isolated or purified polynucleotides that consist of or comprise a polynucleotide sequence capable of encoding the amino acid sequence of "P44 Box 6".

Disclosed herein are isolated or purified polypeptides that consist of or comprise the amino acid sequence of "OMP-1X Box 1". OMP-1X Box 1 includes, but is not limited to, the OMP-1X Box 1 amino acid sequences identified in FIG. 22, for example the sequence from about position 66 to about position 192 of FIG. 22. In addition, OMP-1X Box 1 includes, but is not limited to, the amino acid sequences of SEQ ID NO: 2, SEQ ID NO: 6, or SEQ ID NO: 14. Also disclosed herein are isolated or purified polynucleotides that consist of or comprise a polynucleotide sequence capable of encoding the amino acid sequence of "OMP-1X Box 1".

Disclosed herein are isolated or purified polypeptides that consist of or comprise the amino acid sequence of "OMP-1X Box 2". OMP-1X Box 2 includes, but is not limited to, the OMP-1X Box 2 amino acid sequences identified in FIG. 22, for example the sequence from about position 241 to about position 309 of FIG. 22. In addition, OMP-1X Box 2 includes, but is not limited to, the amino acid sequences of SEQ ID NO: 3, SEQ ID NO: 7, or SEQ ID NO: 15. Also disclosed herein are isolated or purified polynucleotides that consist of or comprise a polynucleotide sequence capable of encoding the amino acid sequence of "OMP-1X Box 2".

Also described herein are purified polypeptides comprising the sequences outlined in FIG. 17, or at least about 10 contiguous amino acids of the sequence from FIG. 17 wherein the at least 10 contiguous amino acids are chosen from amino acids 300-410. In some aspects, the polypeptides described herein also inherently disclose the nucleotide sequence as related to the amino acids sequence 300-410 from FIG. 17.

In one aspect, described herein are purified polypeptides comprising at least about 8, 10, 15, 20, 30, 40, 50, or more contiguous amino acids, wherein the contiguous amino acids can be chosen from amino acids 300-410 from FIG. 17.

Disclosed herein are purified polypeptides that can either be full-length polypeptides or fragments of polypeptides. For example, fragments of polypeptides disclosed herein can comprise about 8, 10, 15, 20, 30, 40, 50, or more amino acids of polypeptides of the aspects described herein. Variant polypeptides can be at least about 90, 96, 98, or 99% identical to the polypeptide sequences shown in FIGS. 17 and 22. Variant polypeptides can have one or more conservative amino acid variations or other minor modifications and retain biological activity, i.e., are biologically functional equivalents. A biologically active equivalent can have substantially equivalent function when compared to the corresponding wild-type polypeptide.

Described herein are isolated or purified polypeptides comprising a sequence chosen from the following: a *Anaplasma platys* P44 protein, a variant of an *Anaplasma platys* P44 protein, or an antigenic fragment of an *Anaplasma platys* P44 protein. In one aspect, the *Anaplasma platys* P44 protein can comprise or consist of: P44 Box 1, P44 Box 2, P44 Box 3, P44 Box 4, P44 Box 5, P44 Box 6, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof.

In a further aspect, the *Anaplasma platys* P44 protein can comprise or consist of a variant of: P44 Box 1, P44, Box 2, P44 Box 3, P44 Box 4, P44 Box 5, P44 Box 6, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof.

It is understood that one way to define the variants and derivatives of the disclosed proteins herein is to define them in terms of homology/identity to specific known sequences. Specifically disclosed are variants of *A. platys* peptides and other proteins or peptides herein disclosed which have at least, 70% or at least 75% or at least 80% or at least 85% or at least 90% or at least 95% homology to the *A. platys* peptides specifically recited herein. Those of skill in the art readily understand how to determine the homology of two proteins.

As this specification discusses various polypeptides and polypeptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

In yet a further aspect, the *Anaplasma platys* P44 protein can comprise or consist of an antigenic fragment of: P44 Box 1, P44, Box 2, P44 Box 3, P44 Box 4, P44 Box 5, P44 Box 6, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, or the amino acid sequence comprising the amino acid from about position 416 to about position 433 of FIG. 19. In still a further aspect, the *Anaplasma platys* P44 proteins described herein can comprise or consist of a combination of one or more of the sequences described herein.

In one aspect, the variants or antigenic fragments of the *Anaplasma platys* P44 proteins described herein can be immunoreactive with at least one antibody that binds to their corresponding peptide sequence.

Also described herein are isolated or purified polypeptides that can comprise a sequence that is at least 95% identical to an *Anaplasma platys* P44 protein, a variant of the *Anaplasma platys* P44 protein, or an antigenic fragment of the *Anaplasma platys* P44 protein. Thus, in one aspect, the polypeptides described herein can be at least 95% identical to: P44 Box 1, P44 Box 2, P44 Box 3, P44 Box 4, P44 Box 5, P44 Box 6, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof.

In a further aspect, the polypeptides described herein can be at least 95% identical to a variant of: P44 Box 1, P44, Box 2, P44 Box 3, P44 Box 4, P44 Box 5, P44 Box 6, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof.

In yet a further aspect, the polypeptides described herein can be at least 95% identical to an antigenic fragment of: P44 Box 1, P44, Box 2, P44 Box 3, P44 Box 4, P44 Box 5, P44 Box 6, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, or the amino acid sequence comprising the amino acid from about position 416 to about position 433 of FIG. 19. In still a further aspect, the polypeptides described herein can be at least 95% identical to one or more of the peptide sequences described herein. In still a further aspect, the *Anaplasma platys* P44 proteins described herein can comprise or consist of a combination of one or more of the sequences described herein.

In one aspect, the variants or antigenic fragments can be at least 95% identical to the *Anaplasma platys* P44 proteins described herein can be immunoreactive with at least one antibody that binds to their corresponding peptide sequence.

In one aspect, the isolated polypeptides described herein can be: the P44 Box 1 protein, the P44 Box 2 protein, the P44 Box 3 protein, the P44 Box 4 protein, the P44 Box 5 protein, the P44 Box 6 protein; a variant of the P44 Box 1 protein, the P44 Box 2 protein, the P44 Box 3 protein, the P44 Box 4 protein, the P44 Box 5 protein, the P44 Box 6 protein; or an antigenic fragment of the P44 Box 1 protein, the P44 Box 2 protein, the P44 Box 3 protein, the P44 Box 4 protein, the P44 Box 5 protein, the P44 Box 6 protein.

Furthermore, described herein are isolated or purified polypeptides comprising a sequence chosen from the following: a *Anaplasma platys* OMP-1X protein, a variant of the *Anaplasma platys* OMP-1X protein, or an antigenic fragment of the *Anaplasma platys* OMP-1X protein. In one aspect, the *Anaplasma platys* OMP-1X protein can comprise or consist of: OMP-1X Box 1, OMP-1X Box 2, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof.

In a further aspect, the *Anaplasma platys* OMP-1X protein can comprise or consist of a variant of: OMP-1X Box 1, OMP-1X Box 2, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof.

In yet a further aspect, the *Anaplasma platys* OMP-1X protein can comprise or consist of an antigenic fragment of: OMP-1X Box 1, OMP-1X Box 2, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, or a combination of the amino acid from about position 240 to about position 312 and the amino acid from about position 230 to about position 300 of FIG. 22. In still a further aspect, the *Anaplasma platys* OMP-1X proteins described herein can comprise or consist of a combination of one or more of the sequences described herein.

In one aspect, the variants or antigenic fragments of the *Anaplasma platys* OMP-1X proteins described herein can be immunoreactive with at least one antibody that binds to their corresponding peptide sequence.

Also described herein are isolated or purified polypeptides that can comprise a sequence that is at least 95% identical to an *Anaplasma platys* OMP-1X protein, a variant of the *Anaplasma platys* OMP-1X protein, or an antigenic fragment of the *Anaplasma platys* OMP-1X protein. Thus, in one aspect, the polypeptides described herein can be at least 95% identical to: OMP-1X Box 1, OMP-1X Box 2, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof.

In a further aspect, the polypeptides described herein can be at least 95% identical to a variant of: OMP-1X Box 1, OMP-1X Box 2, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof.

In yet a further aspect, the polypeptides described herein can be at least 95% identical to an antigenic fragment of: OMP-1X Box 1, OMP-1X Box 2, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, or a combination of the amino acid from about position 240 to about position 312 and the amino acid from about position 230 to about position 300 of FIG. 22. In still a further aspect, the *Anaplasma platys* OMP-1X proteins described herein can comprise or consist of a combination of one or more of the sequences described herein. In still a further aspect, the polypeptides described herein can be at least 95% identical to one or more of the peptide sequences described herein. In still a further aspect, the *Anaplasma platys* OMP-1X proteins described herein can comprise or consist of a combination of one or more of the sequences described herein.

In one aspect, the variants or antigenic fragments can be at least 95% identical to the *Anaplasma platys* OMP-1X proteins described herein can be immunoreactive with at least one antibody that binds to their corresponding peptide sequence.

In one aspect, the isolated polypeptides described herein can be: the OMP-1X protein, the OMP-1X Box 1 protein, or the OMP-1X Box 2 protein; a variant of the OMP-1X protein, the OMP-1X Box 1 protein, or the OMP-1X Box 2 protein; or an antigenic fragment of the OMP-1X protein, the OMP-1X Box 1 protein, or the OMP-1X Box 2 protein.

Also disclosed herein are isolated polynucleotides that encode the polypeptides described herein. A purified polypeptide can further comprising a carrier. A purified polypeptide can be in a multimeric form. A purified polypeptide can be linked to an indicator reagent, an amino acid spacer, an amino acid linker, a signal sequence, a stop transfer sequence, a transmembrane domain, a protein purification ligand, a heterologous polypeptide or a combination thereof.

Purified polypeptides described herein can either be full-length polypeptides or fragments of polypeptides. For example, fragments of polypeptides described herein can comprise about 10, 15, 20, 50, 75, 100, 150, 200, 250 or more amino acids of polypeptides of the invention. For example, and not to be limiting, variant polypeptides can be at least about 80, or about 90, 96, 98, or 99% identical to the polypeptide sequences shown in SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, or a fragment thereof, and are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, New Jersey, (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J. Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide or polypeptide and that gaps in identity of up to 5% of the total number of nucleotides or amino acids in the reference polynucleotide or polypeptide are allowed.

Variants can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide. Variant polypeptides of the invention can comprise about 1, 2, 3, 4, 5, 10, or 20 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

The polypeptides described herein can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

The polypeptides described herein can be covalently or non-covalently linked to an amino acid sequence to which the polypeptide is not normally associated with in nature, i.e., a heterologous amino acid sequence. A heterologous amino acid sequence can be from a non-*Anaplasma platys* organism (e.g., an *Anaplasma phagocytophilum* organism), a synthetic sequence, or an *Anaplasma platys* sequence not usually located at the carboxy or amino terminus of a polypeptide of the invention. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. In one embodiment of the invention a protein purification ligand can be one or more C amino acid residues at, for example, the amino terminus or carboxy terminus of a polypeptide of the invention. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and Staphylococcal protein A, or combinations thereof. More than one polypeptide of the invention can be present in a fusion protein. Fragments of polypeptides of the invention can be present in a fusion protein of the invention. A fusion protein of the invention can comprise one or more of *Anaplasma platys* polypeptides described herein, fragments thereof, or combinations thereof. A fusion protein can also comprise multiple copies of a same *Anaplasma platys* polypeptide or combination of different *Anaplasma platys* polypeptides described herein.

Polypeptides of the invention can be in a multimeric form. That is, a polypeptide can comprise one or more copies of an *Anaplasma platys* polypeptide of the invention or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody specific for *Anaplasma platys* P44 or *Anaplasma platys* OMP-1X. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, CABIOS 4:181-186 (1988). For example, a polypeptide of the invention can be isolated and screened. A series of short peptides, which together span an entire polypeptide sequence, can be prepared by proteolytic cleavage. By starting with, for example, 100-mer polypeptide fragments, each fragment can be tested for the presence of epitopes recognized in an ELISA. For example, in an ELISA assay an *Anaplasma platys* polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

The polypeptides described herein can be produced recombinantly. A polynucleotide encoding a polypeptide described herein can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from *Anaplasma platys* cells.

For example, and not to be limiting, an immunogenic polypeptide of the invention can comprise an amino acid sequence shown in SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, or fragments thereof. An immunogenic polypeptide can elicit antibodies or other immune responses (e.g., T-cell responses of the immune system) that recognize epitopes of a polypeptide having a SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, or fragments thereof. An immunogenic polypeptide of the invention can also be a fragment of a polypeptide that has an amino acid sequence shown in SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8. An immunogenic polypeptide fragment of the invention can be about 10, 15, 20, 25, 30, 40, 50 or more amino acids in length.

Polypeptide Production

Polypeptides that can be used in the disclosed methods can be produced by any method known in the art. One method of producing the disclosed polypeptides is to link two or more amino acid residues, peptides or polypeptides together by protein chemistry techniques. For example, peptides or polypeptides are chemically synthesized using currently available laboratory equipment using either Fmoc (9-fluorenylmethyloxycarbonyl) or Boc (tert-butyloxycarbonyl) chemistry (Applied Biosystems, Inc., Foster City, Calif.). A peptide or polypeptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively, (Grant G A (1992) *Synthetic Peptides: A User Guide*. W.H. Freeman and Co., N.Y. (1992); Bodansky M and Trost B., Ed. (1993) *Principles of Peptide Synthesis*. Springer-Verlag Inc., NY). Alternatively, the peptide or polypeptide is independently synthesized in vivo. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two-step chemical reaction (Dawson et al. *Science*, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolim M et al. (1992) *FEBS Lett*. 307:97-101; Clark-Lewis I et al., *J. Biol. Chem.*, 269:16075 (1994); Clark-Lewis I et al., *Biochem.*, 30:3128 (1991); Rajarathnam K et al., *Biochem*. 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

Also disclosed are the components to be used to prepare the disclosed *A. platys* peptides that can be used in the disclosed methods as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polynucleotide is disclosed and discussed and a number of modifications that can be made to a number of molecules including the polynucleotide are discussed, specifically contemplated is each and every combination and permutation of polynucleotide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that one way to define any known variants and derivatives or those that might arise, of the disclosed genes and proteins herein is through defining the variants and derivatives in terms of homology to specific known sequences. Specifically disclosed are variants of the genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence. Those of skill in the art readily understand how to determine the homology of two proteins or nucleic acids, such as genes. For example, the homology can be calculated after aligning the two sequences so that the homology is at its highest level.

Antibodies

Described herein are isolated or purified antibodies that selectively hybridize to a peptide chosen from: *Anaplasma platys* P44 protein, *Anaplasma platys* OMP-1X, P44 Box 1, P44, Box 2, P44 Box 3, P44 Box 4, P44 Box 5, P44 Box 6, OMP-1X Box 1, OMP-1X Box 2, or a fragment thereof. In one aspect, the antibodies described herein can hybridize to a peptide chosen from one or more of: P44 Box 1, P44 Box 2, P44 Box 3, P44 Box 4, P44 Box 5, P44 Box 6, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, OMP-1X Box 1, OMP-1X Box 2, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof. In a further aspect, the antibodies described herein can hybridize to one or more of a peptide that is at least 95% identical to the P44 or OMP-1X peptide sequences described herein. In a further aspect, the antibodies described herein can hybridize to one or more of a variant or antigenic fragment of the P44 or OMP-1X peptide sequences described herein. In still a further aspect, the antibodies described herein can hybridize to one or more of a variant or antigenic fragment of a peptide that is at least 95% identical to the P44 or OMP-1X peptide sequences described herein.

Disclosed herein are antibodies that specifically and stably bind to an *Anaplasma platys* p44 polypeptide, an *Anaplasma platys* OMP-1X peptide, or fragment thereof. Antibodies can also specifically and stably bind to an *Anaplasma platys* P44 Box 1, P44 Box 2, P44 Box 3, P44 Box 4, P44 Box 5, P44 Box 6 polypeptide or fragment thereof. Antibodies can also specifically and stably bind to an *Anaplasma platys* OMP-1X Box 1 polypeptide, an OMP-1X Box 2 polypeptide or fragment thereof. One of skill in the art can easily determine if an antibody is specific for an *Anaplasma platys* polypeptide using assays described herein. An antibody can be a polyclonal antibody, a monoclonal antibody, a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

The antibodies described herein can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, Methods Mol. Biol. 80:23-37 (1998); Dean, Methods Mol. Biol. 32:361-79 (1994); Baileg, Methods Mol. Biol. 32:381-88 (1994); Gullick, Methods Mol. Biol. 32:389-99 (1994); Drenckhahn et al. Methods Cell. Biol. 37:7-56 (1993); Morrison, Ann. Rev. Immunol. 10:239-65 (1992); Wright et al. Crit. Rev. Immunol. 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that a first antigen, e.g., an *Anaplasma platys* polypeptide, recognizes and binds to an antibody of the invention with greater affinity than other, non-specific molecules. A non-specific molecule is an antigen that shares no common epitope with the first antigen. In this case, *Anaplasma platys* polypeptides would not generally be desirable choices for non-specific control molecules. For example, an antibody raised against a first antigen (e.g., a polypeptide) to which it binds more efficiently than to a non-specific antigen can be described as specifically binding to the first antigen. In a preferred embodiment, an antibody or antigen-binding portion thereof specifically binds to a polypeptide of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, or fragments thereof. Specific binding can be tested using, for example, an enzyme-linked immunosorbant assay (ELISA), a radioimmunoassay (RIA), or a western blot assay using methodology well known in the art.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing *Anaplasma platys*-specific antibodies can be identified using RIA or ELISA and isolated by cloning in semi-solid agar or by limiting dilution. Clones producing *Anaplasma platys*-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., P.N.A.S. U.S.A. 82:8653 1985; Spria et al., J. Immunolog. Meth. 74:307, 1984. Monoclonal antibodies of the invention can also be recombinant monoclonal antibodies. See, e.g., U.S. Pat. Nos. 4,474,893; 4,816,567. Antibodies of the invention can also be chemically constructed. See, e.g., U.S. Pat. No. 4,676,980.

Antibodies can be chimeric (see, e.g., U.S. Pat. No. 5,482,856), humanized (see, e.g., Jones et al., Nature 321: 522 (1986); Reichmann et al., Nature 332:323 (1988); Presta, Curr. Op. Struct. Biol. 2:593 (1992)), caninized, canine, or human antibodies. Human antibodies can be made by, for example, direct immortilization, phage display, transgenic mice, or a Trimera methodology, see e.g., Reisener et al., Trends Biotechnol. 16:242-246 (1998).

Antibodies that specifically bind *Anaplasma platys* antigens (e.g., *Anaplasma platys* polypeptides), are particularly useful for detecting the presence of Apl or Apl antigens in a sample, such as a serum, blood, plasma, urine, fecal, or saliva sample from an Apl- or Aph-infected animal. An immunoassay for *Anaplasma platys* antigen can utilize one antibody or several antibodies. An immunoassay for *Anaplasma platys* antigen can use, for example, a monoclonal antibody specific for an *Anaplasma platys* epitope, a combination of monoclonal antibodies specific for epitopes of one *Anaplasma platys* polypeptide, monoclonal antibodies specific for epitopes of different *Anaplasma platys* polypeptides, polyclonal antibodies specific for the same *Anaplasma platys* antigen, polyclonal antibodies specific for different *Anaplasma platys* antigens, or a combination of monoclonal and polyclonal antibodies. Immunoassay protocols can be based upon, for example, competition, direct reaction, or sandwich type assays using, for example, labeled antibody. Antibodies can be labeled with any type of label known in the art, including, for example, fluorescent, chemiluminescent, radioactive, enzyme, colloidal metal, radioisotope and bioluminescent labels.

Antibodies or fragments thereof can be bound to a support and used to detect the presence of *Anaplasma platys* antigen. Supports include, for example, glass, polystyrene, polypropylene, polyethylene, dextran, nylon, amylases, natural and modified celluloses, polyacrylamides, agaroses and magletite.

Antibodies can further be used to isolate *Anaplasma platys* organisms or *Anaplasma platys* antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind *Anaplasma platys* organisms or *Anaplasma platys* antigens from a sample, such as a biological sample including saliva, serum, sputum, blood, urine, feces, cerebrospinal fluid, amniotic fluid, wound exudate, or tissue. The bound *Anaplasma platys* organisms or *Anaplasma platys* antigens are recovered from the column matrix by, for example, a change in pH.

Antibodies can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies, including, for example, monoclonal antibodies and single chain antibodies, can be used to monitor the course of amelioration of a disease caused by *Anaplasma platys*. By measuring the increase or decrease of *Anaplasma platys* antibodies to *Anaplasma platys* antigens in a test sample from an animal, it can be determined whether a particular therapeutic regiment aimed at ameliorating the disorder is effective. Antibodies can be detected and/or quantified using for example, direct binding assays such as RIA, ELISA, or western blot assays.

In one aspect, the antibodies can be immunoglobulin molecules that specifically and stably bind to *A. platys* P44 or OMP-1X polypeptide or fragment thereof. In a further aspect, the antibody can be monoclonal, polyclonal, or a single chain antibody. In yet a further aspect, an antibody can be an antigen-binding fragments, which is a portion of an intact antibody comprising the antigen binding site or variable region of an intact antibody, wherein the portion is free of the constant heavy chain domains of the Fc region of the intact antibody.

In one aspect, monoclonal antibodies directed against epitopes present on a polypeptide discussed herein can be produced. In a further aspect, clones producing *A. platys*-specific antibodies can be isolated via additional screening. In yet a further aspect, monoclonal antibodies can also be recombinant monoclonal antibodies. Monoclonal antibodies can be screened for specificity using standard techniques known in the art.

In one aspect, an antibody can belong to any antibody class. In a further aspect, an antibody or fragment thereof can bind to an epitope of a polypeptide disclosed herein. An antibody can be made in vivo in suitable laboratory animals or in vitro via recombinant DNA techniques known in the art.

Means for preparing and characterizing antibodies are well known in the art. For example, polyclonal antibodies can be produced by administering a polypeptide described herein to an animal, such as a human or other primate, mouse, rat, rabbit, dog, cow, sheep, or horse. Serum from the immunized animal can be collected and the antibodies can be purified from the plasma.

In one aspect, antibodies can be chimeric, canine, or human antibodies. In a further aspect, antibodies or fragments thereof can be bound to a support. Supports can include, glass, polystyrene, polypropylene, polyethylene, nylon, celluloses, or polyacrylamides.

Vaccines

In one aspect, described herein are *Anaplasma platys* P44 protein based vaccines. Thus, described herein are peptides comprising one or more amino-acid sequences selected from the group consisting of P44 Box 1, P44 Box 2, P44 Box 3, P44 Box 4, P44 Box 5, P44 Box 6, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof. In a further aspect, the peptides disclosed herein can comprise one or more amino-acid sequences selected from the group consisting of a combination of any P44 peptide sequences described herein.

In yet a further aspect, the vaccines described herein can comprise one or more amino-acid sequences selected from the group consisting of a variant of the P44 proteins described herein, or an antigenic fragment of the P44 proteins described herein. In still a further aspect, the vaccines described herein can comprise one or more amino-acid sequences selected from the group consisting of a sequence that is at least 95% identical to a P44 protein, a variant of the P44 protein, or an antigenic fragment of the P44 protein sequences described herein. The peptides described herein can also be any antigenically related variant of the peptide sequences which have an identity of 95% and are capable of immunologically mimicking the corresponding antigenic determinant site of the P44 protein of *Anaplasma platys*.

In one aspect, the vaccines described herein can be *Anaplasma platys* OMP-1X protein based vaccines. Thus, described herein are peptides comprising one or more amino-acid sequences selected from the group consisting of OMP-1X Box 1, OMP-1X Box 2, SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, SEQ ID NO: 2, SEQ ID NO: 6, SEQ ID NO: 3, SEQ ID NO: 7, SEQ ID NO: 4, SEQ ID NO: 8, the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof. In a further aspect, the peptides disclosed herein can comprise one or more amino-acid sequences selected from the group consisting of a combination of any OMP-1X peptide sequences described herein.

In yet a further aspect, the vaccines described herein can comprise one or more amino-acid sequences selected from the group consisting of a variant of the OMP-1X proteins described herein, or an antigenic fragment of the OMP-1X proteins described herein. In still a further aspect, the vaccines described herein can comprise one or more amino-acid sequences selected from the group consisting of a sequence that is at least 95% identical to a OMP-1X protein, a variant of the OMP-1X protein, or an antigenic fragment of the OMP-1X protein sequences described herein. The peptides described herein can also be any antigenically related variant of the peptide sequences which have an identity of 95% and are capable of immunologically mimicking the corresponding antigenic determinant site of the OMP-1X protein of *Anaplasma platys*. Antigenically related variants can have amino acids added, inserted, substituted or deleted.

Furthermore, described herein are chimeric peptides comprising: one or more *Anaplasma platys* P44 proteins or *Anaplasma platys* OMP-1X proteins described herein; one or more variants of the *Anaplasma platys* P44 proteins or *Anaplasma platys* OMP-1X proteins described herein; one or more antigenic fragments of the *Anaplasma platys* P44 proteins or *Anaplasma platys* OMP-1X proteins described herein; or one or more proteins that are at least 95% identical to the *Anaplasma platys* P44 proteins or *Anaplasma platys* OMP-1X proteins described herein, linked to a carrier polypeptide that can comprise at least one T-cell epitope. In one aspect, the chimeric peptides described herein can further comprise a purification tag peptide sequence. For example, and not to be limiting, the purification tag sequence can be a Histidine-tag sequence. Also disclosed herein are purified antibodies that are immunospecific to the chimeric peptides described herein. In one aspect, a purification tag peptide sequence (such as a Histidine tag or a Glutathione-S-transferase tag) can be used in order to aid subsequent purification of the polypeptide. Optional short peptide spacer sequences can be introduced between elements of the chimeric polypeptide. When one is required a Histidine tag sequence can be located at the C-terminus of the polypeptide.

Further described herein are vaccine compositions comprising an immunogenic amount of at least: one *Anaplasma platys* P44 protein or *Anaplasma platys* OMP-1X protein described herein; one variant of the *Anaplasma platys* P44 proteins or *Anaplasma platys* OMP-1X proteins described herein; one antigenic fragment of the *Anaplasma platys* P44 proteins or *Anaplasma platys* OMP-1X proteins described herein; or one protein that is at least 95% identical to the *Anaplasma platys* P44 proteins or *Anaplasma platys* OMP-1X proteins described herein, wherein the protein or peptide can be in a pharmaceutically acceptable excipient, and an optional adjuvant. Vaccine preparation is generally described in Vaccine Design ("The subunit and adjuvant approach" (eds. Powell M. F. & Newman M. J). (1995) Plenum Press New York), which is hereby incorporated in its entirety by this reference. Suitable adjuvants include, but are not limited to an aluminium salt such as aluminium hydroxide gel (alum) or aluminium phosphate, but can also be a salt of calcium, iron or zinc, or can be an insoluble suspension of acylated tyrosine, or acylated sugars, cationically or anionically derivatised polysaccharides, or polyphosphazenes. Other known adjuvants include CpG containing oligonucleotides. The oligonucleotides can be characterized in that the CpG dinucleotide is unmethylated. Such oligonucleotides are well known in the art and are described in, for example WO96/02555. In one aspect, the adjuvants can induce an immune response, for example, of the TH1 type. High levels of Th1-type cytokines can favor the induction of cell mediated immune responses to the given antigen, while high levels of Th2-type cytokines can favor the induction of humoral immune responses to the antigen. Suitable adjuvant systems can include, for example, monophosphoryl lipid A, 3-de-O-acylated monophosphoryl lipid A (3D-MPL), or a combination of 3D-MPL together with an aluminium salt. CpG oligonucleotides can also induce a TH1 response. An enhanced system can involve the combination of a monophosphoryl lipid A and a saponin derivative, for example, the combination of QS21 and 3D-MPL as disclosed in WO 94/00153, or a less reactogenic composition where the QS21 can be quenched with cholesterol as described in WO 96/33739. Another adjuvant formulation involving QS21 3D-MPL & tocopherol in an oil in water emulsion is described in WO 95/17210.

Also described herein are methods of inducing an immune response in a mammal susceptible to *Anaplasma platys* infection comprising administering to the mammal an effective amount of the vaccine compositions described herein. As used herein, "infection" can also mean "exposure," and the terms can be used interchangeably.

Additionally, described herein are methods of preventing *Anaplasma platys* infection comprising administering to a mammal an effective amount of the vaccine compositions described herein.

Vectors

Also described herein are vectors for transformation of a host cell comprising an isolated polynucleotide that can encode an outer membrane protein of *Anaplasma platys*, a variant of said outer membrane protein, or an immunogenic fragment of said outer membrane protein. In one aspect, the outer membrane protein can be the P44 protein, P44 Box 1, P44 Box 2, P44 Box 3, P44 Box 4, P44 Box 5, P44 Box 6, OMP-1X protein, OMP-1X Box 1, OMP-1X Box 2, OMP-1X Box 1 and OMP-1X Box 2, or a fragment thereof. The vectors disclosed herein can comprise any of the isolated polynucleotide sequences disclosed or described herein.

The polynucleotides described herein can comprise coding sequences for naturally occurring polypeptides or can encode altered sequences that do not occur in nature. If desired, polynucleotides can be cloned into an expression vectors comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

In a further aspect, the vectors described herein can be used in a process for making a corresponding outer membrane protein of *Anaplasma platys*, a variant of said outer membrane protein, or an immunogenic fragment of said outer membrane protein. For example, and not to be limiting, the process can comprise transfecting host cells with any of the vectors described herein and inducing expression of the outer membrane protein or the variant or immunogenic fragment thereof in any of the host cells described herein.

Expression vectors for production of proteins and peptides are well known in the art (see Ausubel et al., 2004, Current Protocols In Molecular Biology, Greene Publishing and Wiley-Interscience, New York). Such expression vectors can include the nucleic acid sequence encoding the *Anaplasma platys* polypeptides linked to regulatory elements, such as a promoter, which drives transcription of the DNA and can be adapted for expression in prokaryotic (e.g., *E. coli*) and eukaryotic (e.g., yeast, insect or mammalian cells) hosts. A variant *Anaplasma platys* polypeptide can also be expressed in an expression vector in which a variant *Anaplasma platys* gene is operably linked to a promoter. The promoter can be a eukaryotic promoter for expression in a mammalian cell. The transcription regulatory sequences can comprise a heterologous promoter and optionally an enhancer, which is recognized by the host cell. Commercially available expression vectors can also be used. Expression vectors can include host-recognized replication systems, amplifiable genes, selectable markers, host sequences useful for insertion into the host genome, and the like.

Host Cells

Also disclosed herein are host cells comprising any of the vectors disclosed or described herein. Suitable host cells can include, but are not limited to, bacteria such as *E. coli*, yeast, filamentous fungi, mollusk cells, snail cells, insect cells, and mammalian cells, which are typically immortalized, including mouse, hamster, human, and monkey cell lines, and derivatives thereof. Host cells may be able to process the *Anaplasma platys* gene product to produce an appropriately processed, mature polypeptide. Such processing can include glycosylation, ubiquitination, disulfide bond formation, and the like.

Kits

Described herein are kits for diagnosing *Anaplasma platys* in a subject, wherein the kit can comprise the *Anaplasma platys* P44 protein, an antigenic fragment of the *Anaplasma platys* P44 protein, or both. In one aspect, in the kits disclosed herein, the protein can comprise: one or more *Anaplasma platys* P44 proteins described herein; one or more variants of the *Anaplasma platys* P44 proteins described herein; one or more antigenic fragments of the *Anaplasma platys* P44 proteins described herein; or one or more proteins that are at least 95% identical to the *Anaplasma platys* P44 proteins described herein.

Also described herein are kits for diagnosing *Anaplasma platys* in a subject, wherein the kit can comprise the *Anaplasma platys* OMP-1X protein, an antigenic fragment of the *Anaplasma platys* OMP-1X protein, or both. In one aspect, in the kits disclosed herein, the protein can comprise: one or more *Anaplasma platys* OMP-1X proteins described herein; one or more variants of the *Anaplasma platys* OMP-1X proteins described herein; one or more antigenic fragments of the *Anaplasma platys* OMP-1X proteins described herein; or one or more proteins that are at least 95% identical to the *Anaplasma platys* OMP-1X proteins described herein.

Further described herein are kits for diagnosing *Anaplasma platys* in a subject comprising one or more of the antibodies described herein. In one aspect, the kits described herein can further comprise a biomolecule for detecting an interaction between the reagent and antibodies in a sample from an animal.

Also described herein are reagent kits for diagnosing infection or exposure with *Anaplasma platys* in a subject comprising a DNA probe or primer constructed to correspond to the P44 protein, P44 Box 1, P44 Box 2, P44 Box 3, P44 Box 4, P44 Box 5, or P44 Box 6 of *Anaplasma platys*, characterized in that the probe or primer comprises one or more of the nucleotides or polynucleotides described herein.

Also described herein are reagent kits for diagnosing infection or exposure with *Anaplasma platys* in a subject comprising a DNA probe or primer constructed to correspond to the OMP-1X protein, OMP-1X Box 1, or OMP-1X Box 2 of *Anaplasma platys*, characterized in that the probe or primer comprises one or more of the nucleotides or polynucleotides described herein.

The kits described herein can comprise one or more of the polypeptides described herein and means for determining binding of the polypeptide to anti-*Anaplasma platys* or antibody fragments in the sample. A kit or article of manufacture can also comprise one or more antibodies or antibody fragments described herein and means for determining binding of the antibodies or antibody fragments to *Anaplasma platys* and/or *Anaplasma platys* polypeptides in the sample. A kit can comprise a device containing one or more polypeptides or antibodies described herein and instructions for use of the one or more polypeptides or antibodies for, e.g., the identification of an *Anaplasma platys* infection in a mammal. The kit can also comprise packaging material comprising a label that indicates that the one or more polypeptides or antibodies of the kit can be used for the identification of *Anaplasma platys* infection. Other components such as buffers, controls, and the like, known to those of ordinary skill in art, can be included in such test kits. The polypeptides, antibodies, assays, and kits of the invention are useful, for example, in the diagnosis of individual cases of *Anaplasma platys* infection in a subject, as well as epidemiological studies of *Anaplasma platys* outbreaks. Exposure to *Anaplasma platys* can also be detected. Exposure would include the presence of *Anaplasma platys* organisms without clinical symptoms and prior infection with *Anaplasma platys*.

Samples

Vertebrate host samples are collected from body tissue or bodily fluid, such as for example, blood, plasma, saliva, and peripheral blood mononuclear cells. For the invertebrate vectors which can transmit the pathogen from one vertebrate host to another, the sample can be from dissected ticks (e.g., midgut, salivary glands, and hemolymph), tick pieces, and frozen and smashed ticks in preparation for PCR assays. Further preparation of tick tissues can involve heating the sample, digesting the samples with proteases, and isolating pure DNA from the tick tissues. Other suitable samples include, but are not limited to, saliva, cheek scrapings, biopsies of retina, kidney or liver or other organs or tissues; skin biopsies; amniotic fluid; or CNS samples; and the like.

Methods

PCR Based Diagnostics

Described herein are methods for detecting *Anaplasma platys* in a sample obtained from a subject, comprising (a) providing a primer set comprising: (i) one or more forward primers comprising the sequence of: SEQ ID NO: 82, SEQ ID NO: 83, SEQ ID NO:84, or SEQ ID NO: 90 and (ii) one or more reverse primers comprising the sequence of: SEQ ID NO: 85, SEQ ID NO: 86, SEQ ID NO: 87, SEQ ID NO:88, SEQ ID NO: 89 or SEQ ID NO: 91; (b) amplifying DNA in the sample with the said primer set and a polymerase chain reaction, and (c) determining the length or sequence of the PCR products of step (b), wherein the presence of a PCR product having a length or sequence which corresponds to the length or sequence, respectively, of that region of the *Anaplasma platys* p44 gene which is located between the regions to which the one or more forward primers and the one or more reverse primers bind is indicative of the presence of *Anaplasma platys* in the sample. For example, and not to be limiting, the one or more forward or reverse primers can be from 15 to 35 nucleotides in length. In one aspect, the forward and the reverse primer can comprise SEQ ID NO: 90 and SEQ ID NO: 91, respectively.

Further described herein are primer sets for detecting *Anaplasma platys* in a sample, the primer set comprising: (a) one or more forward primers comprising the sequence of: SEQ ID NO: 82, SEQ ID NO: 83, SEQ ID NO:84, or SEQ ID NO: 90 and (ii) one or more reverse primers comprising the sequence of: SEQ ID NO: 85, SEQ ID NO: 86, SEQ ID NO: 87, SEQ ID NO:88, SEQ ID NO: 89 or SEQ ID NO: 91. For example, and not to be limiting, the one or more forward or reverse primers can be from 15 to 35 nucleotides in length. In one aspect, the forward and the reverse primer can comprise SEQ ID NO: 90 and SEQ ID NO: 91, respectively.

Also described herein are methods for detecting *Anaplasma platys* in a sample obtained from a subject, comprising (a) providing a primer set comprising: (i) one or more forward primers comprising the sequence of: SEQ ID NO: 52, SEQ ID NO: 54, SEQ ID NO:56, SEQ ID NO: 58, SEQ ID NO: 60, or SEQ ID NO: 62 and (ii) one or more reverse primers comprising the sequence of: SEQ ID NO: 53, SEQ ID NO: 55, SEQ ID NO:57, SEQ ID NO: 59, SEQ ID NO: 61, or SEQ ID NO: 63; (b) amplifying DNA in the sample with the said primer set and a polymerase chain reaction, and (c) determining the length or sequence of the PCR products of step (b), wherein the presence of a PCR product having a length or sequence which corresponds to the length or sequence, respectively, of that region of the *Anaplasma platys* p44 gene which is located between the regions to which the one or more forward primers and the one or more reverse primers bind is indicative of the presence of *Anaplasma platys* in the sample. For example, and not to be limiting, the one or more forward or reverse primers can be from 15 to 35 nucleotides in length. In one aspect, the forward and the reverse primer can comprise one or more of pairs of sequences described herein, including, but not limited to: PAIR 1: SEQ ID NO: 52 and SEQ ID NO: 53; PAIR 2: SEQ ID NO: 54 and SEQ ID NO: 55; PAIR 3: SEQ ID NO: 56 and SEQ ID NO: 57; PAIR 4: SEQ ID NO: 58 and SEQ ID NO: 59; PAIR 5: SEQ ID NO: 60 and SEQ ID NO: 61; or PAIR 6: SEQ ID NO: 62 and SEQ ID NO: 63.

Further described herein are primer sets for detecting *Anaplasma platys* in a sample, the primer set comprising: (a) one or more forward primers comprising the sequence of: SEQ ID NO: 82, SEQ ID NO: 83, SEQ ID NO:84, or SEQ ID NO: 90 and (ii) one or more reverse primers comprising the sequence of: SEQ ID NO: 85, SEQ ID NO: 86, SEQ ID NO: 87, SEQ ID NO:88, SEQ ID NO: 89 or SEQ ID NO: 91. For example, and not to be limiting, the one or more forward or reverse primers can be from 15 to 35 nucleotides in length.

Described herein are methods for detecting *Anaplasma platys* in a sample obtained from a subject, comprising (a) providing a primer set comprising: (i) one or more forward primers comprising the sequence of: SEQ ID NO: 64, SEQ ID NO: 18, or SEQ ID NO: 20 and (ii) one or more reverse primers comprising the sequence of: SEQ ID NO: 65, SEQ ID NO: 19, or SEQ ID NO: 99; (b) amplifying DNA in the sample with the said primer set and a polymerase chain reaction, and (c) determining the length or sequence of the PCR products of step (b), wherein the presence of a PCR product having a length or sequence which corresponds to the length or sequence, respectively, of that region of the *Anaplasma platys* OMP-1X gene which is located between the regions to which the one or more forward primers and the one or more reverse primers bind is indicative of the presence of *Anaplasma platys* in the sample. For example, and not to be limiting, the one or more forward or reverse primers can be from 15 to 35 nucleotides in length. In one aspect, the forward and reverse primers can comprise one or more pairs of sequences described herein, including, but not limited to: PAIR 1: SEQ ID NO: 64 and SEQ ID NO: 65; PAIR 2: SEQ ID NO: 18 and SEQ ID NO: 19; or PAIR 3: SEQ ID NO: 20 and SEQ ID NO: 99, respectively.

Further described herein are primer sets for detecting *Anaplasma platys* in a sample, the primer set comprising: (a) one or more forward primers comprising the sequence of: SEQ ID NO: 64, SEQ ID NO: 18, or SEQ ID NO: 20 and (ii) one or more reverse primers comprising the sequence of: SEQ ID NO: 65, SEQ ID NO: 19, or SEQ ID NO: 99. For example, and not to be limiting, the one or more forward or reverse primers can be from 15 to 35 nucleotides in length.

Also described herein are methods of detecting the presence of *Anaplasma platys* in a sample by contacting the sample with a DNA probe or primer constructed to correspond to the P44 protein of *Anaplasma platys*, characterized in that the probe or primer comprises one or more of the nucleotides or polynucleotides described herein.

Further described herein are methods of detecting the presence of *Anaplasma platys* in a sample by contacting the sample with a DNA probe or primer constructed to correspond to the OMP-1X protein, OMP-1X Box 1, or OMP-1X Box 2 of *Anaplasma platys*, characterized in that the probe or primer comprises one or more of the nucleotides or polynucleotides described herein.

PCR assays are well known in the art, including, for example, U.S. Pat. Nos. 4,683,195; 4,683,202; 4,965,188. Generally, polynucleotide primers are annealed to denatured strands of a target nucleic acid. Primer extension products are formed by polymerization of deoxynucleoside triphosphates by a polymerase. PCR then involves repetitive cycles of template nucleic acid denaturation, primer annealing and extension of the annealed primers by the action of a thermostable polymerase. The process results in exponential amplification of the target *Anaplasma platys* nucleic acids in the test sample, which allows for the detection of target polynucleotides existing in very low concentrations in a sample.

Real-time PCR assays are based on the detection of a signal, e.g., a fluorescent reporter signal. This signal increases in direct proportion to the amount of PCR product in a reaction. Real-time PCR is any amplification technique that makes it possible to monitor the evolution of an ongoing amplification reaction. See, Quantitation of DNA/RNA Using Real-Time PCR Detection, Perkin Elmer Applied Biosystems (1999); PCR Protocols (Academic Press New York, 1989). By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

Described herein are methods for detecting and/or quantifying *Anaplasma platys* polynucleotides in a test sample. Sense primers and antisense primers can be added to a test sample under conditions suitable for a polymerase chain reaction. The primers hybridize with *Anaplasma platys* P44 or OMP-1X polynucleotides such that an amplification product is formed if *Anaplasma platys* P44 or OMP-1X polynucleotides are present in the test sample. In one aspect, the primers can be SEQ ID NOs: 90 and 91. Amplification products are detected and the presence and/or quantity of *Anaplasma platys* P44 or OMP-1X polynucleotides is determined. Amplification products can be detected with a polynucleotide probe that hybridizes, under conditions suitable for a polymerase chain reaction, with an *Anaplasma platys* P44 or OMP-1X polynucleotide sequence. Examples of probes include SEQ ID NOs: 17 which can be used to identify the presence of an OMP-1X polynucleotide. The amplification product can be quantified by measuring a detection signal from the probe and comparing said detection signal to a second probe detection signal from a quantification standard. The quantification standard can be extracted in parallel with the test sample.

Also disclosed are methods wherein the PCR primers can be selected from the variable regions of an *Anaplasma platys* P44 or OMP-1X polynucleotide. For example, primers of 10, 15, 20, 25, 30, or 40 contiguous nucleotides can be selected from the regions of P44 Boxes 1-6 or OMP-1X Boxes 1 or 2.

The polynucleotides described herein can be used to detect the presence of *Anaplasma platys* polynucleotides in a sample. The polynucleotides can be used to detect *Anaplasma platys* polynucleotides in a sample by a simple hybridization reaction and can also be used in, e.g., polymerase chain reactions (PCR) such as a real-time PCR reaction. The methods and compositions described herein can also be used to differentially detect the presence *Anaplasma platys* from *Anaplasma phagocytophilum* or other *Anaplasma* species.

Antibody Based Diagnostics

Also described herein are methods for detecting *Anaplasma platys* in a sample by contacting the sample with one or more of the antibodies described herein. In one aspect, to the *Anaplasma platys* in a sample of a bodily fluid from a patient. The method comprises providing an isolated outer membrane protein of *Anaplasma platys*, for example, a recombinant form of the isolated protein, contacting the outer membrane protein or polypeptide with a sample taken from the patient; and assaying for the formation of a complex between the outer membrane protein or polypeptide and antibodies in the sample. In one aspect, the isolated protein or polypeptide be attached to a substrate such as a column, plastic dish, matrix, or membrane, preferably nitrocellulose. The sample can be a tissue or a biological fluid, including urine, whole blood, exudate, or serum. The sample can be untreated, subjected to precipitation, fractionation, separation, or purification before combining with the isolated protein or peptide. Interactions between antibodies in the sample and the isolated protein or peptide can be detected by radiometric, colorimetric, or fluorometric means, size-separation, or precipitation. In one aspect, detection of the antibody-outer membrane protein complex can be by addition of a secondary antibody that can be coupled to a detectable tag, such as for example, an enzyme, fluorophore, or chromophore. Formation of the complex is indicative of the presence of anti-*Anaplasma platys* antibodies, either IgM or IgG, in the patient. Thus, the method can be used to determine whether a subject is infected with *Anaplasma platys*.

In one aspect, the method can employ an enzyme-linked immunosorbent assay (ELISA) or a Western immunoblot procedure. Such methods can be relatively simple to perform and do not require special equipment as long as membrane strips are coated with a high quality antigen. Accordingly, in one aspect, it can be advantageous to use a recombinant form of the outer membrane protein of *Anaplasma platys* since such proteins, typically, are more pure and consistent in quality than a purified form of such protein.

Peptide Based Diagnostics

Described herein are methods of detecting antibodies that specifically bind an *Anaplasma platys* polypeptide, comprising: (a) contacting a purified polypeptide comprising the amino acid sequence of one or more of the following: (i) P44 Box 1, P44 Box 2, P44 Box 3, P44 Box 4, P44 Box 5, P44 Box 6, or a fragment thereof; (ii) a variant of P44 Box 1, P44, Box 2, P44 Box 3, P44 Box 4, P44 Box 5, P44 Box 6, or a fragment thereof; (iii) an antigenic fragment of P44 Box 1, P44 Box 2, P44 Box 3, P44 Box 4, P44 Box 5, P44 Box 6, or a fragment thereof; (iv) SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, or a fragment thereof; (v) a variant of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, or a fragment thereof; (vi) an antigenic fragment of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, or SEQ ID NO: 45; (vii) SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, or a fragment thereof; (viii) a variant of SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, or a fragment thereof; (ix) an antigenic fragment of SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, or SEQ ID NO: 97; (x) the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xi) a variant of the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xii) an antigenic fragment of the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xii) a combination of one or more of the sequences in (i)-(xii); (xiv) OMP-1X Box 1, OMP-1X Box 2, or a fragment thereof; (xv) a variant of OMP-1X Box 1, OMP-1X Box 2, or a fragment thereof; (xvi) an antigenic fragment of OMP-1X Box 1, OMP-1X Box 2, or a fragment thereof; (xvii) SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, or a fragment thereof; (xviii) a variant of SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, or a fragment thereof; (xix) an antigenic fragment of SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, or SEQ ID NO: 9; (xx) SEQ ID NO: 2, SEQ ID NO: 6, SEQ ID NO: 3, SEQ ID NO: 7, SEQ ID NO: 4, SEQ ID NO: 8, or a fragment thereof; (xxi) a variant of SEQ ID NO: 2, SEQ ID NO: 6, SEQ ID NO: 3, SEQ ID NO: 7, SEQ ID NO: 4, SEQ ID NO: 8, or a fragment thereof; (xxii) an antigenic fragment of SEQ ID NO: 2, SEQ ID NO: 6, SEQ ID NO: 3, SEQ ID NO: 7, SEQ ID NO: 4, or SEQ ID NO: 8; (xxiii) the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; (xxiv) a variant of the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; (xxv) an antigenic fragment of the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; or (xxvi) a combination of one or more of the sequences in (xiv)-(xxv); with a test sample, under conditions that allow polypeptide/antibody complex to form; (b) detecting polypeptide/antibody complexes; wherein the detection of polypeptide/antibody complexes is an indication that antibodies specific for an *Anaplasma platys* polypeptide is present in the test sample. For example, and not to be limiting, the test sample can be a biological sample from a subject, and the detection of polypeptide/antibody complexes can be an indication that the subject has an *Anaplasma platys* infection or has been exposed to *Anaplasma platys*.

In one aspect, the methods of detecting antibodies that specifically bind an *Anaplasma platys* polypeptide described herein can further comprise determining the amount of antibody in the test sample. In yet a further aspect, the purified polypeptide can be attached to a substrate. In still a further aspect, the purified protein can be a fusion protein. For example, and not to be limiting, the purified polypeptide can be fused to an indicator reagent, an amino acid spacer, an amino acid linker, a signal sequence, a stop transfer sequence, a transmembrane domain, a protein purification ligand, a heterologous protein, or a combination thereof. In a further aspect, the purified polypeptide can be in multimeric form.

In yet a further aspect, the methods of detecting antibodies that specifically bind an *Anaplasma platys* polypeptide described herein can further comprise a microtiter plate assay, reversible flow chromatographic binding assay, an enzyme linked immunosorbent assay, a radioimmunoassay, a hemagglutination assay, a western blot assay, a fluorescence polarization immunoassay, or an indirect immunofluorescence assay.

Also described herein are methods of detecting an *Anaplasma platys* infection or exposure to *Anaplasma platys* in a subject comprising: (a) obtaining a biological sample from the subject; (b) contacting a purified polypeptide comprising the amino acid sequence of one or more of the following: (i) P44 Box 1, P44 Box 2, P44 Box 3, P44 Box 4, P44 Box 5, P44 Box 6, or a fragment thereof (ii) a variant of P44 Box 1, P44, Box 2, P44 Box 3, P44 Box 4, P44 Box 5, P44 Box 6, or a fragment thereof (iii) an antigenic fragment of P44 Box 1, P44 Box 2, P44 Box 3, P44 Box 4, P44 Box 5, P44 Box 6, or a fragment thereof (iv) SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, or a fragment thereof (v) a variant of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, or a fragment thereof (vi) an antigenic fragment of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, or SEQ ID NO: 45; (vii) SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, or a fragment thereof; (viii) a variant of SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, or a fragment thereof; (ix) an antigenic fragment of SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, or SEQ ID NO: 97; (x) the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xi) a variant of the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xii) an antigenic fragment of the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xiii) a combination of one or more of the sequences in (i)-(xii); (xiv) OMP-1X Box 1, OMP-1X Box 2, or a fragment thereof; (xv) a variant of OMP-1X Box 1, OMP-1X Box 2, or a fragment thereof; ((xvi) an antigenic fragment of OMP-1X Box 1, OMP-1X Box 2, or a fragment thereof; (xvii) SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, or a fragment thereof; (xviii) a variant of SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, or a fragment thereof; (xix) an antigenic fragment of SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, or SEQ ID NO: 9; (xx) SEQ ID NO: 2, SEQ ID NO: 6, SEQ ID NO: 3, SEQ ID NO: 7, SEQ ID NO: 4, SEQ ID NO: 8, or a fragment thereof; (xxi) a variant of SEQ ID NO: 2, SEQ ID NO: 6, SEQ ID NO: 3, SEQ ID NO: 7, SEQ ID NO: 4, SEQ ID NO: 8, or a fragment thereof; (xxii) an antigenic fragment of SEQ ID NO: 2, SEQ ID NO: 6, SEQ ID NO: 3, SEQ ID NO: 7, SEQ ID NO: 4, or SEQ ID NO: 8; (xxiii) the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; (xxiv) a variant of the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; (xxv) an antigenic fragment of the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; or (xxvi) a combination of one or more of the sequences in (xiv)-(xxv); with the biological sample under conditions that allow polypeptide/antibody complexes to form; and (c) detecting polypeptide/antibody complexes; wherein the detection of polypeptide/antibody complexes is an indication that the subject has an *Anaplasma platys* infection or exposure to *Anaplasma platys*. In one aspect, the methods of detecting an *Anaplasma platys* infection or exposure to *Anaplasma platys* in a subject can further comprise contacting the polypeptide/antibody complexes of step (b) with an indicator reagent that generates a measurable signal prior to the performance of step (c).

In a further aspect, the purified protein can be a fusion protein. For example, and not to be limiting, the purified polypeptide can be fused to an indicator reagent, an amino acid spacer, an amino acid linker, a signal sequence, a stop transfer sequence, a transmembrane domain, a protein purification ligand, a heterologous protein, or a combination thereof. In yet a further aspect, the polypeptide/antibody complexes can be detected at about 10 days after exposure or infection of the subject by *Anaplasma platys*.

Further described herein are methods of detecting *Anaplasma platys* polypeptides in a test sample comprising: (a) contacting one or more antibodies that specifically bind to a *Anaplasma platys* polypeptide with the test sample under conditions that allow polypeptide/antibody complexes to form; wherein the *Anaplasma platys* polypeptide comprises the amino acid sequence of one or more of the following: (i) P44 Box 1, P44 Box 2, P44 Box 3, P44 Box 4, P44 Box 5, P44 Box 6, or a fragment thereof, (ii) a variant of P44 Box 1, P44, Box 2, P44 Box 3, P44 Box 4, P44 Box 5, P44 Box 6, or a fragment thereof, (iii) an antigenic fragment of P44 Box 1, P44 Box 2, P44 Box 3, P44 Box 4, P44 Box 5, P44 Box 6, or a fragment thereof, (iv) SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, or a fragment thereof, (v) a variant of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, SEQ ID NO: 45, or a fragment thereof, (vi) an antigenic fragment of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 39, SEQ ID NO: 40, SEQ ID NO: 41, SEQ ID NO: 42, SEQ ID NO: 43, SEQ ID NO: 44, or SEQ ID NO: 45; (vii) SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, or a fragment thereof; (viii) a variant of SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, SEQ ID NO: 97, or a fragment thereof; (ix) an antigenic fragment of SEQ ID NO: 39, SEQ ID NO: 42, SEQ ID NO: 40, SEQ ID NO: 93, SEQ ID NO: 41, SEQ ID NO: 94, SEQ ID NO: 42, SEQ ID NO: 95, SEQ ID NO: 43, SEQ ID NO: 96, SEQ ID NO: 44, or SEQ ID NO: 97; (x) the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xi) a variant of the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xii) an antigenic fragment of the amino acid sequence comprising the amino acid from about position 20 to about position 40 of FIG. 23, the amino acid sequence comprising the amino acid from about position 40 to about position 64 of FIG. 23, the amino acid from about position 75 to about position 85 of FIG. 23, the amino acid sequence comprising the amino acid from about position 102 to about position 111 of FIG. 23, the amino acid from about position 170 to about position 190 of FIG. 23, the amino acid sequence comprising the amino acid from about position 178 to about position 222 of FIG. 23, the amino acid from about position 205 to about position 215 of FIG. 23, the amino acid sequence comprising the amino acid from about position 259 to about position 266 of FIG. 23, the amino acid from about position 270 to about position 290 of FIG. 23, the amino acid sequence comprising the amino acid from about position 319 to about position 340 of FIG. 23, the amino acid from about position 365 to about position 380 of FIG. 23, the amino acid sequence comprising the amino acid from about position 451 to about position 460 of FIG. 23, the amino acid from about position 1 to about position 41 of FIG. 19, the amino acid sequence comprising the amino acid from about position 78 to about position 85 of FIG. 19, the amino acid from about position 174 to about position 192 of FIG. 19, the amino acid sequence comprising the amino acid from about position 227 to about position 234 of FIG. 19 the amino acid from about position 276 to about position 294 of FIG. 19, the amino acid sequence comprising the amino acid from about position 416 to about position 433 of FIG. 19, or a fragment thereof; (xiii) a combination of one or more of the sequences in (i)-(xii); (xiv) OMP-1X Box 1, OMP-1X Box 2, or a fragment thereof; (xv) a variant of OMP-1X Box 1, OMP-1X Box 2, or a fragment thereof; ((xvi) an antigenic fragment of OMP-1X Box 1, OMP-1X Box 2, or a fragment thereof; (xvii) SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, or a fragment thereof; (xviii) a variant of SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, SEQ ID NO: 9, or a fragment thereof; (xix) an antigenic fragment of SEQ ID NO: 1, SEQ ID NO: 5, SEQ ID NO: 10, SEQ ID NO: 2, SEQ ID NO: 6, SEQ ID NO: 3, SEQ ID NO: 7, SEQ ID NO: 4, SEQ ID NO: 8, or SEQ ID NO: 9; (xx) SEQ ID NO: 2, SEQ ID NO: 6, SEQ ID NO: 3, SEQ ID NO: 7, SEQ ID NO: 4, SEQ ID NO: 8, or a fragment thereof; (xxi) a variant of SEQ ID NO: 2, SEQ ID NO: 6, SEQ ID NO: 3, SEQ ID NO: 7, SEQ ID NO: 4, SEQ ID NO: 8, or a fragment thereof; (xxii) an antigenic fragment of SEQ ID NO: 2, SEQ ID NO: 6, SEQ ID NO: 3, SEQ ID NO: 7, SEQ ID NO: 4, or SEQ ID NO: 8; (xxiii) the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; (xxiv) a variant of the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; (xxv) an antigenic fragment of the amino acid from about position 66 to about position 192 of FIG. 22, the amino acid from about position 70 to about position 180 of FIG. 22, a combination of the amino acid from about position 66 to about position 192 and the amino acid from about position 70 to about position 180 of FIG. 22, the amino acid from about position 240 to about position 312 of FIG. 22, the amino acid from about position 230 to about position 300 of FIG. 22, a combination of the amino acid from about position 240 to about position 312 and the amino acid from about position 230 to about position 300 of FIG. 22, or a fragment thereof; or (xxvi) a combination of one or more of the sequences in (xiv)-(xxv); (b) detecting polypeptide/antibody complexes; wherein the detection of polypeptide/antibody complexes is an indication that an *Anaplasma platys* polypeptide is present in the test sample. For example, and not to be limiting, the one or more antibodies can be monoclonal antibodies, polyclonal antibodies, Fab fragments, Fab' fragments, Fab'-SH fragments, F(ab')2 fragments, Fv fragments, or single chain antibodies. In one aspect, the complexes of step (a) can be contacted with an indicator reagent prior to the performance of step (b).

In one aspect, the methods of detecting *Anaplasma platys* polypeptides in a test sample can further comprise determining the amount of *Anaplasma platys* polypeptides in the test sample. In yet a further aspect, the one or more antibodies can be attached to a substrate.

In a further aspect, the methods of detecting *Anaplasma platys* polypeptides in a test sample can further comprise a microtiter plate assay, reversible flow chromatographic binding assay, an enzyme linked immunosorbent assay, a radioimmunoassay, a hemagglutination assay, a western blot assay, a fluorescence polarization immunoassay, or an indirect immunofluorescence assay.

The methods described herein can be used to detect antibodies or antibody fragments specific for *Anaplasma platys* polypeptides, *Anaplasma platys* polynucleotides, or a combination thereof in a test sample, such as a biological sample, an environmental sample, or a laboratory sample. A test sample can potentially comprise *Anaplasma platys* polynucleotides, *Anaplasma platys* polypeptides, or antibodies specific for *Anaplasma platys*. A biological sample can include, for example, sera, blood, cells, plasma, or tissue from a mammal such as a horse, cat, dog or human. The test sample can be untreated, precipitated, fractionated, separated, diluted, concentrated, or purified.

Disclosed herein are methods that comprise contacting an *Anaplasma platys* polypeptide with a test sample under conditions that allow a polypeptide/antibody complex, i.e., an immunocomplex, to form. That is, one or more of the polypeptides described herein specifically binds to an antibody specific for *Anaplasma platys* antigens located in the sample. One of skill in the art is familiar with assays and conditions that are used to detect antibody/polypeptide complex binding. The formation of a complex between polypeptides and anti-*Anaplasma platys* in the sample is detected. In one embodiment of the invention antibody-polypeptide complexes can be detected at about 10, 15, 20, 25, 30 or less days after exposure or infection of the subject by *Anaplasma platys*.

The antibodies described herein can be used in a method of the diagnosis of *Anaplasma platys* infection by obtaining a test sample from, e.g., a human or animal suspected of having an *Anaplasma platys* infection. Exposure to *Anaplasma platys* can also be detected. Exposure would include the presence of *Anaplasma platys* organisms without clinical symptoms and prior infection with *Anaplasma platys*. The test sample is contacted with antibodies of the invention under conditions enabling the formation of antibody-antigen complexes (i.e., immunocomplexes). The amount of antibody-antigen complexes can be determined by methodology known in the art. A level that is higher than that formed in a control sample indicates an *Anaplasma platys* infection. A control sample is a sample that does not comprise any *Anaplasma platys* polypeptides or antibodies specific for *Anaplasma platys*. In one embodiment of the invention an antibody is specific for *Anaplasma platys* P44 or *Anaplasma platys* OMP-1X antigens only. Alternatively, a polypeptide of the invention can be contacted with a test sample. *Anaplasma platys* antibodies in a positive body sample will form an antigen-antibody complex under suitable conditions. The amount of antibody-antigen complexes can be determined by methods known in the art.

Also disclosed herein are methods wherein the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

Disclosed herein are methods wherein one or more of the antibodies disclosed herein are attached to a solid phase or substrate. A test sample potentially comprising a protein comprising one or more of the polypeptides described herein is added to the substrate. Antibodies that specifically bind to one or more of the polypeptides described herein are added. The antibodies can be the same antibodies used on the solid phase or can be from a different source or species and can be linked to an indicator reagent, such as an enzyme conjugate. Wash steps can be performed prior to each addition. A chromophore or enzyme substrate can be added and color is allowed to develop. The color reaction can be stopped and the color can be quantified using, for example, a spectrophotometer.

Also disclosed herein are methods wherein one or more of the antibodies described herein are attached to a solid phase or substrate. A test sample potentially comprising a protein comprising one or more of the polypeptides described herein is added to the substrate. Second anti-species antibodies that specifically bind one or more of the polypeptides described herein are added. These second antibodies can be from a different species than the solid phase antibodies. Third anti-species antibodies can also be added that specifically bind the second antibodies and that do not specifically bind the solid phase antibodies are added. The third antibodies can comprise an indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

Disclosed herein are methods of detecting antibodies that specifically bind an *Anaplasma platys* polypeptide or both. The method comprises contacting one or more of the purified polypeptides described herein with a test sample, under conditions that allow polypeptide/antibody complexes to form and detecting polypeptide/antibody complexes. The detection of polypeptide/antibody complexes is an indication that antibodies specific for *Anaplasma platys* are present in the test sample, and the absence of polypeptide/antibody complexes is an indication that antibodies specific for *Anaplasma platys* are not present in the test sample. The complexes can be contacted with an indicator reagent prior to the detection step. The amount of antibody in the test sample can be determined. The purified polypeptide can be attached to a substrate. The purified polypeptide can be a fusion protein wherein the purified polypeptide is fused to an indicator reagent, an amino acid spacer, an amino acid linker, a signal sequence, a stop transfer sequence, a transmembrane domain, a protein purification ligand, a heterologous protein, or a combination thereof. The purified polypeptide can be in multimeric form. The method can comprise a microtiter plate assay, reversible flow chromatographic binding assay, an enzyme linked immunosorbent assay, a radioimmunoassay, a hemagglutination assay a western blot assay, a fluorescence polarization immunoassay, or an indirect immunofluorescence assay.

Disclosed herein are methods of detecting an *Anaplasma platys* infection and/or exposure to *Anaplasma platys* in a subject. The method can comprise obtaining a biological sample from the subject; contacting a purified polypeptide of the invention with the biological sample under conditions that allow polypeptide/antibody complexes to form; and detecting polypeptide/antibody complexes. The detection of polypeptide/antibody complexes is an indication that the subject has an *Anaplasma platys* infection and/or exposure to *Anaplasma platys*. The absence of polypeptide/antibody complexes is an indication that the mammal has not had an *Anaplasma platys* infection and/or exposure to *Anaplasma*

*platys*. The polypeptide/antibody complexes can be contacted with an indicator reagent that generates a measurable signal prior to the performance of the detection step. The purified polypeptide can be a fusion protein wherein the purified polypeptide is fused to an indicator reagent, an amino acid spacer, an amino acid linker, a signal sequence, a stop transfer sequence, a transmembrane domain, a protein purification ligand, a heterologous protein or a combination thereof. The polypeptide/antibody complexes can detected at about 10 days after exposure or infection of subject by *Anaplasma platys*.

Also described herein are assays that include, but are not limited to those based on competition, direct reaction or sandwich-type assays, including, but not limited to enzyme linked immunosorbent assay (ELISA), western blot, IFA, radioimmunoassay (RIA), hemagglutination (HA), fluorescence polarization immunoassay (FPIA), and microtiter plate assays (any assay done in one or more wells of a microtiter plate). One assay comprises a reversible flow chromatographic binding assay. For example, described herein are assays similar to those described in U.S. Pat. No. 5,726,010.

Assays can use solid phases or substrates or can be performed by immunoprecipitation or any other methods that do not utilize solid phases. Where a solid phase or substrate is used, one or more of the polypeptides described herein can be directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). For example, the substrate can be sintered, fine particles of polyethylene, commonly known as porous polyethylene, for example, 10-15 micron porous polyethylene from Chromex Corporation (Albuquerque, N. Mex.). All substrate materials can be used in suitable shapes, such as films, sheets, or plates, or they can be coated onto or bonded or laminated to appropriate inert carriers, such as paper, glass, plastic films, or fabrics. Suitable methods for immobilizing peptides on solid phases include ionic, hydrophobic, covalent interactions and the like.

Disclosed herein is an assay format, wherein one or more polypeptides can be coated on a solid phase or substrate. A test sample suspected of containing an anti-*Anaplasma platys* antibody or fragment thereof is incubated with an indicator reagent comprising a signal generating compound conjugated to an antibody or antibody fragment specific for *Anaplasma platys* for a time and under conditions sufficient to form antigen/antibody complexes of either antibodies of the test sample to the polypeptides of the solid phase or the indicator reagent compound conjugated to an antibody specific for *Anaplasma platys* to the polypeptides of the solid phase. The reduction in binding of the indicator reagent conjugated to an anti-*Anaplasma platys* antibody to the solid phase can be quantitatively measured. A measurable reduction in the signal compared to the signal generated from a confirmed negative *Anaplasma platys* test sample indicates the presence of anti-*Anaplasma platys* antibody in the test sample. This type of assay can quantitate the amount of anti-*Anaplasma platys* antibodies in a test sample.

Disclosed herein is an assay format, wherein one or more of the polypeptides disclosed herein are coated onto a support or substrate. One or more of the polypeptides disclosed herein can be conjugated to an indicator reagent and added to a test sample. This mixture can then be applied to the support or substrate. If *Anaplasma platys* antibodies are present in the test sample they will bind the polypeptide conjugated to an indicator reagent and to the polypeptide immobilized on the support. The polypeptide/antibody/indicator complex can then be detected. This type of assay can quantitate the amount of anti-*Anaplasma platys* antibodies in a test sample.

Disclosed herein is an assay format, wherein one or more polypeptides disclosed herein are coated onto a support or substrate. The test sample can be applied to the support or substrate and incubated. Unbound components from the sample can be washed away by washing the solid support with a wash solution. If *Anaplasma platys* specific antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-*Anaplasma platys* antibodies in a test sample.

The formation of a polypeptide/antibody complex or a polypeptide/antibody/indicator complex can be detected by radiometric, colorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Disclosed herein is an assay format wherein the *Anaplasma platys* polypeptides, polynucleotides, antibodies or combinations thereof can be used in conjunction with Raman spectroscopy. Raman spectroscopy is an analytical technique for chemical and biological analysis due to the wealth of information on molecular structures, surface processes, and interface reactions that can be extracted from experimental data. The Raman technique has been used with gene probe biosensors. U.S. Pat. No. 5,814,516 ('516 patent) discloses a gene probe biosensor comprising a support means, a SERS gene probe having at least one oligonucleotide strand having at least one SERS label, and a SERS active substrate disposed on the support means. The support means has at least one SERS gene probe adsorbed thereon. Biotargets such as bacterial and viral DNA, RNA and PNA are detected using a SERS gene probe via hybridization to oligonucleotide strands complementary to the SERS gene probe. U.S. Pat. No. 5,814,516 is hereby incorporated by reference in its entirety for it's teaching of the Raman technique.

The '516 patent does not disclose or suggest operatively connecting a Raman gene probe with an integrated circuit detection system to produce a biochip capable of SERS detection. U.S. Pat. No. 7,267,948 ('948 patent) provides another assay format wherein the *Anaplasma platys* polypeptides, polynucleotides, antibodies or combinations thereof can be used. This '948 patent describes Raman and SERS assay methods and systems including microarrays, biosensors and biochips for the detection of biotargets such as DNA, proteins and pathogens using receptor probes. Receptor probes may include one or more bioreceptors selected from antibodies, DNA, enzymes, tissues, organelles, as well as other receptor probes, and combinations thereof described herein. U.S. Pat. No. 7,267,948 is hereby incorporated by reference in its entirety for it's teaching of the Raman and SERS assay methods and systems.

Formation of the complex is indicative of the presence of anti-*Anaplasma platys* antibodies in a test sample. Therefore, the methods of the invention can be used to diagnose *Anaplasma platys* infection or exposure in a patient.

The methods described herein can also indicate the amount or quantity of anti-*Anaplasma platys* antibodies in a test sample. With many indicator reagents, such as enzyme conjugates, the amount of antibody present is proportional to the signal generated. Depending upon the type of test sample, it can be diluted with a suitable buffer reagent, concentrated, or contacted with a solid phase without any manipulation. For example, serum or plasma samples that previously have been diluted, or concentrate specimens such as urine, can be tested in order to determine the presence and/or amount of antibody present.

The polypeptides and assays described herein can be combined with other polypeptides or assays to detect the presence of *Anaplasma platys* along with other organisms. For example, polypeptides and assays of the invention can be combined with reagents that detect heartworm and/or *Borrelia burgdorferi* and/or *Anaplasma phagocytophilium* and/or *Ehrlichia canis*.

Also disclosed herein are methods of detecting an *Anaplasma* infection or exposure to *Anaplasma* in a subject. These methods can be used as an initial or final method to identify the presence of one or more species of *Anaplasma*. *Anaplasma* is a genus of rickettsiales bacteria. Anaplasmas can reside in host red blood cells and lead to the disease anaplasmosis.

Anaplasmas can require intermediate tick hosts for maturation, and flies may act as mechanical vectors. Species of *Anaplasma* include, but are not limited to, *Anaplasma marginate, Anaplasma centrale, Anaplasma mesaeterum, Anaplasma ovis*, and *Anaplasma platys*.

Disclosed herein are methods of detecting an *Anaplasma* infection or exposure to *Anaplasma* in a subject comprising: (a) obtaining a biological sample from the subject; (b) contacting a purified polypeptide encoded by one or more of the nucleotides of the following: SEQ ID NOs: 124-132 or a combination of one or more of the sequences of SEQ ID NOs: 124-132; with the biological sample under conditions that allow polypeptide complexes to form; and (c) detecting polypeptide complexes; wherein the detection of polypeptide complexes is an indication that the subject has an *Anaplasma* infection or exposure to *Anaplasma*. In addition, the methods can further comprise contacting the polypeptide complexes with an antibody that recognizes the polypeptide or polypeptide complex.

Also disclosed are methods of detecting the presence of *Anaplasma* in a sample by contacting said sample with a DNA probe or primer constructed to correspond to an *Anaplasma* P44 nucleotide sequence, characterized in that the probe or primer comprises one or more of the nucleotides of SEQ ID NOs: 124-132.

Also disclosed are methods of detecting the presence of *Anaplasma* in a sample by contacting said sample with a DNA probe or primer constructed to correspond to an *Anaplasma* P44 nucleotide sequence, characterized in that the probe or primer comprises one or more nucleotides capable of hybridizing to one or more of the nucleotides of SEQ ID NOs: 124-132.

A method for detecting *Anaplasma* in a sample obtained from a subject, comprising (a) providing a primer set comprising: (i) one or more forward primers capable of hybridizing to or amplifying: one or more of the nucleotides of SEQ ID NOs: 124-132 and (ii) one or more forward primers capable of hybridizing to or amplifying: one or more of the nucleotides of SEQ ID NOs: 124-132; (b) amplifying DNA in the sample with the said primer set and a polymerase chain reaction, and (c) determining the length or sequence of the PCR products of step (b), wherein the presence of a PCR product having a length or sequence which corresponds to the length or sequence, respectively, of that region of the *Anaplasma* nucleotide sequence which is located between the regions to which the one or more forward primers and the one or more reverse primers bind is indicative of the presence of *Anaplasma* in the sample.

Also disclosed herein are isolated or purified polynucleotides comprising the sequence of one or more of the polynucleotide sequences of SEQ ID NOs: 124-132, or a fragment thereof. Also disclosed herein are isolated or purified polynucleotides comprising 80%, 85%, 90%, 95%, or 100% sequence identity to the sequence of one or more of the polynucleotide sequences of SEQ ID NOs: 124-132, or a fragment thereof.

Also disclosed are vectors for transformation of a host cell, said vector comprising the sequence of one or more of the polynucleotide sequences of SEQ ID NOs: 124-132, or a fragment thereof.

Also disclosed herein are isolated or purified polypeptides encoded by a polynucleotide sequences wherein the polynucleotide sequence comprises the sequence of one or more of the polynucleotide sequences of SEQ ID NOs: 124-132, or a fragment thereof. Also disclosed herein are isolated or purified polypeptides encoded by a polynucleotide sequences wherein the polynucleotide sequence comprises 80%, 85%, 90%, 95%, or 100% sequence identity to the sequence of one or more of the polynucleotide sequences of SEQ ID NOs: 124-132, or a fragment thereof.

EXAMPLES

Example 1

Materials and Methods

*A. platys*-Infected Dogs.

Dogs that were naturally infected with *A. platys* were identified in Lara, Venezuela, in 2007 by observation of bacterial inclusions (morulae) in platelets from blood smears, and cases were confirmed by PCR and sequencing using primer pairs specific for *A. platys* 16S rRNA (EP1-EP3 and EP2-EP3).[29] Naturally infected dogs in Taichung, Taiwan and the Democratic Republic of Congo were identified and confirmed by PCR using primer pair EPLATS-EPLAT.[42]

Cloning of p44 Expression Locus from *A. platys*.

DNA samples from three dogs from Venezuela and one dog from Taiwan were used as templates. By aligning the p44/msp2 expression loci from *A. phagocytophilum* and *A. marginate*, several degenerate primers were designed for conserved regions of the locus (FIG. 1, Table 1). Using the first and the second primer pairs F1-R1 and F1-R2, (hemi-) nested touchdown PCR[52] was used to amplify the tr1 and omp-1X gene sequences from *A. platys*. In order to avoid truncating p44 pseudogenes in the *A. platys* genome, primer F3 was designed to be upstream of the predicted p44 open reading frame. p44ES sequences were amplified by nested touchdown PCR using primer pairs F2-R3 and F3-R4. Amplification was performed as previously described.[68] The amplified DNA fragments were cloned using the TA cloning kit (Invitrogen, Carlsbad, Calif.) and sequenced with M13 forward or M13 reverse sequencing primers. All sequencing data were assembled using the SeqMan program (DNASTAR Inc., Madison, Wis.). To confirm the assembly the entire locus was amplified using primers F1 and R5 (Table 1).

Phylogenetic Analysis.

The deduced amino acid sequences for Tr1, OMP-1/OMP-1X, and P44ES from *A. marginate, A. phagocytophilum*, and *A. platys* were aligned using the MegAlign program (DNASTAR Inc.) by the Clustal W method.

Protein Structure Analysis Using Bioinformatics Tools.

SignalP 3.0 server trained on Gram-negative bacteria (http://www.cbs.dtu.dk/services/SignalP/) was used for signal peptide sequence analysis. The secondary structures of P44 and OMP-1X were predicted by PRED-TMBB[4] and hydrophobicity analysis and the hydrophobic moment profile method, as previously described.[30, 35] The antigenic index and surface probability were determined using the Protean program (DNASTAR Inc.).

ELISA Analysis of OMP-1X-Specific Peptide.

The OMP-1X peptide from *A. platys* was synthesized at Biomatik (Wilmington, Del.). The purity of the peptide was greater than 98%, as assessed by high-performance liquid chromatography. The wells of a 96-well microtiter plate were coated with 200 ng peptide/well and the ELISA was performed as previously described.[60] Samples were from three dogs that were PCR-positive for *A. platys* (TW 431, TW 270, and TW 210), and three dogs that were both PCR-negative for *A. platys* and antigen dot blot—negative for *A. phagocytophilum* (E05-290, E10-0062, and E10-0075). In addition, horse anti-*A. phagocytophilum* positive sera (EQ002, EQ006, and E09-0011)[65, 71] were used to confirm the absence of OMP-1X peptide antigen cross-reactivity with anti-*A. phagocytophilum* antibodies. The horseradish peroxidase substrate 2,2'-azido-di-(3-ethyl)-benzthiazoline-6-sulfonic acid (Sigma, St. Louis, Mo.) in 70 mM citrate buffer (pH 4.2) applied, and absorbance values at 415 and 492 nm were measured in an ELISA plate reader (Molecular Devices, Sunnyvale, Calif.) as previously described.[68] Results were presented as optical density at 415 nm minus that at 492 nm ($OD_{415}$-$OD_{492}$), and the cutoff for a positive reaction was set at greater than the mean $OD_{415}$-$OD_{492}$+3 SD for the negative control samples (OD>0.165). The assay was repeated at least three times.

Nucleotide Sequence Accession Number.

The *A. platys* tr1-omp-1X-p44ES sequences from two naturally infected dogs from Venezuela were assembled and deposited at GenBank under accession numbers GQ868750 and GU357491. Additional p44ES and p44 sequences were deposited at GenBank under accession numbers GU357492, GU357493, GU357494, GU357495, GU357496, GU357497, and HQ738571.

Results

*A. platys* tr1-omp1-p44ES cluster sequencing and assembly. Three degenerate primers and one primer at a highly conserved region of tr1 upstream region were designed based on conserved regions of the aligned tr1-omp1X-omp1N-p44 cluster of *A. phagocytophilum* and YP_154239 (hypothetical protein AM1138; transcriptional regulator)-YP_154240 (outer membrane protein 1; outer membrane protein 4)-YP_154241 (msp2 operon associated gene 3; outer membrane protein 3)-YP_154243 (msp2 operon associated gene 2)-YP_154244 (msp2 operon associated gene 1)-YP_154245 (msp2) cluster of *A. marginate* (FIG. 1, Table 1). The first touchdown PCR was designed to amplify the entire fragment using primers F1 and R1. The PCR products from the two dog DNA specimens were then used as templates for hemi-nested touchdown PCRs using primers F1 and R2 (FIG. 1, Table 1). As a result, a single band of about 2,100 bp was amplified (fragment A). The PCR products were TA cloned and sequenced. The sequence results showed this fragment contained *A. platys* tr1 and omp-1X. The downstream region of fragment A was amplified by nested touchdown PCR, using the PCR products obtained with primers F1 and R1 as templates, with primer F2 designed based on the fragment A sequence and primer R3 designed based on p44 (msp2) sequences conserved between *A. phagocytophilum* and *A. marginate*. As a result, a single band of approximately 1,100 bp was amplified (fragment B). The PCR products were TA cloned and sequenced. The sequence results showed that this fragment contained a partial *A. platys* p44 sequence. To amplify *A. platys* full-length p44, primer F3 was designed based on fragment B sequence and primer R4 was designed based on the conserved region of valS found downstream of p44 (msp2) in both *A. phagocytophilum* and *A. marginate*. Further touchdown PCR was done using primers F1 and R4. The PCR products were then used as templates for hemi-nested touchdown PCRs using primers F3 and R4. As a result, a single band of about 1,700 bp was amplified (fragment C). The PCR products were TA cloned and sequenced. The sequence results showed this fragment contained full length *A. platys* p44 sequences. The final assembled sequences 3,957 bp from dogs 1 and 2, respectively contained the entire *A. platys* p44ES locus, and the G+C content was 47.46~47.51%.

The final assembled sequence of 3957 bp from Venezuelan dogs 1 and 2 contained the entire *A. platys* p44ES locus. The sequence average coverage of the entire locus was 8.3 fold (5 to 15 fold). To confirm the assembly was from a complete genomic locus, primer R5 was designed to be downstream of the predicted p44 open reading frame and one more touchdown PCR was conducted using primers F1 and R5. A single band, approximately 3.9 kb was amplified (fragment D), indicating the fragment containing the entire locus was amplified from the blood of dog 2 (FIG. 1C). The G+C content was determined to be 47.46% to 47.51%. The synteny among the entire outer membrane protein gene clusters of *A. platys* and the two previously sequenced *Anaplasma* species was analyzed using the Artemis Comparison Tool.[14] The tr1 sequences were conserved among the three *Anaplasma* species (FIG. 2). The 5' and 3' regions of p44ES were conserved between *A. platys* and *A. phagocytophilum*, but not between *A. platys* and *A. marginate* (FIG. 2).

*A. platys* Tr1 Structure.

Three similar (97.8% to 99.5%) *A. platys* tr1 sequences were obtained from two dogs from Venezuela and one dog from Taiwan. The predicted molecular mass of *A. platys* Tr1 was 21.0 to 21.1 kDa with an isoelectric point of 5.50 to 5.80

(Table 2). Tr1 was not predicted to have a signal peptide, thus was a cytoplasmic protein, as analyzed by SignalP 3.0. Tr1 was predicted to contain a putative N-terminal helix-turn-helix DNA-binding domain based on the analysis of the NCBI conserved domain database, suggesting that it was a transcriptional regulator. The amino acid sequence identity between *A. platys* Tr1 and *A. phagocytophilum* Tr1 (YP_505749) was 84.8% to 86.4%, and that between *A. platys* Tr1 and *A. marginate* Tr (YP_154239) was 73.1% to 74.1%.

Figure 2:
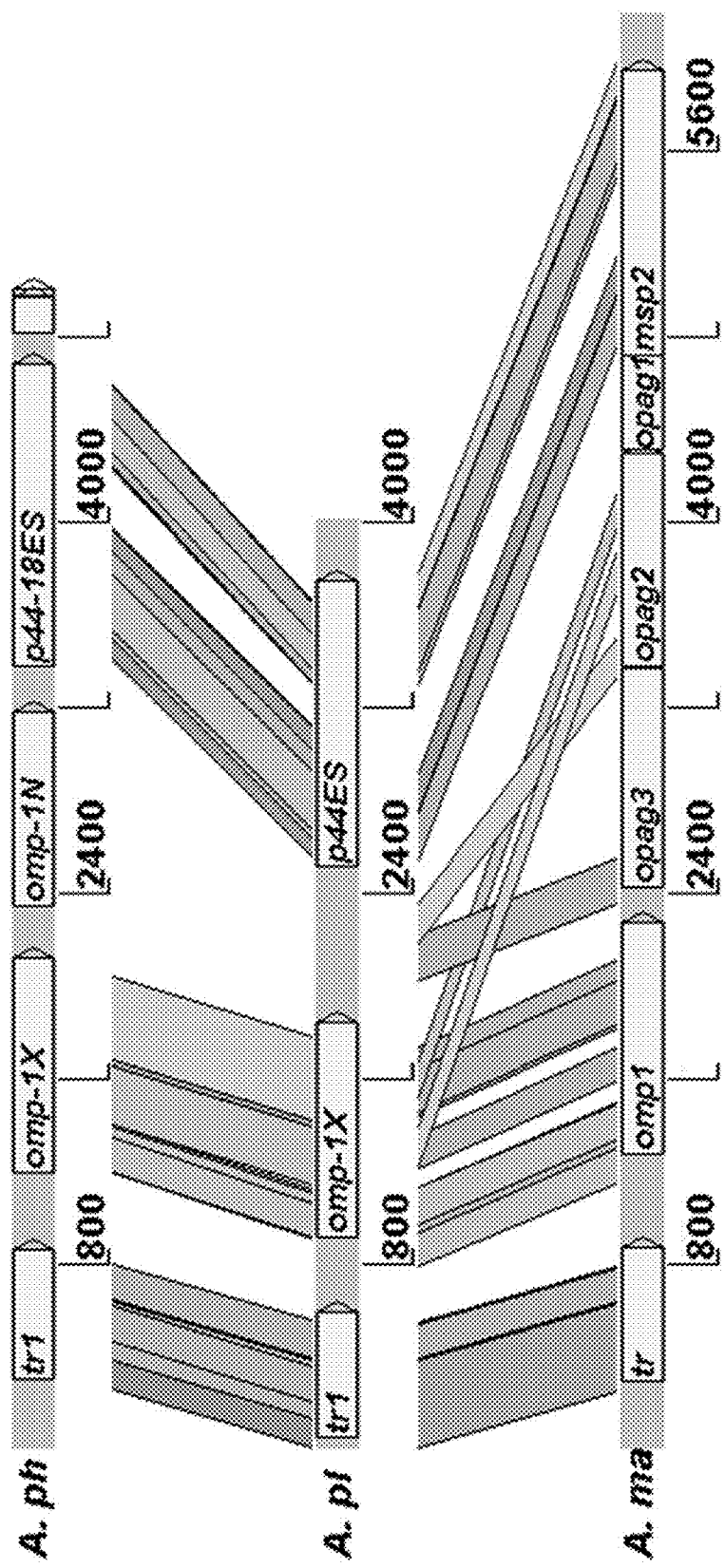
FIG. 2 depicts the synteny analysis, using the Artemis comparison tool, of the *A. platys* (*A. pl*) p44ES cluster relative to *A. phagocytophilum* (*A. ph*) and *A. marginate* (*A. ma*). Each bar corresponds to a good match. Numbers indicate bp. Score cutoffs: 140.
Figure 3:
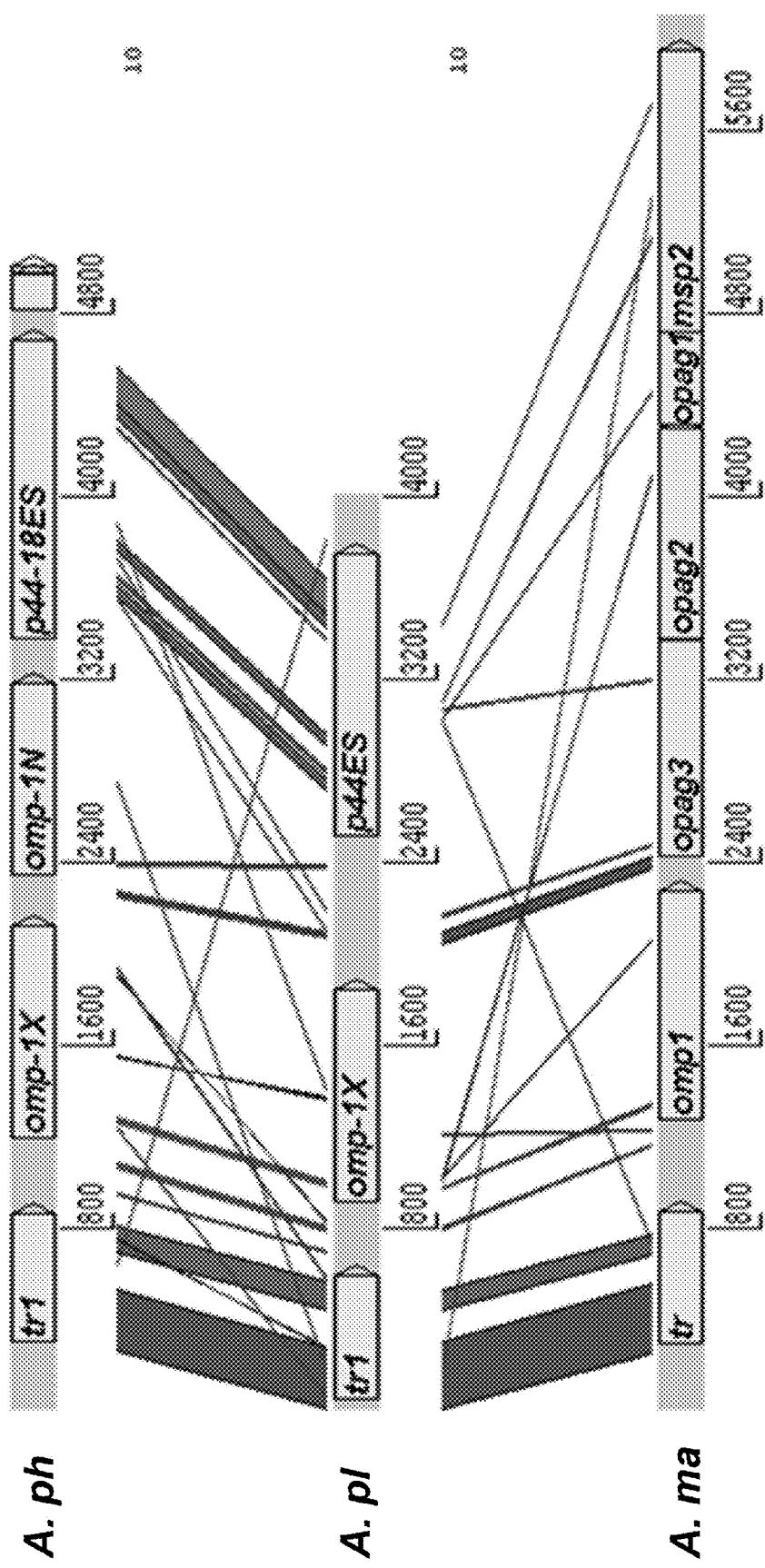
FIG. 3 depicts the synteny analysis, using the Artemis comparison tool, of the *A. platys* (*A. pl*) p44ES cluster relative to *A. phagocytophilum* (*A. ph*) and *A. marginate* (*A.* ma). Each bar corresponds to a good match. Numbers indicate bp. Score cutoffs: 140 using the Artemis Comparison Tool.

A. platys OMP-1X structure. Three nearly identical (99.1%) *A. platys* omp-1X sequences were obtained from two dogs from Venezuela and one dog from Taiwan. Using SignalP 3.0 server, OMP-1X was predicted to have a signal peptide with a cleavage site between positions 23 and 24. The predicted molecular mass of mature *A. platys* OMP-1X was 31.9 kDa with an isoelectric point of 7.27 to 7.92 (Table 2). The secondary structure of OMP-1X was then examined, using PRED-TMBB.[4] The discrimination value of the OMP-1X amino acid sequence was 2.907, which is below the threshold value of 2.965, making OMP-1X likely to be a β-barrel protein localized to the outer membrane. Hydrophobicity analysis and the hydrophobic moment profile program developed for the porin structure prediction,[35] predicted 14 β-strands in OMP-1X. The protein sequences most closely related to *A. platys* OMP-1X were *A. phagocytophilum* OMP-1X (YP_505750; 45.9%-46.3% identity) and *A. marginate* OMP-1 (YP_154240; 39.8% identity). A phylogenetic analysis showed that OMP-1X homologs in *Anaplasma* spp. formed a cluster that was distinct from the cluster of most closely related OMP-1X homologs in each *Ehrlichia* spp. (FIG. 3).

A. platys P44ES Structure.

Four P44ES sequences (GQ868750, GU357491, GU357492, and GU357493) were obtained from three dogs from Venezuela. Using SignalP 3.0 sever P44ES was predicted to have a putative signal peptide with a cleavage site between positions 21 and 22. The molecular mass of the mature P44ES protein was predicted to be 41.2 to 41.4 kDa with an isoelectric point of 5.30 to 5.72 (Table 2). By PRED-TMBB[4] analysis, the discrimination value of the P44 amino acid sequence was 2.920 which was below the threshold value of 2.965, making P44 likely to be a β-barrel protein localized to the outer membrane. Hydrophobicity analysis and the hydrophobic moment profile predicted 16 β-strands in P44. Alignment of total nine *A. platys* P44 sequences (the four P44 full-length proteins from dogs 1, 2, and 3, and the five partial P44 sequences obtained from dogs 1, 2 and Taiwan) using HVF and HVR primers, revealed a single central hypervariable region (aa position 193-247) of approximately 55 amino acid residues, and N-terminal and C-terminal conserved regions of approximately 192 and 159 amino acid residues, respectively. The conserved amino acids C, C, W, and A from the P44 hypervariable region of *A. phagocytophilum* P44[41] were also detected in the hypervariable region of *A. platys* P44. The C terminus of *A. platys* P44 ends with phenylalanine, as does the C terminus of *A. phagocytophilum* P44.[30] The amino acid sequence identity between *A. platys* P44ES and *A. phagocytophilum* P44-18ES (YP_505752) was 55.0% to 56.9%, and that between *A. platys* P44ES and *A. marginate* Msp2 (YP_154245) was 41.5% to 42.1%. Phylogenetic analysis placed full-length *A. platys* p44s between *A. phagocytophilum* p44s and *A. marginate* msp2s (FIG. 4). The sequence identities of the conserved N-terminal 192 amino acids and the conserved C-terminal 159 amino acids of *A. platys* and *A. phagocytophilum* P44s were 57.3% and 66.7%, respectively.

Primer pairs (HVF and HVR, Table 1) designed based on *A. platys* p44 conserved region amplified only *A. platys* DNA, but not *A. phagocytophilum* and *A. marginate* DNA. Alignment of a total of nine *A. platys* P44 hypervariable regions and flanking conserved regions with P44/Msp2 sequences among *A. phagocytophilum* P44s and *A. marginate* Msp2s revealed several *A. platys*-specific sequences: TGTAAGSDVDYVSKF (SEQ ID NO: 92; aa position 23-37), TRVEWKAE (SEQ ID NO: 93; aa position 78-85), AAEIVKFAEAVGTSAK (SEQ ID NO: 94; aa position 174-189), SWKCTQTG (SEQ ID NO: 95; aa position 207-214), AAKAEDLS (SEQ ID NO: 96; aa position 248-255) and ATTNKTKEF (SEQ ID NO: 97; aa position 378-386). These *A. platys*-specific p44 regions were utilized as serologic test antigens to distinguish from *A. phagocytophilum* or *A. marginate* infections.

TABLE 1

Primers used for PCR amplification of *A. platys* P44ES cluster

| Primer | Sequence | Note |
|---|---|---|
| F1 | 5'-ATTATGTATGATTTATCCTAAGTTATCTGAG-3' (SEQ ID NO: 82) | tr 1/tr highly conserved upstream region |
| F2 | 5-GGGATATCGGCGTTGATAGGG-3' (SEQ ID NO: 83) | *A. platys* omp-1X downstream genomic walking |
| F3 | 5'-GGTTTGTGTTGCTGGTGATTGGAGG-3' (SEQ ID NO: 84) | *A. platys* p44 upstream genomic walking |
| R1 | 5'-GCAAACCTAACACCMAAYTCMCCACC-3' (SEQ ID NO: 85) | p44ES/Msp2 C-terminal highly conserved region |
| R2 | 5'-TATACTAAAAAAGAATTAAGTCAAGAG-3' (SEQ ID NO: 86) | Conserved intergenetic region between omp-1X/omp1 and omp-1N/opag3 |
| R3 | 5'-ATGGTAGAAASCCCCAGCAAA-3' (SEQ ID NO: 87) | p44ES/Msp2 N-terminal conserved region |
| R4 | 5'-CACGTNTTTAGTTACTGCCA-3' (SEQ ID NO: 88) | p44ES/Msp2ES from downstream conserved valS gene |

TABLE 1-continued

Primers used for PCR amplification of A. platys P44ES cluster

| Primer | Sequence | Note |
|---|---|---|
| R5 | 5'-GTACTAGTCAGCGCCACTAACATCAA-3'<br>(SEQ ID NO: 89) | p44ES/Msp2ES downstream region for complete locus confirmation |
| HVF | 5'-GAAGAATACGAAAGCGGCGG-3'<br>(SEQ ID NO: 90) | A. platys P44 hypervariable cloning region |
| HVR | 5'-TACTTAGGTCTTCCGCTTTCGC-3'<br>(SEQ ID NO: 91) | A. platys P44 hypervariable cloning region |

ELISA Analysis of OMP-1X.

When the Clustal W method was used to compare A. platys OMP-1X to its phylogenetically closest OMP-1 homologs-A. phagocytophilum OMP-1X (YP_505750), A. marginate OMP1 (YP_154240), E. canis P30-19 (AAK28680), E. ruminantium Map1-related protein (YP_180721), E. ewingii OMP-1-1 (AB036240), and E. chaffeensis OMP-1M (YP_507903), we identified a unique region in the A. platys OMP-1X amino acid sequence. This sequence, AVQEKKPPEA (SEQ ID NO: 98), is within the 2nd external loop from the N-terminus based on the hydrophobicity analysis and the hydrophobic moment profile program. The sequence is predicted to be highly antigenic and surface exposed by Protean program may aid in differential serodiagnosis (FIG. 14). The A. platys OMP-1X peptide was synthesized and its reactivity to known infected dog sera was tested by ELISA. Three A. platys PCR-positive dog sera reacted with the synthesized OMP-1X peptide antigen. Sera from A. platys PCR-negative dogs and horse anti-A. phagocytophilum serum did not react with the OMP-1X peptide antigen (FIG. 15), suggesting that this antigen can be used for species-specific serodiagnosis of A. platys.

locus of A. platys is also the site of active recombination, and multiple p44 donor sequences also exist in the A. platys genome.

The synteny analysis suggested that the major outer membrane expression locus existed in a common ancestor of the three Anaplasma species in existence today. Furthermore, the locus appears to have diverged primarily by duplicating omp-1-like sequences between tr1 and p44/msp2ES; A. marginate, A. phagocytophilum, and A. platys have 4, 2, and 1 omp-1-like sequences, respectively.

Three species of Anaplasma infect different host cells, namely neutrophils, erythrocytes, and platelets. The comparative study of between A. phagocytophilum, A. marginate, and A. platys P44/Msp2s, and OMP-1 homologs provided a new window of opportunity to investigate different Anaplasma host cell tropism.

Tr1, a putative transcription factor, is more highly expressed in tick cells infected with A. phagocytophilum than in human leukemic HL-60 cells infected with A. phagocytophilum, which suggested that Tr1 may regulate genes involved in the bacterial infection cycle in ticks.[44, 64]

TABLE 2

Properties of A. platys p44ES cluster

| Protein | Upstream intergenic space (bp) | Gene Length (bp) | Protein Size (amino acids)[a] | Signal peptide (amino acids)[b] | Molecular mass[a] (Da) | Isoelectric point | Protein | Upstream intergenic space (bp) |
|---|---|---|---|---|---|---|---|---|
| Tr1 | NA[c] | 558 | 185 | NA | 21010.6-20952.6[d] | 5.50-5.80[d] | Tr1 | NA[c] |
| OMP-1X | 306 | 933 | 301 | 23 | 31885.0-31942.1[d] | 7.27-7.92[d] | OMP-1X | 306 |
| P44ES | 682 | 1221 | 380-386[d] | 21 | 41167.3-41359.5[d] | 5.30-5.72[d] | P44ES | 682 |

[a]Mature protein.
[b]Predicted cleavage site.
[c]Not applicable.
[d]Range among strains.

Discussion

In the present study, the entire 4 kb A. platys p44ES locus, containing tr1, omp-1X and p44 genes, was sequenced, providing new insight into the p44 expression locus and the major surface antigen of A. platys. From each infected dog different p44ES sequences were detected, showing mixed P44 allele population of A. platys is present in the dog blood in a given time point similar to A. phagocytophilum p44 expression in humans and horses[38, 39, 65] or A. marginate msp2 in the blood of cattle.[18, 21, 47] In addition three more different hypervariable regions were detected in partial A. platys p44 gene sequences, suggesting the p44-expression In contrast, Tr is expressed similarly in bovine red blood cells and IDE8 tick cell cultures infected with A. marginale.[5]

In A. phagocytophilum tr1, two omp-1s and p44E were co-expressed.[39] In the cattle blood, the aforementioned and related genes were co-expressed with the exception of the third msp2-associated genes.[48] Omp-1s are major surface antigens of Ehrlichia species, also has a role in A. platys infection cycle. OMP-1 homologous proteins are major surface antigens in Ehrlichia species,[23, 46, 57, 62, 66] and OMP-1X functions similarly in the A. platys infection cycle. A. platys OMP-1X is predicted to have a β-barrel structure similar to that of E. chaffeensis P28 and OMP-1F,[37] and is thus a porin.

The fact that *A. phagocytophilum* and *A. marginate* P44/Msp2 transcripts were distinct between mammals and ticks advocates multiple physiological adaptations between different host environments.[44, 53, 71] Furthermore, *A. phagocytophilum* p44 gene conversion in mammalian hosts suggested its role in antigenic variation.[8, 19, 38, 65] In cattle, *A. marginate* MSP2s allows antigenic variation for persistent infection.[6, 11, 47] *A. platys* P44, therefore, plays an important role in determining persistent or cyclical rickettsemia.

It is not known whether *A. platys* p44ES undergoes nonsegmental gene conversion (as in *A. phagocytophilum* to generate identical P44s from a large number of donor loci) or segmental gene conversion (as in *A. marginate* to generate mosaic Msp2ES from a small number of donor loci).[39, 47] P44 has a role in the interaction between *A. phagocytophilum* and host cells.[36, 49, 64] The P44 of *A. phagocytophilum* is the major surface antigen useful for serologic diagnosis of human granulocytic anaplasmosis, and has a role in the interaction between *A. phagocytophilum* and host cells. P44s also elicits a porin activity for passive diffusion of hydrophilic solutes.

Based on the present study, recombinant or peptide-based OMP-1X and P44 antigen can be prepared for testing the applicability of *A. platys* serodiagnosis. P44 can also serve as a specific and sensitive target for PCR diagnosis for human granulocytic anaplasmosis, and thus can be tested for *A. platys* infection or exposure.

*A. phagocytophilum* is known to infect dogs in regions where the *Ixodes* tick is endemic.[2, 24, 50, 51] *A. platys* inclusions in the platelets of a naturally infected dog cross-reacted with mouse anti-*A. phagocytophilum* serum.[32] It was important, therefore, to develop a method for distinguishing *A. platys* infection from *A. phagocytophilum* infection. Since the p44 primer pair: HVF and HVR described herein, is specific to *A. platys*, it was expected to be useful for species-specific PCR diagnosis. P44 of *A. phagocytophilum* is the major surface antigen used for serologic diagnosis of human granulocytic anaplasmosis.[1, 16, 27, 31, 70] In the present study, several *A. platys*-specific amino acid sequences were identified within P44 proteins that can be used as serologic test antigens to provide differential diagnosis from other *Anaplasma* species infection. Additionally, *Ehrlichia* OMP-1/P28/P30/MAP families are immunodominant major outer membrane proteins useful for serodiagnosis.[45, 62, 63, 68] The alignment results showed a distinct fragment (~20 amino acids) in *A. platys* Omp-1X that was not observed in the closest homologs from *Anaplasma* and *Ehrlichia* spp. Furthermore, this region was identical in *A. platys* samples from the geographically separated regions of Venezuela and Taiwan. This specific OMP-1X peptide antigen did not cross-react with anti-*A. phagocytophilum* serum, and therefore can be suitable for species-specific differential serodiagnosis of *A. platys*.

Since the only available source of *A. platys* DNA was a small amount of DNA purified from infected dog blood specimens, touchdown PCR was employed to amplify the available canine DNA. Incorrect base pairings resulting from amplification were minimized by using a high-fidelity Taq polymerase Example 2

*A. platys* Expression Locus Analysis.

DNA specimens from three dogs naturally infected with *A. platys* at Lara, Venezuela in 2007 were used as the template for the amplification and sequencing process. *A. platys* infection of the dog was confirmed by PCR and sequencing of the 16S rRNA of *A. platys* as well as by observation of bacterial inclusions (morulae) in platelets in the blood smear. By aligning *A. phagocytophilum* and *A. marginate* p44/msp2 expression loci, several degenerate primers were designed based upon conserved regions (FIG. 1, Table 1). Using the first primer pair F1 and R1, and the second primer pair F1 and R2, (hemi-) nested touchdown PCR amplified the *A. platys* tr1 and omp-1X sequences. In order to avoid truncated p44 pseudogenes in *A. platys* genome, primer F3 for the 5' upstream of the predicted p44 ORF was designed. p44ES sequences were amplified by nested touchdown PCR with primer pairs F2 and R3, and F3 and R4. Amplification was performed as previously described. The amplified DNA fragments were cloned using a TA cloning kit (Invitrogen, Carlsbad, Calif.) and sequenced with M13 Forward or M13 Reverse sequencing primers. All sequencing data was assembled using SeqMan program of DNASTAR software (DNASTAR Inc., Madison, Wis.). The deduced amino acid sequences of *A. marginate*, *A. phagocytophilum*, and *A. platys* tr1, Omp-1X and p44ES were aligned using the MegAlign program of DNASTAR software by the Clustal W method.

P44 Secondary Structure Prediction.

The P44 secondary structure was predicted by hydrophobicity and the hydrophobic moment profile method as previously described. Antigenic Index and surface probability were examined by Protean program of DNASTAR.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed can be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Nothing herein is to be construed as an admission that the present invention is not entitled to antedate such publication by virtue of prior invention. Further, the dates of publication provided herein may be different from the actual publication dates, which can require independent confirmation.

REFERENCES

1. Aguero-Rosenfeld, M. E., F. Kalantarpour, M. Baluch, H. W. Horowitz, D. F. McKenna, J. T. Raffalli, T. Hsieh, J. Wu, J. S. Dumler, and G. P. Wormser. 2000. Serology of culture-confirmed cases of human granulocytic ehrlichiosis. J Clin Microbiol 38: 635-8.
2. Alberti, A., R. Zobba, B. Chessa, M. F. Addis, O. Sparagano, M. L. Pinna Parpaglia, T. Cubeddu, G. Pintori, and M. Pittau. 2005. Equine and canine *Anaplasma phagocytophilum* strains isolated on the island of Sardinia (Italy) are phylogenetically related to pathogenic strains from the United States. Appl Environ Microbiol 71: 6418-22.
3. Anderson, B. E., C. E. Greene, D. C. Jones, and J. E. Dawson. 1992. *Ehrlichia ewingii* sp. nov., the etiologic agent of canine granulocytic ehrlichiosis. Int J Syst Bacteriol 42: 299-302.
4. Bagos, P. G., T. D. Liakopoulos, I. C. Spyropoulos, and S. J. Hamodrakas. 2004. PRED-TMBB: a web server for predicting the topology of beta-barrel outer membrane proteins. Nucleic Acids Res 32: W400-4.
5. Barbet, A. F., J. T. Agnes, A. L. Moreland, A. M. Lundgren, A. R. Alleman, S. M. Noh, K. A. Brayton, U. G. Munderloh, and G. H. Palmer. 2005. Identification of functional promoters in the msp2 expression loci of *Anaplasma marginate* and *Anaplasma phagocytophilum*. Gene 353: 89-97.
6. Barbet, A. F., A. Lundgren, J. Yi, F. R. Rurangirwa, and G. H. Palmer. 2000. Antigenic variation of *Anaplasma marginate* by expression of MSP2 mosaics. Infect Immun 68: 6133-8.
7. Barbet, A. F., A. M. Lundgren, A. R. Alleman, S. Stuen, A. Bjoersdorff, R. N. Brown, N. L. Drazenovich, and J. E. Foley. 2006. Structure of the expression site reveals global diversity in MSP2 (P44) variants in *Anaplasma phagocytophilum*. Infect Immun 74: 6429-37.
8. Barbet, A. F., P. F. Meeus, M. Belanger, M. V. Bowie, J. Yi, A. M. Lundgren, A. R. Alleman, S. J. Wong, F. K. Chu, U. G. Munderloh, and S. D. Jauron. 2003. Expression of multiple outer membrane protein sequence variants from a single genomic locus of *Anaplasma phagocytophilum*. Infect Immun 71: 1706-18.
9. Barbet, A. F., J. Yi, A. Lundgren, B. R. McEwen, E. F. Blouin, and K. M. Kocan. 2001. Antigenic variation of *Anaplasma marginate*: major surface protein 2 diversity during cyclic transmission between ticks and cattle. Infect Immun 69: 3057-66.
10. Brayton, K. A., L. S. Kappmeyer, D. R. Herndon, M. J. Dark, D. L. Tibbals, G. H. Palmer, T. C. McGuire, and D. P. Knowles, Jr. 2005. Complete genome sequencing of *Anaplasma marginate* reveals that the surface is skewed to two superfamilies of outer membrane proteins. Proc Natl Acad Sci USA 102: 844-9.
11. Brayton, K. A., G. H. Palmer, A. Lundgren, J. Yi, and A. F. Barbet. 2002. Antigenic variation of *Anaplasma marginate* msp2 occurs by combinatorial gene conversion. Mol Microbiol 43: 1151-9.
12. Brown, G. K., A. R. Martin, T. K. Roberts, and R. J. Aitken. 2001. Detection of *Ehrlichia platys* in dogs in Australia. Aust Vet J 79: 554-8.
13. Cardoso, L., J. Tuna, L. Vieira, Y. Yisaschar-Mekuzas, and G. Baneth. 2008. Molecular detection of *Anaplasma platys* and *Ehrlichia canis* in dogs from the North of Portugal. Vet J.
14. Carver, T. J., K. M. Rutherford, M. Berriman, M. A. Rajandream, B. G. Barrell, and J. Parkhill. 2005. ACT: the Artemis Comparison Tool. Bioinformatics 21: 3422-3.
15. Chang, W. L., and M. J. Pan. 1996. Specific amplification of *Ehrlichia platys* DNA from blood specimens by two-step PCR. J Clin Microbiol 34: 3142-6.
16. Dumler, J. S., K. M. Asanovich, J. S. Bakken, P. Richter, R. Kimsey, and J. E. Madigan. 1995. Serologic cross-reactions among *Ehrlichia equi*, *Ehrlichia phagocytophila*, and human granulocytic *Ehrlichia*. J Clin Microbiol 33: 1098-103.
17. Dumler, J. S., A. F. Barbet, C. P. Bekker, G. A. Dasch, G. H. Palmer, S. C. Ray, Y. Rikihisa, and F. R. Rurangirwa. 2001. Reorganization of genera in the families Rickettsiaceae and Anaplasmataceae in the order Rickettsiales: unification of some species of *Ehrlichia* with *Anaplasma*, *Cowdria* with *Ehrlichia* and *Ehrlichia* with *Neorickettsia*, descriptions of six new species combinations and designation of *Ehrlichia equi* and 'HGE agent' as subjective synonyms of *Ehrlichia phagocytophila*. Int J Syst Evol Microbiol 51: 2145-65.
18. Eid, G., D. M. French, A. M. Lundgren, A. F. Barbet, T. F. McElwain, and G. H. Palmer. 1996. Expression of major surface protein 2 antigenic variants during acute *Anaplasma marginate* rickettsemia. Infect Immun 64: 836-41.
19. Felek, S., S. Telford, 3rd, R. C. Falco, and Y. Rikihisa. 2004. Sequence analysis of p44 homologs expressed by *Anaplasma phagocytophilum* in infected ticks feeding on naive hosts and in mice infected by tick attachment. Infect Immun 72: 659-66.
20. Ferreira, R. F., A. M. Cerqueira, A. M. Pereira, C. M. Guimaraes, A. Garcia, F. S. Abreu, C. L. Massard, and N. R. P. Almosny. 2007. *Anaplasma platys* Diagnosis in Dogs: Comparison Between Morphological and Molecular Tests. Intern J Appl Res Vet Med 5: 7.
21. French, D. M., T. F. McElwain, T. C. McGuire, and G. H. Palmer. 1998. Expression of *Anaplasma marginate* major surface protein 2 variants during persistent cyclic rickettsemia. Infect Immun 66: 1200-7.
22. French, T. W., and J. W. Harvey. 1983. Serologic diagnosis of infectious cyclic thrombocytopenia in dogs using an indirect fluorescent antibody test. Am J Vet Res 44: 2407-11.
23. Ganta, R. R., C. Cheng, E. C. Miller, B. L. McGuire, L. Peddireddi, K. R. Sirigireddy, and S. K. Chapes. 2007. Differential clearance and immune responses to tick cell-derived versus macrophage culture-derived *Ehrlichia chaffeensis* in mice. Infect Immun 75: 135-45.
24. Greig, B., K. M. Asanovich, P. J. Armstrong, and J. S. Dumler. 1996. Geographic, clinical, serologic, and molecular evidence of granulocytic ehrlichiosis, a likely zoonotic disease, in Minnesota and Wisconsin dogs. J Clin Microbiol 34: 44-8.
25. Harvey, J. W., C. F. Simpson, and J. M. Gaskin. 1978. Cyclic thrombocytopenia induced by a *Rickettsia*-like agent in dogs. J Infect Dis 137: 182-8.
26. Hotopp, J. C., M. Lin, R. Madupu, J. Crabtree, S. V. Angiuoli, J. A. Eisen, R. Seshadri, Q. Ren, M. Wu, T. R. Utterback, S. Smith, M. Lewis, H. Khouri, C. Zhang, H. Niu, Q. Lin, N. Ohashi, N. Zhi, W. Nelson, L. M. Brinkac, R. J. Dodson, M. J. Rosovitz, J. Sundaram, S. C. Daugherty, T. Davidsen, A. S. Durkin, M. Gwinn, D. H. Haft, J.

26. (cont.) D. Selengut, S. A. Sullivan, N. Zafar, L. Zhou, F. Benahmed, H. Forberger, R. Halpin, S. Mulligan, J. Robinson, O. White, Y. Rikihisa, and H. Tettelin. 2006. Comparative genomics of emerging human ehrlichiosis agents. PLoS Genet 2: e21.

27. Hsieh, T., A. M. DiPietrantonio, H. W. Horowitz, J. S. Dumler, M. E. Aguero-Rosenfeld, G. P. Wormser, and J. M. Wu. 1999. Changes in expression of the 44-kilodalton outer surface membrane antigen (p44 kD) for monitoring progression of infection and antimicrobial susceptibility of the human granulocytic ehrlichiosis (HGE) agent in HL-60 cells. Biochem Biophys Res Commun 257: 351-5.

28. Hua, P., M. Yuhai, T. Shide, S. Yang, W. Bohai, and C. Xiangrui. 2000. Canine ehrlichiosis caused simultaneously by *Ehrlichia canis* and *Ehrlichia platys*. Microbiol Immunol 44: 737-9.

29. Huang, H., A. Unver, M. J. Perez, N. G. *Orellana*, and Y. Rikihisa 2005. Prevalence and molecular analysis of *Anaplasma platys* from dogs in Lara, Venezuela. Brazilian J. Microbiol 36: 211-216.

30. Huang, H., X. Wang, T. Kikuchi, Y. Kumagai, and Y. Rikihisa. 2007. Porin activity of *Anaplasma phagocytophilum* outer membrane fraction and purified P44. J Bacteriol 189: 1998-2006.

31. Ijdo, J. W., C. Wu, L. A. Magnarelli, and E. Fikrig. 1999. Serodiagnosis of human granulocytic ehrlichiosis by a recombinant HGE-44-based enzyme-linked immunosorbent assay. J Clin Microbiol 37: 3540-4.

32. Inokuma, H., K. Fujii, K. Matsumoto, M. Okuda, K. Nakagome, R. Kosugi, M. Hirakawa, and T. Onishi. 2002. Demonstration of *Anaplasma (Ehrlichia) platys* inclusions in peripheral blood platelets of a dog in Japan. Vet Parasitol 110: 145-52.

33. Inokuma, H., K. Fujii, M. Okuda, T. Onishi, J. P. Beaufils, D. Raoult, and P. Brouqui. 2002. Determination of the nucleotide sequences of heat shock operon groESL and the citrate synthase gene (gltA) of *Anaplasma (Ehrlichia) platys* for phylogenetic and diagnostic studies. Clin Diagn Lab Immunol 9: 1132-6.

34. Inokuma, H., D. Raoult, and P. Brouqui. 2000. Detection of *Ehrlichia platys* DNA in brown dog ticks (*Rhipicephalus sanguineus*) in Okinawa Island, Japan. J Clin Microbiol 38: 4219-21.

35. Jeanteur, D., J. H. Lakey, and F. Pattus. 1991. The bacterial porin superfamily: sequence alignment and structure prediction. Mol Microbiol 5: 2153-64.

36. Kim, H. Y., and Y. Rikihisa. 1998. Characterization of monoclonal antibodies to the 44-kilodalton major outer membrane protein of the human granulocytic ehrlichiosis agent. J Clin Microbiol 36: 3278-84.

37. Kumagai, Y., H. Huang, and Y. Rikihisa. 2008. Expression and porin activity of P28 and OMP-1F during intracellular *Ehrlichia chaffeensis* development. J Bacteriol 190: 3597-605.

38. Lin, Q., and Y. Rikihisa. 2005. Establishment of cloned *Anaplasma phagocytophilum* and analysis of p44 gene conversion within an infected horse and infected SCID mice. Infect Immun 73: 5106-14.

39. Lin, Q., Y. Rikihisa, N. Ohashi, and N. Zhi. 2003. Mechanisms of variable p44 expression by *Anaplasma phagocytophilum*. Infect Immun 71: 5650-61.

40. Lin, Q., C. Zhang, and Y. Rikihisa. 2006. Analysis of involvement of the RecF pathway in p44 recombination in *Anaplasma phagocytophilum* and in *Escherichia coli* by using a plasmid carrying the p44 expression and p44 donor loci. Infect Immun 74: 2052-62.

41. Lin, Q., N. Zhi, N. Ohashi, H. W. Horowitz, M. E. Aguero-Rosenfeld, J. Raffalli, G. P. Wormser, and Y. Rikihisa. 2002. Analysis of sequences and loci of p44 homologs expressed by *Anaplasma phagocytophila* in acutely infected patients. J Clin Microbiol 40: 2981-8.

42. Mathew, J. S., S. A. Ewing, G. L. Murphy, K. M. Kocan, R. E. Corstvet, and J. C. Fox. 1997. Characterization of a new isolate of *Ehrlichia platys* (Order Rickettsiales) using electron microscopy and polymerase chain reaction. Vet Parasitol 68: 1-10.

43. Mylonakis, M. E., A. F. Koutinas, E. B. Breitschwerdt, B. C. Hegarty, C. D. Billinis, L. S. Leontides, and V. S. Kontos. 2004. Chronic canine ehrlichiosis (*Ehrlichia canis*): a retrospective study of 19 natural cases. J Am Anim Hosp Assoc 40: 174-84.

44. Nelson, C. M., M. J. Herron, R. F. Felsheim, B. R. Schloeder, S. M. Grindle, A. O. Chavez, T. J. Kurtti, and U. G. Munderloh. 2008. Whole genome transcription profiling of *Anaplasma phagocytophilum* in human and tick host cells by tiling array analysis. BMC Genomics 9: 364.

45. Ohashi, N., A. Unver, N. Zhi, and Y. Rikihisa. 1998. Cloning and characterization of multigenes encoding the immunodominant 30-kilodalton major outer membrane proteins of *Ehrlichia canis* and application of the recombinant protein for serodiagnosis. J Clin Microbiol 36: 2671-80.

46. Ohashi, N., N. Zhi, Y. Zhang, and Y. Rikihisa. 1998. Immunodominant major outer membrane proteins of *Ehrlichia chaffeensis* are encoded by a polymorphic multigene family. Infect Immun 66: 132-9.

47. Palmer, G. H., T. Bankhead, and S. A. Lukehart. 2009. 'Nothing is permanent but change'—antigenic variation in persistent bacterial pathogens. Cell Microbiol 11: 1697-705.

48. Palmer, G. H., J. E. Futse, D. P. Knowles, Jr., and K. A. Brayton. 2006. Insights into mechanisms of bacterial antigenic variation derived from the complete genome sequence of *Anaplasma marginate*. Ann N Y Acad Sci 1078: 15-25.

49. Park, J., K. S. Choi, and J. S. Dumler. 2003. Major surface protein 2 of *Anaplasma phagocytophilum* facilitates adherence to granulocytes. Infect Immun 71: 4018-25.

50. Poitout, F. M., J. K. Shinozaki, P. J. Stockwell, C. J. Holland, and S. K. Shukla. 2005. Genetic variants of *Anaplasma phagocytophilum* infecting dogs in Western Washington State. J Clin Microbiol 43: 796-801.

51. Pusterla, N., J. Huder, C. Wolfensberger, B. Litschi, A. Parvis, and H. Lutz. 1997. Granulocytic ehrlichiosis in two dogs in Switzerland. J Clin Microbiol 35: 2307-9.

52. Roux, K. H., and K. H. Hecker. 1997. One-step optimization using touchdown and stepdown PCR. Methods Mol Biol 67: 39-45.

53. Rurangirwa, F. R., D. Stiller, D. M. French, and G. H. Palmer. 1999. Restriction of major surface protein 2 (MSP2) variants during tick transmission of the *ehrlichia Anaplasma marginate*. Proc Natl Acad Sci USA 96: 3171-6.

54. Sainz, A., I. Amusategui, and M. A. Tesouro. 1999. *Ehrlichia platys* infection and disease in dogs in Spain. J Vet Diagn Invest 11: 382-4.

55. Sanogo, Y. O., B. Davoust, H. Inokuma, J. L. Camicas, P. Parola, and P. Brouqui. 2003. First evidence of *Anaplasma platys* in *Rhipicephalus sanguineus* (Acari: Ixodida) collected from dogs in Africa. Onderstepoort J Vet Res 70: 205-12.

56. Simpson, R. M., S. D. Gaunt, J. A. Hair, K. M. Kocan, W. G. Henk, and H. W. Casey. 1991. Evaluation of *Rhipicephalus sanguineus* as a potential biologic vector of *Ehrlichia platys*. Am J Vet Res 52: 1537-41.
57. Singu, V., H. Liu, C. Cheng, and R. R. Ganta. 2005. *Ehrlichia chaffeensis* expresses macrophage- and tick cell-specific 28-kilodalton outer membrane proteins. Infect Immun 73: 79-87.
58. Sparagano, O. A., A. P. de Vos, B. Paoletti, C. Camma, P. de Santis, D. Otranto, and A. Giangaspero. 2003. Molecular detection of *Anaplasma platys* in dogs using polymerase chain reaction and reverse line blot hybridization. J Vet Diagn Invest 15: 527-34.
59. Suksawat, J., C. Pitulle, C. Arraga-Alvarado, K. Madrigal, S. I. Hancock, and E. B. Breitschwerdt. 2001. Coinfection with three *Ehrlichia* species in dogs from Thailand and Venezuela with emphasis on consideration of 16S ribosomal DNA secondary structure. J Clin Microbiol 39: 90-3.
60. Tajima, T., N. Zhi, Q. Lin, Y. Rikihisa, H. W. Horowitz, J. Ralfalli, G. P. Wormser, and K. E. Hechemy. 2000. Comparison of two recombinant major outer membrane proteins of the human granulocytic ehrlichiosis agent for use in an enzyme-linked immunosorbent assay. Clin Diagn Lab Immunol 7: 652-7.
61. Unver, A., Y. Rikihisa, M. Kawahara, and S. Yamamoto. 2003. Analysis of 16S rRNA gene sequences of *Ehrlichia canis*, *Anaplasma platys*, and *Wolbachia* species from canine blood in Japan. Ann N Y Acad Sci 990: 692-8.
62. Unver, A., Y. Rikihisa, N. Ohashi, L. C. Cullman, R. Buller, and G. A. Storch. 1999. Western and dot blotting analyses of *Ehrlichia chaffeensis* indirect fluorescent-antibody assay-positive and -negative human sera by using native and recombinant *E. chaffeensis* and *E. canis* antigens. J Clin Microbiol 37: 3888-95.
63. van Vliet, A. H., F. Jongejan, M. van Kleef, and B. A. van der Zeijst. 1994. Molecular cloning, sequence analysis, and expression of the gene encoding the immunodominant 32-kilodalton protein of *Cowdria ruminantium*. Infect Immun 62: 1451-6.
64. Wang, X., Z. Cheng, C. Zhang, T. Kikuchi, and Y. Rikihisa. 2007. *Anaplasma phagocytophilum* p44 mRNA expression is differentially regulated in mammalian and tick host cells: involvement of the DNA binding protein ApxR. J Bacteriol 189: 8651-9.
65. Wang, X., Y. Rikihisa, T. H. Lai, Y. Kumagai, N. Zhi, and S. M. Reed. 2004. Rapid sequential changeover of expressed p44 genes during the acute phase of *Anaplasma phagocytophilum* infection in horses. Infect Immun 72: 6852-9.
66. Yu, X., J. W. McBride, X. Zhang, and D. H. Walker. 2000. Characterization of the complete transcriptionally active *Ehrlichia chaffeensis* 28 kDa outer membrane protein multigene family. Gene 248: 59-68.
67. Yu, X. J., X. F. Zhang, J. W. McBride, Y. Zhang, and D. H. Walker. 2001. Phylogenetic relationships of *Anaplasma marginate* and '*Ehrlichia platys*' to other *Ehrlichia* species determined by GroEL amino acid sequences. Int J Syst Evol Microbiol 51: 1143-6.
68. Zhang, C., Q. Xiong, T. Kikuchi, and Y. Rikihisa. 2008. Identification of 19 polymorphic major outer membrane protein genes and their immunogenic peptides in *Ehrlichia ewingii* for use in a serodiagnostic assay. Clin Vaccine Immunol 15: 402-11.
69. Zhi, N., N. Ohashi, and Y. Rikihisa. 1999. Multiple p44 genes encoding major outer membrane proteins are expressed in the human granulocytic ehrlichiosis agent. J Biol Chem 274: 17828-36.
70. Zhi, N., N. Ohashi, Y. Rikihisa, H. W. Horowitz, G. P. Wormser, and K. Hechemy. 1998. Cloning and expression of the 44-kilodalton major outer membrane protein gene of the human granulocytic ehrlichiosis agent and application of the recombinant protein to serodiagnosis. J Clin Microbiol 36: 1666-73.
71. Zhi, N., N. Ohashi, T. Tajima, J. Mott, R. W. Stich, D. Grover, S. R. Telford, 3rd, Q. Lin, and Y. Rikihisa. 2002. Transcript heterogeneity of the p44 multigene family in a human granulocytic ehrlichiosis agent transmitted by ticks. Infect Immun 70: 1175-84.

---

What is claimed is:

1. A method for diagnosing an infection with *Anaplasma platys* in a subject comprising the steps of: (a) providing a test sample from the subject; (b) providing an isolated or purified P44 protein of *Anaplasma platys*; (c) contacting the test sample with the P44 protein; and (d) assaying for the formation of a complex between antibodies in the test sample and the P44 protein, wherein formation of said complex is indicative of infection with *Anaplasma platys*, wherein the *Anaplasma platys* P44 protein comprises SEQ ID NO: 39, SEQ ID NO: 92 or SEQ ID NO:44.

2. The method of claim 1, wherein the *Anaplasma platys* P44 protein comprises SEQ ID NO: 39 or SEQ ID NO: 44.

3. The method of claim 1, wherein the test sample comprises a serum sample or a plasma sample.

* * * * *

UNITED STATES PATENT AND TRADEMARK OFFICE
CERTIFICATE OF CORRECTION

PATENT NO. : 10,393,741 B2
APPLICATION NO. : 14/993678
DATED : August 27, 2019
INVENTOR(S) : Yasuko Rikihisa Page 1 of 1

It is certified that error appears in the above-identified patent and that said Letters Patent is hereby corrected as shown below:

In the Specification

Column 1, Line 10 add the Government Support Clause:
--This invention was made with government support under grant number AI054476 awarded by the National Institutes of Health. The government has certain rights in the invention.--

Signed and Sealed this
Sixth Day of October, 2020

Andrei Iancu
*Director of the United States Patent and Trademark Office*

SEQUENCE LISTING

```
<160> NUMBER OF SEQ ID NOS: 212

<210> SEQ ID NO 1
<211> LENGTH: 324
<212> TYPE: PRT
<213> ORGANISM: Artificial Sequence
<220> FEATURE:
<223> OTHER INFORMATION: Synthetic construct

<400> SEQUENCE: 1

Met Lys Lys Arg Ile Arg Val Phe Ala Phe Ala Val Phe Met Leu Gly
1               5                   10                  15

Leu Pro Ser Val Ser Phe Ala Ser Pro Gln Pro Val Asp Phe Ser Tyr
            20                  25                  30

His Glu Gly Ala Ser Gly Phe Phe Ala Ser Val Gln Tyr Lys Tyr Gly
        35                  40                  45

Ala Pro Tyr Phe Gly Ser Leu Thr Leu Glu Ser Gly Gly Lys Thr Leu
    50                  55                  60

Asn Leu Val Ser Ala Val Gln Glu Lys Lys Pro Pro Glu Ala Pro Ala
65                  70                  75                  80

Ala Asp Glu Ala Ala Glu Pro Ala Thr Pro Ala Pro Ser Ser Pro Glu
                85                  90                  95
```

```
Gly Phe Gly Ser Ser Thr Asp Asp Phe Gln Gly Arg Tyr Ser Pro Thr
                100                 105                 110

Tyr Leu Lys Asp Ala Gly Ala Phe Ser Ile Thr Ala Gly Tyr Thr Ile
            115                 120                 125

Gly Ile Met Arg Phe Glu Ala Glu Ala Met Arg Ser Arg Phe Gln Val
        130                 135                 140

Asn Gly Ser Lys Trp Asn Pro Val Glu Asn Ala Tyr Ile Phe Ala Ala
145                 150                 155                 160

Ala Lys Pro Ser Glu Asn Ile Ser Tyr Pro Ala Gln Ile Leu Glu Ala
                165                 170                 175

Gln Lys Tyr Phe Val Thr Leu Glu Asn Arg Asp Val Ala Ile Thr Ser
            180                 185                 190

Leu Val Ala Asn Ala Cys Tyr Asp Met Met Pro Ala Thr Ser Ser Ile
        195                 200                 205

Ala Pro Ser Ala Cys Val Gly Val Gly Val Ser Phe Ala Lys Leu Leu
210                 215                 220

Gly Val Leu Glu Gln Arg Leu Thr Tyr Gln Phe Lys Gly Gly Leu Gln
225                 230                 235                 240

Tyr Phe Val Gly Lys Lys Thr Val Ile Phe Leu Ser Gly Tyr Val Ser
                245                 250                 255

Thr Ile Gly Gly Arg Lys Ile Thr Gln Val Lys Val Lys His Arg Leu
            260                 265                 270

Ser Thr Pro Gln Thr Ala Ser Val Gly Ala Glu Gly Ser Gly Ala Gly
        275                 280                 285

Ala Ala Ala Thr Ser Ser Ala Pro Pro Ala Pro Ile His Leu Leu Tyr
        290                 295                 300

Pro Asp Ala Asn Leu Ser Leu Ala Tyr Tyr Gly Phe Glu Leu Gly Val
305                 310                 315                 320

Arg Leu Val Phe

<210> SEQ ID NO 2
<211> LENGTH: 117
<212> TYPE: PRT
<213> ORGANISM: Artificial Sequence
<220> FEATURE:
<223> OTHER INFORMATION: Synthetic construct

<400> SEQUENCE: 2

Leu Val Ser Ala Val Gln Glu Lys Lys Pro Pro Glu Ala Pro Ala Ala
1               5                   10                  15

Asp Glu Ala Ala Glu Pro Ala Thr Pro Ala Pro Ser Ser Pro Glu Gly
            20                  25                  30

Phe Gly Ser Ser Thr Asp Asp Phe Gln Gly Arg Tyr Ser Pro Thr Tyr
        35                  40                  45

Leu Lys Asp Ala Gly Ala Phe Ser Ile Thr Ala Gly Tyr Thr Thr Gly
    50                  55                  60

Ile Met Arg Phe Glu Ala Glu Ala Met Arg Ser Arg Phe Gln Val Asn
65                  70                  75                  80

Gly Ser Lys Trp Asn Pro Val Glu Asn Ala Tyr Ile Phe Ala Ala Ala
                85                  90                  95

Lys Pro Ser Glu Asn Ile Ser Tyr Pro Ala Gln Ile Leu Glu Ala Gln
            100                 105                 110

Lys Tyr Phe Val Thr
            115
```

<210> SEQ ID NO 3
<211> LENGTH: 68
<212> TYPE: PRT
<213> ORGANISM: Artificial Sequence
<220> FEATURE:
<223> OTHER INFORMATION: Synthetic construct

<400> SEQUENCE: 3

```
Leu Thr Tyr Gln Phe Lys Gly Gly Leu Gln Tyr Phe Val Gly Lys Lys
1               5                   10                  15

Thr Val Ile Phe Leu Ser Gly Tyr Val Ser Thr Ile Gly Gly Arg Lys
            20                  25                  30

Ile Thr Gln Val Lys Val Lys His Arg Leu Ser Thr Pro Gln Thr Ala
        35                  40                  45

Ser Val Gly Ala Glu Gly Ser Gly Ala Gly Ala Ala Thr Ser Ser
    50                  55                  60

Ala Pro Pro Ala
65
```

<210> SEQ ID NO 4
<211> LENGTH: 185
<212> TYPE: PRT
<213> ORGANISM: Artificial Sequence
<220> FEATURE:
<223> OTHER INFORMATION: Synthetic construct

<400> SEQUENCE: 4

```
Leu Val Ser Ala Val Gln Glu Lys Lys Pro Pro Glu Ala Pro Ala Ala
1               5                   10                  15

Asp Glu Ala Ala Glu Pro Ala Thr Pro Ala Pro Ser Ser Pro Glu Gly
            20                  25                  30

Phe Gly Ser Ser Thr Asp Asp Phe Gln Gly Arg Tyr Ser Pro Thr Tyr
        35                  40                  45

Leu Lys Asp Ala Gly Ala Phe Ser Ile Thr Ala Gly Tyr Thr Thr Gly
    50                  55                  60

Ile Met Arg Phe Glu Ala Glu Ala Met Arg Ser Arg Phe Gln Val Asn
65                  70                  75                  80

Gly Ser Lys Trp Asn Pro Val Glu Asn Ala Tyr Ile Phe Ala Ala Ala
                85                  90                  95

Lys Pro Ser Glu Asn Ile Ser Tyr Pro Ala Gln Ile Leu Glu Ala Gln
            100                 105                 110

Lys Tyr Phe Val Thr Leu Thr Tyr Gln Phe Lys Gly Gly Leu Gln Tyr
        115                 120                 125

Phe Val Gly Lys Lys Thr Val Ile Phe Leu Ser Gly Tyr Val Ser Thr
    130                 135                 140

Ile Gly Gly Arg Lys Ile Thr Gln Val Lys Val Lys His Arg Leu Ser
145                 150                 155                 160

Thr Pro Gln Thr Ala Ser Val Gly Ala Glu Gly Ser Gly Ala Gly Ala
                165                 170                 175

Ala Ala Thr Ser Ser Ala Pro Pro Ala
            180                 185
```

<210> SEQ ID NO 5
<211> LENGTH: 324
<212> TYPE: PRT
<213> ORGANISM: Artificial Sequence
<220> FEATURE:
<223> OTHER INFORMATION: Synthetic construct -continued

```
<400> SEQUENCE: 5

Met Lys Lys Arg Ile Arg Val Phe Ala Phe Ala Val Phe Met Leu Gly
1               5                   10                  15

Leu Pro Ser Val Ser Phe Ala Ser Pro Gln Pro Val Asp Phe Ser Tyr
            20                  25                  30

His Glu Gly Ala Ser Gly Phe Phe Ala Ser Val Gln Tyr Lys Tyr Gly
        35                  40                  45

Ala Pro Tyr Phe Gly Ser Leu Thr Leu Glu Ser Gly Gly Lys Ile Leu
    50                  55                  60

Asn Leu Val Ser Ala Val Gln Glu Lys Lys Pro Pro Glu Ala Pro Ala
65                  70                  75                  80

Ala Asp Glu Ala Ala Gly Pro Ala Thr His Ala Pro Ser Ser Pro Glu
                85                  90                  95

Gly Phe Gly Ser Ser Thr Asp Asp Phe Gln Gly Arg Tyr Ser Pro Thr
            100                 105                 110

Tyr Leu Lys Asp Ala Gly Ala Phe Ser Ile Thr Ala Gly Tyr Thr Ile
        115                 120                 125

Gly Ile Met Arg Phe Glu Ala Glu Ala Met Arg Ser Arg Phe Gln Val
    130                 135                 140

Asn Gly Ser Lys Trp Asn Pro Val Glu Asn Ala Tyr Ile Phe Ala Ala
145                 150                 155                 160

Ala Lys Pro Ser Glu Asn Ile Ser Tyr Pro Ala Gln Ile Leu Glu Thr
                165                 170                 175

Gln Lys Tyr Phe Val Thr Leu Glu Asn Arg Asp Val Ala Ile Thr Ser
            180                 185                 190

Leu Val Ala Ser Ala Cys Tyr Asp Met Met Pro Ala Thr Ser Ser Ile
        195                 200                 205

Ala Pro Ser Ala Cys Val Gly Val Gly Val Ser Phe Ala Lys Leu Leu
    210                 215                 220

Gly Val Leu Glu Gln Arg Leu Thr Tyr Gln Phe Lys Gly Gly Leu Gln
225                 230                 235                 240

Tyr Phe Val Gly Lys Lys Thr Val Ile Phe Leu Ser Gly Tyr Val Ser
                245                 250                 255

Thr Ile Gly Gly Arg Lys Ile Ser Gln Val Lys Val Lys His Arg Leu
            260                 265                 270

Pro Thr Pro Gln Thr Ala Ser Val Gly Ala Glu Gly Ser Gly Ser Gly
        275                 280                 285

Ala Ala Ala Thr Ser Ser Ala Pro Pro Ala Leu Ile His Leu Leu Tyr
    290                 295                 300

Pro Asp Ala Asn Leu Ser Leu Ala Tyr Tyr Gly Phe Glu Leu Gly Val
305                 310                 315                 320

Arg Leu Val Phe

<210> SEQ ID NO 6
<211> LENGTH: 117
<212> TYPE: PRT
<213> ORGANISM: Artificial Sequence
<220> FEATURE:
<223> OTHER INFORMATION: Synthetic construct

<400> SEQUENCE: 6

Leu Val Ser Ala Val Gln Glu Lys Lys Pro Pro Glu Ala Pro Ala Ala
1               5                   10                  15

Asp Glu Ala Ala Gly Pro Ala Thr His Ala Pro Ser Ser Pro Glu Gly
            20                  25                  30
```

```
Phe Gly Ser Ser Thr Asp Asp Phe Gln Gly Arg Tyr Ser Pro Thr Tyr
            35                  40                  45

Leu Lys Asp Ala Gly Ala Phe Ser Ile Thr Ala Gly Tyr Thr Thr Gly
    50                  55                  60

Ile Met Arg Phe Glu Ala Glu Ala Met Arg Ser Arg Phe Gln Val Asn
65                  70                  75                  80

Gly Ser Lys Trp Asn Pro Val Glu Asn Ala Tyr Ile Phe Ala Ala Ala
                85                  90                  95

Lys Pro Ser Glu Asn Ile Ser Tyr Pro Ala Gln Ile Leu Glu Thr Gln
            100                 105                 110

Lys Tyr Phe Val Thr
            115

<210> SEQ ID NO 7
<211> LENGTH: 68
<212> TYPE: PRT
<213> ORGANISM: Artificial Sequence
<220> FEATURE:
<223> OTHER INFORMATION: Synthetic construct

<400> SEQUENCE: 7

Leu Thr Tyr Gln Phe Lys Gly Gly Leu Gln Tyr Phe Val Gly Lys Lys
1               5                   10                  15

Thr Val Ile Phe Leu Ser Gly Tyr Val Ser Thr Ile Gly Gly Arg Lys
            20                  25                  30

Ile Ser Gln Val Lys Val Lys His Arg Leu Pro Thr Pro Gln Thr Ala
            35                  40                  45

Ser Val Gly Ala Glu Gly Ser Gly Ser Gly Ala Ala Ala Thr Ser Ser
    50                  55                  60

Ala Pro Pro Ala
65

<210> SEQ ID NO 8
<211> LENGTH: 185
<212> TYPE: PRT
<213> ORGANISM: Artificial Sequence
<220> FEATURE:
<223> OTHER INFORMATION: Synthetic construct

<400> SEQUENCE: 8

Leu Val Ser Ala Val Gln Glu Lys Lys Pro Pro Glu Ala Pro Ala Ala
1               5                   10                  15

Asp Glu Ala Ala Gly Pro Ala Thr His Ala Pro Ser Ser Pro Glu Gly
            20                  25                  30

Phe Gly Ser Ser Thr Asp Asp Phe Gln Gly Arg Tyr Ser Pro Thr Tyr
            35                  40                  45

Leu Lys Asp Ala Gly Ala Phe Ser Ile Thr Ala Gly Tyr Thr Thr Gly
    50                  55                  60

Ile Met Arg Phe Glu Ala Glu Ala Met Arg Ser Arg Phe Gln Val Asn
65                  70                  75                  80

Gly Ser Lys Trp Asn Pro Val Glu Asn Ala Tyr Ile Phe Ala Ala Ala
                85                  90                  95

Lys Pro Ser Glu Asn Ile Ser Tyr Pro Ala Gln Ile Leu Glu Thr Gln
            100                 105                 110

Lys Tyr Phe Val Thr Leu Thr Tyr Gln Phe Lys Gly Gly Leu Gln Tyr
            115                 120                 125

Phe Val Gly Lys Lys Thr Val Ile Phe Leu Ser Gly Tyr Val Ser Thr
```

```
                130                 135                 140
Ile Gly Gly Arg Lys Ile Ser Gln Val Lys Val Lys His Arg Leu Pro
145                 150                 155                 160

Thr Pro Gln Thr Ala Ser Val Gly Ala Glu Gly Ser Gly Ser Gly Ala
                165                 170                 175

Ala Ala Thr Ser Ser Ala Pro Pro Ala
            180                 185

<210> SEQ ID NO 9
<211> LENGTH: 23
<212> TYPE: PRT
<213> ORGANISM: Artificial Sequence
<220> FEATURE:
<223> OTHER INFORMATION: Synthetic construct

<400> SEQUENCE: 9

Gly Gly Lys Thr Leu Asn Ala Val Gln Glu Lys Lys Pro Pro Glu Ala
1               5                   10                  15

Pro Ala Ala Asp Glu Ala Ala
            20

<210> SEQ ID NO 10
<211> LENGTH: 324
<212> TYPE: PRT
<213> ORGANISM: Artificial Sequence
<220> FEATURE:
<223> OTHER INFORMATION: Synthetic construct

<400> SEQUENCE: 10

Met Lys Lys Arg Ile Arg Val Phe Ala Phe Ala Val Phe Met Leu Gly
1               5                   10                  15

Leu Pro Ser Val Ser Phe Ala Ser Pro Gln Pro Val Asp Phe Ser Tyr
            20                  25                  30

His Glu Gly Ala Ser Gly Phe Phe Ala Ser Val Gln Tyr Lys Tyr Gly
        35                  40                  45

Ala Pro Tyr Phe Gly Ser Leu Thr Leu Glu Ser Gly Gly Lys Thr Leu
    50                  55                  60

Asn Leu Val Ser Ala Val Gln Glu Lys Lys Pro Pro Glu Ala Pro Ala
65                  70                  75                  80

Ala Asp Glu Ala Ala Glu Pro Ala Thr Pro Ala Pro Ser Ser Pro Glu
                85                  90                  95

Gly Phe Gly Ser Ser Thr Asp Asp Phe Gln Gly Arg Tyr Ser Pro Ala
            100                 105                 110

Tyr Leu Lys Asp Ala Gly Ala Phe Ser Ile Thr Ala Gly Tyr Thr Thr
        115                 120                 125

Gly Ile Met Arg Phe Glu Ala Glu Ala Met Arg Ser Arg Phe Gln Val
    130                 135                 140

Asn Gly Ser Lys Trp Asn Pro Val Glu Asn Ala Tyr Ile Phe Ala Ala
145                 150                 155                 160

Ala Lys Pro Ser Glu Asn Ile Ser Tyr Pro Ala Gln Ile Leu Glu Ala
                165                 170                 175

Gln Lys Tyr Phe Val Thr Leu Glu Asn Arg Asp Val Ala Ile Thr Ser
            180                 185                 190

Leu Val Ala Asn Ala Cys Tyr Asp Met Met Pro Ala Thr Ser Ser Ile
        195                 200                 205

Ala Pro Ser Ala Cys Val Gly Val Gly Val Ser Phe Ala Lys Leu Leu
    210                 215                 220
```

Gly Val Leu Glu Gln Arg Leu Thr Tyr Gln Phe Lys Gly Gly Ser Gln
225                 230                 235                 240

Tyr Phe Val Gly Lys Lys Thr Val Ile Phe Leu Ser Gly Tyr Val Ser
            245                 250                 255

Thr Ile Gly Gly Arg Lys Ile Thr Gln Val Lys Val Lys His Arg Leu
        260                 265                 270

Pro Thr Pro Gln Thr Ala Ser Val Gly Ala Glu Gly Ser Gly Ala Gly
    275                 280                 285

Ala Ala Ala Thr Ser Ser Ala Pro Pro Ala Pro Ile His Leu Leu Tyr
    290                 295                 300

Pro Asp Ala Asn Leu Ser Leu Ala Tyr Tyr Gly Phe Glu Leu Gly Val
305                 310                 315                 320

Arg Leu Val Phe

<210> SEQ ID NO 11
<211> LENGTH: 975
<212> TYPE: DNA
<213> ORGANISM: Artificial Sequence
<220> FEATURE:
<223> OTHER INFORMATION: Synthetic construct

<400> SEQUENCE: 11
atgaagaaga gaatccgggt tttcgcgttt gcagtgttca tgcttgggtt gccctccgta      60
tcatttgctt ctccacaacc cgtggatttt tcgtaccacg agggtgcatc cggcttttt     120 gccagcgttc agtataagta cggtgcaccc tatttcggaa gccttacact ggaaagcggc     180
gggaagacgc tgaatcttgt gagcgcggtg caggaaaaga accccccgga agccccgca     240 gctgacgaag ctgctgaacc tgccaccccct gctccctcaa gccctgaagg gtttggttca     300
tctaccgatg attttcaagg taggtactcg ccaacctatt taaggacgc aggagccttt     360 tcaataacag cgggttatac caccggtatt atgagatttg aagcagaggc tatgcgttcg     420
cgtttccagg taaatggcag taatggaat cctgtagaga acgcttatat atttgccgct     480
gctaaaccca gtgagaatat atcgtaccct gctcagatac tggaggcaca aaagtacttc     540
gtcaccttgg aaaacaggga tgttgccatc acttcgctgg tggcaaatgc ctgctacgac     600
atgatgccag caacctctag catcgcacct agtgcgtgcg tgggtgtagg ggttagcttt     660
gccaaactgt taggtgttct ggaacaaagg ctaacctatc aattcaaagg tggattgcaa     720
tattttgtcg gcaaaaagac cgtcatcttc ctatctggat acgtatccac aataggtgga     780
aggaaaatca ctcaggtaaa agtgaaacat cgtttgtcca cgcctcagac cgcgtcagtt     840
ggtgcagaag cagtggagc aggtgctgct gcaacatctt ctgctccccc agcccccatt     900
cacctgttgt acccagatgc aaatttatcg ctagcgtact acgggtttga gcttggggtg     960
cgtcttgttt tctaa                                                      975

<210> SEQ ID NO 12
<211> LENGTH: 975
<212> TYPE: DNA
<213> ORGANISM: Artificial Sequence
<220> FEATURE:
<223> OTHER INFORMATION: Synthetic construct

<400> SEQUENCE: 12
atgaagaaga gaatccgggt tttcgcgttt gcagtgttca tgcttgggtt gccctccgta      60
tcatttgctt ctccacaacc cgtggatttt tcgtaccacg agggtgcatc cggcttttt     120 gccagcgttc agtataagta cggtgcaccc tatttcggaa gccttacact ggaaagcggc     180

```
gggaagattc tgaatcttgt gagcgcggtg caggaaaaga accccccgga agcccccgca    240
gctgacgaag ctgctggacc tgccacccat gctccctcaa gccctgaagg gtttggttca    300
tctaccgatg attttcaagg taggtactcg ccaacctatt taaaggacgc aggagccttt    360
tcaataacag cgggttatac caccggtatt atgagatttg aagcagaggc tatgcgttcg    420
cgtttccagg taaatggcag taaatggaat cctgtagaga acgcttatat atttgccgct    480
gctaaaccca gtgagaatat atcgtaccct gctcagatac tggagacaca aaagtacttc    540
gtcaccttgg aaaacaggga tgttgccatc acttcgctgg tggcaagtgc ctgctacgac    600
atgatgccag caacctctag catcgcacct agtgcgtgcg tgggtgtagg ggttagcttt    660
gccaaactgt taggtgttct ggaacaaagg ctaacctatc aattcaaagg tggattgcaa    720
tattttgtcg gcaaaaagac cgtcatcttc ctatctggat acgtatccac aataggtgga    780
aggaaaatct ctcaggtaaa agtgaaacat cgtttgccca cgcctcagac cgcgtcagtt    840
ggtgcagaag gcagtggatc aggtgctgct gcaacatctt ctgctccccc agccctcatc    900
cacctgttgt acccagatgc aaatttatcg ctagcgtact acgggtttga gcttggggtg    960
cgtcttgttt tctaa                                                    975

<210> SEQ ID NO 13
<211> LENGTH: 975
<212> TYPE: DNA
<213> ORGANISM: Artificial Sequence
<220> FEATURE:
<223> OTHER INFORMATION: Synthetic construct

<400> SEQUENCE: 13
atgaagaaga gaatccgggt tttcgcgttt gcagtgttca tgcttgggtt gccctccgta     60
tcatttgctt ctccacaacc cgtggatttt tcgtaccacg agggtgcatc cggcttttttt   120 gccagcgttc agtataagta cggtgcaccc tatttcggaa gccttacact ggaaagcggc    180
gggaagacgc tgaatcttgt gagcgcggtg caggaaaaga accccccgga agcccccgca    240
gctgacgaag ctgctgaacc tgccaccccct gctccctcaa gccctgaagg gtttggttca   300
tctaccgatg attttcaagg taggtactcg ccagcctatt taaaggacgc aggagccttt    360
tcaataacag cgggttatac caccggtatt atgagatttg aagcagaggc tatgcgttcg    420
cgtttccagg taaatggcag taaatggaat cctgtagaga acgcttatat atttgccgct    480
gctaaaccca gtgagaatat atcgtaccct gctcagatac tggaggcaca aaagtacttc    540
gtcaccttgg aaaacaggga tgttgccatc acttcgctgg tggcaaatgc ctgctacgac    600
atgatgccag caacctctag catcgcacct agtgcgtgcg tgggtgtagg ggttagcttt    660
gccaaactgt taggtgttct ggaacaaagg ctaacctatc aattcaaagg tggatcgcaa    720
tattttgtcg gcaaaaagac cgtcatcttc ctatctggat acgtatccac aataggtgga    780
aggaaaatca ctcaggtaaa agtgaaacat cgtttgccca cgcctcagac cgcgtcagtt    840
ggtgcagaag gcagtggagc aggtgctgct gcaacatctt ctgctccccc agccccccatt   900 cacctgttgt acccagatgc aaatttatcg ctagcgtact acgggtttga gcttggggtg    960
cgtcttgttt tctaa                                                    975

<210> SEQ ID NO 14
<211> LENGTH: 360
<212> TYPE: DNA
<213> ORGANISM: Artificial Sequence
<220> FEATURE:
```

<223> OTHER INFORMATION: Synthetic construct

<400> SEQUENCE: 14

```
ctgaatcttg tgagcgcggt gcaggaaaag aaaccccggg aagcccccgc agctgacgaa      60
gctgctgaac ctgccacccc tgctccctca agccctgaag ggtttggttc atctaccgat     120
gattttcaag gtaggtactc gccaacctat ttaaaggacg caggagcctt ttcaataaca     180
gcgggttata ccaccggtat tatgagattt gaagcagagg ctatgcgttc gcgtttccag     240
gtaaatggca gtaaatggaa tcctgtagag aacgcttata tatttgccgc tgctaaaccc     300
agtgagaata tatcgtaccc tgctcagata ctggaggcac aaaagtactt cgtcaccttg     360
```

<210> SEQ ID NO 15
<211> LENGTH: 204
<212> TYPE: DNA
<213> ORGANISM: Artificial Sequence
<220> FEATURE:
<223> OTHER INFORMATION: Synthetic construct

<400> SEQUENCE: 15

```
ctaacctatc aattcaaagg tggattgcaa tattttgtcg gcaaaaagac cgtcatcttc      60
ctatctggat acgtatccac aataggtgga aggaaaatca ctcaggtaaa agtgaaacat     120
cgtttgtcca cgcctcagac cgcgtcagtt ggtgcagaag gcagtggagc aggtgctgct     180
gcaacatctt ctgctccccc agcc                                            204
```

<210> SEQ ID NO 16
<211> LENGTH: 564
<212> TYPE: DNA
<213> ORGANISM: Artificial Sequence
<220> FEATURE:
<223> OTHER INFORMATION: Synthetic construct

<400> SEQUENCE: 16

```
ctgaatcttg tgagcgcggt gcaggaaaag aaaccccggg aagcccccgc agctgacgaa      60
gctgctgaac ctgccacccc tgctccctca agccctgaag ggtttggttc atctaccgat     120
gattttcaag gtaggtactc gccaacctat ttaaaggacg caggagcctt ttcaataaca     180
gcgggttata ccaccggtat tatgagattt gaagcagagg ctatgcgttc gcgtttccag     240
gtaaatggca gtaaatggaa tcctgtagag aacgcttata tatttgccgc tgctaaaccc     300
agtgagaata tatcgtaccc tgctcagata ctggaggcac aaaagtactt cgtcaccttg     360
ctaacctatc aattcaaagg tggattgcaa tattttgtcg gcaaaaagac cgtcatcttc     420
ctatctggat acgtatccac aataggtgga aggaaaatca ctcaggtaaa agtgaaacat     480
cgtttgtcca cgcctcagac cgcgtcagtt ggtgcagaag gcagtggagc aggtgctgct     540
gcaacatctt ctgctccccc agcc                                            564
```

<210> SEQ ID NO 17
<211> LENGTH: 51
<212> TYPE: DNA
<213> ORGANISM: Artificial Sequence
<220> FEATURE:
<223> OTHER INFORMATION: Synthetic construct

<400> SEQUENCE: 17

```
gcggtgcagg aaaagaaacc cccggaagcc cccgcagctg acgaagctgc t               51
```

<210> SEQ ID NO 18
<211> LENGTH: 19

```
<212> TYPE: DNA
<213> ORGANISM: Artificial Sequence
<220> FEATURE:
<223> OTHER INFORMATION: Synthetic construct

<400> SEQUENCE: 18
ctgaatcttg tgagcgcgg                                                    19

<210> SEQ ID NO 19
<211> LENGTH: 23
<212> TYPE: DNA
<213> ORGANISM: Artificial Sequence
<220> FEATURE:
<223> OTHER INFORMATION: Synthetic construct

<400> SEQUENCE: 19
caaggtgacg aagtactttt gtg                                               23

<210> SEQ ID NO 20
<211> LENGTH: 27
<212> TYPE: DNA
<213> ORGANISM: Artificial Sequence
<220> FEATURE:
<223> OTHER INFORMATION: Synthetic construct

<400> SEQUENCE: 20
ctaacctatc aattcaaagg tggattg                                           27

<210> SEQ ID NO 21
<211> LENGTH: 406
<212> TYPE: PRT
<213> ORGANISM: Artificial Sequence
<220> FEATURE:
<223> OTHER INFORMATION: Synthetic construct

<400> SEQUENCE: 21
```

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ser Asp Val Asp
            20                  25                  30

Tyr Val Ser Lys Phe Gly Glu Gly Ser Phe Tyr Val Gly Leu Asn Tyr
        35                  40                  45

Ser Pro Ala Phe Ser Lys Ile Asn Gly Phe Glu Ile Arg Glu Ser Thr
    50                  55                  60

Gly Glu Thr Ala Ala Val Tyr Pro Tyr Met Lys Asp Gly Thr Arg Val
65                  70                  75                  80

Glu Trp Lys Ala Glu Lys Phe Asp Trp Asn Thr Pro Asp Pro Arg Ile
                85                  90                  95

Lys Phe Lys Asn Asn Pro Ile Val Ala Leu Glu Gly Ser Val Gly Tyr
            100                 105                 110

Ser Ile Gly Val Ala Arg Val Glu Leu Glu Ile Gly Tyr Glu Gln Phe
        115                 120                 125

Lys Thr Lys Gly Ile Arg Asp Thr Gly Ser Lys Glu Glu Ala Asp
    130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
            180                 185                 190

-continued

```
Gly Lys Val Cys Lys Lys Gly Gly Ser Gly Asn Ala Ala Gly Ser Trp
            195                 200                 205
Lys Cys Thr Gln Thr Gly Ser Asn Gly Val Ser Thr Ala Glu Phe Ser
210                 215                 220
Lys Ile Phe Thr Lys Ala Asp Val Asn Thr Asp Asn Lys Gly Lys Ala
225                 230                 235                 240
Trp Pro Asn Gly Asn Asn Asp Ala Ala Lys Ala Glu Asp Leu Ser Ile
                245                 250                 255
Ala Leu Asn Arg Glu Leu Thr Ser Ala Glu Lys Asn Lys Val Ala Gly
            260                 265                 270
Leu Leu Thr Arg Thr Ile Ser Gly Gly Glu Val Val Glu Ile Arg Ala
        275                 280                 285
Val Ser Thr Thr Ser Val Met Leu Asn Gly Cys Tyr Asp Leu Gln Ser
    290                 295                 300
Glu Gly Phe Ser Ile Val Pro Tyr Ala Cys Leu Gly Val Gly Ala Asn
305                 310                 315                 320
Phe Val Gly Ile Val Asp Gly His Val Thr Pro Lys Leu Ala Tyr Lys
                325                 330                 335
Val Lys Ala Gly Leu Ser Tyr Glu Leu Ser Pro Glu Ile Ser Met Phe
            340                 345                 350
Ala Gly Gly Phe Tyr His Arg Val Leu Gly Glu Gly Glu Tyr Asp Asp
        355                 360                 365
Leu Pro Val Gln Arg Leu Val Asp Asp Ala Thr Thr Asn Lys Thr Lys
    370                 375                 380
Glu Phe Ala Lys Ala Ser Phe Lys Met Ala Tyr Thr Gly Ala Glu Ile
385                 390                 395                 400
Gly Val Arg Ser Ala Phe
                405

<210> SEQ ID NO 22
<211> LENGTH: 406
<212> TYPE: PRT
<213> ORGANISM: Artificial Sequence
<220> FEATURE:
<223> OTHER INFORMATION: Synthetic construct

<400> SEQUENCE: 22

Met Lys Glu Arg Lys Leu Ala Leu Ser Gly Ala Val Ala Met Thr Val
1               5                   10                  15
Leu Val Ser Thr Ala Gly Thr Gly Thr Ala Ala Gly Ser Asp Val Asp
            20                  25                  30
Tyr Val Ser Lys Phe Gly Glu Gly Ser Phe Tyr Val Gly Leu Asn Tyr
        35                  40                  45
Ser Pro Ala Phe Ser Lys Ile Asn Gly Phe Glu Ile Arg Glu Ser Thr
    50                  55                  60
Gly Glu Thr Ala Ala Val Tyr Pro Tyr Met Lys Asp Gly Thr Arg Val
65                  70                  75                  80
Glu Trp Lys Ala Glu Lys Phe Asp Trp Asn Thr Asp Pro Arg Ile
                85                  90                  95
Lys Phe Lys Asn Asn Pro Ile Val Ala Leu Glu Gly Ser Val Gly Tyr
                100                 105                 110
Ser Ile Gly Val Ala Arg Val Glu Leu Glu Ile Gly Tyr Glu Gln Phe
            115                 120                 125
Lys Thr Lys Gly Ile Arg Asp Thr Gly Ser Lys Glu Glu Glu Ala Asp
        130                 135                 140
```

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
            165                 170                 175

Ile Val Lys Phe Ala Glu Ala Val Gly Thr Ser Ala Lys Asp Ile Asp
        180                 185                 190

Gly Lys Val Cys Lys Lys Gly Gly Ser Gly Asn Ala Ala Gly Ser Trp
    195                 200                 205

Lys Cys Thr Gln Thr Gly Ser Asn Gly Val Ser Thr Ala Glu Phe Ser
210                 215                 220

Lys Ile Phe Thr Lys Ala Asp Val Asn Thr Asp Asn Lys Gly Lys Ala
225                 230                 235                 240

Arg Pro Asn Gly Asn Asn Asp Ala Ala Lys Ala Glu Asp Leu Ser Ile
            245                 250                 255

Ala Leu Asn Arg Glu Leu Thr Ser Ala Glu Lys Asn Lys Val Ala Gly
        260                 265                 270

Leu Leu Thr Arg Thr Ile Ser Gly Gly Glu Val Val Glu Ile Arg Ala
    275                 280                 285

Val Ser Thr Thr Ser Val Met Leu Asn Gly Cys Tyr Asp Leu Gln Ser
290                 295                 300

Glu Gly Phe Ser Ile Val Pro Tyr Ala Cys Leu Gly Val Gly Ala Asn
305                 310                 315                 320

Phe Val Gly Ile Val Asp Gly His Val Thr Pro Lys Leu Ala Tyr Lys
            325                 330                 335

Val Lys Ala Gly Leu Ser Tyr Glu Leu Ser Pro Glu Ile Ser Met Phe
        340                 345                 350

Ala Gly Gly Phe Tyr His Arg Val Leu Gly Glu Gly Tyr Asp Asp
    355                 360                 365

Leu Pro Val Gln Arg Leu Val Asp Asp Ala Thr Thr Asn Lys Thr Lys
370                 375                 380

Glu Phe Ala Lys Ala Ser Phe Lys Met Ala Tyr Thr Gly Ala Glu Ile
385                 390                 395                 400

Gly Val Arg Phe Ala Phe
            405

<210> SEQ ID NO 23
<211> LENGTH: 400
<212> TYPE: PRT
<213> ORGANISM: Artificial Sequence
<220> FEATURE:
<223> OTHER INFORMATION: Synthetic construct

<400> SEQUENCE: 23

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ser Asp Val Asp
            20                  25                  30

Tyr Val Ser Lys Phe Gly Glu Gly Ser Phe Tyr Val Gly Leu Asn Tyr
        35                  40                  45

Ser Pro Ala Phe Ser Lys Ile Asn Gly Phe Glu Ile Arg Glu Ser Thr
    50                  55                  60

Gly Glu Thr Ala Ala Val Tyr Pro Tyr Met Lys Asp Gly Thr Arg Val
65                  70                  75                  80

Glu Trp Lys Ala Glu Lys Phe Asp Trp Asn Thr Pro Asp Pro Arg Ile
                85                  90                  95

Lys Phe Lys Asn Asn Pro Ile Val Ala Leu Glu Gly Ser Val Gly Tyr
            100                 105                 110

Ser Ile Gly Val Ala Arg Val Glu Leu Glu Ile Gly Tyr Glu Gln Phe
        115                 120                 125

Lys Thr Lys Gly Ile Arg Asp Thr Gly Ser Lys Glu Glu Ala Asp
    130                 135                 140

Ala Val Tyr Leu Leu Ala Lys Lys Leu Pro His Thr Leu Val Ser Asp
145                 150                 155                 160

Gln Ser Asp Lys Phe Leu Glu Leu Lys Asn Thr Lys Ala Ala Glu
                165                 170                 175

Ile Val Lys Phe Ala Glu Ala Val Gly Thr Ser Ala Lys Asp Ile Asp
                180                 185                 190

Lys Lys Val Cys Lys Lys Thr Glu Asn Thr Glu Asp Ser Trp Lys Cys
                195                 200                 205

Thr Gln Thr Gly Asn Asp Gly Ser Asp Lys Glu Phe Ser Lys Ile Phe
            210                 215                 220

Thr Lys Lys Asn Val Asp Thr Ser Gly Lys Ala Trp Pro Asn Gly Ser
225                 230                 235                 240

Asp Ala Ala Lys Ala Glu Asp Leu Ser Thr Ala Leu Asn Arg Glu Leu
                245                 250                 255

Thr Ser Ala Glu Lys Asn Lys Val Ala Gly Leu Leu Thr Arg Thr Ile
            260                 265                 270

Ser Gly Gly Glu Val Val Glu Ile Arg Ala Val Ser Thr Thr Ser Val
        275                 280                 285

Met Leu Asn Gly Cys Tyr Asp Leu Gln Ser Gly Phe Ser Ile Val
    290                 295                 300

Pro Tyr Ala Cys Leu Gly Val Gly Ala Asn Phe Val Gly Ile Val Asp
305                 310                 315                 320

Gly His Val Thr Ser Lys Leu Ala Tyr Lys Val Lys Ala Gly Leu Ser
                325                 330                 335

Tyr Glu Leu Ser Pro Glu Ile Ser Met Phe Ala Gly Gly Phe Tyr His
                340                 345                 350

Arg Val Leu Gly Glu Gly Glu Tyr Asp Asp Leu Pro Val Gln Arg Leu
            355                 360                 365

Val Asp Asp Ala Thr Thr Asn Lys Thr Lys Glu Phe Ala Lys Ala Ser
    370                 375                 380

Phe Lys Met Ala Tyr Thr Gly Ala Glu Ile Gly Val Arg Phe Ala Phe
385                 390                 395                 400

<210> SEQ ID NO 24
<211> LENGTH: 400
<212> TYPE: PRT
<213> ORGANISM: Artificial Sequence
<220> FEATURE:
<223> OTHER INFORMATION: Synthetic construct

<400> SEQUENCE: 24

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ser Asp Val Asp
                20                  25                  30

Tyr Val Ser Lys Phe Gly Glu Gly Ser Phe Tyr Val Gly Leu Asn Tyr
            35                  40                  45

Ser Pro Ala Phe Ser Lys Ile Asn Gly Phe Glu Ile Arg Glu Ser Thr
        50                  55                  60

Gly Glu Thr Ala Ala Val Tyr Pro Tyr Met Lys Asp Gly Thr Arg Val
65                  70                  75                  80

Glu Trp Lys Ala Glu Lys Phe Asp Trp Asn Thr Pro Asp Pro Arg Ile
                85                  90                  95

Lys Phe Lys Asn Asn Pro Ile Val Ala Leu Glu Gly Ser Val Gly Tyr
            100                 105                 110

Ser Ile Gly Val Ala Arg Val Glu Leu Glu Ile Gly Tyr Glu Gln Phe
        115                 120                 125

Lys Thr Lys Gly Ile Arg Asp Thr Gly Ser Lys Glu Glu Ala Asp
130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
            180                 185                 190

Lys Lys Val Cys Lys Lys Thr Glu Asn Thr Glu Asp Ser Trp Lys Cys
        195                 200                 205

Thr Gln Thr Gly Asn Asp Gly Gly Asp Lys Glu Phe Ser Lys Ile Phe
210                 215                 220

Thr Lys Lys Asn Val Asp Thr Ser Gly Lys Ala Trp Pro Asn Gly Ser
225                 230                 235                 240

Asp Ala Ala Lys Ala Glu Asp Leu Ser Thr Ala Leu Asn Arg Glu Leu
                245                 250                 255

Thr Ser Ala Glu Lys Asn Lys Val Ala Gly Leu Leu Thr Arg Thr Ile
            260                 265                 270

Ser Gly Gly Glu Val Val Glu Ile Arg Ala Val Ser Thr Thr Ser Val
        275                 280                 285

Met Leu Asn Gly Cys Tyr Asp Leu Gln Ser Glu Gly Phe Ser Ile Val
290                 295                 300

Pro Tyr Ala Cys Leu Gly Val Gly Ala Asn Phe Val Gly Ile Val Asp
305                 310                 315                 320

Gly His Val Thr Pro Lys Leu Ala Tyr Lys Val Lys Ala Gly Leu Ser
                325                 330                 335

Tyr Glu Leu Ser Pro Glu Ile Ser Met Phe Ala Gly Gly Phe Tyr His
            340                 345                 350

Arg Val Leu Gly Glu Gly Tyr Asp Asp Leu Pro Val Leu Arg Leu
        355                 360                 365

Val Asp Asp Ala Thr Thr Asn Lys Thr Lys Glu Phe Ala Lys Ala Ser
370                 375                 380

Phe Lys Met Ala Tyr Thr Gly Ala Glu Ile Gly Val Arg Phe Ala Phe
385                 390                 395                 400

<210> SEQ ID NO 25
<211> LENGTH: 280
<212> TYPE: PRT
<213> ORGANISM: Artificial Sequence
<220> FEATURE:
<223> OTHER INFORMATION: Synthetic construct

<400> SEQUENCE: 25

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ala Asp Val Asp
            20                  25                  30

```
Tyr Val Ser Lys Phe Gly Glu Gly Ser Phe Tyr Val Gly Leu Asn Tyr
             35                  40                  45

Ser Pro Ala Phe Ser Lys Ile Asn Gly Phe Glu Ile Arg Glu Ser Thr
 50                  55                  60

Gly Glu Thr Ala Ala Val Tyr Pro Tyr Met Lys Asp Gly Thr Arg Val
 65                  70                  75                  80

Glu Trp Lys Ala Glu Lys Phe Asp Trp Asn Thr Pro Asp Pro Arg Ile
                 85                  90                  95

Lys Phe Lys Asn Asn Pro Ile Val Ala Leu Glu Gly Ser Val Gly Tyr
                100                 105                 110

Ser Ile Gly Ile Ala Arg Val Glu Leu Glu Ile Gly Tyr Glu Gln Phe
            115                 120                 125

Lys Thr Lys Gly Ile Arg Asp Thr Gly Ser Lys Glu Glu Ala Asp
        130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
                180                 185                 190

Gly Lys Val Cys Lys Lys Thr Gly Asn Glu Ala Asp Ser Trp Lys Cys
            195                 200                 205

Thr Gln Thr Gly Asn Gly Ser Gly Asn Ala Thr Glu Phe Ser Lys Ile
        210                 215                 220

Phe Thr Lys Lys Asn Val Asp Ala Glu Gly Lys Gly Lys Ala Trp Pro
225                 230                 235                 240

Asn Gly His Thr Asp Ser Ala Ala Lys Ala Glu Asp Leu Ser Thr Ala
                245                 250                 255

Leu Asn Arg Glu Leu Thr Ser Ala Glu Lys Asn Lys Val Ala Gly Leu
                260                 265                 270

Leu Thr Arg Thr Ile Ser Gly Gly
                275                 280

<210> SEQ ID NO 26
<211> LENGTH: 86
<212> TYPE: PRT
<213> ORGANISM: Artificial Sequence
<220> FEATURE:
<223> OTHER INFORMATION: Synthetic construct

<400> SEQUENCE: 26

Lys Asn Thr Lys Ala Ala Glu Ile Val Lys Phe Ala Glu Ala Val Gly
 1               5                  10                  15

Thr Ser Ala Lys Asp Ile Asp Gly Lys Val Cys Lys Lys Gly Gly Ser
                 20                  25                  30

Gly Asn Ala Ala Gly Ser Trp Lys Cys Thr Gln Thr Gly Ser Asn Gly
             35                  40                  45

Val Ser Thr Ala Glu Phe Ser Lys Ile Phe Phe Lys Ala Asp Val Asn
         50                  55                  60

Thr Asp Asn Lys Gly Lys Ala Trp Pro Asn Gly Asn Asn Asp Ala Ala
 65                  70                  75                  80

Lys Ala Glu Asp Leu Ser
                 85

<210> SEQ ID NO 27
<211> LENGTH: 84
```

```
<212> TYPE: PRT
<213> ORGANISM: Artificial Sequence
<220> FEATURE:
<223> OTHER INFORMATION: Synthetic construct

<400> SEQUENCE: 27

Lys Asn Thr Lys Ala Ala Glu Ile Val Lys Phe Ala Glu Ala Val Gly
1               5                   10                  15

Thr Ser Ala Lys Asp Ile Asp Lys Lys Val Cys Lys Lys Thr Asp Asn
            20                  25                  30

Thr Glu Gly Ser Trp Lys Cys Thr Gln Thr Gly Asn Asp Gly Gly Asp
        35                  40                  45

Lys Glu Phe Ser Lys Thr Phe Thr Lys Thr Gly Val Asn Glu Ala Thr
    50                  55                  60

Lys Gly Lys Ala Trp Pro Asn Gly His Thr Asp Ser Ala Ala Lys Ala
65                  70                  75                  80

Glu Asp Leu Ser

<210> SEQ ID NO 28
<211> LENGTH: 84
<212> TYPE: PRT
<213> ORGANISM: Artificial Sequence
<220> FEATURE:
<223> OTHER INFORMATION: Synthetic construct

<400> SEQUENCE: 28

Lys Asn Thr Lys Ala Ala Glu Ile Val Lys Phe Ala Glu Ala Val Gly
1               5                   10                  15

Thr Ser Ala Lys Asn Ile Asp Lys Val Cys Lys Lys Thr Gly Asn
            20                  25                  30

Asp Ala Asn Ser Trp Lys Cys Leu Gln Thr Gly Arg Asp Asp Ser Thr
        35                  40                  45

Ser Gly Lys Lys Phe Ser Glu Ile Phe Thr Lys Ala Asp Val Asn Thr
    50                  55                  60

Asp Asn Lys Gly Lys Ala Trp Pro Asn Gly Asn Glu Ala Ala Lys Ala
65                  70                  75                  80

Glu Asp Leu Ser

<210> SEQ ID NO 29
<211> LENGTH: 86
<212> TYPE: PRT
<213> ORGANISM: Artificial Sequence
<220> FEATURE:
<223> OTHER INFORMATION: Synthetic construct

<400> SEQUENCE: 29

Lys Asn Thr Lys Ala Ala Glu Ile Val Lys Phe Ala Glu Ala Val Gly
1               5                   10                  15

Thr Ser Ala Lys Asn Ile Asp Lys Lys Val Cys Lys Lys Thr Gly Asn
            20                  25                  30

Asp Ala Asn Ser Trp Lys Cys Glu Gln Thr Gly Ser Gly Ala Glu Thr
        35                  40                  45

Ser Ala Lys Ala Phe Ser Glu Ile Phe Thr Lys Ala Gly Val Asn Glu
    50                  55                  60

Ala Thr Lys Gly Lys Ala Trp Pro Asn Gly His Thr Gly Gly Ala Ala
65                  70                  75                  80

Lys Ala Glu Asp Leu Ser
                85
```

<210> SEQ ID NO 30
<211> LENGTH: 1221
<212> TYPE: DNA
<213> ORGANISM: Artificial Sequence
<220> FEATURE:
<223> OTHER INFORMATION: Synthetic construct

<400> SEQUENCE: 30

| | | | | | |
|---|---|---|---|---|---|
| atgaaggaaa | gaaaacttgc | gctaagtgga | gcggtggcga | tgacagtttt | ggtgtcgact | 60 |
| gctggtaccg | ggactgcggc | agggtcggac | gtggactatg | taagtaagtt | cggtgagggc | 120 |
| agcttctacg | taggtctaaa | ctatagtccg | gcgtttagta | agataaatgg | gtttgagata | 180 |
| agagagagta | ccggggaaac | tgcggcagta | tatccgtaca | tgaaagatgg | aactagagtg | 240 |
| gagtggaaag | ctgagaagtt | cgactggaac | acaccagatc | cgaggattaa | gtttaaaaac | 300 |
| aatcctatcg | tggcgttaga | aggaagtgtg | ggctacagta | tcggggtagc | gagagtagaa | 360 |
| ctggagatcg | gctatgaaca | gttcaagacg | aaaggaataa | gagatacggg | aagtaaggaa | 420 |
| gaagaagctg | atgccgtgta | cctgttggct | aagaagctac | cgcataccct | ggtgagtgac | 480 |
| cagagcgata | aattcctgga | ggagctgaag | aatacgaaag | cggcggagat | cgttaaattt | 540 |
| gctgaggctg | ttggcacatc | ggcaaaggat | attgatggaa | aggtttgtaa | gaagggcggc | 600 |
| agcggcaatg | ccgcgggcag | ctggaagtgt | acgcagactg | gcagcaacgg | cgtcagcacc | 660 |
| gcagagttca | gtaaaatatt | tacgaaggca | gacgtaaata | ctgacaacaa | aggcaaagca | 720 |
| tggcctaacg | ggaacaacga | cgctgcgaaa | gcggaagacc | taagtattgc | gttgaataga | 780 |
| gaactaacca | gcgccgaaaa | gaacaaggta | gctggcctac | taaccaggac | tatatccggt | 840 |
| ggtgaggtag | tggagatccg | tgcggtgtcg | acaacgtcag | taatgttgaa | tggttgttat | 900 |
| gatctgcaga | gtgaagggtt | tagtatagta | ccttatgcat | gtcttggtgt | aggtgctaac | 960 |
| ttcgttggca | ttgttgacgg | acacgtcact | cctaaactgg | cttacaaggt | caaggctggt | 1020 |
| ttgagttatg | agttgtcgcc | ggaaatctca | atgttcgctg | gtgggttcta | tcatcgggtg | 1080 |
| ctgggtgaag | gtgagtacga | tgatctgcca | gtgcagaggc | ttgtagacga | tgcgactacg | 1140 |
| aacaagacta | aagagttcgc | taaagcgtcg | ttcaagatgg | cgtacactgg | tgctgaaatc | 1200 |
| ggtgttaggt | ctgcgttcta | a | | | | 1221 |

<210> SEQ ID NO 31
<211> LENGTH: 1221
<212> TYPE: DNA
<213> ORGANISM: Artificial Sequence
<220> FEATURE:
<223> OTHER INFORMATION: Synthetic construct

<400> SEQUENCE: 31

| | | | | | |
|---|---|---|---|---|---|
| atgaaggaaa | gaaaacttgc | gctaagtgga | gcggtggcga | tgacagtttt | ggtgtcgact | 60 |
| gctggtaccg | ggactgcggc | agggtcggac | gtggactatg | taagtaagtt | cggtgagggc | 120 |
| agcttctacg | taggtctaaa | ctatagtccg | gcgtttagta | agataaatgg | gtttgagata | 180 |
| agagagagta | ccggggaaac | tgcggcagta | tatccgtaca | tgaaagatgg | aactagagtg | 240 |
| gagtggaaag | ctgagaagtt | cgactggaac | acaccagatc | cgaggattaa | gtttaaaaac | 300 |
| aatcctatcg | tggcgttaga | aggaagtgtg | ggctacagta | tcggggtagc | gagagtagaa | 360 |
| ctggagatcg | gctatgaaca | gttcaagacg | aaaggaataa | gagatacggg | aagtaaggaa | 420 |
| gaagaagctg | atgccgtgta | cctgttggct | aagaagctac | cgcataccct | ggtgagtgac | 480 |
| cagagcgata | aattcctgga | ggagctgaag | aatacgaaag | cggcggagat | cgttaaattt | 540 |

```
gctgaggctg ttggcacatc ggcaaaggat attgatggaa aggtttgtaa gaagggcggc      600
agcggcaatg ccgcgggcag ctggaagtgt acgcagactg cagcaacgg cgtcagcacc       660 gcagagttca gtaaaatatt tacgaaggca gacgtaaata ctgacaacaa aggcaaagca      720
cggcctaacg ggaacaacga cgctgcgaaa gcggaagacc taagtattgc gttgaataga     780
gaactaacca gcgccgaaaa gaacaaggta gctggcctac taaccaggac tatatccggt     840
ggtgaggtag tggagatccg tgcggtgtcg acaacgtcag taatgttgaa tggttgttat      900
gatctgcaga gtgaagggtt tagtatagta ccttatgcat gtcttggtgt aggtgctaac    960
ttcgttggca ttgttgacgg acacgtcact cctaaactgg cttacaaggt caaggctggt    1020
ttgagttatg aattgtcgcc ggaaatctca atgttcgctg gtgggttcta tcatcgggtg    1080
ctgggtgaag gtgagtacga tgatctgcca gtgcagaggc ttgtagacga tgcgactacg    1140
aacaagacta aagagttcgc taaagcgtcg ttcaagatgg cgtacactgg tgctgaaatc    1200
ggtgttaggt ttgcgttcta a                                              1221
```

<210> SEQ ID NO 32
<211> LENGTH: 1203
<212> TYPE: DNA
<213> ORGANISM: Artificial Sequence
<220> FEATURE:
<223> OTHER INFORMATION: Synthetic construct

<400> SEQUENCE: 32

```
atgaaggaaa gaaaacttgc gctaagtgga gcggtggcga tgacagtttt ggtgtcgact       60
gctggtaccg ggactgcggc agggtcggac gtggactatg taagtaagtt cggtgagggc     120
agcttctacg taggtctaaa ctatagtccg gcgtttagta agataaatgg gtttgagata     180
agagagagta ccggggaaac tgcggcagta tatccgtaca tgaaagatgg aactagagtg     240
gagtggaaag ctgagaagtt cgactggaac acaccagatc cgaggattaa gtttaaaaac    300
aatcctatcg tggcgttaga aggaagtgtg ggctacagta tcggggtagc gagagtagaa    360
ctggagatcg gctatgaaca gttcaagacg aaaggaataa gagatacggg aagtaaggaa   420
gaagaagctg atgccgtgta cctgttggct aagaagctac cgcataccct ggtgagtgac    480
cagagcgata aattcctgga ggagctgaag aatacgaaag cggcggagat cgttaagttt     540
gctgaggctg tcggtacatc ggcaaaggat attgataaga aggtttgtaa gaagactgaa     600
aatacagaag acagttggaa gtgtacgcag actggcaacg acggcagcga caaggagttc    660
agtaaaatat ttacgaagaa aaacgtagat actagcggca aagcatggcc taacggaagc     720
gacgccgcga aagcggaaga cctaagtact gcgctgaata gagaactaac cagcgccgaa     780
aagaacaagg tagctggcct actaaccagg actatatccg gtggtgaggt agtggagatc   840
cgtgcggtgt cgacaacgtc agtaatgttg aatggttgtt atgatctgca gagtgaaggg     900
tttagtatag taccttatgc atgtcttggt gtaggtgcta acttcgttgg cattgttgac     960
ggacacgtca cttctaaact ggcttacaag gtcaaggctg gtttgagtta tgagttgtcg    1020
ccggaaatct caatgttcgc tggtgggttc tatcatcggg tgctgggtga aggtgagtac    1080
gatgatctgc cagtgcagag gcttgtagac gatgcgacta cgaacaagac taaagagttc     1140
gctaaagcgt cgttcaagat ggcgtacact ggtgctgaaa tcggtgttag gtttgcgttc     1200
taa                                                                 1203
```

<210> SEQ ID NO 33

<211> LENGTH: 1203
<212> TYPE: DNA
<213> ORGANISM: Artificial Sequence
<220> FEATURE:
<223> OTHER INFORMATION: Synthetic construct

<400> SEQUENCE: 33

| | | | | | | |
|---|---|---|---|---|---|---|
| atgaaggaaa | gaaaacttgc | gctaagtgga | gcggtggcga | tgacagtttt | ggtgtcgact | 60 |
| gctggtaccg | ggactgcggc | agggtcggac | gtggactatg | taagtaagtt | cggtgagggc | 120 |
| agcttctacg | taggtctaaa | ctatagtccg | gcgtttagta | agataaatgg | gtttgagata | 180 |
| agagagagta | ccggggaaac | tgcggcagta | tatccgtaca | tgaaagatgg | aactagagtg | 240 |
| gagtggaaag | ctgagaagtt | cgactggaac | acaccagatc | cgaggattaa | gtttaaaaac | 300 |
| aatcctatcg | tggcgttaga | aggaagtgtg | ggctacagta | tcggggtagc | gagagtagaa | 360 |
| ctggagatcg | gctatgaaca | gttcaagacg | aaaggaataa | gagatacggg | aagtaaggaa | 420 |
| gaagaagctg | atgccgtgta | cctattggct | aagaagctac | cgcataccct | ggtgagtgac | 480 |
| cagagcgata | aattcctgga | ggagctgaag | aatacgaaag | cggcggagat | cgttaagttt | 540 |
| gctgaggctg | ttggtacatc | ggcaaaggat | attgataaga | aggtttgtaa | gaagactgaa | 600 |
| aatacagaag | acagttggaa | gtgtacgcag | actggcaacg | acgcggcga | caaggagttc | 660 |
| agtaaaatat | ttacgaagaa | aaacgtagat | actagcggca | agcatggcc | taacggaagc | 720 |
| gacgccgcga | aagcggaaga | cctaagtact | gcgctgaata | gagaactaac | cagcgccgaa | 780 |
| aagaacaagg | tagctggcct | actaaccagg | actatatccg | gtggtgaggt | agtggagatc | 840 |
| cgtgcggtgt | cgacaacgtc | agtaatgttg | aatggttgtt | atgatctgca | gagtgaaggg | 900 |
| tttagtatag | taccttatgc | atgtcttggt | gtaggtgcta | acttcgttgg | cattgttgac | 960 |
| ggacacgtca | ctcctaaact | ggcttacaag | gtcaaggctg | gtttgagtta | tgagttgtcg | 1020 |
| ccggaaatct | caatgttcgc | tggtgggttc | tatcatcggg | tgctgggtga | aggtgagtac | 1080 |
| gatgatctgc | cagtgctgag | gcttgtagac | gatgcgacta | cgaacaagac | taagagttc | 1140 |
| gctaaagcgt | cgttcaagat | ggcgtacact | ggtgctgaaa | tcggtgttag | gtttgcgttc | 1200 |
| taa | | | | | | 1203 |

<210> SEQ ID NO 34
<211> LENGTH: 260
<212> TYPE: DNA
<213> ORGANISM: Artificial Sequence
<220> FEATURE:
<223> OTHER INFORMATION: Synthetic construct

<400> SEQUENCE: 34

| | | | | | | |
|---|---|---|---|---|---|---|
| gaagaatacg | aaagcggcgg | agatcgttaa | atttgctgag | gctgttggca | catcggcaaa | 60 |
| ggatattgat | ggaaaggttt | gtaagaaggg | cggcagcggc | aatgccgcgg | gcagctggaa | 120 |
| gtgtacgcag | actggcagca | acggcgtcag | caccgcagag | ttcagtaaaa | tatttacgaa | 180 |
| ggcagacgta | aatactgaca | acaaaggcaa | agcatggcct | aacgggaaca | acgacgctgc | 240 |
| gaaagcggaa | gacctaagta | | | | | 260 |

<210> SEQ ID NO 35
<211> LENGTH: 254
<212> TYPE: DNA
<213> ORGANISM: Artificial Sequence
<220> FEATURE:
<223> OTHER INFORMATION: Synthetic construct

<400> SEQUENCE: 35

```
gaagaatacg aaagcggcgg agatcgttaa atttgctgag gctgttggta catcggcaaa    60
ggatattgat aagaaggttt gtaagaagac tgacaataca gaaggcagtt ggaagtgtac   120
gcagactggc aacgacggcg gcgacaagga gttcagtaaa acatttacga agacgggcgt   180
gaatgaggcc accaagggca aagcatggcc taacgggcac accgacagcg ccgcgaaagc   240
ggaagaccta agta                                                    254
```

<210> SEQ ID NO 36
<211> LENGTH: 254
<212> TYPE: DNA
<213> ORGANISM: Artificial Sequence
<220> FEATURE:
<223> OTHER INFORMATION: Synthetic construct

<400> SEQUENCE: 36

```
gaagaatacg aaagcggcgg agatcgttaa atttgctgag gctgttggca catcggcaaa    60
gaatattgat aagaaggttt gtaagaagac tggaaatgac gcgaacagtt ggaagtgctt   120
gcagactggc agagacgaca gcacgtcggg gaaaaagttc agtgaaatat ttacgaaggc   180
agacgtaaat actgacaaca aaggcaaagc atggcctaac gggaacgaag ccgcgaaagc   240
ggaagaccta agta                                                    254
```

<210> SEQ ID NO 37
<211> LENGTH: 260
<212> TYPE: DNA
<213> ORGANISM: Artificial Sequence
<220> FEATURE:
<223> OTHER INFORMATION: Synthetic construct

<400> SEQUENCE: 37

```
gaagaatacg aaagcggcgg agatcgttaa atttgctgag gctgttggca catcggcaaa    60
gaatattgat aagaaggttt gtaagaagac tggaaatgac gcgaacagtt ggaagtgcga   120
gcagactggc agcggcgccg agacaagcgc caaggcgttc agtgaaatat ttacgaaggc   180
gggcgtgaat gaggccacca agggcaaagc atggcctaac gggcacaccg cggcgccgc   240 gaaagcggaa gacctaagta                                              260
```

<210> SEQ ID NO 38
<211> LENGTH: 842
<212> TYPE: DNA
<213> ORGANISM: Artificial Sequence
<220> FEATURE:
<223> OTHER INFORMATION: Synthetic construct

<400> SEQUENCE: 38

```
atgaaggaaa gaaaacttgc gctaagtgga gcggtggcga tgacagtttt ggtgtcgact    60
gctggtaccg ggactgcggc aggggcggac gtggactatg taagtaagtt cggtgagggc   120
agcttctacg taggtctaaa ctatagtccg gcgtttagta agataaatgg gtttgagata   180
agagagagta ccggggaaac tgcggcagta tatccgtaca tgaaagatgg aactagagtg   240
gagtggaaag ctgagaagtt cgactggaac acaccagatc cgaggattaa gtttaaaaac   300
aatcctatcg tggcgttgga aggaagtgtg ggctacagta tcgggatagc gagagtagaa   360
ctagagatcg gctatgaaca gttcaagacg aaaggaataa gagatacggg aagtaaggaa   420
gaagaagctg atgccgtgta cctgttggct aagaagctac cgcatacccg ggtgagtgac   480
cagagcgata aattcctgga ggagctgaag aatacgaaag cggcggagat cgttaagttt   540
```

```
gctgaggctg ttggtacatc ggcaaaggat attgatggaa aggtttgtaa gaagactgga    600
aatgaggcgg acagttggaa gtgtacgcag actggcaacg gcagcggcaa cgccacagag    660
tttagtaaaa tatttacgaa gaaaaacgta gatgctgagg gcaaaggcaa agcatggcct    720
aacgggcaca ccgacagcgc cgcgaaagcg gaagacctaa gtactgcgtt gaatagagaa    780
ctaaccagcg ccgaaaagaa caaggtagct ggcctactaa ccaggactat atccggtggc    840
ga                                                                   842
```

<210> SEQ ID NO 39
<211> LENGTH: 18
<212> TYPE: PRT
<213> ORGANISM: Artificial Sequence
<220> FEATURE:
<223> OTHER INFORMATION: Synthetic construct

<400> SEQUENCE: 39

Gly Thr Gly Thr Ala Ala Gly Ser Asp Val Asp Tyr Val Ser Lys Phe
1               5                   10                  15

Gly Glu

<210> SEQ ID NO 40
<211> LENGTH: 9
<212> TYPE: PRT
<213> ORGANISM: Artificial Sequence
<220> FEATURE:
<223> OTHER INFORMATION: Synthetic construct

<400> SEQUENCE: 40

Gly Thr Arg Val Glu Trp Lys Ala Glu
1               5

<210> SEQ ID NO 41
<211> LENGTH: 40
<212> TYPE: PRT
<213> ORGANISM: Artificial Sequence
<220> FEATURE:
<223> OTHER INFORMATION: Synthetic construct

<400> SEQUENCE: 41

Lys Lys Leu Pro His Thr Leu Val Ser Asp Gln Ser Asp Lys Phe Leu
1               5                   10                  15

Glu Glu Leu Lys Asn Thr Lys Ala Ala Glu Ile Val Lys Phe Ala Glu
            20                  25                  30

Ala Val Gly Thr Ser Ala Lys Asp
        35                  40

<210> SEQ ID NO 42
<211> LENGTH: 8
<212> TYPE: PRT
<213> ORGANISM: Artificial Sequence
<220> FEATURE:
<223> OTHER INFORMATION: Synthetic construct

<400> SEQUENCE: 42

Ser Trp Lys Cys Thr Gln Thr Gly
1               5

<210> SEQ ID NO 43
<211> LENGTH: 22
<212> TYPE: PRT
<213> ORGANISM: Artificial Sequence
<220> FEATURE:
<223> OTHER INFORMATION: Synthetic construct

<400> SEQUENCE: 43

Ala Ala Lys Ala Glu Asp Leu Ser Ile Ala Leu Asn Arg Glu Leu Thr
1               5                   10                  15

Ser Ala Glu Lys Asn Lys
            20

<210> SEQ ID NO 44
<211> LENGTH: 9
<212> TYPE: PRT
<213> ORGANISM: Artificial Sequence
<220> FEATURE:
<223> OTHER INFORMATION: Synthetic construct

<400> SEQUENCE: 44

Ala Thr Thr Asn Lys Thr Lys Glu Phe
1               5

<210> SEQ ID NO 45
<211> LENGTH: 106
<212> TYPE: PRT
<213> ORGANISM: Artificial Sequence
<220> FEATURE:
<223> OTHER INFORMATION: Synthetic construct

<400> SEQUENCE: 45

Gly Thr Gly Thr Ala Ala Gly Ser Asp Val Asp Tyr Val Ser Lys Phe
1               5                   10                  15

Gly Glu Gly Thr Arg Val Glu Trp Lys Ala Glu Lys Lys Leu Pro His
            20                  25                  30

Thr Leu Val Ser Asp Gln Ser Asp Lys Phe Leu Glu Glu Leu Lys Asn
        35                  40                  45

Thr Lys Ala Ala Glu Ile Val Lys Phe Ala Glu Ala Val Gly Thr Ser
    50                  55                  60

Ala Lys Asp Ser Trp Lys Cys Thr Gln Thr Gly Ala Ala Lys Ala Glu
65                  70                  75                  80

Asp Leu Ser Ile Ala Leu Asn Arg Glu Leu Thr Ser Ala Glu Lys Asn
                85                  90                  95

Lys Ala Thr Thr Asn Lys Thr Lys Glu Phe
            100                 105

<210> SEQ ID NO 46
<211> LENGTH: 54
<212> TYPE: DNA
<213> ORGANISM: Artificial Sequence
<220> FEATURE:
<223> OTHER INFORMATION: Synthetic construct

<400> SEQUENCE: 46
ggtaccggga ctgcggcagg gtcggacgtg actatgtaa gtaagttcgg tgag          54

<210> SEQ ID NO 47
<211> LENGTH: 27
<212> TYPE: DNA
<213> ORGANISM: Artificial Sequence
<220> FEATURE:
<223> OTHER INFORMATION: Synthetic construct

<400> SEQUENCE: 47
ggaactagag tggagtggaa agctgag                                       27

<210> SEQ ID NO 48

```
<211> LENGTH: 120
<212> TYPE: DNA
<213> ORGANISM: Artificial Sequence
<220> FEATURE:
<223> OTHER INFORMATION: Synthetic construct

<400> SEQUENCE: 48
aagaagctac cgcataccct ggtgagtgac cagagcgata aattcctgga ggagctgaag     60
aatacgaaag cggcggagat cgttaaattt gctgaggctg ttggcacatc ggcaaaggat    120

<210> SEQ ID NO 49
<211> LENGTH: 24
<212> TYPE: DNA
<213> ORGANISM: Artificial Sequence
<220> FEATURE:
<223> OTHER INFORMATION: Synthetic construct

<400> SEQUENCE: 49
agctggaagt gtacgcagac tggc                                            24

<210> SEQ ID NO 50
<211> LENGTH: 66
<212> TYPE: DNA
<213> ORGANISM: Artificial Sequence
<220> FEATURE:
<223> OTHER INFORMATION: Synthetic construct

<400> SEQUENCE: 50
gctgcgaaag cggaagacct aagtattgcg ttgaatagag aactaaccag cgccgaaaag     60
aacaag                                                                66

<210> SEQ ID NO 51
<211> LENGTH: 27
<212> TYPE: DNA
<213> ORGANISM: Artificial Sequence
<220> FEATURE:
<223> OTHER INFORMATION: Synthetic construct

<400> SEQUENCE: 51
gcgactacga acaagactaa agagttc                                         27

<210> SEQ ID NO 52
<211> LENGTH: 17
<212> TYPE: DNA
<213> ORGANISM: Artificial Sequence
<220> FEATURE:
<223> OTHER INFORMATION: Synthetic construct

<400> SEQUENCE: 52
ggtaccggga ctgcggc                                                    17

<210> SEQ ID NO 53
<211> LENGTH: 27
<212> TYPE: DNA
<213> ORGANISM: Artificial Sequence
<220> FEATURE:
<223> OTHER INFORMATION: Synthetic construct

<400> SEQUENCE: 53
ctcaccgaac ttacttacat agtccac                                         27

<210> SEQ ID NO 54
<211> LENGTH: 23
<212> TYPE: DNA
<213> ORGANISM: Artificial Sequence
```

```
<220> FEATURE:
<223> OTHER INFORMATION: Synthetic construct

<400> SEQUENCE: 54
ggaactagag tggagtggaa agc                                    23

<210> SEQ ID NO 55
<211> LENGTH: 16
<212> TYPE: DNA
<213> ORGANISM: Artificial Sequence
<220> FEATURE:
<223> OTHER INFORMATION: Synthetic construct

<400> SEQUENCE: 55
ctcagctttc cactcc                                            16

<210> SEQ ID NO 56
<211> LENGTH: 21
<212> TYPE: DNA
<213> ORGANISM: Artificial Sequence
<220> FEATURE:
<223> OTHER INFORMATION: Synthetic construct

<400> SEQUENCE: 56
aagaagctac cgcataccct g                                      21

<210> SEQ ID NO 57
<211> LENGTH: 21
<212> TYPE: DNA
<213> ORGANISM: Artificial Sequence
<220> FEATURE:
<223> OTHER INFORMATION: Synthetic construct

<400> SEQUENCE: 57
atcctttgcc gatgtaccaa c                                      21

<210> SEQ ID NO 58
<211> LENGTH: 22
<212> TYPE: DNA
<213> ORGANISM: Artificial Sequence
<220> FEATURE:
<223> OTHER INFORMATION: Synthetic construct

<400> SEQUENCE: 58
agctggaagt gtacgcagac tg                                     22

<210> SEQ ID NO 59
<211> LENGTH: 20
<212> TYPE: DNA
<213> ORGANISM: Artificial Sequence
<220> FEATURE:
<223> OTHER INFORMATION: Synthetic construct

<400> SEQUENCE: 59
gccagtctgc gtacacttcc                                        20

<210> SEQ ID NO 60
<211> LENGTH: 18
<212> TYPE: DNA
<213> ORGANISM: Artificial Sequence
<220> FEATURE:
<223> OTHER INFORMATION: Synthetic construct

<400> SEQUENCE: 60
gctgcgaaag cggaagac                                          18
```

<210> SEQ ID NO 61
<211> LENGTH: 19
<212> TYPE: DNA
<213> ORGANISM: Artificial Sequence
<220> FEATURE:
<223> OTHER INFORMATION: Synthetic construct

<400> SEQUENCE: 61
cttgttcttt tcggcgctg                                                  19

<210> SEQ ID NO 62
<211> LENGTH: 24
<212> TYPE: DNA
<213> ORGANISM: Artificial Sequence
<220> FEATURE:
<223> OTHER INFORMATION: Synthetic construct

<400> SEQUENCE: 62
gcgactacga acaagactaa agag                                            24

<210> SEQ ID NO 63
<211> LENGTH: 26
<212> TYPE: DNA
<213> ORGANISM: Artificial Sequence
<220> FEATURE:
<223> OTHER INFORMATION: Synthetic construct

<400> SEQUENCE: 63
gaactcttta gtcttgttcg tagtcg                                          26

<210> SEQ ID NO 64
<211> LENGTH: 19
<212> TYPE: DNA
<213> ORGANISM: Artificial Sequence
<220> FEATURE:
<223> OTHER INFORMATION: Synthetic construct

<400> SEQUENCE: 64
gcggtgcagg aaaagaaac                                                  19

<210> SEQ ID NO 65
<211> LENGTH: 18
<212> TYPE: DNA
<213> ORGANISM: Artificial Sequence
<220> FEATURE:
<223> OTHER INFORMATION: Synthetic construct

<400> SEQUENCE: 65
agcagcttcg tcagctgc                                                   18

<210> SEQ ID NO 66
<211> LENGTH: 24
<212> TYPE: DNA
<213> ORGANISM: Artificial Sequence
<220> FEATURE:
<223> OTHER INFORMATION: Synthetic construct

<400> SEQUENCE: 66
aacatatgaa tcttgtgagc gcgg                                            24

<210> SEQ ID NO 67
<211> LENGTH: 25
<212> TYPE: DNA
<213> ORGANISM: Artificial Sequence
<220> FEATURE:
<223> OTHER INFORMATION: Synthetic construct

<400> SEQUENCE: 67
ggggatccgg ctgggggagc agaag                                         25

<210> SEQ ID NO 68
<211> LENGTH: 31
<212> TYPE: DNA
<213> ORGANISM: Artificial Sequence
<220> FEATURE:
<223> OTHER INFORMATION: Synthetic construct

<400> SEQUENCE: 68
aagctagcca aggtgacgaa gtacttttgt g                                  31

<210> SEQ ID NO 69
<211> LENGTH: 35
<212> TYPE: DNA
<213> ORGANISM: Artificial Sequence
<220> FEATURE:
<223> OTHER INFORMATION: Synthetic construct

<400> SEQUENCE: 69
aagctagcct aacctatcaa ttcaaaggtg gattg                              35

<210> SEQ ID NO 70
<211> LENGTH: 24
<212> TYPE: DNA
<213> ORGANISM: Artificial Sequence
<220> FEATURE:
<223> OTHER INFORMATION: Synthetic construct

<400> SEQUENCE: 70
ggccatgggt accgggactg cggc                                          24

<210> SEQ ID NO 71
<211> LENGTH: 24
<212> TYPE: DNA
<213> ORGANISM: Artificial Sequence
<220> FEATURE:
<223> OTHER INFORMATION: Synthetic construct

<400> SEQUENCE: 71
ttcatatgct cagctttcca ctcc                                          24

<210> SEQ ID NO 72
<211> LENGTH: 35
<212> TYPE: DNA
<213> ORGANISM: Artificial Sequence
<220> FEATURE:
<223> OTHER INFORMATION: Synthetic construct

<400> SEQUENCE: 72
ccctgcagct caccgaactt acttacatag tccac                              35

<210> SEQ ID NO 73
<211> LENGTH: 31
<212> TYPE: DNA
<213> ORGANISM: Artificial Sequence
<220> FEATURE:
<223> OTHER INFORMATION: Synthetic construct

<400> SEQUENCE: 73
ggctgcaggg aactagagtg gagtggaaag c                                  31

<210> SEQ ID NO 74

```
<211> LENGTH: 29
<212> TYPE: DNA
<213> ORGANISM: Artificial Sequence
<220> FEATURE:
<223> OTHER INFORMATION: Synthetic construct

<400> SEQUENCE: 74
aaggatccaa gaagctaccg catacccctg                                    29

<210> SEQ ID NO 75
<211> LENGTH: 28
<212> TYPE: DNA
<213> ORGANISM: Artificial Sequence
<220> FEATURE:
<223> OTHER INFORMATION: Synthetic construct

<400> SEQUENCE: 75
ccgtcgacgc cagtctgcgt acacttcc                                      28

<210> SEQ ID NO 76
<211> LENGTH: 29
<212> TYPE: DNA
<213> ORGANISM: Artificial Sequence
<220> FEATURE:
<223> OTHER INFORMATION: Synthetic construct

<400> SEQUENCE: 76
aagaattcat cctttgccga tgtaccaac                                     29

<210> SEQ ID NO 77
<211> LENGTH: 30
<212> TYPE: DNA
<213> ORGANISM: Artificial Sequence
<220> FEATURE:
<223> OTHER INFORMATION: Synthetic construct

<400> SEQUENCE: 77
ttgaattcag ctggaagtgt acgcagactg                                    30

<210> SEQ ID NO 78
<211> LENGTH: 26
<212> TYPE: DNA
<213> ORGANISM: Artificial Sequence
<220> FEATURE:
<223> OTHER INFORMATION: Synthetic construct

<400> SEQUENCE: 78
aaaagcttgc tgcgaaagcg gaagac                                        26

<210> SEQ ID NO 79
<211> LENGTH: 34
<212> TYPE: DNA
<213> ORGANISM: Artificial Sequence
<220> FEATURE:
<223> OTHER INFORMATION: Synthetic construct

<400> SEQUENCE: 79
ccctcgagga actctttagt cttgttcgta gtcg                               34

<210> SEQ ID NO 80
<211> LENGTH: 27
<212> TYPE: DNA
<213> ORGANISM: Artificial Sequence
<220> FEATURE:
<223> OTHER INFORMATION: Synthetic construct

<400> SEQUENCE: 80
```
ttggatccct tgttctttc ggcgctg                                        27

<210> SEQ ID NO 81
<211> LENGTH: 32
<212> TYPE: DNA
<213> ORGANISM: Artificial Sequence
<220> FEATURE:
<223> OTHER INFORMATION: Synthetic construct

<400> SEQUENCE: 81
aaggatccgc gactacgaac aagactaaag ag                                 32

<210> SEQ ID NO 82
<211> LENGTH: 31
<212> TYPE: DNA
<213> ORGANISM: Artificial Sequence
<220> FEATURE:
<223> OTHER INFORMATION: Synthetic construct

<400> SEQUENCE: 82
attatgtatg atttatccta agttatctga g                                  31

<210> SEQ ID NO 83
<211> LENGTH: 21
<212> TYPE: DNA
<213> ORGANISM: Artificial Sequence
<220> FEATURE:
<223> OTHER INFORMATION: Synthetic construct

<400> SEQUENCE: 83
gggatatcgg cgttgatagg g                                             21

<210> SEQ ID NO 84
<211> LENGTH: 25
<212> TYPE: DNA
<213> ORGANISM: Artificial Sequence
<220> FEATURE:
<223> OTHER INFORMATION: Synthetic construct

<400> SEQUENCE: 84
ggtttgtgtt gctggtgatt ggagg                                         25

<210> SEQ ID NO 85
<211> LENGTH: 26
<212> TYPE: DNA
<213> ORGANISM: Artificial Sequence
<220> FEATURE:
<223> OTHER INFORMATION: Synthetic construct

<400> SEQUENCE: 85
gcaaacctaa caccmaaytc mccacc                                        26

<210> SEQ ID NO 86
<211> LENGTH: 27
<212> TYPE: DNA
<213> ORGANISM: Artificial Sequence
<220> FEATURE:
<223> OTHER INFORMATION: Synthetic construct

<400> SEQUENCE: 86
tatactaaaa aagaattaag tcaagag                                       27

<210> SEQ ID NO 87
<211> LENGTH: 21
<212> TYPE: DNA

```
<213> ORGANISM: Artificial Sequence
<220> FEATURE:
<223> OTHER INFORMATION: Synthetic construct

<400> SEQUENCE: 87
atggtagaaa sccccagcaa a                                              21

<210> SEQ ID NO 88
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: n is a, c, g or t

<400> SEQUENCE: 88
cacgtnttta gttactgcca                                                20

<210> SEQ ID NO 89
<211> LENGTH: 26
<212> TYPE: DNA
<213> ORGANISM: Artificial Sequence
<220> FEATURE:
<223> OTHER INFORMATION: Synthetic construct

<400> SEQUENCE: 89
gtactagtca gcgccactaa catcaa                                         26

<210> SEQ ID NO 90
<211> LENGTH: 20
<212> TYPE: DNA
<213> ORGANISM: Artificial Sequence
<220> FEATURE:
<223> OTHER INFORMATION: Synthetic construct

<400> SEQUENCE: 90
gaagaatacg aaagcggcgg                                                20

<210> SEQ ID NO 91
<211> LENGTH: 22
<212> TYPE: DNA
<213> ORGANISM: Artificial Sequence
<220> FEATURE:
<223> OTHER INFORMATION: Synthetic construct

<400> SEQUENCE: 91
tacttaggtc ttccgctttc gc                                             22

<210> SEQ ID NO 92
<211> LENGTH: 15
<212> TYPE: PRT
<213> ORGANISM: Artificial Sequence
<220> FEATURE:
<223> OTHER INFORMATION: Synthetic construct

<400> SEQUENCE: 92

Thr Gly Thr Ala Ala Gly Ser Asp Val Asp Tyr Val Ser Lys Phe
1               5                   10                  15

<210> SEQ ID NO 93
<211> LENGTH: 8
<212> TYPE: PRT
<213> ORGANISM: Artificial Sequence
<220> FEATURE:
```

```
<223> OTHER INFORMATION: Synthetic construct

<400> SEQUENCE: 93

Thr Arg Val Glu Trp Lys Ala Glu
1               5

<210> SEQ ID NO 94
<211> LENGTH: 16
<212> TYPE: PRT
<213> ORGANISM: Artificial Sequence
<220> FEATURE:
<223> OTHER INFORMATION: Synthetic construct

<400> SEQUENCE: 94

Ala Ala Glu Ile Val Lys Phe Ala Glu Ala Val Gly Thr Ser Ala Lys
1               5                   10                  15

<210> SEQ ID NO 95
<211> LENGTH: 8
<212> TYPE: PRT
<213> ORGANISM: Artificial Sequence
<220> FEATURE:
<223> OTHER INFORMATION: Synthetic construct

<400> SEQUENCE: 95

Ser Trp Lys Cys Thr Gln Thr Gly
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic construct

<400> SEQUENCE: 96

Ala Ala Lys Ala Glu Asp Leu Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic construct

<400> SEQUENCE: 97

Ala Thr Thr Asn Lys Thr Lys Glu Phe
1               5

<210> SEQ ID NO 98
<211> LENGTH: 10
<212> TYPE: PRT
<213> ORGANISM: Artificial Sequence
<220> FEATURE:
<223> OTHER INFORMATION: Synthetic construct

<400> SEQUENCE: 98

Ala Val Gln Glu Lys Lys Pro Pro Glu Ala
1               5                   10

<210> SEQ ID NO 99
<211> LENGTH: 17
<212> TYPE: DNA
<213> ORGANISM: Artificial Sequence
<220> FEATURE:
<223> OTHER INFORMATION: Synthetic construct
```

<400> SEQUENCE: 99
ggctggggga gcagaag                                                    17

<210> SEQ ID NO 100
<211> LENGTH: 18
<212> TYPE: PRT
<213> ORGANISM: Artificial Sequence
<220> FEATURE:
<223> OTHER INFORMATION: Synthetic construct

<400> SEQUENCE: 100

Gly Thr Gly Thr Ala Ala Gly Ser Asp Val Asp Tyr Val Ser Lys Phe
1               5                   10                  15

Gly Glu

<210> SEQ ID NO 101
<211> LENGTH: 18
<212> TYPE: PRT
<213> ORGANISM: Artificial Sequence
<220> FEATURE:
<223> OTHER INFORMATION: Synthetic construct

<400> SEQUENCE: 101

Gly Thr Gly Thr Ala Ala Gly Ser Asp Val Asp Tyr Val Ser Lys Phe
1               5                   10                  15

Gly Glu

<210> SEQ ID NO 102
<211> LENGTH: 18
<212> TYPE: PRT
<213> ORGANISM: Artificial Sequence
<220> FEATURE:
<223> OTHER INFORMATION: Synthetic construct

<400> SEQUENCE: 102

Gly Thr Gly Thr Ala Ala Gly Ser Asp Val Asp Tyr Val Ser Lys Phe
1               5                   10                  15

Gly Glu

<210> SEQ ID NO 103
<211> LENGTH: 18
<212> TYPE: PRT
<213> ORGANISM: Artificial Sequence
<220> FEATURE:
<223> OTHER INFORMATION: Synthetic construct

<400> SEQUENCE: 103

Gly Thr Gly Thr Ala Ala Gly Ser Asp Val Asp Tyr Val Ser Lys Phe
1               5                   10                  15

Gly Glu

<210> SEQ ID NO 104
<211> LENGTH: 9
<212> TYPE: PRT
<213> ORGANISM: Artificial Sequence
<220> FEATURE:
<223> OTHER INFORMATION: Synthetic construct

<400> SEQUENCE: 104

Gly Thr Arg Val Glu Trp Lys Ala Glu
1               5

```
<210> SEQ ID NO 105
<211> LENGTH: 9
<212> TYPE: PRT
<213> ORGANISM: Artificial Sequence
<220> FEATURE:
<223> OTHER INFORMATION: Synthetic construct

<400> SEQUENCE: 105

Gly Thr Arg Val Glu Trp Lys Ala Glu
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic construct

<400> SEQUENCE: 106

Gly Thr Arg Val Glu Trp Lys Ala Glu
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic construct

<400> SEQUENCE: 107

Gly Thr Arg Val Glu Trp Lys Ala Glu
1               5

<210> SEQ ID NO 108
<211> LENGTH: 40
<212> TYPE: PRT
<213> ORGANISM: Artificial Sequence
<220> FEATURE:
<223> OTHER INFORMATION: Synthetic construct

<400> SEQUENCE: 108

Lys Lys Leu Pro His Thr Leu Val Ser Asp Gln Ser Asp Lys Phe Leu
1               5                   10                  15

Glu Glu Leu Lys Asn Thr Lys Ala Ala Glu Ile Val Lys Phe Ala Glu
            20                  25                  30

Ala Val Gly Thr Ser Ala Lys Asp
        35                  40

<210> SEQ ID NO 109
<211> LENGTH: 41
<212> TYPE: PRT
<213> ORGANISM: Artificial Sequence
<220> FEATURE:
<223> OTHER INFORMATION: Synthetic construct

<400> SEQUENCE: 109

Ala Lys Lys Leu Pro His Thr Leu Val Ser Asp Gln Ser Asp Lys Phe
1               5                   10                  15

Leu Glu Glu Leu Lys Asn Thr Lys Ala Ala Glu Ile Val Lys Phe Ala
            20                  25                  30

Glu Ala Val Gly Thr Ser Ala Lys Asp
        35                  40

<210> SEQ ID NO 110
<211> LENGTH: 40
```

<212> TYPE: PRT
<213> ORGANISM: Artificial Sequence
<220> FEATURE:
<223> OTHER INFORMATION: Synthetic construct

<400> SEQUENCE: 110

Lys Lys Leu Pro His Thr Leu Val Ser Asp Gln Ser Asp Lys Phe Leu
1               5                   10                  15
Glu Glu Leu Lys Asn Thr Lys Ala Ala Glu Ile Val Lys Phe Ala Glu
            20                  25                  30
Ala Val Gly Thr Ser Ala Lys Asp
        35                  40

<210> SEQ ID NO 111
<211> LENGTH: 41
<212> TYPE: PRT
<213> ORGANISM: Artificial Sequence
<220> FEATURE:
<223> OTHER INFORMATION: Synthetic construct

<400> SEQUENCE: 111

Ala Lys Lys Leu Pro His Thr Leu Val Ser Asp Gln Ser Asp Lys Phe
1               5                   10                  15
Leu Glu Glu Leu Lys Asn Thr Lys Ala Ala Glu Ile Val Lys Phe Ala
            20                  25                  30
Glu Ala Val Gly Thr Ser Ala Lys Asp
        35                  40

<210> SEQ ID NO 112
<211> LENGTH: 8
<212> TYPE: PRT
<213> ORGANISM: Artificial Sequence
<220> FEATURE:
<223> OTHER INFORMATION: Synthetic construct

<400> SEQUENCE: 112

Ser Trp Lys Cys Thr Gln Thr Gly
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic construct

<400> SEQUENCE: 113

Ser Trp Lys Cys Thr Gln Thr Gly
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic construct

<400> SEQUENCE: 114

Ser Trp Lys Cys Thr Gln Thr Gly
1               5

<210> SEQ ID NO 115
<211> LENGTH: 8
<212> TYPE: PRT
<213> ORGANISM: Artificial Sequence

```
<220> FEATURE:
<223> OTHER INFORMATION: Synthetic construct

<400> SEQUENCE: 115

Ser Trp Lys Cys Thr Gln Thr Gly
1               5

<210> SEQ ID NO 116
<211> LENGTH: 22
<212> TYPE: PRT
<213> ORGANISM: Artificial Sequence
<220> FEATURE:
<223> OTHER INFORMATION: Synthetic construct

<400> SEQUENCE: 116

Ala Ala Lys Ala Glu Asp Leu Ser Ile Ala Leu Asn Arg Glu Leu Thr
1               5                   10                  15

Ser Ala Glu Lys Asn Lys
            20

<210> SEQ ID NO 117
<211> LENGTH: 22
<212> TYPE: PRT
<213> ORGANISM: Artificial Sequence
<220> FEATURE:
<223> OTHER INFORMATION: Synthetic construct

<400> SEQUENCE: 117

Ala Ala Lys Ala Glu Asp Leu Ser Ile Ala Leu Asn Arg Glu Leu Thr
1               5                   10                  15

Ser Ala Glu Lys Asn Lys
            20

<210> SEQ ID NO 118
<211> LENGTH: 22
<212> TYPE: PRT
<213> ORGANISM: Artificial Sequence
<220> FEATURE:
<223> OTHER INFORMATION: Synthetic construct

<400> SEQUENCE: 118

Ala Ala Lys Ala Glu Asp Leu Ser Thr Ala Leu Asn Arg Glu Leu Thr
1               5                   10                  15

Ser Ala Glu Lys Asn Lys
            20

<210> SEQ ID NO 119
<211> LENGTH: 21
<212> TYPE: PRT
<213> ORGANISM: Artificial Sequence
<220> FEATURE:
<223> OTHER INFORMATION: Synthetic construct

<400> SEQUENCE: 119

Ala Lys Ala Glu Asp Leu Ser Thr Ala Leu Asn Arg Glu Leu Thr Ser
1               5                   10                  15

Ala Glu Lys Asn Lys
            20

<210> SEQ ID NO 120
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 120

Ala Thr Thr Asn Lys Thr Lys Glu Phe
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic construct

<400> SEQUENCE: 121

Ala Thr Thr Asn Lys Thr Lys Glu Phe
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic construct

<400> SEQUENCE: 122

Ala Thr Thr Asn Lys Thr Lys Glu Phe
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic construct

<400> SEQUENCE: 123

Ala Thr Thr Asn Lys Thr Lys Glu Phe
1               5

<210> SEQ ID NO 124
<211> LENGTH: 11
<212> TYPE: DNA
<213> ORGANISM: Artificial Sequence
<220> FEATURE:
<223> OTHER INFORMATION: Synthetic construct

<400> SEQUENCE: 124
ggtggtgagg t                                                              11

<210> SEQ ID NO 125
<211> LENGTH: 15
<212> TYPE: DNA
<213> ORGANISM: Artificial Sequence
<220> FEATURE:
<223> OTHER INFORMATION: Synthetic construct

<400> SEQUENCE: 125
gttgttatga tctgc                                                          15

<210> SEQ ID NO 126
<211> LENGTH: 11
<212> TYPE: DNA
<213> ORGANISM: Artificial Sequence
<220> FEATURE:
<223> OTHER INFORMATION: Synthetic construct

<400> SEQUENCE: 126
```
ccttatgcat g                                    11

<210> SEQ ID NO 127
<211> LENGTH: 14
<212> TYPE: DNA
<213> ORGANISM: Artificial Sequence
<220> FEATURE:
<223> OTHER INFORMATION: Synthetic construct

<400> SEQUENCE: 127
cctcctaact tcct                                 14

<210> SEQ ID NO 128
<211> LENGTH: 14
<212> TYPE: DNA
<213> ORGANISM: Artificial Sequence
<220> FEATURE:
<223> OTHER INFORMATION: Synthetic construct

<400> SEQUENCE: 128
ttgttatgat ctgc                                 14

<210> SEQ ID NO 129
<211> LENGTH: 14
<212> TYPE: DNA
<213> ORGANISM: Artificial Sequence
<220> FEATURE:
<223> OTHER INFORMATION: Synthetic construct

<400> SEQUENCE: 129
gtaccttatg catg                                 14

<210> SEQ ID NO 130
<211> LENGTH: 14
<212> TYPE: DNA
<213> ORGANISM: Artificial Sequence
<220> FEATURE:
<223> OTHER INFORMATION: Synthetic construct

<400> SEQUENCE: 130
cctcctaact tcct                                 14

<210> SEQ ID NO 131
<211> LENGTH: 17
<212> TYPE: DNA
<213> ORGANISM: Artificial Sequence
<220> FEATURE:
<223> OTHER INFORMATION: Synthetic construct

<400> SEQUENCE: 131
aaggctggtt tgagtta                              17

<210> SEQ ID NO 132
<211> LENGTH: 14
<212> TYPE: DNA
<213> ORGANISM: Artificial Sequence
<220> FEATURE:
<223> OTHER INFORMATION: Synthetic construct

<400> SEQUENCE: 132
ccctcttacc tctg                                 14

<210> SEQ ID NO 133
<211> LENGTH: 183
<212> TYPE: PRT
<213> ORGANISM: Artificial Sequence

```
<220> FEATURE:
<223> OTHER INFORMATION: Synthetic construct
<220> FEATURE:
<221> NAME/KEY: MISC_FEATURE
<222> LOCATION: (105)..(105)
<223> OTHER INFORMATION: any amino acid
<220> FEATURE:
<221> NAME/KEY: MISC_FEATURE
<222> LOCATION: (107)..(109)
<223> OTHER INFORMATION: any amino acid
<220> FEATURE:
<221> NAME/KEY: MISC_FEATURE
<222> LOCATION: (111)..(111)
<223> OTHER INFORMATION: any amino acid
<220> FEATURE:
<221> NAME/KEY: MISC_FEATURE
<222> LOCATION: (116)..(116)
<223> OTHER INFORMATION: any amino acid
<220> FEATURE:
<221> NAME/KEY: MISC_FEATURE
<222> LOCATION: (122)..(122)
<223> OTHER INFORMATION: any amino acid
<220> FEATURE:
<221> NAME/KEY: MISC_FEATURE
<222> LOCATION: (168)..(168)
<223> OTHER INFORMATION: any amino acid
<220> FEATURE:
<221> NAME/KEY: MISC_FEATURE
<222> LOCATION: (171)..(171)
<223> OTHER INFORMATION: any amino acid
<220> FEATURE:
<221> NAME/KEY: MISC_FEATURE
<222> LOCATION: (173)..(173)
<223> OTHER INFORMATION: any amino acid
<220> FEATURE:
<221> NAME/KEY: MISC_FEATURE
<222> LOCATION: (177)..(178)
<223> OTHER INFORMATION: any amino acid
<220> FEATURE:
<221> NAME/KEY: MISC_FEATURE
<222> LOCATION: (180)..(181)
<223> OTHER INFORMATION: any amino acid

<400> SEQUENCE: 133

Met Phe Met Thr Ser Gln Ala Gln Asn Gln Ser Ser Ile Pro Ile Thr
1               5                   10                  15

Val Glu Gly Lys Ala Arg Pro His Pro Val Asp Glu Tyr Val Gly Arg
            20                  25                  30

Glu Ile Lys Lys Gln Arg Ile Met Lys Gly Met Ser Gln Asn Gln Leu
        35                  40                  45

Ala Ser Arg Leu Gly Ile Thr Phe Gln Gln Val Gln Lys Tyr Glu Lys
    50                  55                  60

Gly Thr Asn Arg Ile Val Ile Ser Arg Leu Tyr Glu Leu Ala Arg Val
65                  70                  75                  80

Leu Gly Ile Glu Ile Asn Asp Leu Ile Ser Lys Leu Gln Asn Asp Leu
                85                  90                  95

Arg Ser Ile Thr Glu Gly Thr Asp Xaa Ser Xaa Xaa Xaa Leu Xaa Glu
            100                 105                 110

Gly Asp Glu Xaa Ser Leu Glu Glu Phe Xaa His Asn Tyr Asn Asp Gly
        115                 120                 125

Lys Glu Val Leu Met Leu Val Arg Ala Tyr Arg Arg Ile Lys Ser Glu
    130                 135                 140

Lys Met Arg Gly Ala Ile His Thr Leu Val Lys Val Met Cys Ala Glu
145                 150                 155                 160

Gln Ser Asn Asp Asp Tyr Glu Xaa Ser Tyr Xaa Asp Xaa Glu Tyr Glu
                165                 170                 175

Xaa Xaa Thr Xaa Xaa Glu Asp
```

<210> SEQ ID NO 134
<211> LENGTH: 185
<212> TYPE: PRT
<213> ORGANISM: Artificial Sequence
<220> FEATURE:
<223> OTHER INFORMATION: Synthetic construct

<400> SEQUENCE: 134

Met Phe Met Thr Ser Gln Ala Gln Asn Gln Ser Ser Ile Pro Ile Thr
1               5                   10                  15

Val Glu Gly Lys Val Arg Pro His Pro Val Asp Glu Tyr Val Gly Arg
            20                  25                  30

Glu Ile Lys Lys Gln Arg Ile Met Lys Gly Met Ser Gln Asn Gln Leu
        35                  40                  45

Ala Ser Arg Leu Gly Ile Thr Phe Gln Gln Val Gln Lys Tyr Glu Lys
    50                  55                  60

Gly Thr Asn Arg Ile Val Ile Ser Arg Leu Tyr Glu Leu Ala Arg Val
65                  70                  75                  80

Leu Gly Ile Glu Ile Asn Asp Leu Ile Ser Lys Leu Gln Asn Asp Leu
                85                  90                  95

Arg Ser Ile Thr Glu Gly Thr Asp Thr Ser Gly Thr Ser Phe Leu Lys
            100                 105                 110

Asp Gly Asp Glu Thr Ser Leu Glu Glu Phe Asn His Asn Tyr Asn Asp
        115                 120                 125

Gly Lys Glu Val Leu Met Leu Val Arg Ala Tyr Arg Lys Ile Lys Ser
    130                 135                 140

Glu Lys Met Arg Gly Ala Ile His Thr Leu Val Lys Val Met Cys Ala
145                 150                 155                 160

Glu Gln Ser Ser Asn Asp Asp Tyr Glu Asn Ser Tyr Val Asp Ser Asp
                165                 170                 175

Tyr Glu Ser Gly Thr Gly Thr Glu Asp
            180                 185

<210> SEQ ID NO 135
<211> LENGTH: 183
<212> TYPE: PRT
<213> ORGANISM: Artificial Sequence
<220> FEATURE:
<223> OTHER INFORMATION: Synthetic construct

<400> SEQUENCE: 135

Met Phe Met Thr Ser Gln Ala Gln Asn Gln Asn Ser Ile Pro Ile Thr
1               5                   10                  15

Ile Glu Gly Lys Ala Lys Pro His Pro Val Asp Glu Tyr Val Gly Arg
            20                  25                  30

Glu Ile Lys Lys Gln Arg Ile Met Lys Gly Met Ser Gln Asn Gln Leu
        35                  40                  45

Ala Ser Arg Leu Gly Ile Thr Phe Gln Gln Val Gln Lys Tyr Glu Lys
    50                  55                  60

Gly Thr Asn Arg Ile Val Ile Ser Arg Leu Tyr Glu Leu Ala Arg Val
65                  70                  75                  80

Leu Gly Ile Glu Ile Asn Asp Leu Met Ser Lys Leu Gln Asn Asp Ile
                85                  90                  95

Arg Ser Ile Thr Glu Gly Thr Asp Ile Ser Ile Thr Cys Leu Gln Glu
            100                 105                 110

Gly Asp Glu Ala Ser Leu Glu Glu Phe Asp His Asn Tyr Asn Asp Gly
            115                 120                 125

Lys Glu Val Leu Met Leu Val Arg Ala Tyr Arg Ile Lys Ser Glu
130                 135                 140

Lys Met Arg Gly Ala Ile His Thr Leu Val Lys Val Met Cys Ala Glu
145                 150                 155                 160

Gln Ser Asn Asp Asp Tyr Glu Thr Ser Tyr Arg Gly Pro Glu Tyr Val
                165                 170                 175

Ile Val Thr Asn Gln Glu Asp
            180

<210> SEQ ID NO 136
<211> LENGTH: 185
<212> TYPE: PRT
<213> ORGANISM: Artificial Sequence
<220> FEATURE:
<223> OTHER INFORMATION: Synthetic construct

<400> SEQUENCE: 136

Met Thr Ser Arg Thr Gln Asn Gln Ser Ser Ile Pro Ile Ile Val Glu
1               5                   10                  15

Gly Lys Ala Arg Pro His Pro Val Asp Glu Tyr Val Gly Arg Glu Ile
            20                  25                  30

Lys Lys Gln Arg Ile Met Lys Gly Met Ser Gln Asn Gln Leu Ala Ser
        35                  40                  45

Arg Leu Gly Ile Thr Phe Gln Gln Val Gln Lys Tyr Glu Lys Gly Thr
    50                  55                  60

Asn Arg Ile Val Ile Ser Arg Leu Tyr Glu Leu Ala Arg Val Leu Gly
65                  70                  75                  80

Ile Glu Ile Lys Asp Leu Ile Ala Lys Leu Gln Asn Asp Leu Arg Pro
                85                  90                  95

Ile Thr Asp Ala Gly Asp Ala Thr Asp Ala Ala Leu Arg Glu Gly Glu
            100                 105                 110

Glu Ser Ser Leu Glu Glu Phe Gly Gln Ser Tyr Asn Asp Gly Lys Glu
        115                 120                 125

Val Leu Met Leu Val Arg Ala Tyr Arg Arg Ile Lys Ser Asp Lys Met
    130                 135                 140

Arg Gly Ala Ile His Thr Leu Val Lys Val Met Cys Ala Glu Gln Gln
145                 150                 155                 160

Gln Asp Asp Tyr Glu His Ser Asp Ala Asp Glu Leu Gly Tyr Glu
                165                 170                 175

His Asp Pro Glu Ser Glu Thr Gly Ala
            180                 185

<210> SEQ ID NO 137
<211> LENGTH: 326
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (10)..(10)

```
<223> OTHER INFORMATION: any amino acid
<220> FEATURE:
<221> NAME/KEY: MISC_FEATURE
<222> LOCATION: (12)..(13)
<223> OTHER INFORMATION: any amino acid
<220> FEATURE:
<221> NAME/KEY: MISC_FEATURE
<222> LOCATION: (16)..(16)
<223> OTHER INFORMATION: any amino acid
<220> FEATURE:
<221> NAME/KEY: MISC_FEATURE
<222> LOCATION: (20)..(20)
<223> OTHER INFORMATION: any amino acid
<220> FEATURE:
<221> NAME/KEY: MISC_FEATURE
<222> LOCATION: (26)..(26)
<223> OTHER INFORMATION: any amino acid
<220> FEATURE:
<221> NAME/KEY: MISC_FEATURE
<222> LOCATION: (33)..(33)
<223> OTHER INFORMATION: any amino acid
<220> FEATURE:
<221> NAME/KEY: MISC_FEATURE
<222> LOCATION: (54)..(54)
<223> OTHER INFORMATION: any amino acid
<220> FEATURE:
<221> NAME/KEY: MISC_FEATURE
<222> LOCATION: (56)..(56)
<223> OTHER INFORMATION: any amino acid
<220> FEATURE:
<221> NAME/KEY: MISC_FEATURE
<222> LOCATION: (59)..(59)
<223> OTHER INFORMATION: any amino acid
<220> FEATURE:
<221> NAME/KEY: MISC_FEATURE
<222> LOCATION: (63)..(63)
<223> OTHER INFORMATION: any amino acid
<220> FEATURE:
<221> NAME/KEY: MISC_FEATURE
<222> LOCATION: (66)..(66)
<223> OTHER INFORMATION: any amino acid
<220> FEATURE:
<221> NAME/KEY: MISC_FEATURE
<222> LOCATION: (70)..(71)
<223> OTHER INFORMATION: any amino acid
<220> FEATURE:
<221> NAME/KEY: MISC_FEATURE
<222> LOCATION: (75)..(76)
<223> OTHER INFORMATION: any amino acid
<220> FEATURE:
<221> NAME/KEY: MISC_FEATURE
<222> LOCATION: (78)..(80)
<223> OTHER INFORMATION: any amino acid
<220> FEATURE:
<221> NAME/KEY: MISC_FEATURE
<222> LOCATION: (82)..(82)
<223> OTHER INFORMATION: any amino acid
<220> FEATURE:
<221> NAME/KEY: MISC_FEATURE
<222> LOCATION: (84)..(84)
<223> OTHER INFORMATION: any amino acid
<220> FEATURE:
<221> NAME/KEY: MISC_FEATURE
<222> LOCATION: (86)..(89)
<223> OTHER INFORMATION: any amino acid
<220> FEATURE:
<221> NAME/KEY: MISC_FEATURE
<222> LOCATION: (94)..(95)
<223> OTHER INFORMATION: any amino acid
<220> FEATURE:
<221> NAME/KEY: MISC_FEATURE
<222> LOCATION: (97)..(100)
<223> OTHER INFORMATION: any amino acid
<220> FEATURE:
<221> NAME/KEY: MISC_FEATURE
<222> LOCATION: (102)..(104)
<223> OTHER INFORMATION: any amino acid
<220> FEATURE:
<221> NAME/KEY: MISC_FEATURE
```

-continued

```
<222> LOCATION: (112)..(112)
<223> OTHER INFORMATION: any amino acid
<220> FEATURE:
<221> NAME/KEY: MISC_FEATURE
<222> LOCATION: (115)..(115)
<223> OTHER INFORMATION: any amino acid
<220> FEATURE:
<221> NAME/KEY: MISC_FEATURE
<222> LOCATION: (118)..(118)
<223> OTHER INFORMATION: any amino acid
<220> FEATURE:
<221> NAME/KEY: MISC_FEATURE
<222> LOCATION: (120)..(120)
<223> OTHER INFORMATION: any amino acid
<220> FEATURE:
<221> NAME/KEY: MISC_FEATURE
<222> LOCATION: (122)..(122)
<223> OTHER INFORMATION: any amino acid
<220> FEATURE:
<221> NAME/KEY: MISC_FEATURE
<222> LOCATION: (130)..(130)
<223> OTHER INFORMATION: any amino acid
<220> FEATURE:
<221> NAME/KEY: MISC_FEATURE
<222> LOCATION: (133)..(133)
<223> OTHER INFORMATION: any amino acid
<220> FEATURE:
<221> NAME/KEY: MISC_FEATURE
<222> LOCATION: (139)..(139)
<223> OTHER INFORMATION: any amino acid
<220> FEATURE:
<221> NAME/KEY: MISC_FEATURE
<222> LOCATION: (143)..(143)
<223> OTHER INFORMATION: any amino acid
<220> FEATURE:
<221> NAME/KEY: MISC_FEATURE
<222> LOCATION: (146)..(146)
<223> OTHER INFORMATION: any amino acid
<220> FEATURE:
<221> NAME/KEY: MISC_FEATURE
<222> LOCATION: (151)..(154)
<223> OTHER INFORMATION: any amino acid
<220> FEATURE:
<221> NAME/KEY: MISC_FEATURE
<222> LOCATION: (156)..(156)
<223> OTHER INFORMATION: any amino acid
<220> FEATURE:
<221> NAME/KEY: MISC_FEATURE
<222> LOCATION: (169)..(171)
<223> OTHER INFORMATION: any amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: MISC_FEATURE
<222> LOCATION: (176)..(176)
<223> OTHER INFORMATION: any amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: MISC_FEATURE
<222> LOCATION: (182)..(182)
<223> OTHER INFORMATION: any amino acid
<220> FEATURE:
<221> NAME/KEY: MISC_FEATURE
<222> LOCATION: (191)..(191)
<223> OTHER INFORMATION: any amino acid
<220> FEATURE:
<221> NAME/KEY: MISC_FEATURE
<222> LOCATION: (204)..(204)
<223> OTHER INFORMATION: any amino acid
<220> FEATURE:
<221> NAME/KEY: MISC_FEATURE
<222> LOCATION: (207)..(207)
<223> OTHER INFORMATION: any amino acid
<220> FEATURE:
```

```
<221> NAME/KEY: MISC_FEATURE
<222> LOCATION: (209)..(209)
<223> OTHER INFORMATION: any amino acid
<220> FEATURE:
<221> NAME/KEY: MISC_FEATURE
<222> LOCATION: (218)..(218)
<223> OTHER INFORMATION: any amino acid
<220> FEATURE:
<221> NAME/KEY: MISC_FEATURE
<222> LOCATION: (220)..(220)
<223> OTHER INFORMATION: any amino acid
<220> FEATURE:
<221> NAME/KEY: MISC_FEATURE
<222> LOCATION: (222)..(222)
<223> OTHER INFORMATION: any amino acid
<220> FEATURE:
<221> NAME/KEY: MISC_FEATURE
<222> LOCATION: (225)..(225)
<223> OTHER INFORMATION: any amino acid
<220> FEATURE:
<221> NAME/KEY: MISC_FEATURE
<222> LOCATION: (245)..(245)
<223> OTHER INFORMATION: any amino acid
<220> FEATURE:
<221> NAME/KEY: MISC_FEATURE
<222> LOCATION: (250)..(251)
<223> OTHER INFORMATION: any amino acid
<220> FEATURE:
<221> NAME/KEY: MISC_FEATURE
<222> LOCATION: (259)..(259)
<223> OTHER INFORMATION: any amino acid
<220> FEATURE:
<221> NAME/KEY: MISC_FEATURE
<222> LOCATION: (261)..(261)
<223> OTHER INFORMATION: any amino acid
<220> FEATURE:
<221> NAME/KEY: MISC_FEATURE
<222> LOCATION: (266)..(266)
<223> OTHER INFORMATION: any amino acid
<220> FEATURE:
<221> NAME/KEY: MISC_FEATURE
<222> LOCATION: (269)..(269)
<223> OTHER INFORMATION: any amino acid
<220> FEATURE:
<221> NAME/KEY: MISC_FEATURE
<222> LOCATION: (273)..(275)
<223> OTHER INFORMATION: any amino acid
<220> FEATURE:
<221> NAME/KEY: MISC_FEATURE
<222> LOCATION: (277)..(280)
<223> OTHER INFORMATION: any amino acid
<220> FEATURE:
<221> NAME/KEY: MISC_FEATURE
<222> LOCATION: (282)..(282)
<223> OTHER INFORMATION: any amino acid
<220> FEATURE:
<221> NAME/KEY: MISC_FEATURE
<222> LOCATION: (285)..(285)
<223> OTHER INFORMATION: any amino acid
<220> FEATURE:
<221> NAME/KEY: MISC_FEATURE
<222> LOCATION: (289)..(289)
<223> OTHER INFORMATION: any amino acid
<220> FEATURE:
<221> NAME/KEY: MISC_FEATURE
<222> LOCATION: (291)..(292)
<223> OTHER INFORMATION: any amino acid
<220> FEATURE:
<221> NAME/KEY: MISC_FEATURE
<222> LOCATION: (294)..(294)
<223> OTHER INFORMATION: any amino acid
<220> FEATURE:
<221> NAME/KEY: MISC_FEATURE
<222> LOCATION: (296)..(296)
<223> OTHER INFORMATION: any amino acid
<220> FEATURE:
<221> NAME/KEY: MISC_FEATURE
<222> LOCATION: (298)..(303)
<223> OTHER INFORMATION: any amino acid
```

<220> FEATURE:
<221> NAME/KEY: MISC_FEATURE
<222> LOCATION: (310)..(310)
<223> OTHER INFORMATION: any amino acid
<220> FEATURE:
<221> NAME/KEY: MISC_FEATURE
<222> LOCATION: (314)..(314)
<223> OTHER INFORMATION: any amino acid

<400> SEQUENCE: 137

```
Met Lys Lys Xaa Ile Xaa Val Phe Ala Xaa Ala Xaa Xaa Met Leu Xaa
1               5                   10                  15

Leu Pro Ser Xaa Ser Phe Ala Ser Pro Xaa Pro Val Asp Phe Ser Arg
            20                  25                  30

Xaa Glu Gly Ala Ser Gly Phe Phe Ala Ser Val Gln Tyr Lys Tyr Ala
        35                  40                  45

Val Pro Tyr Phe Gly Xaa Phe Xaa Leu Glu Xaa Gly Gly Lys Xaa Leu
50                  55                  60

Asn Xaa Phe Ser Ala Xaa Xaa Glu Lys Lys Xaa Xaa Glu Xaa Xaa Xaa
65                  70                  75                  80

Ala Xaa Ala Xaa Ala Xaa Xaa Xaa Ala Ala Pro Ser Xaa Xaa Glu
        85                  90                  95

Xaa Xaa Xaa Xaa Ser Xaa Xaa Xaa Phe Gln Gly Lys Tyr Ser Pro Xaa
            100                 105                 110

Tyr Leu Xaa Ser Ala Xaa Ala Xaa Ser Xaa Ser Ala Gly Tyr Ser Thr
        115                 120                 125

Gly Xaa Val Arg Xaa Glu Ala Glu Gly Met Xaa Gln Lys Phe Xaa Val
    130                 135                 140

Asp Xaa Lys Lys Tyr Lys Xaa Xaa Xaa Ala Xaa Ala Tyr Arg Phe
145                 150                 155                 160

Ala Ala Ser Ala Pro Ser Glu Asn Xaa Xaa Pro Xaa Ala Thr Xaa
                165                 170                 175

Pro Xaa Glu Lys Tyr Xaa Ile Thr Leu Glu Asn Arg Asp Val Xaa Ile
    180                 185                 190

Thr Ser Leu Val Ala Asn Leu Cys Tyr Asp Met Xaa Pro Glu Xaa Ser
        195                 200                 205

Xaa Ile Ser Pro Ser Ala Cys Val Gly Xaa Gly Xaa Ser Xaa Val Lys
    210                 215                 220

Xaa Leu Gly Val Leu Glu Gln Arg Trp Ala Tyr Gln Ala Lys Val Gly
225                 230                 235                 240

Val Gln Tyr Phe Xaa Ser Arg Lys Ala Xaa Xaa Phe Leu Ser Ala Tyr
                245                 250                 255

Val Ser Xaa Val Xaa Gly Glu Lys Phe Xaa Asn Val Xaa Val Lys His
            260                 265                 270

Xaa Xaa Xaa Thr Xaa Xaa Xaa Xaa Ser Xaa Gly Ala Xaa Gly Ser Gly
            275                 280                 285

Xaa Gly Xaa Xaa Ser Xaa Ser Xaa Ala Xaa Xaa Xaa Xaa Xaa Xaa Leu
    290                 295                 300

Leu Tyr Pro Asp Ala Xaa Leu Ser Leu Xaa Tyr Tyr Gly Phe Glu Cys
305                 310                 315                 320

Gly Val Arg Leu Val Leu
                325
```

<210> SEQ ID NO 138
<211> LENGTH: 306
<212> TYPE: PRT
<213> ORGANISM: Artificial Sequence
<220> FEATURE:
<223> OTHER INFORMATION: Synthetic construct

<400> SEQUENCE: 138

Met Lys Lys Lys Ile Cys Val Phe Ala Leu Pro Thr Val Met Phe Met
1               5                   10                  15

Leu Pro Ser Leu Ser Phe Ala Ser Pro Lys Pro Val Asp Phe Ser Arg
            20                  25                  30

Gln Ala Gly Ile Glu Gly Phe Phe Ser Ile Gln Tyr Lys Tyr Ala
        35                  40                  45

Val Pro Tyr Phe Gly Ala Phe Ser Leu Val His Gly Gly Asn Pro Leu
50                  55                  60

Asp Val Phe Ser Ala Lys Asp Ala Glu Ser Ser Gly Ile Ala Thr
65                  70                  75                  80

Leu Leu Gln Ser Val Ala Ser Thr Ser Thr Ser Asp Ala Glu Asn Phe
                85                  90                  95

Gln Gly Lys Tyr Asn Pro Ser Tyr Leu His Ser Lys Gln Ala Leu Ser
            100                 105                 110

Ala Ser Ala Gly Tyr Ser Thr Gly Tyr Val Arg Val Glu Val Glu Gly
        115                 120                 125

Met His Gln Lys Phe Leu Val Asp Pro Lys Arg Tyr Lys Glu Arg Asp
130                 135                 140

Lys Ala Lys Ala Tyr Arg Phe Ala Ala Ser Ala Ser Gly Gly Thr
145                 150                 155                 160

Gly Gln Pro Thr Ala Thr His Pro Asn Glu Lys Tyr Tyr Ile Ser Leu
            165                 170                 175

Glu Asn Arg Asp Leu Ile Ile Thr Ser Leu Val Ala Asn Leu Cys Tyr
        180                 185                 190

Asp Met Ile Pro Glu Glu Ser Arg Leu Ser Pro Asn Ile Cys Val Gly
        195                 200                 205

Ala Gly Ile Gly Tyr Val Lys Ala Phe Gly Val Leu Glu Gln Arg Trp
210                 215                 220

Ala Tyr Gln Ala Lys Val Gly Val Gln Tyr Phe Leu Ser Arg Lys Ala
225                 230                 235                 240

Ser Val Phe Leu Ser Ala Tyr Val Asp Lys Val Asn Gly Glu Lys Phe
                245                 250                 255

Lys Asn Val Arg Val Lys His Asn Ile Gly Thr Arg Ser Ser Ser Ser
            260                 265                 270

Gly Gly Thr Ser Gln Ser Ile Ser Thr Asp Ser Ile Leu Tyr Pro Asp
        275                 280                 285

Ala His Leu Ser Leu Leu Tyr Tyr Gly Leu Glu Cys Gly Val Arg Leu
290                 295                 300

Thr Leu
305

<210> SEQ ID NO 139
<211> LENGTH: 330
<212> TYPE: PRT
<213> ORGANISM: Artificial Sequence
<220> FEATURE:
<223> OTHER INFORMATION: Synthetic construct

<400> SEQUENCE: 139

Met Lys Lys Val Tyr Gly Leu Val Tyr Ala Ala Leu Ser Leu Leu Phe
1               5                   10                  15

Thr Pro Cys Gly Ser Phe Ala Ser Pro Arg Pro Ile Asp Phe Ser Arg

```
            20                  25                  30
Gly Glu Gly Ala Ser Gly Phe Phe Ala Ser Val Gln Tyr Lys Leu Ala
            35                  40                  45

Val Pro His Phe Arg Asp Phe Ile Val Glu Asp Lys Gly Lys Ala Leu
 50                      55                  60

Asn Thr Phe Ala Met Lys Glu Lys Gln Gln Gly Thr Ala Lys Ala
 65                  70                  75                  80

Ala Ala Gly Ala Ala Thr Pro Pro Ala Ala Pro Ser Gly Ala Glu Ala
                 85                  90                  95

Pro Pro Ala Lys Gly Pro Asp Leu Ala Ser Gly Gly Ser Phe Glu Gly
                100                 105                 110

Lys Tyr Ser Pro Glu Tyr Leu Arg Ser Ala Lys Ala Gly Ser Val Ser
                115                 120                 125

Val Gly Tyr Ser Ala Gly Asn Val Arg Leu Glu Ala Glu Gly Met Tyr
            130                 135                 140

Gln Lys Phe Pro Val Asp Thr Lys Lys Tyr Lys Asp Asn Pro Glu Arg
145                 150                 155                 160

Ala Tyr Arg Phe Ala Ile Ser Ala Pro Asp Glu Asn Ser Thr Thr Val
                165                 170                 175

Ala Thr Arg Pro Gln Glu Pro Tyr His Ile Thr Ala Glu Asn Lys Glu
                180                 185                 190

Val Thr Thr Ala Ser Leu Met Ala Asn Leu Cys Tyr Asp Leu Leu Pro
                195                 200                 205

Glu Ser Ser Gln Ile Ser Pro Ser Ala Cys Val Gly Gly Gly Ser
    210                 215                 220

Leu Val Arg Phe Leu Gly Val Thr Glu Val Arg Trp Ala Tyr Gln Ala
225                 230                 235                 240

Lys Val Gly Val Gln Tyr Phe Ala Ser Arg Lys Ala Ala Leu Phe Ala
                245                 250                 255

Tyr Ala Tyr Ala Ser Arg Val His Pro Glu Lys Phe Ser Asn Ile Pro
                260                 265                 270

Val Val His His Ile Lys Thr Glu Ser Pro Lys Gly Ser Gln Gly Ala
                275                 280                 285

Ala Gly Ser Gly Gly Glu Ser Ser Ala Gln Ala Ala Gly Gly Lys
                290                 295                 300

Leu Pro Gly Leu Leu Tyr Pro Gln Ala Ser Leu Gly Leu Asp Tyr Phe
305                 310                 315                 320

Gly Phe Glu Cys Gly Ile Arg Leu Val Leu
                325                 330

<210> SEQ ID NO 140
<211> LENGTH: 418
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(3)
<223> OTHER INFORMATION: any amino acid
<220> FEATURE:
<221> NAME/KEY: MISC_FEATURE
<222> LOCATION: (5)..(10)
<223> OTHER INFORMATION: any amino acid
<220> FEATURE:
<221> NAME/KEY: MISC_FEATURE
<222> LOCATION: (12)..(14)
<223> OTHER INFORMATION: any amino acid
<220> FEATURE:
```

```
<221> NAME/KEY: MISC_FEATURE
<222> LOCATION: (16)..(16)
<223> OTHER INFORMATION: any amino acid
<220> FEATURE:
<221> NAME/KEY: MISC_FEATURE
<222> LOCATION: (19)..(20)
<223> OTHER INFORMATION: any amino acid
<220> FEATURE:
<221> NAME/KEY: MISC_FEATURE
<222> LOCATION: (25)..(30)
<223> OTHER INFORMATION: any amino acid
<220> FEATURE:
<221> NAME/KEY: MISC_FEATURE
<222> LOCATION: (33)..(35)
<223> OTHER INFORMATION: any amino acid
<220> FEATURE:
<221> NAME/KEY: MISC_FEATURE
<222> LOCATION: (38)..(39)
<223> OTHER INFORMATION: any amino acid
<220> FEATURE:
<221> NAME/KEY: MISC_FEATURE
<222> LOCATION: (42)..(44)
<223> OTHER INFORMATION: any amino acid
<220> FEATURE:
<221> NAME/KEY: MISC_FEATURE
<222> LOCATION: (46)..(47)
<223> OTHER INFORMATION: any amino acid
<220> FEATURE:
<221> NAME/KEY: MISC_FEATURE
<222> LOCATION: (66)..(66)
<223> OTHER INFORMATION: any amino acid
<220> FEATURE:
<221> NAME/KEY: MISC_FEATURE
<222> LOCATION: (69)..(69)
<223> OTHER INFORMATION: any amino acid
<220> FEATURE:
<221> NAME/KEY: MISC_FEATURE
<222> LOCATION: (74)..(74)
<223> OTHER INFORMATION: any amino acid
<220> FEATURE:
<221> NAME/KEY: MISC_FEATURE
<222> LOCATION: (78)..(78)
<223> OTHER INFORMATION: any amino acid
<220> FEATURE:
<221> NAME/KEY: MISC_FEATURE
<222> LOCATION: (84)..(84)
<223> OTHER INFORMATION: any amino acid
<220> FEATURE:
<221> NAME/KEY: MISC_FEATURE
<222> LOCATION: (88)..(88)
<223> OTHER INFORMATION: any amino acid
<220> FEATURE:
<221> NAME/KEY: MISC_FEATURE
<222> LOCATION: (91)..(92)
<223> OTHER INFORMATION: any amino acid
<220> FEATURE:
<221> NAME/KEY: MISC_FEATURE
<222> LOCATION: (94)..(94)
<223> OTHER INFORMATION: any amino acid
<220> FEATURE:
<221> NAME/KEY: MISC_FEATURE
<222> LOCATION: (107)..(107)
<223> OTHER INFORMATION: any amino acid
<220> FEATURE:
<221> NAME/KEY: MISC_FEATURE
<222> LOCATION: (155)..(155)
<223> OTHER INFORMATION: any amino acid
<220> FEATURE:
<221> NAME/KEY: MISC_FEATURE
<222> LOCATION: (167)..(167)
<223> OTHER INFORMATION: any amino acid
<220> FEATURE:
<221> NAME/KEY: MISC_FEATURE
<222> LOCATION: (169)..(169)
<223> OTHER INFORMATION: any amino acid
<220> FEATURE:
<221> NAME/KEY: MISC_FEATURE
<222> LOCATION: (172)..(172)
<223> OTHER INFORMATION: any amino acid
```

```
<220> FEATURE:
<221> NAME/KEY: MISC_FEATURE
<222> LOCATION: (174)..(174)
<223> OTHER INFORMATION: any amino acid
<220> FEATURE:
<221> NAME/KEY: MISC_FEATURE
<222> LOCATION: (177)..(177)
<223> OTHER INFORMATION: any amino acid
<220> FEATURE:
<221> NAME/KEY: MISC_FEATURE
<222> LOCATION: (180)..(180)
<223> OTHER INFORMATION: any amino acid
<220> FEATURE:
<221> NAME/KEY: MISC_FEATURE
<222> LOCATION: (183)..(185)
<223> OTHER INFORMATION: any amino acid
<220> FEATURE:
<221> NAME/KEY: MISC_FEATURE
<222> LOCATION: (192)..(192)
<223> OTHER INFORMATION: any amino acid
<220> FEATURE:
<221> NAME/KEY: MISC_FEATURE
<222> LOCATION: (196)..(196)
<223> OTHER INFORMATION: any amino acid
<220> FEATURE:
<221> NAME/KEY: MISC_FEATURE
<222> LOCATION: (198)..(199)
<223> OTHER INFORMATION: any amino acid
<220> FEATURE:
<221> NAME/KEY: MISC_FEATURE
<222> LOCATION: (202)..(203)
<223> OTHER INFORMATION: any amino acid
<220> FEATURE:
<221> NAME/KEY: MISC_FEATURE
<222> LOCATION: (208)..(209)
<223> OTHER INFORMATION: any amino acid
<220> FEATURE:
<221> NAME/KEY: MISC_FEATURE
<222> LOCATION: (212)..(214)
<223> OTHER INFORMATION: any amino acid
<220> FEATURE:
<221> NAME/KEY: MISC_FEATURE
<222> LOCATION: (217)..(218)
<223> OTHER INFORMATION: any amino acid
<220> FEATURE:
<221> NAME/KEY: MISC_FEATURE
<222> LOCATION: (222)..(222)
<223> OTHER INFORMATION: any amino acid
<220> FEATURE:
<221> NAME/KEY: MISC_FEATURE
<222> LOCATION: (224)..(225)
<223> OTHER INFORMATION: any amino acid
<220> FEATURE:
<221> NAME/KEY: MISC_FEATURE
<222> LOCATION: (228)..(230)
<223> OTHER INFORMATION: any amino acid
<220> FEATURE:
<221> NAME/KEY: MISC_FEATURE
<222> LOCATION: (232)..(232)
<223> OTHER INFORMATION: any amino acid
<220> FEATURE:
<221> NAME/KEY: MISC_FEATURE
<222> LOCATION: (234)..(234)
<223> OTHER INFORMATION: any amino acid
<220> FEATURE:
<221> NAME/KEY: MISC_FEATURE
<222> LOCATION: (236)..(237)
<223> OTHER INFORMATION: any amino acid
<220> FEATURE:
<221> NAME/KEY: MISC_FEATURE
<222> LOCATION: (240)..(243)
<223> OTHER INFORMATION: any amino acid
<220> FEATURE:
<221> NAME/KEY: MISC_FEATURE
<222> LOCATION: (248)..(248)
<223> OTHER INFORMATION: any amino acid
<220> FEATURE:
<221> NAME/KEY: MISC_FEATURE
<222> LOCATION: (251)..(251)
```

```
<223> OTHER INFORMATION: any amino acid
<220> FEATURE:
<221> NAME/KEY: MISC_FEATURE
<222> LOCATION: (254)..(256)
<223> OTHER INFORMATION: any amino acid
<220> FEATURE:
<221> NAME/KEY: MISC_FEATURE
<222> LOCATION: (258)..(260)
<223> OTHER INFORMATION: any amino acid
<220> FEATURE:
<221> NAME/KEY: MISC_FEATURE
<222> LOCATION: (263)..(265)
<223> OTHER INFORMATION: any amino acid
<220> FEATURE:
<221> NAME/KEY: MISC_FEATURE
<222> LOCATION: (267)..(268)
<223> OTHER INFORMATION: any amino acid
<220> FEATURE:
<221> NAME/KEY: MISC_FEATURE
<222> LOCATION: (271)..(272)
<223> OTHER INFORMATION: any amino acid
<220> FEATURE:
<221> NAME/KEY: MISC_FEATURE
<222> LOCATION: (275)..(276)
<223> OTHER INFORMATION: any amino acid
<220> FEATURE:
<221> NAME/KEY: MISC_FEATURE
<222> LOCATION: (279)..(279)
<223> OTHER INFORMATION: any amino acid
<220> FEATURE:
<221> NAME/KEY: MISC_FEATURE
<222> LOCATION: (318)..(318)
<223> OTHER INFORMATION: any amino acid
<220> FEATURE:
<221> NAME/KEY: MISC_FEATURE
<222> LOCATION: (326)..(326)
<223> OTHER INFORMATION: any amino acid
<220> FEATURE:
<221> NAME/KEY: MISC_FEATURE
<222> LOCATION: (328)..(328)
<223> OTHER INFORMATION: any amino acid
<220> FEATURE:
<221> NAME/KEY: MISC_FEATURE
<222> LOCATION: (355)..(355)
<223> OTHER INFORMATION: any amino acid
<220> FEATURE:
<221> NAME/KEY: MISC_FEATURE
<222> LOCATION: (376)..(376)
<223> OTHER INFORMATION: any amino acid
<220> FEATURE:
<221> NAME/KEY: MISC_FEATURE
<222> LOCATION: (382)..(382)
<223> OTHER INFORMATION: any amino acid
<220> FEATURE:
<221> NAME/KEY: MISC_FEATURE
<222> LOCATION: (390)..(390)
<223> OTHER INFORMATION: any amino acid
<220> FEATURE:
<221> NAME/KEY: MISC_FEATURE
<222> LOCATION: (404)..(404)
<223> OTHER INFORMATION: any amino acid
<220> FEATURE:
<221> NAME/KEY: MISC_FEATURE
<222> LOCATION: (408)..(408)
<223> OTHER INFORMATION: any amino acid
<220> FEATURE:
<221> NAME/KEY: MISC_FEATURE
<222> LOCATION: (412)..(412)
<223> OTHER INFORMATION: any amino acid

<400> SEQUENCE: 140

Xaa Xaa Xaa Val Xaa Xaa Xaa Xaa Xaa Met Xaa Xaa Xaa Lys Xaa
1               5                   10                  15

Ala Leu Xaa Xaa Ala Val Ala Met Xaa Xaa Xaa Xaa Xaa Ala Gly
            20                  25                  30

Xaa Xaa Xaa Ala Ala Xaa Xaa Asp Val Xaa Xaa Xaa Ser Xaa Xaa Gly
```

```
                  35                  40                  45
Ala Gly Ser Phe Tyr Val Gly Leu Asp Tyr Ser Pro Ala Phe Ser Lys
 50                  55                  60

Ile Xaa Asp Phe Xaa Ile Arg Glu Ser Xaa Gly Glu Thr Xaa Ala Val
 65                  70                  75                  80

Tyr Pro Tyr Xaa Lys Asp Gly Xaa Arg Val Xaa Xaa Lys Xaa His Lys
                 85                  90                  95

Phe Asp Trp Asn Thr Pro Asp Pro Arg Ile Xaa Phe Lys Asp Asn Met
                100                 105                 110

Leu Val Ala Leu Glu Gly Ser Val Gly Tyr Ser Ile Gly Gly Ala Arg
            115                 120                 125

Val Glu Leu Glu Ile Gly Tyr Glu Arg Phe Lys Thr Lys Gly Ile Arg
        130                 135                 140

Asp Ser Gly Ser Lys Glu Glu Ala Asp Xaa Val Tyr Leu Leu Ala
145                 150                 155                 160

Lys Glu Leu Ala Tyr Asp Xaa Val Xaa Gly Gln Xaa Asp Xaa Leu Ala
                165                 170                 175

Xaa Ala Leu Xaa Lys Thr Xaa Xaa Xaa Glu Ile Val Lys Phe Ala Xaa
            180                 185                 190

Ala Val Glu Xaa Ser Xaa Xaa Gly Ile Xaa Xaa Lys Val Cys Lys Xaa
        195                 200                 205

Xaa Gly Ser Xaa Xaa Xaa Ala Gly Xaa Xaa Lys Cys Gly Xaa Gln Xaa
    210                 215                 220

Xaa Ser Asp Xaa Xaa Xaa Thr Xaa Glu Xaa Ser Xaa Xaa Phe Thr Xaa
225                 230                 235                 240

Xaa Xaa Xaa Asn Thr Leu Ser Xaa Gly Lys Xaa Trp Pro Xaa Xaa Xaa
                245                 250                 255

Asn Xaa Xaa Xaa Asn Ala Xaa Xaa Ala Xaa Xaa Leu Asn Xaa Xaa
                260                 265                 270

Leu Thr Xaa Xaa Glu Lys Xaa Ile Val Ala Gly Leu Leu Ala Arg Thr
            275                 280                 285

Ile Glu Gly Gly Glu Val Val Glu Ile Arg Ala Val Ser Ser Thr Ser
        290                 295                 300

Val Met Leu Asn Ala Cys Tyr Asp Leu Leu Ser Glu Gly Xaa Gly Val
305                 310                 315                 320

Val Pro Tyr Ala Cys Xaa Gly Xaa Gly Gly Asn Phe Val Gly Val Val
                325                 330                 335

Asp Gly His Ile Thr Pro Lys Leu Ala Tyr Arg Val Lys Ala Gly Leu
            340                 345                 350

Ser Tyr Xaa Leu Ser Pro Glu Ile Ser Ala Phe Ala Gly Gly Phe Tyr
        355                 360                 365

His Arg Val Leu Gly Asp Gly Xaa Tyr Asp Asp Leu Pro Xaa Gln Arg
    370                 375                 380

Leu Val Asp Asp Thr Xaa Thr Ala Gly Lys Thr Lys Asp Thr Ala Ile
385                 390                 395                 400

Ala Ser Phe Xaa Met Ala Tyr Xaa Gly Glu Xaa Gly Val Arg Phe
                405                 410                 415

Ala Phe

<210> SEQ ID NO 141
<211> LENGTH: 407
<212> TYPE: PRT
<213> ORGANISM: Artificial Sequence
<220> FEATURE:
```

<223> OTHER INFORMATION: Synthetic construct

<400> SEQUENCE: 141

```
Met Ser Ala Val Ser Asn Arg Lys Leu Pro Leu Gly Gly Val Leu Met
1               5                   10                  15

Ala Leu Val Ala Ala Val Ala Pro Ile His Ser Leu Leu Ala Ala Pro
            20                  25                  30

Ala Ala Gly Ala Gly Ala Gly Gly Glu Gly Leu Phe Ser Gly Ala Gly
        35                  40                  45

Ala Gly Ser Phe Tyr Ile Gly Leu Asp Tyr Ser Pro Ala Phe Gly Ser
    50                  55                  60

Ile Lys Asp Phe Lys Val Gln Glu Ala Gly Thr Thr Arg Gly Val
65                  70                  75                  80

Phe Pro Tyr Lys Arg Asp Ala Ala Gly Arg Val Asp Phe Lys Val His
                85                  90                  95

Asn Phe Asp Trp Ser Ala Pro Glu Pro Lys Ile Ser Phe Lys Asp Ser
                100                 105                 110

Met Leu Thr Ala Leu Glu Gly Ser Ile Gly Tyr Ser Ile Gly Gly Ala
            115                 120                 125

Arg Val Glu Val Glu Val Gly Tyr Glu Arg Phe Val Ile Lys Gly Gly
        130                 135                 140

Lys Lys Ser Asn Glu Asp Thr Ala Ser Val Phe Leu Leu Gly Lys Glu
145                 150                 155                 160

Leu Ala Tyr Asp Thr Ala Arg Gly Gln Val Asp Arg Leu Ala Thr Ala
                165                 170                 175

Leu Gly Lys Met Thr Lys Gly Glu Ala Lys Lys Trp Gly Asn Ala Val
            180                 185                 190

Glu Asn Ala Thr Asn Gly Asp Lys Val Ser Gln Asn Val Cys Lys Gly
        195                 200                 205

Thr Gly Ser Thr Gly Ser Ser Gly Asn Lys Cys Gly Thr Thr Asp Ser
    210                 215                 220

Thr Ala Thr Thr Lys Ile Ser Ala Val Phe Thr Glu Asp Ala Ala Ala
225                 230                 235                 240

Gln Leu Ser Thr Met Asp Asn Thr Thr Ile Asn Thr Thr Gly Met Ala
                245                 250                 255

Asn Asn Ile Asn Ser Leu Thr Lys Asp Glu Lys Ala Ile Val Ala Gly
            260                 265                 270

Ala Phe Ala Arg Ala Val Glu Gly Ala Glu Val Ile Glu Val Arg Ala
        275                 280                 285

Ile Gly Ser Thr Ser Val Met Leu Asn Ala Cys Tyr Asp Leu Leu Thr
    290                 295                 300

Asp Gly Ile Gly Val Val Pro Tyr Ala Cys Ala Gly Ile Gly Gly Asn
305                 310                 315                 320

Phe Val Ser Val Val Asp Gly His Ile Asn Pro Lys Phe Ala Tyr Arg
                325                 330                 335

Val Lys Ala Gly Leu Ser Tyr Ala Leu Thr Pro Glu Ile Ser Ala Phe
            340                 345                 350

Ala Gly Ala Phe Tyr His Lys Val Leu Gly Asp Gly Asp Tyr Asp Glu
        355                 360                 365

Leu Pro Leu Ser His Ile Ser Asp Tyr Thr Gly Thr Ala Gly Lys Asn
    370                 375                 380

Lys Asp Thr Gly Ile Ala Ser Phe Asn Phe Ala Tyr Phe Gly Gly Glu
385                 390                 395                 400
```

Leu Gly Val Arg Phe Ala Phe
                405

<210> SEQ ID NO 142
<211> LENGTH: 431
<212> TYPE: PRT
<213> ORGANISM: Artificial Sequence
<220> FEATURE:
<223> OTHER INFORMATION: Synthetic construct

<400> SEQUENCE: 142

Met Arg Lys Gly Lys Ile Ile Leu Gly Ser Val Met Met Ser Met Ala
1               5                   10                  15

Ile Val Met Ala Gly Asn Asp Val Arg Ala His Asp Asp Val Ser Ala
            20                  25                  30

Leu Glu Thr Gly Gly Ala Gly Tyr Phe Tyr Val Gly Leu Asp Tyr Ser
        35                  40                  45

Pro Ala Phe Ser Lys Ile Arg Asp Phe Ser Ile Arg Glu Ser Asn Gly
    50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
            100                 105                 110

Ile Gly Gly Ala Arg Val Glu Leu Glu Ile Gly Tyr Glu Arg Phe Lys
        115                 120                 125

Thr Lys Gly Ile Arg Asp Ser Gly Ser Lys Glu Asp Glu Ala Asp Thr
    130                 135                 140

Val Tyr Leu Leu Ala Lys Glu Leu Ala Tyr Asp Val Val Thr Gly Gln
145                 150                 155                 160

Thr Asp Asn Leu Ala Ala Ala Leu Ala Lys Thr Ser Gly Lys Asp Ile
                165                 170                 175

Val Gln Phe Ala Lys Ala Val Glu Ile Ser Asn Ser Gly Ile Gly Lys
            180                 185                 190

Lys Val Cys Glu Thr Lys Arg Lys Asp Gly Asp Thr Thr Asn Arg Phe
        195                 200                 205

Ala Lys Tyr Ile Val Gly Ala Gly Asp Ser Ser Asn Ala Gly Thr Ser
    210                 215                 220

Leu Cys Gly Gly Lys Asn Gln Lys Ser Ser Asp Thr Asp Thr Gly Val
225                 230                 235                 240

Glu Lys Ala Gln Ala Leu His Asp Phe Val Ser Asn Thr Leu Ser Asp
                245                 250                 255

Gly Thr Lys Asn Trp Pro Thr Ser Ser Glu Thr Ser Lys Ser Asn Asn
            260                 265                 270

Asp Asn Ala Lys Ala Val Ala Gly Asp Leu Thr Lys Lys Leu Thr Pro
        275                 280                 285

Glu Glu Lys Thr Ile Val Ala Gly Leu Leu Ala Lys Thr Ile Glu Gly
    290                 295                 300

Gly Glu Val Val Glu Ile Arg Ala Val Ser Ser Thr Ser Val Met Val
305                 310                 315                 320

Asn Ala Cys Tyr Asp Leu Leu Ser Glu Gly Leu Gly Val Val Pro Tyr
                325                 330                 335

Ala Cys Val Gly Leu Gly Gly Asn Phe Val Gly Val Val Asp Gly His
            340                 345                 350

-continued

Ile Thr Pro Lys Leu Ala Tyr Arg Leu Lys Ala Gly Leu Ser Tyr Gln
        355                 360                 365

Leu Ser Pro Glu Ile Ser Ala Phe Ala Gly Gly Phe Tyr His Arg Val
    370                 375                 380

Val Gly Asp Gly Val Tyr Asp Leu Pro Ala Gln Arg Leu Val Asp
385                 390                 395                 400

Asp Thr Ser Pro Ala Gly Arg Thr Lys Asp Thr Ala Ile Ala Asn Phe
                405                 410                 415

Ser Met Ala Tyr Val Gly Gly Glu Phe Gly Val Arg Phe Ala Phe
            420                 425                 430

<210> SEQ ID NO 143
<211> LENGTH: 458
<212> TYPE: PRT
<213> ORGANISM: Artificial Sequence
<220> FEATURE:
<223> OTHER INFORMATION: Synthetic construct

<400> SEQUENCE: 143

Met Leu Cys Leu Leu Val Val Glu Leu Trp Asn Val Lys Leu Val Ser
1               5                   10                  15

Val Gly Glu Ser Thr Gly Glu Ser Arg Asn Thr Val Glu Val Cys Cys
            20                  25                  30

Ala Arg Glu Lys Gly Val Arg Arg Glu Ala Ile Val Lys Gly Ser
        35                  40                  45

Glu Val Lys Gly Met Lys Glu Arg Lys Leu Ala Leu Ser Gly Ala Val
    50                  55                  60

Ala Met Thr Val Leu Val Ser Thr Ala Gly Thr Gly Thr Ala Ala Gly
65                  70                  75                  80

Ser Asp Val Asp Tyr Val Ser Lys Phe Gly Glu Gly Ser Phe Tyr Val
                85                  90                  95

Gly Leu Asn Tyr Ser Pro Ala Phe Ser Lys Ile Asn Gly Phe Glu Ile
            100                 105                 110

Arg Glu Ser Thr Gly Glu Thr Ala Ala Val Tyr Pro Tyr Met Lys Asp
        115                 120                 125

Gly Thr Arg Val Glu Trp Lys Ala Glu Lys Phe Asp Trp Asn Thr Pro
    130                 135                 140

Asp Pro Arg Ile Lys Phe Lys Asn Asn Pro Ile Val Ala Leu Glu Gly
145                 150                 155                 160

Ser Val Gly Tyr Ser Ile Gly Val Ala Arg Val Glu Leu Glu Ile Gly
                165                 170                 175

Tyr Glu Gln Phe Lys Thr Lys Gly Ile Arg Asp Thr Gly Ser Lys Glu
            180                 185                 190

Glu Glu Ala Asp Ala Val Tyr Leu Leu Ala Lys Lys Leu Pro His Thr
        195                 200                 205

Leu Val Ser Asp Gln Ser Asp Lys Phe Leu Glu Glu Leu Lys Asn Thr
    210                 215                 220

Lys Ala Ala Glu Ile Val Lys Phe Ala Glu Ala Val Gly Thr Ser Ala
225                 230                 235                 240

Lys Asp Ile Asp Gly Lys Val Cys Lys Lys Gly Gly Ser Gly Asn Ala
                245                 250                 255

Ala Gly Ser Trp Lys Cys Thr Gln Thr Gly Ser Asn Gly Val Ser Thr
            260                 265                 270

Ala Glu Phe Ser Lys Ile Phe Thr Lys Ala Asp Val Asn Thr Asp Asn
        275                 280                 285

```
Lys Gly Lys Ala Trp Pro Asn Gly Asn Asn Asp Ala Ala Lys Ala Glu
    290                 295                 300

Asp Leu Ser Ile Ala Leu Asn Arg Glu Leu Thr Ser Ala Glu Lys Asn
305                 310                 315                 320

Lys Val Ala Gly Leu Leu Thr Arg Thr Ile Ser Gly Gly Glu Val Val
                325                 330                 335

Glu Ile Arg Ala Val Ser Thr Thr Ser Val Met Leu Asn Gly Cys Tyr
            340                 345                 350

Asp Leu Gln Ser Glu Gly Phe Ser Ile Val Pro Tyr Ala Cys Leu Gly
        355                 360                 365

Val Gly Ala Asn Phe Val Gly Ile Val Asp Gly His Val Thr Pro Lys
    370                 375                 380

Leu Ala Tyr Lys Val Lys Ala Gly Leu Ser Tyr Glu Leu Ser Pro Glu
385                 390                 395                 400

Ile Ser Met Phe Ala Gly Gly Phe Tyr His Arg Val Leu Gly Glu Gly
                405                 410                 415

Glu Tyr Asp Asp Leu Pro Val Gln Arg Leu Val Asp Asp Ala Thr Thr
            420                 425                 430

Asn Lys Thr Lys Glu Phe Ala Lys Ala Ser Phe Lys Met Ala Tyr Thr
        435                 440                 445

Gly Ala Glu Ile Gly Val Arg Ser Ala Phe
    450                 455

<210> SEQ ID NO 144
<211> LENGTH: 36
<212> TYPE: PRT
<213> ORGANISM: Artificial Sequence
<220> FEATURE:
<223> OTHER INFORMATION: Synthetic construct

<400> SEQUENCE: 144

Asn Leu Val Ser Ala Val Gln Glu Lys Lys Pro Pro Glu Ala Pro Ala
1               5                   10                  15

Ala Asp Glu Ala Ala Glu Pro Ala Thr Pro Ala Pro Ser Ser Pro Glu
            20                  25                  30

Gly Phe Gly Ser
        35

<210> SEQ ID NO 145
<211> LENGTH: 22
<212> TYPE: PRT
<213> ORGANISM: Artificial Sequence
<220> FEATURE:
<223> OTHER INFORMATION: Synthetic construct

<400> SEQUENCE: 145

Glu Asn Thr Glu Lys Glu Leu Thr Leu Phe Thr Leu Lys Glu Ser Thr
1               5                   10                  15

Asp Thr Pro Thr Phe Lys
            20

<210> SEQ ID NO 146
<211> LENGTH: 27
<212> TYPE: PRT
<213> ORGANISM: Artificial Sequence
<220> FEATURE:
<223> OTHER INFORMATION: Synthetic construct

<400> SEQUENCE: 146

Asp Val Phe Ser Ala Lys Asp Ala Glu Ser Ser Ser Gly Ile Ala Thr
```

```
                1               5                  10                  15
Leu Leu Gln Ser Val Ala Ser Thr Ser Thr Ser
                20                  25

<210> SEQ ID NO 147
<211> LENGTH: 22
<212> TYPE: PRT
<213> ORGANISM: Artificial Sequence
<220> FEATURE:
<223> OTHER INFORMATION: Synthetic construct

<400> SEQUENCE: 147

Glu Lys Ser Glu Lys Glu Leu Thr Leu Phe Ser Leu Lys Glu Glu Thr
1               5                  10                  15

Glu Thr Ile Asp Leu Lys
                20

<210> SEQ ID NO 148
<211> LENGTH: 21
<212> TYPE: PRT
<213> ORGANISM: Artificial Sequence
<220> FEATURE:
<223> OTHER INFORMATION: Synthetic construct

<400> SEQUENCE: 148

Lys Gln Asp Lys Glu Leu Thr Leu Phe Ser Leu Lys Glu Glu Asn Thr
1               5                  10                  15

Glu Leu Lys Leu Asn
                20

<210> SEQ ID NO 149
<211> LENGTH: 37
<212> TYPE: PRT
<213> ORGANISM: Artificial Sequence
<220> FEATURE:
<223> OTHER INFORMATION: Synthetic construct

<400> SEQUENCE: 149

Asn Thr Phe Ala Met Lys Glu Lys Gln Gln Gly Gly Thr Ala Lys Ala
1               5                  10                  15

Ala Ala Gly Ala Ala Thr Pro Pro Ala Pro Ser Gly Ala Glu Ala
                20                  25                  30

Pro Pro Ala Lys Gly
            35

<210> SEQ ID NO 150
<211> LENGTH: 25
<212> TYPE: PRT
<213> ORGANISM: Artificial Sequence
<220> FEATURE:
<223> OTHER INFORMATION: Synthetic construct

<400> SEQUENCE: 150

Ser Glu Ala Asp Lys Ser Glu Lys Glu Leu Thr Leu Phe Thr Leu Lys
1               5                  10                  15

Glu Ser Thr Gln Ala Pro Asp Phe Thr
                20                  25

<210> SEQ ID NO 151
<211> LENGTH: 41
<212> TYPE: PRT
<213> ORGANISM: Artificial Sequence
<220> FEATURE:
<223> OTHER INFORMATION: Synthetic construct
```

<400> SEQUENCE: 151

Pro Tyr Phe Gly Ser Leu Thr Leu Glu Ser Gly Gly Lys Thr Leu Asn
1               5                   10                  15

Leu Val Ser Ala Val Gln Glu Lys Lys Pro Pro Glu Ala Pro Ala Ala
            20                  25                  30

Asp Glu Ala Ala Glu Pro Ala Thr Pro
        35                  40

<210> SEQ ID NO 152
<211> LENGTH: 32
<212> TYPE: PRT
<213> ORGANISM: Artificial Sequence
<220> FEATURE:
<223> OTHER INFORMATION: Synthetic construct

<400> SEQUENCE: 152

Pro Tyr Phe Gly Ala Phe Ser Leu Val His Gly Gly Asn Pro Leu Asp
1               5                   10                  15

Val Phe Ser Ala Lys Asp Ala Glu Ser Ser Gly Ile Ala Thr Leu
            20                  25                  30

<210> SEQ ID NO 153
<211> LENGTH: 38
<212> TYPE: PRT
<213> ORGANISM: Artificial Sequence
<220> FEATURE:
<223> OTHER INFORMATION: Synthetic construct

<400> SEQUENCE: 153

Pro His Phe Arg Asp Phe Ile Val Glu Asp Lys Gly Lys Ala Leu Asn
1               5                   10                  15

Thr Phe Ala Met Lys Glu Lys Gln Gln Gly Gly Thr Ala Lys Ala Ala
            20                  25                  30

Ala Gly Ala Ala Thr Pro
        35

<210> SEQ ID NO 154
<211> LENGTH: 22
<212> TYPE: PRT
<213> ORGANISM: Artificial Sequence
<220> FEATURE:
<223> OTHER INFORMATION: Synthetic construct

<400> SEQUENCE: 154

Pro Arg Phe Ser Pro Ile Ser Ala Lys Tyr Lys Thr Asp Glu Lys Ser
1               5                   10                  15

Glu Lys Glu Leu Thr Leu
            20

<210> SEQ ID NO 155
<211> LENGTH: 22
<212> TYPE: PRT
<213> ORGANISM: Artificial Sequence
<220> FEATURE:
<223> OTHER INFORMATION: Synthetic construct

<400> SEQUENCE: 155

Pro Arg Phe Ser Pro Ile Ser Val Lys Tyr Lys Thr Asp Glu Asn Thr
1               5                   10                  15

Glu Lys Glu Leu Thr Leu
            20

<210> SEQ ID NO 156
<211> LENGTH: 27
<212> TYPE: PRT
<213> ORGANISM: Artificial Sequence
<220> FEATURE:
<223> OTHER INFORMATION: Synthetic construct

<400> SEQUENCE: 156

Pro Met Phe Ser Pro Ile Ser Val Lys Tyr Lys Ser Thr Gly Asn Ser
1               5                  10                  15

Glu Ala Asp Lys Ser Glu Lys Glu Leu Thr Leu
            20                  25

<210> SEQ ID NO 157
<211> LENGTH: 21
<212> TYPE: PRT
<213> ORGANISM: Artificial Sequence
<220> FEATURE:
<223> OTHER INFORMATION: Synthetic construct

<400> SEQUENCE: 157

Pro Lys Phe Ser Ala Ile Ser Ala Lys Tyr Lys His Glu Lys Gln Asp
1               5                  10                  15

Lys Glu Leu Thr Leu
            20

<210> SEQ ID NO 158
<211> LENGTH: 273
<212> TYPE: DNA
<213> ORGANISM: Artificial Sequence
<220> FEATURE:
<223> OTHER INFORMATION: Synthetic construct

<400> SEQUENCE: 158
accgtcttgc cactgcttta ggtaagatga ctaagggtga agctaagaag tggggtaatg      60
ccatagagag tgctactggc actactagtg gtgatgaact gagtaagaag gtgtgtggca     120
agggtaccac tagtggtagc accaaccagt gtggtaccac cgatagcact gccaccacca     180
agattagtga ggtgttcact gagggtacag acacactgct ttctgttgag gggaacaaag     240
acaccaccaa cttgcagggg atggcgaata aca                                  273

<210> SEQ ID NO 159
<211> LENGTH: 359
<212> TYPE: DNA
<213> ORGANISM: Artificial Sequence
<220> FEATURE:
<223> OTHER INFORMATION: Synthetic construct

<400> SEQUENCE: 159
ataaccttgc cgctgctctt gccaaaacct caggtaagga catcgttcag tttgctaagg      60
ccgtggagat ttctaattcc ggtattggta agaaggtgtg tgagacaaag cggaaggatg     120
gtgatactac gaacaggttt gcaaagtata tagttggtgc gggtgatagt agcaatgctg     180
gtacatcatt gtgtggtggt aagaaccaaa agagttcgga cacagacacc ggggtggaga     240
aggctcaggc tctgcatgac tttgtttcta acacattgag tgatggtact aagaactggc     300
ctacgtcgag tgaaacgtct aaatcgaata acgacaacgc caaagctgta gcgggagac     359

<210> SEQ ID NO 160
<211> LENGTH: 284
<212> TYPE: DNA
<213> ORGANISM: Artificial Sequence
<220> FEATURE:
<223> OTHER INFORMATION: Synthetic construct

<400> SEQUENCE: 160
ataaattcct ggaggagctg aagaatacga aagcggcgga gatcgttaaa tttgctgagg    60
ctgttggcac atcggcaaag gatattgatg gaaaggtttg taagaagggc ggcagcggca   120
atgccgcggg cagctggaag tgtacgcaga ctggcagcaa cggcgtcagc accgcagagt   180
tcagtaaaat atttacgaag gcagacgtaa atactgacaa caaaggcaaa gcatggccta   240
acgggaacaa cgacgctgcg aaagcggaag acctaagtat tgcg                   284

<210> SEQ ID NO 161
<211> LENGTH: 292
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(5)
<223> OTHER INFORMATION: a, c, g or t
<220> FEATURE:
<221> NAME/KEY: misc_feature
<222> LOCATION: (20)..(20)
<223> OTHER INFORMATION: a, c, g or t
<220> FEATURE:
<221> NAME/KEY: misc_feature
<222> LOCATION: (22)..(23)
<223> OTHER INFORMATION: a, c, g or t
<220> FEATURE:
<221> NAME/KEY: misc_feature
<222> LOCATION: (26)..(26)
<223> OTHER INFORMATION: a, c, g or t
<220> FEATURE:
<221> NAME/KEY: misc_feature
<222> LOCATION: (34)..(34)
<223> OTHER INFORMATION: a, c, g or t
<220> FEATURE:
<221> NAME/KEY: misc_feature
<222> LOCATION: (37)..(37)
<223> OTHER INFORMATION: a, c, g or t
<220> FEATURE:
<221> NAME/KEY: misc_feature
<222> LOCATION: (41)..(41)
<223> OTHER INFORMATION: a, c, g or t
<220> FEATURE:
<221> NAME/KEY: misc_feature
<222> LOCATION: (65)..(65)
<223> OTHER INFORMATION: a, c, g or t
<220> FEATURE:
<221> NAME/KEY: misc_feature
<222> LOCATION: (70)..(70)
<223> OTHER INFORMATION: a, c, g or t
<220> FEATURE:
<221> NAME/KEY: misc_feature
<222> LOCATION: (78)..(79)
<223> OTHER INFORMATION: a, c, g or t
<220> FEATURE:
<221> NAME/KEY: misc_feature
<222> LOCATION: (82)..(82)
<223> OTHER INFORMATION: a, c, g or t
<220> FEATURE:
<221> NAME/KEY: misc_feature
<222> LOCATION: (92)..(92)
<223> OTHER INFORMATION: a, c, g or t
<220> FEATURE:
<221> NAME/KEY: misc_feature
<222> LOCATION: (98)..(98)
<223> OTHER INFORMATION: a, c, g or t
<220> FEATURE:
<221> NAME/KEY: misc_feature
<222> LOCATION: (113)..(113)
<223> OTHER INFORMATION: a, c, g or t
<220> FEATURE:

```
<221> NAME/KEY: misc_feature
<222> LOCATION: (116)..(117)
<223> OTHER INFORMATION: a, c, g or t
<220> FEATURE:
<221> NAME/KEY: misc_feature
<222> LOCATION: (132)..(132)
<223> OTHER INFORMATION: a, c, g or t
<220> FEATURE:
<221> NAME/KEY: misc_feature
<222> LOCATION: (136)..(136)
<223> OTHER INFORMATION: a, c, g or t
<220> FEATURE:
<221> NAME/KEY: misc_feature
<222> LOCATION: (140)..(140)
<223> OTHER INFORMATION: a, c, g or t
<220> FEATURE:
<221> NAME/KEY: misc_feature
<222> LOCATION: (143)..(143)
<223> OTHER INFORMATION: a, c, g or t
<220> FEATURE:
<221> NAME/KEY: misc_feature
<222> LOCATION: (147)..(147)
<223> OTHER INFORMATION: a, c, g or t
<220> FEATURE:
<221> NAME/KEY: misc_feature
<222> LOCATION: (152)..(152)
<223> OTHER INFORMATION: a, c, g or t
<220> FEATURE:
<221> NAME/KEY: misc_feature
<222> LOCATION: (155)..(155)
<223> OTHER INFORMATION: a, c, g or t
<220> FEATURE:
<221> NAME/KEY: misc_feature
<222> LOCATION: (160)..(160)
<223> OTHER INFORMATION: a, c, g or t
<220> FEATURE:
<221> NAME/KEY: misc_feature
<222> LOCATION: (180)..(180)
<223> OTHER INFORMATION: a, c, g or t
<220> FEATURE:
<221> NAME/KEY: misc_feature
<222> LOCATION: (183)..(183)
<223> OTHER INFORMATION: a, c, g or t
<220> FEATURE:
<221> NAME/KEY: misc_feature
<222> LOCATION: (194)..(194)
<223> OTHER INFORMATION: a, c, g or t
<220> FEATURE:
<221> NAME/KEY: misc_feature
<222> LOCATION: (201)..(201)
<223> OTHER INFORMATION: a, c, g or t
<220> FEATURE:
<221> NAME/KEY: misc_feature
<222> LOCATION: (203)..(203)
<223> OTHER INFORMATION: a, c, g or t
<220> FEATURE:
<221> NAME/KEY: misc_feature
<222> LOCATION: (210)..(210)
<223> OTHER INFORMATION: a, c, g or t
<220> FEATURE:
<221> NAME/KEY: misc_feature
<222> LOCATION: (218)..(218)
<223> OTHER INFORMATION: a, c, g or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (221)..(221)
<223> OTHER INFORMATION: a, c, g or t
<220> FEATURE:
<221> NAME/KEY: misc_feature
<222> LOCATION: (226)..(227)
<223> OTHER INFORMATION: a, c, g or t
<220> FEATURE:
<221> NAME/KEY: misc_feature
<222> LOCATION: (230)..(230)
<223> OTHER INFORMATION: a, c, g or t
```

```
<220> FEATURE:
<221> NAME/KEY: misc_feature
<222> LOCATION: (238)..(238)
<223> OTHER INFORMATION: a, c, g or t
<220> FEATURE:
<221> NAME/KEY: misc_feature
<222> LOCATION: (245)..(247)
<223> OTHER INFORMATION: a, c, g or t
<220> FEATURE:
<221> NAME/KEY: misc_feature
<222> LOCATION: (258)..(259)
<223> OTHER INFORMATION: a, c, g or t
<220> FEATURE:
<221> NAME/KEY: misc_feature
<222> LOCATION: (261)..(261)
<223> OTHER INFORMATION: a, c, g or t
<220> FEATURE:
<221> NAME/KEY: misc_feature
<222> LOCATION: (263)..(263)
<223> OTHER INFORMATION: a, c, g or t
<220> FEATURE:
<221> NAME/KEY: misc_feature
<222> LOCATION: (269)..(269)
<223> OTHER INFORMATION: a, c, g or t
<220> FEATURE:
<221> NAME/KEY: misc_feature
<222> LOCATION: (278)..(278)
<223> OTHER INFORMATION: a, c, g or t
<220> FEATURE:
<221> NAME/KEY: misc_feature
<222> LOCATION: (281)..(282)
<223> OTHER INFORMATION: a, c, g or t
<220> FEATURE:
<221> NAME/KEY: misc_feature
<222> LOCATION: (288)..(288)
<223> OTHER INFORMATION: a, c, g or t
<220> FEATURE:
<221> NAME/KEY: misc_feature
<222> LOCATION: (290)..(290)
<223> OTHER INFORMATION: a, c, g or t

<400> SEQUENCE: 161
ataancttgc cgctgctctn gnnaanacga cagnggngga natcgttaag tttgctaagg      60
ccgtngagan ttctactnnc gntattggtg gnaaggtntg tgagaaaagc ggnagnntgg    120
caatgctacg ancagntggn agngtanaca gntgnggtgn cagcaacagc gctggcaccn    180
canagtttag tganaagatc nangagggtn cagacacana nactgnngtn gagaaggnca    240
aagcnnngcc taacttgnnc nangacacng cgagtganag nnctaagnan tg            292

<210> SEQ ID NO 162
<211> LENGTH: 399
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(4)
<223> OTHER INFORMATION: any amino acid
<220> FEATURE:
<221> NAME/KEY: MISC_FEATURE
<222> LOCATION: (6)..(7)
<223> OTHER INFORMATION: any amino acid
<220> FEATURE:
<221> NAME/KEY: MISC_FEATURE
<222> LOCATION: (10)..(10)
<223> OTHER INFORMATION: any amino acid
<220> FEATURE:
<221> NAME/KEY: MISC_FEATURE
<222> LOCATION: (22)..(22)
<223> OTHER INFORMATION: any amino acid
<220> FEATURE:
<221> NAME/KEY: misc_feature
<222> LOCATION: (172)..(172)
```

```
<223> OTHER INFORMATION: Xaa can be any naturally occurring amino acid
<220> FEATURE:
<221> NAME/KEY: misc_feature
<222> LOCATION: (184)..(185)
<223> OTHER INFORMATION: Xaa can be any naturally occurring amino acid
<220> FEATURE:
<221> NAME/KEY: MISC_FEATURE
<222> LOCATION: (194)..(195)
<223> OTHER INFORMATION: any amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: MISC_FEATURE
<222> LOCATION: (213)..(213)
<223> OTHER INFORMATION: any amino acid
<220> FEATURE:
<221> NAME/KEY: MISC_FEATURE
<222> LOCATION: (220)..(220)
<223> OTHER INFORMATION: any amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: MISC_FEATURE
<222> LOCATION: (239)..(239)
<223> OTHER INFORMATION: any amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: MISC_FEATURE
<222> LOCATION: (248)..(248)
<223> OTHER INFORMATION: any amino acid
<220> FEATURE:
<221> NAME/KEY: MISC_FEATURE
<222> LOCATION: (250)..(250)
<223> OTHER INFORMATION: any amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: MISC_FEATURE
<222> LOCATION: (391)..(391)
<223> OTHER INFORMATION: any amino acid
<220> FEATURE:
<221> NAME/KEY: MISC_FEATURE
<222> LOCATION: (409)..(409)
<223> OTHER INFORMATION: any amino acid

<400> SEQUENCE: 162

Xaa Xaa Xaa Xaa Lys Xaa Xaa Leu Gly Xaa Val Met Met Ser Leu Ala
1               5                   10                  15

Ile Val Met Ala Gly Xaa Asp Val Arg Ala His Asp Asp Val Ser Ala
            20                  25                  30

Leu Gly Thr Gly Gly Ala Gly Ser Phe Tyr Val Gly Leu Asp Tyr Ser
        35                  40                  45

Pro Ala Phe Ser Lys Ile Arg Asp Phe Ser Ile Arg Glu Ser Asn Gly
    50                  55                  60
```

Glu Thr Lys Ala Val Tyr Pro Tyr Leu Lys Asp Gly Lys Arg Val Lys
65                  70                  75                  80

Leu Lys Ser His Lys Phe Asp Trp Asn Thr Pro Asp Pro Arg Ile Gly
                85                  90                  95

Phe Lys Asp Asn Met Leu Val Ala Leu Glu Gly Ser Val Gly Tyr Ser
            100                 105                 110

Ile Gly Gly Ala Arg Val Glu Leu Glu Ile Gly Tyr Glu Arg Phe Lys
        115                 120                 125

Thr Lys Gly Ile Arg Asp Ser Gly Ser Lys Glu Glu Ala Asp Thr
    130                 135                 140

Val Tyr Leu Leu Ala Lys Glu Leu Ala Tyr Asp Val Val Thr Gly Gln
145                 150                 155                 160

Thr Asp Lys Leu Ala Ala Leu Ala Lys Thr Xaa Gly Lys Glu Ile
                165                 170                 175

Val Lys Phe Ala Asn Ala Val Xaa Xaa Ser Ala Lys Asp Ile Asp Lys
            180                 185                 190

Lys Val Cys Lys Lys Gly Thr Gly Asn Thr Xaa Ser Ser Trp Lys Cys
            195                 200                 205

Gly Xaa Thr Gly Ser Thr Ala Thr Thr Lys Lys Phe Ser Ala Phe Phe
    210                 215                 220

Thr Lys Ala Val Xaa Glu Gly Lys Asn Trp Pro Thr Gly Xaa Asn Xaa
225                 230                 235                 240

Asn Ala Asn Ala Glu Asp Met Ala Thr Asp Leu Asn Glu Leu Thr Lys
                245                 250                 255

Glu Glu Lys Thr Ile Val Ala Gly Leu Leu Ala Arg Thr Ile Glu Gly
            260                 265                 270

Gly Glu Val Val Glu Ile Arg Ala Val Ser Ser Thr Ser Val Met Leu
        275                 280                 285

Asn Ala Cys Tyr Asp Leu Leu Ser Glu Gly Leu Gly Val Val Pro Tyr
290                 295                 300

Ala Cys Val Gly Leu Gly Gly Asn Phe Val Gly Val Val Asp Gly His
305                 310                 315                 320

Ile Thr Pro Lys Leu Ala Tyr Arg Val Lys Ala Gly Leu Ser Tyr Gln
                325                 330                 335

Leu Ser Pro Glu Ile Ser Ala Phe Ala Gly Gly Phe Tyr His Arg Val
            340                 345                 350

Leu Gly Asp Gly Val Tyr Asp Asp Leu Pro Leu Gln Arg Leu Val Asp
        355                 360                 365

Asp Thr Xaa Thr Ala Gly Lys Thr Lys Asp Thr Ala Ile Ala Ser Phe
    370                 375                 380

Ser Met Ala Tyr Xaa Gly Gly Glu Phe Gly Val Arg Phe Ala Phe
385                 390                 395

<210> SEQ ID NO 163
<211> LENGTH: 80
<212> TYPE: PRT
<213> ORGANISM: Artificial Sequence
<220> FEATURE:
<223> OTHER INFORMATION: Synthetic construct

<400> SEQUENCE: 163

Glu Ile Val Lys Phe Ala Glu Ala Val Gly Thr Ser Ala Lys Asp Ile
1               5                   10                  15

Asp Gly Lys Val Cys Lys Lys Gly Gly Ser Gly Asn Ala Ala Gly Ser
            20                  25                  30

```
Trp Lys Cys Thr Gln Thr Gly Ser Asn Gly Val Ser Thr Ala Glu Phe
            35                  40                  45

Ser Lys Ile Phe Thr Lys Ala Asp Val Asn Thr Asp Asn Lys Gly Lys
 50                  55                  60

Ala Trp Pro Asn Gly Asn Asn Asp Ala Ala Lys Ala Glu Asp Leu Ser
 65                  70                  75                  80
```

<210> SEQ ID NO 164
<211> LENGTH: 78
<212> TYPE: PRT
<213> ORGANISM: Artificial Sequence
<220> FEATURE:
<223> OTHER INFORMATION: Synthetic construct

<400> SEQUENCE: 164

```
Glu Ile Val Lys Phe Ala Glu Ala Val Gly Thr Ser Ala Lys Asp Ile
 1               5                  10                  15

Asp Lys Lys Val Cys Lys Lys Thr Asp Asn Thr Glu Gly Ser Trp Lys
                20                  25                  30

Cys Thr Gln Thr Gly Asn Asp Gly Gly Asp Lys Glu Phe Ser Lys Thr
            35                  40                  45

Phe Thr Lys Thr Gly Val Asn Glu Ala Thr Lys Gly Lys Ala Trp Pro
 50                  55                  60

Asn Gly His Thr Asp Ser Ala Lys Ala Glu Asp Leu Ser
 65                  70                  75
```

<210> SEQ ID NO 165
<211> LENGTH: 78
<212> TYPE: PRT
<213> ORGANISM: Artificial Sequence
<220> FEATURE:
<223> OTHER INFORMATION: Synthetic construct

<400> SEQUENCE: 165

```
Glu Ile Val Lys Phe Ala Glu Ala Val Gly Thr Ser Ala Lys Asn Ile
 1               5                  10                  15

Asp Lys Lys Val Cys Lys Lys Thr Gly Asn Asp Ala Asn Ser Trp Lys
                20                  25                  30

Cys Leu Gln Thr Gly Arg Asp Asp Ser Thr Ser Gly Lys Lys Phe Ser
            35                  40                  45

Glu Ile Phe Thr Lys Ala Asp Val Asn Thr Asp Asn Lys Gly Lys Ala
 50                  55                  60

Trp Pro Asn Gly Asn Gly Ala Ala Lys Ala Glu Asp Leu Ser
 65                  70                  75
```

<210> SEQ ID NO 166
<211> LENGTH: 80
<212> TYPE: PRT
<213> ORGANISM: Artificial Sequence
<220> FEATURE:
<223> OTHER INFORMATION: Synthetic construct

<400> SEQUENCE: 166

```
Glu Ile Val Lys Phe Ala Glu Ala Val Gly Thr Ser Ala Lys Asn Ile
 1               5                  10                  15

Asp Lys Lys Val Cys Lys Lys Thr Gly Asn Asp Ala Asn Ser Trp Lys
                20                  25                  30

Cys Glu Gln Thr Gly Ser Gly Ala Glu Thr Ser Ala Lys Ala Phe Ser
            35                  40                  45
```

-continued

```
Glu Ile Phe Thr Lys Ala Gly Val Asn Glu Ala Thr Lys Gly Lys Ala
 50                  55                  60

Trp Pro Asn Gly His Thr Gly Gly Ala Ala Lys Ala Glu Asp Leu Ser
 65                  70                  75                  80
```

<210> SEQ ID NO 167
<211> LENGTH: 79
<212> TYPE: PRT
<213> ORGANISM: Artificial Sequence
<220> FEATURE:
<223> OTHER INFORMATION: Synthetic construct

<400> SEQUENCE: 167

```
Glu Ile Val Lys Phe Ala Glu Ala Val Gly Thr Ser Ala Lys Asp Ile
 1               5                  10                  15

Asp Gly Lys Val Cys Lys Lys Thr Gly Asn Glu Ala Asp Ser Trp Lys
                 20                  25                  30

Cys Thr Gln Thr Gly Asn Gly Ser Gly Asn Ala Thr Glu Phe Ser Lys
             35                  40                  45

Ile Phe Thr Lys Lys Asn Val Asp Ala Glu Gly Lys Gly Lys Ala Trp
 50                  55                  60

Pro Asn Gly His Thr Asp Ser Ala Ala Lys Ala Glu Asp Leu Ser
 65                  70                  75
```

<210> SEQ ID NO 168
<211> LENGTH: 406
<212> TYPE: PRT
<213> ORGANISM: Artificial Sequence
<220> FEATURE:
<223> OTHER INFORMATION: Synthetic construct

<400> SEQUENCE: 168

```
Met Lys Glu Arg Lys Leu Ala Leu Ser Gly Ala Val Ala Met Thr Val
 1               5                  10                  15

Leu Val Ser Thr Ala Gly Thr Gly Thr Ala Ala Gly Ser Asp Val Asp
                 20                  25                  30

Tyr Val Ser Lys Phe Gly Glu Gly Ser Phe Tyr Val Gly Leu Asn Tyr
             35                  40                  45

Ser Pro Ala Phe Ser Lys Ile Asn Gly Phe Glu Ile Arg Glu Ser Thr
 50                  55                  60

Gly Glu Thr Ala Ala Val Tyr Pro Tyr Met Lys Asp Gly Thr Arg Val
 65                  70                  75                  80

Glu Trp Lys Ala Glu Lys Phe Asp Trp Asn Thr Pro Asp Pro Arg Ile
                 85                  90                  95

Lys Phe Lys Asn Asn Pro Ile Val Ala Leu Glu Gly Ser Val Gly Tyr
                100                 105                 110

Ser Ile Gly Val Ala Arg Val Glu Leu Glu Ile Gly Tyr Glu Gln Phe
            115                 120                 125

Lys Thr Lys Gly Ile Arg Asp Thr Gly Ser Lys Glu Glu Glu Ala Asp
130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
            180                 185                 190

Gly Lys Val Cys Lys Lys Gly Gly Ser Gly Asn Ala Ala Gly Ser Trp
            195                 200                 205
```

```
Lys Cys Thr Gln Thr Gly Ser Asn Gly Val Ser Thr Ala Glu Phe Ser
    210                 215                 220

Lys Ile Phe Thr Lys Ala Asp Val Asn Thr Asp Asn Lys Gly Lys Ala
225                 230                 235                 240

Trp Pro Asn Gly Asn Asn Asp Ala Ala Lys Ala Glu Asp Leu Ser Ile
                245                 250                 255

Ala Leu Asn Arg Glu Leu Thr Ser Ala Glu Lys Asn Lys Val Ala Gly
            260                 265                 270

Leu Leu Thr Arg Thr Ile Ser Gly Gly Glu Val Val Glu Ile Arg Ala
        275                 280                 285

Val Ser Thr Thr Ser Val Met Leu Asn Gly Cys Tyr Asp Leu Gln Ser
    290                 295                 300

Glu Gly Phe Ser Ile Val Pro Tyr Ala Cys Leu Gly Val Gly Ala Asn
305                 310                 315                 320

Phe Val Gly Ile Val Asp Gly His Val Thr Pro Lys Leu Ala Tyr Lys
                325                 330                 335

Val Lys Ala Gly Leu Ser Tyr Glu Leu Ser Pro Glu Ile Ser Met Phe
            340                 345                 350

Ala Gly Gly Phe Tyr His Arg Val Leu Gly Gly Glu Gly Tyr Asp Asp
        355                 360                 365

Leu Pro Val Gln Arg Leu Val Asp Asp Ala Thr Thr Asn Lys Thr Lys
    370                 375                 380

Glu Phe Ala Lys Ala Ser Phe Lys Met Ala Tyr Thr Gly Ala Glu Ile
385                 390                 395                 400

Gly Val Arg Phe Ala Phe
                405

<210> SEQ ID NO 169
<211> LENGTH: 410
<212> TYPE: PRT
<213> ORGANISM: Artificial Sequence
<220> FEATURE:
<223> OTHER INFORMATION: Synthetic construct

<400> SEQUENCE: 169

Met Ser Ala Val Ser Asn Arg Lys Leu Pro Leu Gly Val Leu Met
1               5                   10                  15

Ala Leu Ala Ala Val Ala Pro Ile His Ser Leu Leu Ala Ala Pro
                20                  25                  30

Ala Ala Gly Ala Gly Ala Gly Gly Glu Gly Leu Phe Ser Gly Ala Gly
            35                  40                  45

Ala Gly Ser Phe Tyr Ile Gly Leu Asp Tyr Ser Pro Ala Phe Gly Ser
    50                  55                  60

Ile Lys Asp Phe Lys Val Gln Glu Ala Gly Thr Thr Arg Gly Val
65                  70                  75                  80

Phe Pro Tyr Lys Arg Asp Ala Ala Gly Arg Val Asp Phe Lys Val His
                85                  90                  95

Asn Phe Asp Trp Ser Ala Pro Glu Pro Lys Ile Ser Phe Lys Asp Ser
                100                 105                 110

Met Leu Thr Ala Leu Glu Gly Ser Ile Gly Tyr Ser Ile Gly Gly Ala
            115                 120                 125

Arg Val Glu Val Glu Val Gly Tyr Glu Arg Phe Val Ile Lys Gly Gly
        130                 135                 140

Lys Lys Ser Asn Glu Asp Thr Ala Ser Val Phe Leu Leu Gly Lys Glu
145                 150                 155                 160
```

Leu Ala Tyr Asp Thr Ala Arg Gly Gln Val Asp Arg Leu Ala Thr Ala
				165					170					175

Leu Gly Lys Met Thr Lys Gly Glu Ala Lys Lys Trp Gly Asn Ala Ile
				180					185					190

Glu Ser Ala Thr Gly Thr Thr Ser Gly Asp Glu Leu Ser Lys Lys Val
				195					200					205

Cys Gly Lys Gly Thr Thr Ser Gly Ser Thr Asn Gln Cys Gly Thr Thr
				210					215					220

Asp Ser Thr Ala Thr Thr Lys Ile Ser Glu Val Phe Thr Glu Gly Thr
225					230					235					240

Asp Thr Leu Leu Ser Val Glu Gly Asn Lys Asp Thr Thr Asn Leu Gln
				245					250					255

Gly Met Ala Asn Asn Ile Asn Asn Leu Ser Lys Glu Asp Lys Ala Val
				260					265					270

Val Ala Gly Ala Phe Ala Arg Ala Val Glu Gly Ala Glu Val Ile Glu
				275					280					285

Val Arg Ala Ile Gly Ser Thr Ser Val Met Leu Asn Ala Cys Tyr Asp
				290					295					300

Leu Leu Thr Asp Gly Ile Gly Val Val Pro Tyr Ala Cys Ala Gly Ile
305					310					315					320

Gly Gly Asn Phe Val Ser Val Val Asp Gly His Ile Asn Pro Lys Phe
				325					330					335

Ala Tyr Arg Val Lys Ala Gly Leu Ser Tyr Ala Leu Thr Pro Glu Ile
				340					345					350

Ser Ala Phe Ala Gly Ala Phe Tyr His Lys Val Leu Gly Asp Gly Asp
				355					360					365

Tyr Asp Glu Leu Pro Leu Ser His Ile Ser Asp Tyr Thr Gly Thr Ala
				370					375					380

Gly Lys Asn Lys Asp Thr Gly Ile Ala Ser Phe Asn Phe Ala Tyr Phe
385					390					395					400

Gly Gly Glu Leu Gly Val Arg Phe Ala Phe
				405					410

<210> SEQ ID NO 170
<211> LENGTH: 406
<212> TYPE: PRT
<213> ORGANISM: Artificial Sequence
<220> FEATURE:
<223> OTHER INFORMATION: Synthetic construct

<400> SEQUENCE: 170

Met Ser Ala Val Ser Asn Arg Lys Leu Pro Leu Gly Gly Val Leu Met
1					5					10					15

Ala Leu Val Ala Ala Val Ala Pro Ile His Ser Leu Leu Ala Ala Pro
				20					25					30

Ala Ala Gly Ala Gly Ala Gly Gly Glu Gly Leu Phe Ser Gly Ala Gly
				35					40					45

Ala Gly Ser Phe Tyr Ile Gly Leu Asp Tyr Ser Pro Ala Phe Gly Ser
				50					55					60

Ile Lys Asp Phe Lys Val Gln Glu Ala Gly Thr Thr Arg Gly Val
65					70					75					80

Phe Pro Tyr Lys Arg Asp Ala Ala Gly Arg Val Asp Phe Lys Val His
				85					90					95

Asn Phe Asp Trp Ser Ala Pro Glu Pro Lys Ile Ser Phe Lys Asp Ser
				100					105					110

```
Met Leu Thr Ala Leu Glu Gly Ser Ile Gly Tyr Ser Ile Gly Gly Ala
        115                 120                 125
Arg Val Glu Val Glu Val Gly Tyr Glu Arg Phe Val Ile Lys Gly Gly
    130                 135                 140
Lys Lys Ser Asn Glu Asp Thr Ala Ser Val Phe Leu Leu Gly Lys Glu
145                 150                 155                 160
Leu Ala Tyr Asp Thr Ala Arg Gly Gln Val Asp Arg Leu Ala Ala Ala
                165                 170                 175
Leu Gly Lys Met Thr Lys Gly Glu Ala Lys Lys Trp Gly Thr Thr Val
            180                 185                 190
Glu Ala Ala Thr Asn Gly Gln Thr Val Ser Gln Asn Val Cys Lys Gly
        195                 200                 205
Asp Ser Gly Lys Cys Gly Val Asn Ala Asn Ser Gly Ser Thr Thr Ala
    210                 215                 220
Thr Thr Lys Ile Ser Ala Val Phe Thr Glu Gly Thr Asp Thr Ala Thr
225                 230                 235                 240
Gln Leu Ser Ala Asp Thr Asn Asn Val Ser Thr Ser Gly Met Ala Asn
                245                 250                 255
Asn Ile Asn Ser Leu Ser Lys Glu Glu Lys Ala Val Val Ala Gly Ala
            260                 265                 270
Phe Ala Arg Ala Val Glu Gly Ala Glu Val Ile Glu Val Arg Ala Ile
        275                 280                 285
Gly Ser Thr Ser Val Met Leu Asn Ala Cys Tyr Asp Leu Leu Thr Asp
    290                 295                 300
Gly Ile Gly Val Val Pro Tyr Ala Cys Ala Gly Ile Gly Gly Asn Phe
305                 310                 315                 320
Val Ser Val Val Asp Gly His Ile Asn Pro Lys Phe Ala Tyr Arg Val
                325                 330                 335
Lys Ala Gly Leu Ser Tyr Ala Leu Thr Pro Glu Ile Ser Ala Ser Ala
            340                 345                 350
Gly Ala Phe Tyr His Lys Val Leu Gly Asp Gly Asp Tyr Asp Glu Leu
        355                 360                 365
Pro Leu Ser His Ile Ser Asp Tyr Thr Gly Thr Ala Gly Lys Asn Lys
    370                 375                 380
Asp Thr Gly Ile Ala Ser Phe Asn Phe Ala Tyr Phe Gly Gly Glu Leu
385                 390                 395                 400
Gly Val Arg Phe Ala Phe
                405

<210> SEQ ID NO 171
<211> LENGTH: 410
<212> TYPE: PRT
<213> ORGANISM: Artificial Sequence
<220> FEATURE:
<223> OTHER INFORMATION: Synthetic construct

<400> SEQUENCE: 171

Met Ser Ala Val Ser Asn Arg Lys Leu Pro Leu Gly Gly Val Leu Met
1               5                   10                  15
Ala Leu Val Ala Ala Val Ala Pro Ile His Ser Leu Leu Ala Ala Pro
            20                  25                  30
Ala Ala Gly Ala Gly Ala Gly Gly Glu Gly Leu Phe Ser Gly Ala Gly
        35                  40                  45
Ala Gly Ser Phe Tyr Ile Gly Leu Asp Tyr Ser Pro Ala Phe Gly Ser
    50                  55                  60
```

```
Ile Lys Asp Phe Lys Val Gln Glu Ala Gly Gly Thr Thr Arg Gly Val
 65                  70                  75                  80

Phe Pro Tyr Lys Arg Asp Ala Ala Gly Arg Val Asp Phe Lys Val His
                 85                  90                  95

Asn Phe Asp Trp Ser Ala Pro Glu Pro Lys Ile Ser Phe Lys Asp Ser
                100                 105                 110

Met Leu Thr Ala Leu Glu Gly Ser Ile Gly Tyr Ser Ile Gly Gly Ala
                115                 120                 125

Arg Val Glu Val Glu Val Gly Tyr Glu Arg Phe Val Ile Lys Gly Gly
                130                 135                 140

Lys Lys Ser Asn Glu Asp Thr Ala Ser Val Phe Leu Leu Gly Lys Glu
145                 150                 155                 160

Leu Ala Tyr Asp Thr Ala Arg Gly Gln Val Asp Arg Leu Ala Thr Ala
                165                 170                 175

Leu Gly Lys Met Thr Lys Ser Glu Ala Lys Lys Trp Gly Asn Ala Ile
                180                 185                 190

Glu Ser Ala Thr Gly Thr Thr Ser Gly Asp Glu Leu Ser Lys Lys Val
                195                 200                 205

Cys Gly Lys Gly Thr Thr Ser Gly Asn Gln Cys Gly Lys Asn Ser Gly
210                 215                 220

Asp Thr Asn Gly Ser Ser Thr Thr Gln His Lys Ile Gly Ala Val Phe
225                 230                 235                 240

Thr Asp Glu Ala Thr Leu Leu Ser Ala Ala Gly Asp Thr Ile Asn Thr
                245                 250                 255

Thr Gly Met Ala Gly Asn Ile Asn Ser Leu Thr Lys Asp Glu Lys Ala
                260                 265                 270

Ile Val Ala Gly Ala Phe Ala Arg Ala Val Glu Gly Ala Glu Val Ile
                275                 280                 285

Glu Val Arg Ala Ile Gly Ser Thr Ser Val Met Leu Asn Ala Cys Tyr
290                 295                 300

Asp Leu Leu Thr Asp Gly Ile Gly Val Val Pro Tyr Ala Cys Ala Gly
305                 310                 315                 320

Ile Gly Gly Asn Phe Val Ser Val Val Asp Gly His Ile Asn Pro Lys
                325                 330                 335

Phe Ala Tyr Arg Val Lys Ala Gly Leu Ser Tyr Ala Leu Thr Pro Glu
                340                 345                 350

Ile Ser Ala Phe Ala Gly Ala Phe Tyr His Lys Val Leu Gly Asp Gly
                355                 360                 365

Asp Tyr Asp Glu Leu Pro Leu Ser His Ile Ser Asp Tyr Thr Thr Ala
                370                 375                 380

Gly Lys Asn Lys Asp Thr Gly Ile Ala Ser Phe Asn Phe Ala Tyr Phe
385                 390                 395                 400

Gly Gly Glu Leu Gly Val Arg Phe Ala Phe
                405                 410

<210> SEQ ID NO 172
<211> LENGTH: 410
<212> TYPE: PRT
<213> ORGANISM: Artificial Sequence
<220> FEATURE:
<223> OTHER INFORMATION: Synthetic construct

<400> SEQUENCE: 172

Met Ser Ala Val Ser Asn Arg Lys Leu Pro Leu Gly Gly Val Leu Met
1                5                  10                  15
```

Ala Leu Val Ala Ala Val Ala Pro Ile His Ser Leu Leu Ala Ala Pro
            20                  25                  30

Ala Ala Gly Ala Gly Ala Gly Glu Gly Leu Phe Ser Gly Ala Gly
        35                  40                  45

Ala Gly Ser Phe Tyr Ile Gly Leu Asp Tyr Ser Pro Ala Phe Gly Ser
50                  55                  60

Ile Lys Asp Phe Lys Val Gln Glu Ala Gly Thr Thr Arg Gly Val
65                  70                  75                  80

Phe Pro Tyr Lys Arg Asp Ala Ala Gly Arg Val Asp Phe Lys Val His
                85                  90                  95

Asn Phe Asp Trp Ser Ala Pro Glu Pro Lys Ile Ser Phe Lys Asp Ser
            100                 105                 110

Met Leu Thr Ala Leu Glu Gly Ser Ile Gly Tyr Ser Ile Gly Gly Ala
            115                 120                 125

Arg Val Glu Val Glu Val Gly Tyr Glu Arg Phe Val Ile Lys Gly Gly
            130                 135                 140

Lys Lys Ser Asn Glu Asp Thr Ala Ser Val Phe Leu Leu Gly Lys Glu
145                 150                 155                 160

Leu Ala Tyr Asp Thr Ala Arg Gly Gln Val Asp Arg Leu Ala Thr Ala
                165                 170                 175

Leu Gly Lys Met Thr Lys Ser Glu Ala Lys Lys Trp Gly Asn Ala Ile
            180                 185                 190

Glu Ser Ala Thr Gly Thr Thr Ser Gly Asp Glu Leu Ser Lys Lys Val
            195                 200                 205

Cys Gly Lys Gly Glu Gly Ser Asn Gly Thr Lys Lys Cys Gly Thr Thr
            210                 215                 220

Asp Ser Thr Ala Thr Thr Lys Ile Ser Glu Val Phe Thr Glu Gly Thr
225                 230                 235                 240

Asp Thr Leu Leu Ser Val Glu Gly Asn Lys Asp Thr Ile Asn Leu Gln
                245                 250                 255

Gly Met Ala Asn Asn Ile Asn Asn Leu Ser Lys Glu Asp Lys Ala Val
            260                 265                 270

Val Ala Gly Ala Phe Ala Arg Ala Val Glu Gly Ala Glu Val Ile Glu
            275                 280                 285

Val Arg Ala Ile Gly Ser Thr Ser Val Met Leu Asn Ala Cys Tyr Asp
            290                 295                 300

Leu Leu Thr Asp Gly Ile Gly Val Val Pro Tyr Ala Cys Ala Gly Ile
305                 310                 315                 320

Gly Gly Asn Phe Val Ser Val Val Asp Gly His Ile Asn Pro Lys Phe
                325                 330                 335

Ala Tyr Arg Val Lys Ala Gly Leu Ser Tyr Ala Leu Thr Pro Glu Ile
            340                 345                 350

Ser Ala Phe Ala Gly Ala Phe Tyr His Lys Val Leu Gly Asp Ser Gly
            355                 360                 365

Tyr Asp Glu Leu Pro Leu Ser His Ile Ser Asp Tyr Thr Gly Thr Ala
            370                 375                 380

Gly Lys Asn Lys Asp Thr Gly Ile Ala Ser Phe Asn Phe Ala Tyr Phe
385                 390                 395                 400

Gly Gly Glu Leu Gly Val Arg Phe Ala Phe
                405                 410

<210> SEQ ID NO 173
<211> LENGTH: 409

<212> TYPE: PRT
<213> ORGANISM: Artificial Sequence
<220> FEATURE:
<223> OTHER INFORMATION: Synthetic construct

<400> SEQUENCE: 173

Met Ser Ala Val Ser Asn Arg Lys Leu Pro Leu Gly Gly Val Leu Met
1               5                   10                  15

Ala Leu Val Ala Ala Val Ala Pro Ile His Ser Leu Leu Ala Ala Pro
            20                  25                  30

Ala Ala Gly Ala Gly Ala Gly Glu Gly Leu Phe Ser Gly Ala Gly
        35                  40                  45

Ala Gly Ser Phe Tyr Ile Gly Leu Asp Tyr Ser Pro Ala Phe Gly Ser
        50                  55                  60

Ile Lys Asp Phe Lys Val Gln Glu Ala Gly Gly Thr Thr Arg Gly Val
65                  70                  75                  80

Phe Pro Tyr Lys Arg Asp Ala Ala Gly Arg Val Asp Phe Lys Val His
                85                  90                  95

Asn Phe Asp Trp Ser Ala Pro Glu Pro Lys Ile Ser Phe Lys Asp Ser
                100                 105                 110

Met Leu Thr Ala Leu Glu Gly Ser Ile Gly Tyr Ser Ile Gly Gly Ala
            115                 120                 125

Arg Val Glu Val Glu Val Gly Tyr Glu Arg Phe Val Ile Lys Gly Gly
        130                 135                 140

Lys Lys Ser Asn Glu Asp Thr Ala Ser Val Phe Leu Leu Gly Lys Glu
145                 150                 155                 160

Leu Ala Tyr Asp Thr Ala Arg Gly Gln Val Asp Arg Leu Ala Thr Ala
                165                 170                 175

Leu Gly Lys Met Thr Lys Ser Glu Ala Lys Lys Trp Gly Asn Ala Ile
            180                 185                 190

Glu Ser Ala Thr Gly Thr Thr Ser Gly Asp Glu Leu Ser Lys Lys Val
        195                 200                 205

Cys Gly Lys Gly Thr Gly Ser Ser Gly Ser Ser Gly Asn Lys Cys Gly
210                 215                 220

Thr Thr Asp Ser Thr Ala Thr Thr Lys Ile Ser Ala Val Phe Thr Asp
225                 230                 235                 240

Glu Ala Thr Leu Leu Ser Ala Ala Gly Asp Thr Ile Asn Thr Thr Gly
                245                 250                 255

Met Ala Gly Asn Ile Asn Ser Leu Ser Lys Glu Asp Lys Ala Val Val
            260                 265                 270

Ala Gly Ala Phe Ala Arg Ala Val Glu Gly Ala Glu Val Ile Glu Val
        275                 280                 285

Arg Ala Ile Gly Ser Thr Ser Val Met Leu Asn Ala Cys Tyr Asp Leu
290                 295                 300

Leu Thr Asp Gly Ile Gly Val Val Pro Tyr Ala Cys Ala Gly Ile Gly
305                 310                 315                 320

Gly Asn Phe Val Ser Val Val Asp Gly His Ile Asn Pro Lys Phe Ala
                325                 330                 335

Tyr Arg Val Lys Ala Gly Leu Ser Tyr Ala Leu Thr Pro Glu Ile Ser
            340                 345                 350

Ala Phe Ala Gly Ala Phe Tyr His Lys Val Leu Gly Asp Gly Asp Tyr
        355                 360                 365

Asp Glu Leu Pro Leu Ser His Ile Ser Asp Tyr Thr Gly Thr Ala Gly
370                 375                 380

```
Lys Asn Lys Asp Thr Gly Ile Ala Ser Phe Asn Phe Ala Tyr Phe Gly
385                 390                 395                 400

Gly Glu Leu Gly Val Arg Phe Ala Phe
                405
```

<210> SEQ ID NO 174
<211> LENGTH: 405
<212> TYPE: PRT
<213> ORGANISM: Artificial Sequence
<220> FEATURE:
<223> OTHER INFORMATION: Synthetic construct

<400> SEQUENCE: 174

```
Met Ser Ala Val Ser Asn Arg Lys Leu Pro Leu Gly Gly Val Leu Met
1               5                   10                  15

Ala Leu Val Ala Ala Val Ala Pro Ile His Ser Leu Leu Ala Ala Pro
                20                  25                  30

Ala Ala Gly Ala Gly Ala Gly Gly Glu Gly Leu Phe Ser Gly Ala Gly
            35                  40                  45

Ala Gly Ser Phe Tyr Ile Gly Leu Asp Tyr Ser Pro Ala Phe Gly Ser
        50                  55                  60

Ile Lys Asp Phe Lys Val Gln Glu Ala Gly Thr Thr Arg Gly Val
65                  70                  75                  80

Phe Pro Tyr Lys Arg Asp Ala Ala Gly Arg Val Asp Phe Lys Val His
                85                  90                  95

Asn Phe Asp Trp Ser Ala Pro Glu Pro Lys Ile Ser Phe Lys Asp Ser
                100                 105                 110

Met Leu Thr Ala Leu Glu Gly Ser Ile Gly Tyr Ser Ile Gly Gly Ala
                115                 120                 125

Arg Val Glu Val Glu Val Gly Tyr Glu Arg Phe Val Ile Lys Gly Gly
            130                 135                 140

Lys Lys Ser Asn Glu Asp Thr Ala Ser Val Phe Leu Leu Gly Lys Glu
145                 150                 155                 160

Leu Ala Tyr Asp Thr Ala Arg Gly Gln Val Asp Arg Leu Ala Thr Ala
                165                 170                 175

Leu Gly Lys Met Thr Lys Gly Glu Ala Lys Lys Trp Gly Asn Ala Val
                180                 185                 190

Glu Asn Ala Thr Asn Gly Asp Lys Val Ser Gln Asn Val Cys Lys Gly
            195                 200                 205

Thr Gly Ser Thr Gly Ser Ser Gly Asn Lys Cys Gly Thr Thr Asp Ser
        210                 215                 220

Thr Ala Thr Thr Lys Ile Ser Ala Val Phe Thr Asp Glu Ala Thr Leu
225                 230                 235                 240

Leu Ser Ala Ala Gly Asp Thr Ile Asn Thr Thr Gly Met Ala Gly Asn
                245                 250                 255

Ile Asn Ser Leu Thr Lys Asp Glu Lys Ala Ile Val Ala Gly Ala Phe
                260                 265                 270

Ala Arg Ala Val Glu Gly Ala Glu Val Ile Glu Val Arg Ala Ile Gly
            275                 280                 285

Ser Thr Ser Val Met Leu Asn Ala Cys Tyr Asp Leu Leu Thr Asp Gly
        290                 295                 300

Ile Gly Val Val Pro Tyr Ala Cys Ala Gly Ile Gly Gly Asn Phe Val
305                 310                 315                 320

Ser Val Val Asp Gly His Ile Asn Pro Lys Phe Ala Tyr Arg Val Lys
                325                 330                 335
```

-continued

Ala Gly Leu Ser Tyr Ala Leu Thr Pro Glu Ile Ser Ala Phe Ala Gly
            340                 345                 350

Ala Phe Tyr His Lys Val Leu Gly Asp Gly Asp Tyr Asp Glu Leu Pro
        355                 360                 365

Leu Ser His Ile Ser Asp Tyr Thr Gly Thr Ala Gly Lys Asn Lys Asp
    370                 375                 380

Thr Gly Ile Ala Ser Phe Asn Phe Ala Tyr Phe Gly Gly Glu Leu Gly
385                 390                 395                 400

Val Arg Phe Ala Phe
            405

<210> SEQ ID NO 175
<211> LENGTH: 407
<212> TYPE: PRT
<213> ORGANISM: Artificial Sequence
<220> FEATURE:
<223> OTHER INFORMATION: Synthetic construct

<400> SEQUENCE: 175

Met Ser Ala Val Ser Asn Arg Lys Leu Pro Leu Gly Gly Val Leu Met
1               5                   10                  15

Ala Leu Val Ala Ala Val Ala Pro Ile His Ser Leu Leu Ala Ala Pro
            20                  25                  30

Ala Ala Gly Ala Gly Ala Gly Gly Glu Gly Leu Phe Ser Gly Ala Gly
        35                  40                  45

Ala Gly Ser Phe Tyr Ile Gly Leu Asp Tyr Ser Pro Ala Phe Gly Ser
    50                  55                  60

Ile Lys Asp Phe Lys Val Gln Glu Ala Gly Thr Thr Arg Gly Val
65                  70                  75                  80

Phe Pro Tyr Lys Arg Asp Ala Ala Gly Arg Val Asp Phe Lys Val His
                85                  90                  95

Asn Phe Asp Trp Ser Ala Pro Glu Pro Lys Ile Ser Phe Lys Asp Ser
            100                 105                 110

Met Leu Thr Ala Leu Glu Gly Ser Ile Gly Tyr Ser Ile Gly Gly Ala
        115                 120                 125

Arg Val Glu Val Glu Val Gly Tyr Glu Arg Phe Val Ile Lys Gly Gly
    130                 135                 140

Lys Lys Ser Asn Glu Asp Thr Ala Ser Val Phe Leu Leu Gly Lys Glu
145                 150                 155                 160

Leu Ala Tyr Asp Thr Ala Arg Gly Gln Val Asp Arg Leu Ala Thr Ala
                165                 170                 175

Leu Gly Lys Met Thr Lys Ser Glu Ala Lys Lys Trp Gly Asn Ala Val
            180                 185                 190

Glu Asn Ala Thr Asn Gly Asp Lys Val Ser Gln Asn Val Cys Lys Gly
        195                 200                 205

Thr Gly Ser Thr Gly Ser Ser Gly Asn Lys Cys Gly Thr Thr Asp Ser
    210                 215                 220

Thr Ala Thr Thr Lys Ile Ser Ala Val Phe Thr Glu Asp Ala Ala Ala
225                 230                 235                 240

Gln Leu Ser Thr Met Asp Asn Thr Thr Ile Asp Thr Thr Gly Met Ala
                245                 250                 255

Asn Asn Ile Asn Ser Leu Thr Lys Asp Glu Lys Ala Ile Val Ala Gly
            260                 265                 270

Ala Phe Ala Arg Ala Val Glu Gly Ala Glu Val Ile Glu Val Arg Ala
        275                 280                 285

```
Ile Gly Ser Thr Ser Val Met Leu Asn Ala Cys Tyr Asp Leu Leu Thr
        290                 295                 300

Asp Gly Ile Gly Val Val Pro Tyr Ala Cys Ala Gly Ile Gly Gly Asn
305                 310                 315                 320

Phe Val Ser Val Val Asp Gly His Ile Asn Pro Lys Phe Ala Tyr Arg
                325                 330                 335

Val Lys Ala Gly Leu Ser Tyr Ala Leu Thr Pro Glu Ile Ser Ala Phe
                340                 345                 350

Ala Gly Ala Phe Tyr His Lys Val Leu Gly Asp Gly Asp Tyr Asp Glu
            355                 360                 365

Leu Pro Leu Ser His Ile Ser Asp Tyr Thr Gly Thr Ala Gly Lys Asn
370                 375                 380

Lys Asp Thr Gly Ile Ala Ser Phe Asn Phe Ala Tyr Phe Gly Gly Glu
385                 390                 395                 400

Leu Gly Val Arg Phe Ala Phe
                405

<210> SEQ ID NO 176
<211> LENGTH: 431
<212> TYPE: PRT
<213> ORGANISM: Artificial Sequence
<220> FEATURE:
<223> OTHER INFORMATION: Synthetic construct

<400> SEQUENCE: 176

Met Arg Lys Gly Lys Ile Ile Leu Gly Ser Val Met Ser Met Ala
1                 5                  10                  15

Ile Val Met Ala Gly Asn Asp Val Arg Ala His Asp Val Ser Ala
                20                  25                  30

Leu Glu Thr Gly Gly Ala Gly Tyr Phe Tyr Val Gly Leu Asp Tyr Ser
            35                  40                  45

Pro Ala Phe Ser Lys Ile Arg Asp Phe Ser Ile Arg Glu Ser Asn Gly
        50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
                100                 105                 110

Ile Gly Gly Ala Arg Val Glu Leu Glu Ile Gly Tyr Glu Arg Phe Lys
            115                 120                 125

Thr Lys Gly Ile Arg Asp Ser Gly Ser Lys Glu Asp Glu Ala Asp Thr
130                 135                 140

Val Tyr Leu Leu Ala Lys Glu Leu Ala Tyr Asp Val Val Thr Gly Gln
145                 150                 155                 160

Thr Asp Asn Leu Ala Ala Ala Leu Ala Lys Thr Ser Gly Lys Asp Ile
                165                 170                 175

Val Gln Phe Ala Lys Ala Val Glu Ile Ser Asn Ser Gly Ile Gly Lys
                180                 185                 190

Lys Val Cys Glu Thr Lys Arg Lys Asp Gly Asp Thr Thr Asn Arg Phe
            195                 200                 205

Ala Lys Tyr Ile Val Gly Ala Gly Asp Ser Ser Asn Ala Gly Thr Ser
        210                 215                 220

Leu Cys Gly Gly Lys Asn Gln Lys Ser Ser Asp Thr Asp Thr Gly Val
225                 230                 235                 240
```

```
Glu Lys Ala Gln Ala Leu His Asp Phe Val Ser Asn Thr Leu Ser Asp
                245                 250                 255

Gly Thr Lys Asn Trp Pro Thr Ser Ser Glu Thr Ser Lys Ser Asn Asn
            260                 265                 270

Asp Asn Ala Lys Ala Val Ala Gly Asp Leu Thr Lys Lys Leu Thr Pro
        275                 280                 285

Glu Glu Lys Thr Ile Val Ala Gly Leu Leu Ala Lys Thr Ile Glu Gly
290                 295                 300

Gly Glu Val Val Glu Ile Arg Ala Val Ser Thr Ser Val Met Val
305                 310                 315                 320

Asn Ala Cys Tyr Asp Leu Leu Ser Glu Gly Leu Gly Val Val Pro Tyr
                325                 330                 335

Ala Cys Val Gly Leu Gly Gly Asn Phe Val Gly Val Val Asp Gly His
            340                 345                 350

Ile Thr Pro Lys Leu Ala Tyr Arg Leu Lys Ala Gly Leu Ser Tyr Gln
        355                 360                 365

Leu Ser Pro Glu Ile Ser Ala Phe Ala Gly Gly Phe Tyr His Arg Val
370                 375                 380

Val Gly Asp Gly Val Tyr Asp Asp Leu Pro Ala Gln Arg Leu Val Asp
385                 390                 395                 400

Asp Thr Ser Pro Ala Gly Arg Thr Lys Asp Thr Ala Ile Ala Asn Phe
                405                 410                 415

Ser Met Ala Tyr Val Gly Gly Glu Phe Gly Val Arg Phe Ala Phe
            420                 425                 430

<210> SEQ ID NO 177
<211> LENGTH: 433
<212> TYPE: PRT
<213> ORGANISM: Artificial Sequence
<220> FEATURE:
<223> OTHER INFORMATION: Synthetic construct

<400> SEQUENCE: 177

Met Met Ser Met Ala Ile Val Met Ala Gly Ser Asp Val Arg Ala His
1               5                   10                  15

Asp Asp Val Ser Ala Leu Asp Thr Gly Gly Ala Gly Tyr Phe Tyr Val
            20                  25                  30

Gly Leu Asp Tyr Ser Pro Ala Phe Ser Lys Ile Arg Asp Phe Ser Ile
        35                  40                  45

Arg Glu Ser Asn Gly Glu Thr Lys Ala Val Tyr Pro Tyr Leu Lys Asp
    50                  55                  60

Gly Lys Ser Val Lys Leu Glu Ser His Lys Phe Asp Trp Asn Thr Pro
65                  70                  75                  80

Asp Pro Arg Ile Gly Phe Lys Asp Asn Met Leu Val Ala Met Glu Gly
                85                  90                  95

Ser Val Gly Tyr Gly Ile Gly Gly Ala Arg Val Glu Leu Glu Ile Gly
            100                 105                 110

Tyr Glu Arg Phe Lys Thr Lys Gly Ile Arg Asp Ser Gly Ser Lys Glu
        115                 120                 125

Asp Glu Ala Asp Thr Val Tyr Leu Leu Ala Lys Glu Leu Ala Tyr Asp
    130                 135                 140

Val Val Thr Gly Gln Thr Asp Lys Leu Thr Ala Ala Leu Ala Lys Thr
145                 150                 155                 160

Ser Gly Lys Asp Ile Val Gln Phe Ala Lys Thr Leu Gly Ile Ser His
                165                 170                 175
```

Ser Glu Ile Asp Lys Lys Val Cys Ser Gly Ser His Ala Lys Gly Asn
                180                 185                 190

Ser Glu Thr Thr Lys Asn Asn Thr Val Ala Ser Tyr Thr Glu Lys Pro
            195                 200                 205

Thr Ala Ala Thr Ala Thr Ala Gln Cys Ser Gly Phe Pro Asp Glu Ala
        210                 215                 220

Ala Gly Asn Lys Ala Gly Gly Leu Asn Arg Phe Val Ser Glu Thr Lys
225                 230                 235                 240

Val Glu Glu Gly Lys Asn Trp Pro Thr Gly Lys Ile His Ser Gly Ser
                245                 250                 255

Ser Thr Asn Asn Val Asp Gly Thr His Asn Gly Asn Ala Lys Ala Val
            260                 265                 270

Ala Thr Asp Leu Val Asn Leu Asn Arg Asp Glu Lys Thr Ile Val Ala
        275                 280                 285

Gly Leu Leu Ala Lys Thr Ile Glu Gly Gly Glu Val Val Glu Ile Arg
        290                 295                 300

Ala Val Ser Ser Thr Ser Val Met Val Asn Ala Cys Tyr Asp Leu Leu
305                 310                 315                 320

Ser Glu Gly Leu Gly Val Val Pro Tyr Ala Cys Val Gly Leu Gly Gly
                325                 330                 335

Asn Phe Val Gly Val Val Asp Gly His Ile Thr Pro Lys Leu Ala Tyr
            340                 345                 350

Arg Leu Lys Ala Gly Leu Ser Tyr Gln Leu Ser Pro Glu Ile Ser Ala
        355                 360                 365

Phe Ala Gly Gly Phe Tyr His Arg Val Val Gly Asp Gly Val Tyr Asp
        370                 375                 380

Asp Leu Pro Ala Gln Arg Leu Val Asp Asp Thr Ser Pro Ala Gly Arg
385                 390                 395                 400

Thr Lys Asp Thr Ala Ile Ala Asn Phe Ser Met Ala Tyr Val Gly Ala
                405                 410                 415

Ser Phe Gln Pro Tyr Tyr Ala Val Leu Leu Val Glu Leu Tyr Glu Tyr
            420                 425                 430

Arg

<210> SEQ ID NO 178
<211> LENGTH: 359
<212> TYPE: PRT
<213> ORGANISM: Artificial Sequence
<220> FEATURE:
<223> OTHER INFORMATION: Synthetic construct

<400> SEQUENCE: 178

Met Met Ser Met Ala Ile Val Met Ala Gly Asn Asp Val Arg Ala His
1               5                   10                  15

Asp Asp Val Ser Ala Leu Glu Thr Gly Gly Ala Gly Tyr Phe Tyr Val
                20                  25                  30

Gly Leu Asp Tyr Ser Pro Ala Phe Ser Lys Ile Arg Asp Phe Ser Ile
            35                  40                  45

Arg Glu Ser Asn Gly Glu Thr Lys Ala Val Tyr Pro Tyr Leu Lys Asp
        50                  55                  60

Gly Lys Ser Val Lys Leu Glu Ser His Lys Phe Asp Trp Asn Thr Pro
65                  70                  75                  80

Asp Pro Arg Ile Gly Phe Lys Asp Asn Met Leu Val Ala Met Glu Gly
                85                  90                  95

Ser Val Gly Tyr Gly Ile Gly Gly Ala Arg Val Glu Leu Glu Ile Gly

```
                    100                 105                 110
Tyr Glu Arg Phe Lys Thr Lys Gly Ile Arg Asp Ser Gly Ser Lys Glu
            115                 120                 125

Asp Glu Ala Asp Thr Val Tyr Leu Leu Ala Lys Glu Leu Ala Tyr Asp
        130                 135                 140

Val Val Thr Gly Gln Thr Asp Lys Leu Thr Ala Ala Leu Ala Lys Thr
145                 150                 155                 160

Ser Gly Lys Asp Ile Val Gln Phe Ala Asn Ala Val Lys Ile Ser Ser
                165                 170                 175

Ser Ala Ile Asp Gly Lys Val Cys Thr Gly Ser His Ala Asp Leu Ala
            180                 185                 190

Pro Gly Thr Asn Ala Gly Lys Lys Phe Val Val Asn Pro Glu Ala Ser
        195                 200                 205

Gly Ser Thr Asp Gly Asp Thr Ser Gln Cys Ser Gly Leu Gly His Ser
    210                 215                 220

Ser Gly Val Thr Gln Asn Pro Lys Leu Phe Ser Thr Phe Val Asp Thr
225                 230                 235                 240

Val Lys Ile Ala Glu Asp Lys Asn Trp Pro Thr Gly Arg Ala Lys Ser
                245                 250                 255

Asn Thr Ser Leu Lys Thr Gly Asp Thr Asn Ser Asn Ala Lys Ala Val
            260                 265                 270

Ala Thr Asp Leu Val Gln Glu Leu Thr Pro Glu Glu Lys Thr Ile Val
        275                 280                 285

Ala Gly Leu Leu Ala Lys Thr Ile Glu Gly Gly Glu Val Val Glu Ile
    290                 295                 300

Arg Ala Val Ser Ser Thr Phe Ile Arg Ile Arg Asp Lys Leu Ile Ser
305                 310                 315                 320

Leu Leu Pro Leu Leu Thr Trp Glu Trp Lys Ile Val His Ser Val Cys
                325                 330                 335

Ala Ala Gly Val Arg Tyr Ser Asn Leu Arg Leu Leu Val Leu Leu Ser
            340                 345                 350

Gly Thr Trp Phe Ile Pro Gly
        355

<210> SEQ ID NO 179
<211> LENGTH: 422
<212> TYPE: PRT
<213> ORGANISM: Artificial Sequence
<220> FEATURE:
<223> OTHER INFORMATION: Synthetic construct

<400> SEQUENCE: 179

Met Met Ser Leu Ala Ile Val Met Ala Gly Asn Asp Val Arg Ala His
1               5                   10                  15

Asp Asp Val Ser Ala Leu Asp Thr Gly Gly Ala Gly Tyr Phe Tyr Val
            20                  25                  30

Gly Leu Asp Tyr Ser Pro Ala Phe Ser Lys Ile Arg Asp Phe Ser Ile
        35                  40                  45

Arg Glu Ser Asn Gly Glu Thr Lys Ala Val Tyr Pro Tyr Leu Lys Asp
    50                  55                  60

Gly Lys Ser Val Lys Leu Glu Ser His Lys Phe Asp Trp Asn Thr Pro
65                  70                  75                  80

Asp Pro Arg Ile Gly Phe Lys Asp Asn Met Leu Val Ala Met Glu Gly
                85                  90                  95

Ser Val Gly Tyr Gly Ile Gly Gly Ala Arg Val Glu Leu Glu Ile Gly
```

```
                100                 105                 110
Tyr Glu Arg Phe Lys Thr Lys Gly Ile Arg Asp Ser Gly Ser Lys Glu
            115                 120                 125

Asp Glu Ala Asp Thr Val Tyr Leu Leu Ala Lys Glu Leu Ala Tyr Asp
130                 135                 140

Val Val Thr Gly Gln Thr Asp Lys Leu Thr Ala Ala Leu Ala Lys Thr
145                 150                 155                 160

Ser Gly Lys Asp Ile Val Gln Phe Ala Asn Ala Val Lys Ile Thr Asn
            165                 170                 175

Ser Thr Ile Asp Gly Lys Val Cys Ser Gly Lys His Ala Ala Leu Val
        180                 185                 190

Pro Asn Lys Gly Lys Asp Tyr Asp Ala Asp Ala Lys Glu Ser Asn Thr
        195                 200                 205

Asn Ala His Lys Thr Ala Gln Cys Ser Gly Leu Ala Asp Ser Ala Ala
        210                 215                 220

Thr Gly Pro Lys Ser Phe Ser Gly Phe Val Gly Ala Val Lys Val Gly
225                 230                 235                 240

Glu Gly Lys Asn Trp Pro Thr Gly Arg Ala Ala Ser Ala Thr Ser Asn
                245                 250                 255

Glu Thr Val Val Gly Pro Thr Asn Ser Asn Ala Thr Ala Val Ala Lys
            260                 265                 270

Asp Leu Val Ala Leu Asn Ser Asp Glu Lys Thr Ile Val Ala Gly Leu
        275                 280                 285

Leu Ala Lys Thr Ile Glu Gly Gly Glu Val Val Glu Ile Arg Ala Val
        290                 295                 300

Ser Ser Thr Ser Val Met Val Asn Ala Cys Tyr Asp Leu Leu Ser Glu
305                 310                 315                 320

Gly Leu Gly Val Val Pro Tyr Ala Cys Val Leu Gly Gly Asn Phe
                325                 330                 335

Val Gly Val Val Asp Gly His Ile Thr Pro Lys Leu Ala Tyr Arg Leu
            340                 345                 350

Lys Ala Gly Leu Ser Tyr Gln Leu Ser Pro Glu Ile Ser Ala Phe Ala
        355                 360                 365

Gly Gly Phe Tyr His Arg Val Val Gly Asp Gly Val Tyr Asp Asp Leu
        370                 375                 380

Pro Ala Gln Arg Leu Val Asp Asp Thr Ser Pro Ala Gly Arg Thr Lys
385                 390                 395                 400

Asp Thr Ala Ile Ala Asn Phe Ser Met Ala Tyr Val Gly Gly Glu Phe
                405                 410                 415

Gly Val Arg Phe Ala Phe
            420

<210> SEQ ID NO 180
<211> LENGTH: 355
<212> TYPE: PRT
<213> ORGANISM: Artificial Sequence
<220> FEATURE:
<223> OTHER INFORMATION: Synthetic construct

<400> SEQUENCE: 180

Met Met Ser Met Ala Ile Val Met Ala Gly Asn Asp Val Arg Ala His
1               5                   10                  15

Asp Asp Val Ser Ala Leu Glu Thr Gly Gly Ala Gly Tyr Phe Tyr Val
            20                  25                  30

Gly Leu Asp Tyr Ser Pro Ala Phe Ser Lys Ile Arg Asp Phe Ser Ile
```

```
            35                  40                  45
Arg Glu Ser Asn Gly Glu Thr Lys Ala Val Tyr Pro Tyr Leu Lys Asp
 50                  55                  60
Gly Lys Ser Val Lys Leu Glu Ser His Lys Phe Asp Trp Asn Thr Pro
65                  70                  75                  80
Asp Pro Arg Ile Gly Phe Lys Asp Asn Met Leu Val Ala Met Glu Gly
                 85                  90                  95
Ser Val Gly Tyr Gly Ile Gly Gly Ala Arg Val Glu Leu Glu Ile Gly
                100                 105                 110
Tyr Glu Arg Phe Lys Thr Lys Gly Ile Arg Asp Ser Gly Ser Lys Glu
                115                 120                 125
Asp Glu Ala Asp Thr Val Tyr Leu Leu Ala Lys Glu Leu Ala Tyr Asp
                130                 135                 140
Val Val Thr Gly Gln Thr Asp Asn Leu Ala Ala Ala Leu Ala Lys Thr
145                 150                 155                 160
Ser Gly Lys Asp Ile Val Gln Phe Ala Lys Ala Val Glu Ile Ser Asn
                165                 170                 175
Ser Thr Ile Gly Asp Lys Val Cys Arg Thr Arg Tyr Asp Thr Ala Lys
                180                 185                 190
Lys Asp His Tyr Ala Lys Tyr Ala Lys Thr Thr Asp Lys Gly Ser Ala
                195                 200                 205
Ser Lys Asn Asp Thr Ser Leu Cys Gly Asp Ile Gly His Ser Thr Val
                210                 215                 220
Thr Ser Gly His Ser Thr Thr Pro Gln Val Leu Lys Asn Phe Ile Ser
225                 230                 235                 240
Ala Thr Leu Gly Asn Gly Ser Gln Asn Trp Pro Thr Ser Thr Gly Thr
                245                 250                 255
Gly Ser Ser Thr Asn Asp Asn Ala Glu Ala Val Ala Lys Asp Leu Thr
                260                 265                 270
Lys Leu Thr Thr Glu Glu Lys Thr Ile Val Ala Gly Leu Leu Ala Lys
                275                 280                 285
Thr Ile Glu Gly Gly Glu Val Val Glu Ile Arg Ala Val Ser Ser Thr
                290                 295                 300
Ser Val Met Val Asn Ala Cys Tyr Asp Leu Leu Ser Glu Gly Leu Gly
305                 310                 315                 320
Val Val Pro Tyr Ala Cys Val Gly Leu Gly Gly Asn Phe Val Gly Val
                325                 330                 335
Val Asp Gly Thr Arg Cys Thr Ile Arg Pro Ser Leu Thr Leu Tyr Ala
                340                 345                 350
His Ser Lys
    355

<210> SEQ ID NO 181
<211> LENGTH: 435
<212> TYPE: PRT
<213> ORGANISM: Artificial Sequence
<220> FEATURE:
<223> OTHER INFORMATION: Synthetic construct

<400> SEQUENCE: 181

Met Arg Lys Gly Lys Ile Ile Leu Gly Ser Val Met Met Ser Met Ala
1               5                   10                  15
Ile Val Met Ala Gly Asn Asp Val Arg Ala His Asp Asp Val Ser Ala
                20                  25                  30
Leu Glu Thr Gly Gly Ala Gly Tyr Phe Tyr Val Gly Leu Asp Tyr Ser
```

35                  40                  45
Pro Ala Phe Ser Lys Ile Arg Asp Phe Ser Ile Arg Glu Ser Asn Gly
 50                  55                  60

Glu Thr Lys Ala Val Tyr Pro Tyr Leu Lys Asp Gly Lys Ser Val Lys
 65                  70                  75                  80

Leu Glu Ser Asn Lys Phe Asp Trp Asn Thr Pro Asp Pro Arg Ile Gly
                 85                  90                  95

Phe Lys Asp Asn Met Leu Val Ala Met Glu Gly Ser Val Gly Tyr Gly
                100                 105                 110

Ile Gly Gly Ala Arg Val Glu Leu Glu Ile Gly Tyr Glu Arg Phe Lys
                115                 120                 125

Thr Lys Gly Ile Arg Asp Ser Gly Lys Glu Asp Glu Ala Asp Thr
130                 135                 140

Val Tyr Leu Leu Ala Lys Glu Leu Ala Tyr Asp Val Thr Gly Gln
145                 150                 155                 160

Thr Asp Lys Leu Thr Ala Ala Leu Ala Lys Thr Ser Gly Lys Asp Ile
                165                 170                 175

Val Gln Phe Ala Lys Ala Val Gly Val Ser His Pro Gly Ile Asp Lys
                180                 185                 190

Lys Val Cys Asp Gly Gly His Ala Arg Gly Lys Lys Ser Gly Asp Asn
                195                 200                 205

Gly Ser Leu Ala Asp Tyr Thr Asp Gly Gly Ala Ser Gln Thr Asn Lys
210                 215                 220

Thr Ala Gln Cys Ser Gly Met Gly Thr Gly Lys Ala Gly Lys Arg Gly
225                 230                 235                 240

Leu Gly Leu Thr Glu Phe Val Asn Lys Thr Lys Val Gly Glu Gly Lys
                245                 250                 255

Asn Trp Pro Thr Gly Tyr Val Asn Asp Gly Asp Asn Val Asn Val Leu
                260                 265                 270

Gly Asp Thr Asn Gly Asn Ala Glu Ala Val Ala Lys Asp Leu Val Gln
                275                 280                 285

Glu Leu Thr Pro Glu Glu Lys Thr Ile Val Ala Gly Leu Leu Ala Lys
290                 295                 300

Thr Ile Glu Gly Gly Glu Val Val Glu Ile Arg Ala Val Ser Ser Thr
305                 310                 315                 320

Ser Val Met Val Asn Ala Cys Tyr Asp Leu Leu Ser Glu Gly Leu Gly
                325                 330                 335

Val Val Pro Tyr Ala Cys Val Gly Leu Gly Gly Asn Phe Val Gly Val
                340                 345                 350

Val Asp Gly His Ile Thr Pro Lys Leu Ala Tyr Arg Leu Lys Ala Gly
                355                 360                 365

Leu Ser Tyr Gln Leu Ser Pro Glu Ile Ser Ala Phe Ala Gly Gly Phe
                370                 375                 380

Tyr His Arg Val Val Gly Asp Gly Val Tyr Asp Asp Leu Pro Ala Gln
385                 390                 395                 400

Arg Leu Val Asp Asp Thr Ser Pro Ala Gly Arg Thr Lys Asp Thr Ala
                405                 410                 415

Ile Ala Asn Phe Ser Met Ala Tyr Val Gly Gly Glu Phe Gly Val Arg
                420                 425                 430

Phe Ala Phe
            435

<210> SEQ ID NO 182

<211> LENGTH: 432
<212> TYPE: PRT
<213> ORGANISM: Artificial Sequence
<220> FEATURE:
<223> OTHER INFORMATION: Synthetic construct

<400> SEQUENCE: 182

```
Met Arg Lys Gly Lys Ile Ile Leu Gly Ser Val Met Met Ser Met Ala
1               5                   10                  15

Ile Val Met Ala Gly Asn Asp Val Arg Ala His Asp Asp Val Ser Ala
            20                  25                  30

Leu Glu Thr Gly Gly Ala Gly Tyr Phe Tyr Ile Gly Leu Asp Tyr Ser
        35                  40                  45

Pro Ala Phe Ser Lys Ile Arg Asp Phe Ser Ile Arg Glu Ser Asn Gly
50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
            100                 105                 110

Ile Gly Gly Ala Arg Val Glu Leu Gly Ile Gly Tyr Glu Arg Phe Lys
        115                 120                 125

Thr Lys Gly Ile Arg Asp Ser Gly Ser Lys Glu Asp Glu Ala Asp Thr
130                 135                 140

Val Tyr Leu Leu Ala Lys Glu Leu Ala Tyr Asp Val Val Thr Gly Gln
145                 150                 155                 160

Thr Asp Asn Leu Ala Ala Ala Leu Ala Lys Thr Ser Gly Lys Asp Ile
                165                 170                 175

Val Gln Phe Ala Asn Ala Val Lys Ile Ser Ser Pro Glu Ile Asp Gly
            180                 185                 190

Lys Val Cys Ser Gly Asp His Ala Ala Ile Thr Lys Ala Lys Gly Lys
        195                 200                 205

Lys Tyr Val Ala Glu Leu Ser Thr Thr His Ser Asp Glu Glu Thr Thr
210                 215                 220

Gln Cys Ser Gly Leu Gly Asn Thr Thr Gly Ala Thr Gly Pro Lys Thr
225                 230                 235                 240

Leu Ser Gly Phe Val Asn Thr Val Lys Val Gly Glu Gly Lys Asn Trp
                245                 250                 255

Pro Arg Gly Arg Gly Ser Asn Gly Ser Ser Gln Asn Val Glu Gly Glu
            260                 265                 270

Pro Asn Ser Asn Ala Asn Ala Met Ala Lys Asp Leu Leu Gly Leu Asn
        275                 280                 285

Arg Asp Glu Lys Thr Ile Val Thr Gly Leu Leu Ala Lys Thr Ile Glu
290                 295                 300

Gly Gly Glu Val Val Glu Ile Arg Ala Val Ser Ser Thr Ser Val Met
305                 310                 315                 320

Val Asn Ala Cys Tyr Asp Leu Leu Ser Glu Gly Leu Gly Val Val Pro
                325                 330                 335

Tyr Ala Cys Val Gly Leu Gly Gly Asn Phe Val Gly Val Asp Gly
            340                 345                 350

His Ile Thr Pro Lys Leu Ala Tyr Arg Leu Lys Ala Gly Leu Ser Tyr
        355                 360                 365

Gln Leu Ser Pro Glu Ile Ser Ala Phe Ala Gly Gly Phe Tyr His Arg
370                 375                 380
```

Val Val Gly Asp Gly Val Tyr Asp Asp Leu Pro Ala Gln Arg Leu Val
385                 390                 395                 400

Asp Asp Thr Ser Pro Ala Gly Arg Thr Lys Asp Thr Ala Ile Ala Asn
            405                 410                 415

Phe Ser Met Ala Tyr Val Gly Gly Glu Phe Gly Val Arg Phe Ala Phe
        420                 425                 430

<210> SEQ ID NO 183
<211> LENGTH: 427
<212> TYPE: PRT
<213> ORGANISM: Artificial Sequence
<220> FEATURE:
<223> OTHER INFORMATION: Synthetic construct

<400> SEQUENCE: 183

Met Arg Lys Gly Lys Ile Ile Leu Gly Ser Val Met Met Ser Met Ala
1               5                   10                  15

Ile Val Met Ala Gly Ser Asp Val Arg Ala His Asp Asp Val Ser Ala
            20                  25                  30

Leu Asp Thr Gly Gly Ala Gly Tyr Phe Tyr Val Gly Leu Asp Tyr Ser
        35                  40                  45

Pro Ala Phe Ser Lys Ile Arg Asp Phe Ser Ile Arg Glu Ser Asn Gly
    50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
            100                 105                 110

Ile Gly Gly Ala Arg Val Glu Leu Glu Ile Gly Tyr Glu Arg Phe Lys
        115                 120                 125

Thr Lys Gly Ile Arg Asp Ser Gly Ser Lys Glu Asp Glu Ala Asp Thr
130                 135                 140

Val Tyr Leu Leu Ala Lys Glu Leu Ala Tyr Asp Val Val Thr Gly Gln
145                 150                 155                 160

Thr Asp Asn Leu Ala Ala Ala Leu Ala Lys Thr Ser Gly Lys Asp Leu
                165                 170                 175

Val Gln Phe Ala Asn Ala Val Glu Ile Ser His Ser Glu Ile Gly Lys
            180                 185                 190

Lys Val Cys Val Thr Lys Asn Tyr Asp Ser Gly Ser Asn Phe Ala Lys
        195                 200                 205

Tyr Gly Thr Glu Ser Asn Gly Gln Ser Thr Thr Ser His Arg Val Ala
210                 215                 220

Leu Cys Gly Gly Lys Gly Val Ala Ser Thr Gly Phe Gly Thr Ala Glu
225                 230                 235                 240

Val Leu Arg Asp Phe Val Arg Glu Thr Leu Leu Ser Asn Gly Ser Lys
                245                 250                 255

Asn Trp Pro Thr Ser Thr Gly Thr Gly Ser Ser Ser Asn Asp Asn Ala
            260                 265                 270

Thr Ala Val Ala Gly Asp Leu Thr Lys Leu Thr Pro Glu Glu Lys Thr
        275                 280                 285

Ile Val Ala Gly Leu Leu Ala Lys Thr Ile Glu Gly Gly Glu Val Val
    290                 295                 300

Glu Ile Arg Ala Val Ser Ser Thr Ser Val Met Val Asn Ala Cys Tyr
305                 310                 315                 320

```
Asp Leu Leu Ser Glu Gly Leu Gly Val Val Pro Tyr Ala Cys Val Gly
                325                 330                 335

Leu Gly Gly Asn Phe Val Gly Val Val Asp Gly His Ile Thr Pro Lys
            340                 345                 350

Leu Ala Tyr Arg Leu Lys Ala Gly Leu Ser Tyr Gln Leu Ser Pro Glu
            355                 360                 365

Ile Ser Ala Phe Ala Gly Gly Phe Cys His Arg Val Val Gly Asp Gly
        370                 375                 380

Val Tyr Asp Asp Leu Pro Ala Gln Arg Leu Val Asp Asp Thr Ser Pro
385                 390                 395                 400

Ala Gly Arg Thr Lys Asp Thr Ala Ile Ala Asn Phe Ser Met Ala Tyr
            405                 410                 415

Val Gly Gly Glu Phe Gly Val Arg Phe Ala Phe
            420                 425
```

<210> SEQ ID NO 184
<211> LENGTH: 429
<212> TYPE: PRT
<213> ORGANISM: Artificial Sequence
<220> FEATURE:
<223> OTHER INFORMATION: Synthetic construct

<400> SEQUENCE: 184

```
Met Arg Lys Gly Lys Ile Ile Leu Gly Ser Val Met Met Ser Met Ala
1               5                   10                  15

Ile Val Met Ala Gly Asn Asp Val Arg Ala His Asp Asp Val Ser Ala
            20                  25                  30

Leu Glu Thr Gly Gly Ala Gly Tyr Phe Tyr Val Gly Leu Asp Tyr Ser
        35                  40                  45

Pro Ala Phe Ser Lys Ile Arg Asp Phe Ser Ile Arg Glu Ser Asn Gly
    50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
            100                 105                 110

Ile Gly Gly Ala Arg Val Glu Leu Glu Ile Gly Tyr Glu Arg Phe Lys
        115                 120                 125

Thr Lys Gly Val Arg Asp Ser Gly Ser Lys Glu Asp Glu Ala Asp Thr
130                 135                 140

Val Tyr Leu Leu Ala Lys Glu Leu Ala Tyr Asp Val Val Thr Gly Gln
145                 150                 155                 160

Thr Asp Lys Leu Thr Ala Ala Leu Ala Lys Thr Ser Gly Lys Asp Ile
                165                 170                 175

Val Gln Phe Ala Asn Ala Val Lys Ile Ser His Pro Lys Ile Asp Glu
            180                 185                 190

Gln Val Cys Ser Lys Asn His Thr Val Leu Asn Pro Ser Gln Gly Thr
        195                 200                 205

Thr Tyr Asp Ser Asp Pro Lys Gln Glu Gln Asn Lys Ile Ala Gln Cys
    210                 215                 220

Ser Gly Phe Gly Gly Ala Ala Gly Glu Lys Gln Ala Leu Leu Ser Thr
225                 230                 235                 240

Phe Ala Ser Ala Val Lys Leu Gly Glu Gly Lys Asn Trp Pro Thr Gly
                245                 250                 255
```

```
Gln Ala Gly Lys Ser Gly Ser Gly Pro Val Val Gly Ala Pro Asn Ser
            260                 265                 270

Asn Ala Asn Ala Val Ala Lys Asp Leu Val Ala Leu Asn Arg Glu Glu
        275                 280                 285

Lys Thr Ile Val Ala Gly Leu Leu Ala Lys Thr Ile Glu Gly Gly Glu
    290                 295                 300

Val Val Glu Ile Arg Ala Val Ser Ser Thr Ser Val Met Val Asn Ala
305                 310                 315                 320

Cys Tyr Asp Leu Leu Ser Glu Gly Leu Gly Val Val Pro Tyr Ala Cys
                325                 330                 335

Val Gly Leu Gly Gly Asn Phe Val Gly Val Val Asp Gly His Ile Thr
            340                 345                 350

Pro Lys Leu Ala Tyr Arg Leu Lys Ala Gly Leu Ser Tyr Gln Leu Ser
        355                 360                 365

Pro Glu Ile Ser Ala Phe Ala Gly Gly Phe Tyr His Arg Val Val Gly
    370                 375                 380

Asp Gly Val Tyr Asp Asp Leu Pro Ala Gln Arg Leu Val Asp Asp Thr
385                 390                 395                 400

Ser Pro Ala Gly Arg Thr Lys Asp Thr Ala Ile Ala Asn Phe Ser Met
                405                 410                 415

Ala Tyr Val Gly Gly Glu Phe Gly Val Arg Phe Ala Phe
            420                 425

<210> SEQ ID NO 185
<211> LENGTH: 435
<212> TYPE: PRT
<213> ORGANISM: Artificial Sequence
<220> FEATURE:
<223> OTHER INFORMATION: Synthetic construct

<400> SEQUENCE: 185

Met Arg Lys Gly Lys Ile Ile Leu Gly Ser Val Met Met Ser Met Ala
1               5                   10                  15

Ile Val Met Ala Gly Asn Asp Val Arg Ala His Asp Asp Val Ser Ala
            20                  25                  30

Leu Asp Thr Gly Gly Ala Gly Tyr Phe Tyr Val Gly Leu Asp Tyr Ser
        35                  40                  45

Pro Ala Phe Ser Lys Ile Arg Asp Phe Ser Ile Arg Glu Ser Asn Gly
    50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
            100                 105                 110

Ile Gly Gly Ala Arg Val Glu Leu Glu Ile Gly Tyr Glu Arg Phe Lys
        115                 120                 125

Thr Lys Gly Ile Arg Asp Ser Gly Ser Lys Glu Asp Asp Ala Asp Thr
    130                 135                 140

Val Tyr Leu Leu Ala Lys Glu Leu Ala Tyr Asp Val Val Thr Gly Gln
145                 150                 155                 160

Thr Asp Asn Leu Ala Ala Ala Leu Ala Lys Thr Ser Gly Lys Asp Ile
                165                 170                 175

Val Gln Phe Ala Lys Thr Leu Asn Ile Ser His Ser Asn Ile Asp Gly
            180                 185                 190
```

```
Lys Val Cys Thr Gly Ser His Ala Asp Leu Ala Pro Gly Thr Asn Ala
        195                 200                 205

Gly Lys Lys Phe Val Val Asn Pro Glu Ala Ser Gly Ser Thr Asp Gly
    210                 215                 220

Asp Thr Ser Gln Cys Ser Gly Leu Gly His Ser Ser Gly Val Thr Gln
225                 230                 235                 240

Asn Pro Lys Leu Phe Ser Thr Phe Val Asp Thr Val Lys Ile Ala Glu
                245                 250                 255

Asp Lys Asn Trp Pro Thr Gly Arg Ala Lys Ser Asn Thr Ser Leu Lys
                260                 265                 270

Thr Gly Asp Thr Asn Ser Asn Ala Lys Ala Val Ala Thr Asp Leu Thr
    275                 280                 285

Lys Leu Thr Ala Glu Glu Lys Thr Ile Val Ala Gly Leu Leu Ala Lys
        290                 295                 300

Thr Ile Gly Gly Gly Glu Val Ile Glu Ile Arg Ala Val Ser Ser Thr
305                 310                 315                 320

Ser Val Met Val Asn Ala Cys Tyr Asp Leu Leu Ser Glu Gly Leu Gly
                325                 330                 335

Val Val Pro Tyr Ala Cys Val Gly Leu Gly Gly Asn Phe Val Gly Val
            340                 345                 350

Val Asp Gly His Ile Thr Pro Lys Leu Ala Tyr Arg Leu Lys Ala Gly
        355                 360                 365

Leu Ser Tyr Gln Leu Ser Pro Glu Ile Ser Ala Phe Ala Gly Gly Phe
    370                 375                 380

Tyr His Arg Val Val Gly Asp Gly Val Tyr Asp Leu Pro Ala Gln
385                 390                 395                 400

Arg Leu Val Asp Asp Thr Ser Pro Ala Gly Arg Thr Lys Asp Thr Ala
                405                 410                 415

Ile Ala Asn Phe Ser Met Ala Tyr Val Gly Gly Glu Phe Gly Val Arg
                420                 425                 430

Phe Ala Phe
        435

<210> SEQ ID NO 186
<211> LENGTH: 423
<212> TYPE: PRT
<213> ORGANISM: Artificial Sequence
<220> FEATURE:
<223> OTHER INFORMATION: Synthetic construct

<400> SEQUENCE: 186

Met Lys His Val Val Cys Lys Asn Cys Val Gly Tyr Val Lys Cys Phe
1               5                   10                  15

Thr Val Arg Cys Ala Tyr Lys Arg Val Leu Tyr Met Val Ser Ala Ile
                20                  25                  30

Leu Leu Met Leu Ile Met Gly Glu Asp Ala Lys Ala Val Gly Asp Arg
            35                  40                  45

Ala Val Gln Pro Lys Lys Phe Tyr Val Ala Leu Asp Tyr Thr Pro Ala
        50                  55                  60

Phe Ser Lys Val Arg Asp Phe Tyr Ile Ser Gly Asp Glu Asn Ser Ala
65                  70                  75                  80

Leu Val Met Pro Tyr Pro Lys Ile Lys Glu Glu Asp Val Arg Ala Gln
                85                  90                  95

Gly Trp Gly Val Asp Trp Asn Ala Pro Asn Pro Asn Ile Glu Phe Glu
            100                 105                 110
```

```
Ser Asn Ala Leu Met Ser Trp Glu Gly Ser Leu Gly Tyr Lys Ile Lys
            115                 120                 125

Gly Gly Arg Ile Glu Ile Glu Val Gly Tyr Glu Lys Phe Arg Ala Arg
        130                 135                 140

Val Ser His Asp Ser Gly Gly Glu Ile His Asp Ala Val Tyr Val
145                 150                 155                 160

Phe Met Pro Pro Arg Ala Leu Pro Tyr Phe Val Leu Arg Gly Ser Ser
                165                 170                 175

Glu Arg Leu Lys Ser Glu Leu Ser Ser Val Thr Glu Glu Ile Leu
            180                 185                 190

Thr Phe Ala Lys Gly Leu Ala Asp Gln Arg Pro Asp Ile Asn Arg Lys
            195                 200                 205

Ile Cys Tyr Lys Ala Arg Val Gly Gly Thr Asn Ser His Asn Pro His
        210                 215                 220

Val Arg Ala Ala Cys Gln Asp Ser Thr Leu Gly Lys Tyr Val Gly Gly
225                 230                 235                 240

Leu Tyr Ala Phe Leu Lys Gly Ala Ile Glu Glu His Ser Ile Trp Ile
                245                 250                 255

Ser Glu Gly Ser Gly Gly Arg Val Ala Asn Val Ser Asp Met Val Ser
            260                 265                 270

His Ile Arg Ala Leu Thr Pro Glu Lys Glu Ala Leu Ser Gly Ile
        275                 280                 285

Leu Ala Ile Ala Thr Gly Tyr Gly Arg Thr Val Glu Val Ser Ser Ile
        290                 295                 300

Thr Thr Thr Ser Val Met Val Asn Ala Cys Tyr Asp Arg Asn Ile Lys
305                 310                 315                 320

Lys Met Gln Gly Ile Glu Ala Tyr Ala Cys Met Gly Leu Gly Ser Asn
                325                 330                 335

Leu Val Glu Val Val Asp Lys His Ile Thr Tyr Lys Phe Ala Tyr Arg
            340                 345                 350

Leu Lys Ala Gly Leu Ser Tyr Gln Ile Leu Ser Gly Val Ser Ala Phe
        355                 360                 365

Val Gly Gly Phe Tyr His His Val Ile Gly Asn Gly Val Tyr Asp Glu
        370                 375                 380

Leu Pro Leu Lys Arg Ile Gly Lys Asp Phe Arg Lys Ala Asp Arg Asn
385                 390                 395                 400

Gln Tyr Glu Ala Ile Ala Asn Phe Asp Met Ser Tyr Met Gly Thr Glu
                405                 410                 415

Phe Gly Val Arg Phe Ala Phe
            420

<210> SEQ ID NO 187
<211> LENGTH: 416
<212> TYPE: PRT
<213> ORGANISM: Artificial Sequence
<220> FEATURE:
<223> OTHER INFORMATION: Synthetic construct

<400> SEQUENCE: 187

Met Val Cys Cys Val Ser Arg Val Val Leu Tyr Ile Ala Ser Val Ile
1               5                   10                  15

Leu Leu Met Leu Ile Met Gly Glu Asp Ala Ser Ala Ala Ile Tyr Lys
            20                  25                  30

Asp Asp Leu Pro Pro Asn Ser Lys Lys Phe Tyr Val Ala Leu Asp Tyr
        35                  40                  45
```

Ala Pro Ala Leu Ser Arg Val Ser Thr Phe Asp Ile Val Gly Asp Gly
 50                  55                  60

Lys Thr His Ile Ala Leu Pro Tyr Leu Lys Asn Asp Gln Glu Asp Arg
 65                  70                  75                  80

Phe Asn Ala Glu Ala Ile Asp Trp Asp Ala Pro Asn Leu Ser Val Gln
                 85                  90                  95

Phe Lys Asn Ser Val Leu Met Ser Trp Val Gly Ser Ile Gly Tyr Lys
            100                 105                 110

Met Met Gly Gly Arg Leu Glu Leu Glu Val Gly His Glu Lys Phe Gly
        115                 120                 125

Ala Arg Val Ser Ser Gly Glu Asn Arg Glu Glu Asn Ser Asp Val Ala
    130                 135                 140

Tyr Val Phe Phe Ser Arg Leu Leu Pro Tyr Tyr Leu Val Ser Ala Gln
145                 150                 155                 160

Tyr Glu Lys Leu Ile Ser Gly Leu Ala Asn Leu Thr Glu Asp Glu Ile
                165                 170                 175

Leu Ala Phe Ala Asn Gly Val Ala Asp Gln Arg Pro Asp Leu Asp Lys
            180                 185                 190

Lys Ile Cys Lys Lys Ala Arg Leu Gly Asp Asp Arg Gly Thr Asp
        195                 200                 205

Ala Gln Ala Ala Cys Arg Asp Ser Ile Lys Gly Ala Asp Val Gly Gly
    210                 215                 220

Phe Gly Ala Phe Met Arg Lys Ala Ile Gly Thr Tyr Leu Met Trp Arg
225                 230                 235                 240

Tyr Asn Gly Gly Ser Asp Arg Tyr Gly Leu Glu Arg Gly Arg Ser
                245                 250                 255

Val Asn Ser Lys Asp Ile Val Ser Asp Ile Lys Glu Leu Pro Lys Glu
            260                 265                 270

Glu Arg Lys Ile Leu Ala Gly Ile Leu Ala Ala Thr Gly Tyr Gly
        275                 280                 285

Val Val Val Glu Ile Pro Ser Val Ala Ala Thr Ser Val Met Val Asn
    290                 295                 300

Ala Cys Tyr Asp His Asn Val Ser Leu Thr Arg Lys Arg Ala Ser Ala
305                 310                 315                 320

Tyr Ser Cys Val Gly Leu Gly Ser Thr Phe Val Glu Ile Val Asp Glu
                325                 330                 335

His Arg Ala Ala Lys Leu Ala Tyr Arg Leu Lys Ala Gly Leu Ser Tyr
            340                 345                 350

Asn Phe Ala Ser Gly Val Thr Ala Phe Val Gly Phe Tyr His His
        355                 360                 365

Ile Ile Gly Asp Ser Trp Tyr Asp Arg Val Pro Met Arg Thr Val Phe
    370                 375                 380

Leu Asp Glu Lys Thr Gly Glu Arg Pro Val Lys Thr Gly Lys Val Asp
385                 390                 395                 400

Leu Ser Leu Asp Tyr Ile Gly Ala Glu Cys Gly Ile Arg Leu Ile Leu
                405                 410                 415

<210> SEQ ID NO 188
<211> LENGTH: 254
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature

```
<222> LOCATION: (144)..(144)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (164)..(164)
<223> OTHER INFORMATION: a, c, g or t
<220> FEATURE:
<221> NAME/KEY: misc_feature
<222> LOCATION: (166)..(166)
<223> OTHER INFORMATION: a, c, g or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (215)..(215)
<223> OTHER INFORMATION: a, c, g or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (242)..(242)
<223> OTHER INFORMATION: a, c, g or t

<400> SEQUENCE: 188
gaagaatacg aaagcggcgg agatcgttaa atttgctgag gctgttggca catcggcaaa      60
ggatattgat aagaaggttt gtaagaagac tggaaatgcc gcggacagtt ggaagtgtac     120
gcagactggc agcgacggcg gcancnccaa agagttcagt aaaatattta cgaaggcaga    180
cgtaaatact gacancaaag gcaaagcatg gcctaacggg ancaacgacg ccgcgaaagc    240
ggaagaccta agta                                                       254

<210> SEQ ID NO 189
<211> LENGTH: 257
<212> TYPE: DNA
<213> ORGANISM: Artificial Sequence
<220> FEATURE:
<223> OTHER INFORMATION: Synthetic construct

<400> SEQUENCE: 189
gaagaatacg aaagcggcgg agatcgttaa gtttgctgag gctgttggta catcggcaaa      60
ggatattgat ggaaaggttt gtaagaagac tggaaatgag gcggacagtt ggaagtgtac     120
gcagactggc aacggcagcg gcaacgccac agagtttagt aaaatattta cgaagaaaaa    180
cgtagatgct gagggcaaag gcaaagcatg gcctaacggg cacaccgaca gcgccgcgaa    240
agcggaagac ctaagta                                                    257

<210> SEQ ID NO 190
<211> LENGTH: 242
<212> TYPE: DNA
<213> ORGANISM: Artificial Sequence
<220> FEATURE:
<223> OTHER INFORMATION: Synthetic construct

<400> SEQUENCE: 190
gaagaatacg aaagcggcgg agatcgttaa gtttgctgag gctgtcggta catcggcaaa      60
ggatattgat aagaaggttt gtaagaagac tgaaaataca gaagacagtt ggaagtgtac     120
gcagactggc aacgacggca gcgacaagga gttcagtaaa atatttacga agaaaaacgt    180
```
agatactagc ggcaaagcat ggcctaacgg aagcgacgcc gcgaaagcgg aagacctaag   240
ta   242

<210> SEQ ID NO 191
<211> LENGTH: 242
<212> TYPE: DNA
<213> ORGANISM: Artificial Sequence
<220> FEATURE:
<223> OTHER INFORMATION: Synthetic construct

<400> SEQUENCE: 191
gaagaatacg aaagcggcgg agatcgttaa gtttgctgag gctgttggta catcggcaaa   60
ggatattgat aagaaggttt gtaagaagac tgaaaataca gaagacagtt ggaagtgtac   120
gcagactggc aacgcggcg gcgacaagga gttcagtaaa atatttacga agaaaaacgt   180
agatactagc ggcaaagcat ggcctaacgg aagcgacgcc gcgaaagcgg aagacctaag   240
ta   242

<210> SEQ ID NO 192
<211> LENGTH: 260
<212> TYPE: DNA
<213> ORGANISM: Artificial Sequence
<220> FEATURE:
<223> OTHER INFORMATION: Synthetic construct

<400> SEQUENCE: 192
gaagaatacg aaagcggcgg agatcgttaa atttgctgag gctgttggca catcggcaaa   60
ggatattgat ggaaaggttt gtaagaaggg cggcagcggc aatgccgcgg gcagctggaa   120
gtgtacgcag actggcagca acggcgtcag caccgcagag ttcagtaaaa tatttacgaa   180
ggcagacgta aatactgaca acaaaggcaa agcatggcct aacgggaaca acgacgctgc   240
gaaagcggaa gacctaagta   260

<210> SEQ ID NO 193
<211> LENGTH: 260
<212> TYPE: DNA
<213> ORGANISM: Artificial Sequence
<220> FEATURE:
<223> OTHER INFORMATION: Synthetic construct

<400> SEQUENCE: 193
gaagaatacg aaagcggcgg agatcgttaa atttgctgag gctgttggca catcggcaaa   60
ggatattgat ggaaaggttt gtaagaaggg cggcagcggc aatgccgcgg gcagctggaa   120
gtgtacgcag actggcagca acggcgtcag caccgcagag ttcagtaaaa tatttacgaa   180
ggcagacgta aatactgaca acaaaggcaa agcacggcct aacgggaaca acgacgctgc   240
gaaagcggaa gacctaagta   260

<210> SEQ ID NO 194
<211> LENGTH: 278
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (29)..(29)
<223> OTHER INFORMATION: any amino acid
<220> FEATURE:
<221> NAME/KEY: MISC_FEATURE
<222> LOCATION: (116)..(116)
<223> OTHER INFORMATION: any amino acid

```
<220> FEATURE:
<221> NAME/KEY: MISC_FEATURE
<222> LOCATION: (202)..(202)
<223> OTHER INFORMATION: any amino acid
<220> FEATURE:
<221> NAME/KEY: MISC_FEATURE
<222> LOCATION: (213)..(213)
<223> OTHER INFORMATION: any amino acid
<220> FEATURE:
<221> NAME/KEY: MISC_FEATURE
<222> LOCATION: (214)..(214)
<223> OTHER INFORMATION: any amino acid
<220> FEATURE:
<221> NAME/KEY: MISC_FEATURE
<222> LOCATION: (218)..(218)
<223> OTHER INFORMATION: any amino acid
<220> FEATURE:
<221> NAME/KEY: MISC_FEATURE
<222> LOCATION: (244)..(244)
<223> OTHER INFORMATION: any amino acid

<400> SEQUENCE: 194

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Xaa Asp Val Asp
            20                  25                  30

Tyr Val Ser Lys Phe Gly Glu Gly Ser Phe Tyr Val Gly Leu Asn Tyr
        35                  40                  45

Ser Pro Ala Phe Ser Lys Ile Asn Gly Phe Glu Ile Arg Glu Ser Thr
50                  55                  60

Gly Glu Thr Ala Ala Val Tyr Pro Tyr Met Lys Asp Gly Thr Arg Val
65                  70                  75                  80

Glu Trp Lys Ala Glu Lys Phe Asp Trp Asn Thr Pro Asp Pro Arg Ile
                85                  90                  95

Lys Phe Lys Asn Asn Pro Ile Val Ala Leu Gly Ser Val Gly Tyr
            100                 105                 110

Ser Ile Gly Xaa Ala Arg Val Glu Leu Glu Ile Gly Tyr Glu Gln Phe
        115                 120                 125

Lys Thr Lys Gly Ile Arg Asp Thr Gly Ser Lys Glu Glu Glu Ala Asp
130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
            180                 185                 190

Lys Lys Val Cys Lys Lys Thr Gly Asn Xaa Ala Gly Ser Trp Lys Cys
        195                 200                 205

Thr Gln Thr Gly Xaa Xaa Gly Val Ser Xaa Lys Glu Phe Ser Lys Ile
210                 215                 220

Phe Thr Lys Ala Asp Val Asn Thr Asp Asn Lys Gly Lys Ala Trp Pro
225                 230                 235                 240

Asn Gly Asn Xaa Asp Ala Ala Lys Ala Glu Asp Leu Ser Ala Leu Asn
                245                 250                 255

Arg Glu Leu Thr Ser Ala Glu Leu Asn Lys Val Ala Gly Leu Leu Thr
            260                 265                 270

Arg Thr Ile Ser Gly Gly
        275

<210> SEQ ID NO 195
```

<211> LENGTH: 254
<212> TYPE: PRT
<213> ORGANISM: Artificial Sequence
<220> FEATURE:
<223> OTHER INFORMATION: Synthetic construct

<400> SEQUENCE: 195

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ala Asp Val Asp
            20                  25                  30

Tyr Val Ser Lys Phe Gly Glu Gly Ser Phe Tyr Val Gly Leu Asn Tyr
        35                  40                  45

Ser Pro Ala Phe Ser Lys Ile Asn Gly Phe Glu Ile Arg Glu Ser Thr
    50                  55                  60

Gly Glu Thr Ala Ala Val Tyr Pro Tyr Met Lys Asp Gly Thr Arg Val
65                  70                  75                  80

Glu Trp Lys Ala Glu Lys Phe Asp Trp Asn Thr Pro Asp Pro Arg Ile
                85                  90                  95

Lys Phe Lys Asn Asn Pro Ile Val Ala Leu Glu Gly Ser Val Gly Tyr
            100                 105                 110

Ser Ile Gly Ile Ala Arg Val Glu Leu Glu Ile Gly Tyr Glu Gln Phe
        115                 120                 125

Lys Thr Lys Gly Ile Arg Asp Thr Gly Ser Lys Glu Glu Ala Asp
    130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
            180                 185                 190

Gly Lys Val Cys Lys Lys Thr Gly Asn Glu Ala Asp Ser Trp Lys Cys
        195                 200                 205

Thr Gln Thr Gly Asn Gly Ser Gly Asn Ala Thr Glu Phe Ser Lys Ile
    210                 215                 220

Phe Thr Lys Lys Asn Val Asp Ala Glu Gly Lys Gly Lys Ala Trp Pro
225                 230                 235                 240

Asn Gly His Thr Asp Ser Ala Lys Ala Glu Asp Leu Ser
                245                 250

<210> SEQ ID NO 196
<211> LENGTH: 298
<212> TYPE: PRT
<213> ORGANISM: Artificial Sequence
<220> FEATURE:
<223> OTHER INFORMATION: Synthetic construct

<400> SEQUENCE: 196

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ser Asp Val Asp
            20                  25                  30

Tyr Val Ser Lys Phe Gly Glu Gly Ser Phe Tyr Val Gly Leu Asn Tyr
        35                  40                  45

Ser Pro Ala Phe Ser Lys Ile Asn Gly Phe Glu Ile Arg Glu Ser Thr
    50                  55                  60

Gly Glu Thr Ala Ala Val Tyr Pro Tyr Met Lys Asp Gly Thr Arg Val

```
65                  70                  75                  80
Glu Trp Lys Ala Glu Lys Phe Asp Trp Asn Thr Pro Asp Pro Arg Ile
                85                  90                  95
Lys Phe Lys Asn Asn Pro Ile Val Ala Leu Glu Gly Ser Val Gly Tyr
                100                 105                 110
Ser Ile Gly Val Ala Arg Val Glu Leu Glu Ile Gly Tyr Glu Gln Phe
                115                 120                 125
Lys Thr Lys Gly Ile Arg Asp Thr Gly Ser Lys Glu Glu Glu Ala Asp
    130                 135                 140
Ala Val Tyr Leu Leu Ala Lys Lys Leu Pro His Thr Leu Val Ser Asp
145                 150                 155                 160
Gln Ser Asp Lys Phe Leu Glu Glu Leu Lys Asn Thr Lys Ala Ala Glu
                165                 170                 175
Ile Val Lys Phe Ala Glu Ala Val Gly Thr Ser Ala Lys Asp Ile Asp
                180                 185                 190
Gly Lys Val Cys Lys Lys Gly Gly Ser Gly Asn Ala Ala Gly Ser Trp
                195                 200                 205
Lys Cys Thr Gln Thr Gly Ser Asn Gly Val Ser Thr Ala Glu Phe Ser
    210                 215                 220
Lys Ile Phe Thr Lys Ala Asp Val Asn Thr Asp Asn Lys Gly Lys Ala
225                 230                 235                 240
Trp Pro Asn Gly Asn Asn Asp Ala Ala Lys Ala Glu Asp Leu Ser Ile
                245                 250                 255
Ala Leu Asn Arg Glu Leu Thr Ser Ala Glu Lys Asn Lys Val Ala Gly
                260                 265                 270
Leu Leu Thr Arg Thr Ile Ser Gly Gly Glu Val Val Glu Ile Arg Ala
                275                 280                 285
Val Ser Thr Thr Ser Val Met Leu Asn Gly
    290                 295

<210> SEQ ID NO 197
<211> LENGTH: 292
<212> TYPE: PRT
<213> ORGANISM: Artificial Sequence
<220> FEATURE:
<223> OTHER INFORMATION: Synthetic construct

<400> SEQUENCE: 197

Met Lys Glu Arg Lys Leu Ala Leu Ser Gly Ala Val Ala Met Thr Val
1               5                   10                  15
Leu Val Ser Thr Ala Gly Thr Gly Thr Ala Ala Gly Ser Asp Val Asp
                20                  25                  30
Tyr Val Ser Lys Phe Gly Glu Gly Ser Phe Tyr Val Gly Leu Asn Tyr
                35                  40                  45
Ser Pro Ala Phe Ser Lys Ile Asn Gly Phe Glu Ile Arg Glu Ser Thr
    50                  55                  60
Gly Glu Thr Ala Ala Val Tyr Pro Tyr Met Lys Asp Gly Thr Arg Val
65                  70                  75                  80
Glu Trp Lys Ala Glu Lys Phe Asp Trp Asn Thr Pro Asp Pro Arg Ile
                85                  90                  95
Lys Phe Lys Asn Asn Pro Ile Val Ala Leu Glu Gly Ser Val Gly Tyr
                100                 105                 110
Ser Ile Gly Val Ala Arg Val Glu Leu Glu Ile Gly Tyr Glu Gln Phe
                115                 120                 125
Lys Thr Lys Gly Ile Arg Asp Thr Gly Ser Lys Glu Glu Glu Ala Asp
```

```
                130             135             140
Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
                180                 185                 190

Lys Lys Val Cys Lys Lys Thr Glu Asn Thr Glu Asp Ser Trp Lys Cys
                195                 200                 205

Thr Gln Thr Gly Asn Asp Gly Asp Lys Glu Phe Ser Lys Ile Phe
        210                 215                 220

Thr Lys Lys Asn Val Asp Thr Ser Gly Lys Ala Trp Pro Asn Gly Ser
225                 230                 235                 240

Asp Ala Ala Lys Ala Glu Asp Leu Ser Thr Ala Leu Asn Arg Glu Leu
                245                 250                 255

Thr Ser Ala Glu Lys Asn Lys Val Ala Gly Leu Leu Thr Arg Thr Ile
                260                 265                 270

Ser Gly Gly Glu Val Val Glu Ile Arg Ala Val Ser Thr Thr Ser Val
                275                 280                 285

Met Leu Asn Gly
    290

<210> SEQ ID NO 198
<211> LENGTH: 298
<212> TYPE: PRT
<213> ORGANISM: Artificial Sequence
<220> FEATURE:
<223> OTHER INFORMATION: Synthetic construct

<400> SEQUENCE: 198

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ser Asp Val Asp
                20                  25                  30

Tyr Val Ser Lys Phe Gly Glu Gly Ser Phe Tyr Val Gly Leu Asn Tyr
                35                  40                  45

Ser Pro Ala Phe Ser Lys Ile Asn Gly Phe Glu Ile Arg Glu Ser Thr
50                  55                  60

Gly Glu Thr Ala Ala Val Tyr Pro Tyr Met Lys Asp Gly Thr Arg Val
65                  70                  75                  80

Glu Trp Lys Ala Glu Lys Phe Asp Trp Asn Thr Pro Asp Pro Arg Ile
                85                  90                  95

Lys Phe Lys Asn Asn Pro Ile Val Ala Leu Glu Gly Ser Val Gly Tyr
                100                 105                 110

Ser Ile Gly Val Ala Arg Val Glu Leu Glu Ile Gly Tyr Glu Gln Phe
                115                 120                 125

Lys Thr Lys Gly Ile Arg Asp Thr Gly Ser Lys Glu Glu Glu Ala Asp
                130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
                180                 185                 190

Gly Lys Val Cys Lys Lys Gly Gly Ser Gly Asn Ala Ala Gly Ser Trp
```

```
              195                 200                 205
Lys Cys Thr Gln Thr Gly Ser Asn Gly Val Ser Thr Ala Glu Phe Ser
210                 215                 220

Lys Ile Phe Thr Lys Ala Asp Val Asn Thr Asp Asn Lys Gly Lys Ala
225                 230                 235                 240

Trp Pro Asn Gly Asn Asn Asp Ala Ala Lys Ala Glu Asp Leu Ser Ile
                245                 250                 255

Ala Leu Asn Arg Glu Leu Thr Ser Ala Glu Lys Asn Lys Val Ala Gly
                260                 265                 270

Leu Leu Thr Arg Thr Ile Ser Gly Gly Glu Val Val Glu Ile Arg Ala
                275                 280                 285

Val Ser Thr Thr Ser Val Met Leu Asn Gly
290                 295

<210> SEQ ID NO 199
<211> LENGTH: 298
<212> TYPE: PRT
<213> ORGANISM: Artificial Sequence
<220> FEATURE:
<223> OTHER INFORMATION: Synthetic construct

<400> SEQUENCE: 199

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ser Asp Val Asp
                20                  25                  30

Tyr Val Ser Lys Phe Gly Glu Gly Ser Phe Tyr Val Gly Leu Asn Tyr
                35                  40                  45

Ser Pro Ala Phe Ser Lys Ile Asn Gly Phe Glu Ile Arg Glu Ser Thr
50                  55                  60

Gly Glu Thr Ala Ala Val Tyr Pro Tyr Met Lys Asp Gly Thr Arg Val
65                  70                  75                  80

Glu Trp Lys Ala Glu Lys Phe Asp Trp Asn Thr Pro Asp Pro Arg Ile
                85                  90                  95

Lys Phe Lys Asn Asn Pro Ile Val Ala Leu Glu Gly Ser Val Gly Tyr
                100                 105                 110

Ser Ile Gly Val Ala Arg Val Glu Leu Glu Ile Gly Tyr Glu Gln Phe
                115                 120                 125

Lys Thr Lys Gly Ile Arg Asp Thr Gly Ser Lys Glu Glu Ala Asp
                130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
                180                 185                 190

Gly Lys Val Cys Lys Lys Gly Gly Ser Gly Asn Ala Ala Gly Ser Trp
                195                 200                 205

Lys Cys Thr Gln Thr Gly Ser Asn Gly Val Ser Thr Ala Glu Phe Ser
210                 215                 220

Lys Ile Phe Thr Lys Ala Asp Val Asn Thr Asp Asn Lys Gly Lys Ala
225                 230                 235                 240

Arg Pro Asn Gly Asn Asn Asp Ala Ala Lys Ala Glu Asp Leu Ser Ile
                245                 250                 255

Ala Leu Asn Arg Glu Leu Thr Ser Ala Glu Lys Asn Lys Val Ala Gly
```

```
                    260                 265                 270
Leu Leu Thr Arg Thr Ile Ser Gly Gly Glu Val Val Glu Ile Arg Ala
            275                 280                 285

Val Ser Thr Thr Ser Val Met Leu Asn Gly
            290                 295

<210> SEQ ID NO 200
<211> LENGTH: 396
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: any amino acid
<220> FEATURE:
<221> NAME/KEY: MISC_FEATURE
<222> LOCATION: (77)..(77)
<223> OTHER INFORMATION: any amino acid
<220> FEATURE:
<221> NAME/KEY: MISC_FEATURE
<222> LOCATION: (178)..(178)
<223> OTHER INFORMATION: any amino acid
<220> FEATURE:
<221> NAME/KEY: MISC_FEATURE
<222> LOCATION: (191)..(191)
<223> OTHER INFORMATION: any amino acid
<220> FEATURE:
<221> NAME/KEY: MISC_FEATURE
<222> LOCATION: (203)..(203)
<223> OTHER INFORMATION: any amino acid
<220> FEATURE:
<221> NAME/KEY: MISC_FEATURE
<222> LOCATION: (217)..(217)
<223> OTHER INFORMATION: any amino acid
<220> FEATURE:
<221> NAME/KEY: MISC_FEATURE
<222> LOCATION: (230)..(230)
<223> OTHER INFORMATION: any amino acid
<220> FEATURE:
<221> NAME/KEY: MISC_FEATURE
<222> LOCATION: (233)..(233)
<223> OTHER INFORMATION: any amino acid
<220> FEATURE:
<221> NAME/KEY: MISC_FEATURE
<222> LOCATION: (243)..(243)
<223> OTHER INFORMATION: any amino acid
<220> FEATURE:
<221> NAME/KEY: MISC_FEATURE
<222> LOCATION: (268)..(268)
<223> OTHER INFORMATION: any amino acid

<400> SEQUENCE: 200

Met Lys Leu Val Met Met Ser Met Ala Ile Val Met Ala Gly Asn Asp
1               5                   10                  15

Val Arg Ala His Asp Asp Val Ser Ala Leu Xaa Thr Gly Gly Ala Gly
            20                  25                  30

Tyr Phe Tyr Val Gly Leu Asp Tyr Ser Pro Ala Phe Ser Lys Ile Arg
        35                  40                  45

Asp Phe Ser Ile Arg Glu Ser Asn Gly Glu Thr Lys Ala Val Tyr Pro
50                  55                  60

Tyr Leu Lys Asp Gly Lys Ser Val Lys Leu Glu Ser Xaa Lys Phe Asp
65                  70                  75                  80

Trp Asn Thr Pro Asp Pro Arg Ile Gly Phe Lys Asp Asn Met Leu Val
                85                  90                  95

Ala Met Glu Gly Ser Val Gly Tyr Gly Ile Gly Ala Arg Val Glu
            100                 105                 110
```

```
Leu Glu Ile Gly Tyr Glu Arg Phe Lys Thr Lys Gly Ile Arg Asp Ser
            115                 120                 125

Gly Ser Lys Glu Asp Glu Ala Asp Thr Val Tyr Leu Leu Ala Lys Glu
        130                 135                 140

Leu Ala Tyr Asp Val Val Thr Gly Gln Thr Asp Lys Leu Leu Ala Ala
145                 150                 155                 160

Leu Ala Lys Thr Ser Gly Lys Asp Ile Val Gln Phe Ala Glu Ala Val
                165                 170                 175

Gly Xaa Ser Ala Lys Asp Ile Asp Gly Lys Val Cys Lys Lys Xaa Thr
            180                 185                 190

Gly Asn Ala Ala Asp Ser Trp Gln Cys Ser Xaa Gly Ser Gly Gly Ser
        195                 200                 205

Ser Gly Lys Glu Phe Ser Lys Phe Xaa Thr Lys Val Lys Val Asp Glu
    210                 215                 220

Gly Lys Asn Trp Pro Xaa Gly Arg Xaa Ser Ala Ala Lys Asn Asn Ala
225                 230                 235                 240

Glu Ala Xaa Ala Thr Asp Leu Asn Arg Glu Leu Thr Ser Ala Glu Lys
            245                 250                 255

Thr Ile Val Ala Gly Leu Leu Ala Lys Thr Ile Xaa Gly Gly Glu Val
        260                 265                 270

Val Glu Ile Arg Ala Val Ser Ser Thr Ser Val Met Val Asn Ala Cys
275                 280                 285

Tyr Asp Leu Leu Ser Glu Gly Leu Gly Val Val Pro Tyr Ala Cys Val
            290                 295                 300

Gly Leu Gly Gly Asn Phe Val Gly Val Val Asp Gly His Ile Thr Pro
305                 310                 315                 320

Lys Leu Ala Tyr Arg Leu Lys Ala Gly Leu Ser Tyr Gln Leu Ser Pro
                325                 330                 335

Glu Ile Ser Ala Phe Ala Gly Gly Phe Tyr His Arg Val Val Gly Asp
            340                 345                 350

Gly Val Tyr Asp Asp Leu Pro Ala Gln Arg Leu Val Asp Asp Thr Ser
        355                 360                 365

Pro Ala Gly Arg Thr Lys Asp Thr Ala Ile Ala Asn Phe Ser Met Ala
370                 375                 380

Tyr Val Gly Gly Glu Phe Gly Val Arg Phe Ala Phe
385                 390                 395

<210> SEQ ID NO 201
<211> LENGTH: 243
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid

<400> SEQUENCE: 201

Tyr Phe Tyr Val Gly Leu Asp Tyr Xaa Pro Ala Phe Ser Lys Ile Asn
1               5                   10                  15

Gly Phe Glu Ile Arg Glu Ser Thr Gly Glu Thr Ala Ala Val Tyr Pro
            20                  25                  30

Tyr Met Lys Asp Gly Thr Arg Val Glu Trp Lys Ala Glu Lys Phe Asp
```

```
                35                  40                  45
Trp Asn Thr Pro Asp Pro Arg Ile Lys Phe Lys Asn Asn Pro Ile Val
 50                  55                  60

Ala Leu Glu Gly Ser Val Gly Tyr Ser Ile Gly Val Ala Arg Val Glu
 65                  70                  75                  80

Leu Glu Ile Gly Tyr Glu Gln Phe Lys Thr Lys Gly Ile Arg Asp Thr
                 85                  90                  95

Gly Ser Lys Glu Glu Glu Ala Asp Ala Val Tyr Leu Leu Ala Lys Lys
                100                 105                 110

Leu Pro His Thr Leu Val Ser Asp Gln Ser Asp Lys Phe Leu Glu Glu
                115                 120                 125

Leu Lys Asn Thr Lys Ala Ala Glu Ile Val Lys Phe Ala Glu Ala Val
            130                 135                 140

Gly Thr Ser Ala Lys Asp Ile Asp Lys Lys Val Cys Lys Lys His Thr
145                 150                 155                 160

Asn Asn Ala Ala Asn Ser Trp Lys Cys Glu Gln Pro Gly Ser Lys Gly
                165                 170                 175

Lys Ala Trp Pro Asn Gly His Thr Asp Ser Ala Ala Lys Ala Glu Asp
                180                 185                 190

Leu Ser Thr Ala Leu Asn Arg Glu Leu Thr Ser Ala Glu Lys Asn Lys
            195                 200                 205

Val Ala Gly Leu Leu Thr Arg Thr Ile Ser Gly Gly Glu Val Val Glu
        210                 215                 220

Ile Arg Ala Val Ser Thr Thr Ser Val Met Xaa Asn Ala Cys Tyr Asp
225                 230                 235                 240

Leu Leu Ser

<210> SEQ ID NO 202
<211> LENGTH: 259
<212> TYPE: PRT
<213> ORGANISM: Artificial Sequence
<220> FEATURE:
<223> OTHER INFORMATION: Synthetic construct

<400> SEQUENCE: 202

Tyr Phe Tyr Val Gly Leu Asp Tyr Cys Pro Ala Phe Ser Lys Ile Asn
 1               5                  10                  15

Gly Phe Glu Ile Arg Glu Ser Thr Gly Glu Thr Ala Ala Val Tyr Pro
                20                  25                  30

Tyr Met Lys Asp Gly Thr Arg Val Glu Trp Lys Ala Glu Lys Phe Asp
             35                  40                  45

Trp Asn Thr Pro Asp Pro Arg Ile Lys Phe Lys Asn Asn Pro Ile Val
 50                  55                  60

Ala Leu Glu Gly Ser Val Gly Tyr Ser Ile Gly Val Ala Arg Val Glu
 65                  70                  75                  80

Leu Glu Ile Gly Tyr Glu Gln Phe Lys Thr Lys Gly Ile Arg Asp Thr
                 85                  90                  95

Gly Ser Lys Glu Glu Glu Ala Asp Ala Val Tyr Leu Leu Ala Lys Lys
                100                 105                 110

Leu Pro His Thr Leu Val Ser Asp Gln Ser Asp Lys Phe Leu Glu Glu
                115                 120                 125

Leu Lys Asn Thr Lys Ala Ala Glu Ile Val Lys Phe Ala Glu Ala Val
            130                 135                 140

Gly Thr Ser Ala Lys Asp Ile Asp Gly Lys Val Cys Lys Lys His Asn
145                 150                 155                 160
```

```
Gly Asn Ala Ala Gly Ser Trp Gln Cys Thr Gln Thr Gly Ser Glu Thr
                165                 170                 175

Ser Gly Lys Thr Leu Ser Glu Ile Phe Thr Lys Ala Gly Val Asp Ala
            180                 185                 190

Asn Gly Lys Ala Trp Pro Asn Gly Ser Asp Ala Ala Lys Ala Glu Asp
        195                 200                 205

Leu Ser Thr Ala Leu Asn Arg Glu Leu Thr Ser Ala Glu Lys Asn Lys
    210                 215                 220

Val Ala Gly Leu Leu Thr Arg Thr Ile Ser Gly Gly Glu Val Val Glu
225                 230                 235                 240

Ile Arg Ala Val Ser Thr Thr Ser Val Met Ile Asn Ala Cys Tyr Asp
                245                 250                 255

Leu Leu Ser

<210> SEQ ID NO 203
<211> LENGTH: 263
<212> TYPE: PRT
<213> ORGANISM: Artificial Sequence
<220> FEATURE:
<223> OTHER INFORMATION: Synthetic construct

<400> SEQUENCE: 203

Tyr Phe Tyr Val Gly Leu Asp Tyr Ser Pro Ala Phe Ser Lys Ile Asn
1               5                   10                  15

Gly Phe Glu Ile Arg Glu Ser Thr Gly Glu Thr Ala Ala Val Tyr Pro
            20                  25                  30

Tyr Met Lys Asp Gly Thr Arg Val Glu Trp Lys Ala Glu Lys Phe Asp
        35                  40                  45

Trp Asn Thr Pro Asp Pro Arg Ile Lys Phe Lys Asn Asn Pro Ile Val
    50                  55                  60

Ala Leu Glu Gly Ser Val Gly Tyr Ser Ile Gly Val Ala Arg Val Glu
65                  70                  75                  80

Leu Glu Ile Gly Tyr Glu Gln Phe Lys Thr Lys Gly Ile Arg Asp Thr
                85                  90                  95

Gly Ser Lys Glu Glu Ala Asp Ala Val Tyr Leu Leu Ala Lys Lys
            100                 105                 110

Leu Pro His Thr Leu Val Ser Asp Gln Ser Asp Lys Phe Leu Glu Glu
        115                 120                 125

Leu Lys Asn Thr Lys Ala Ala Glu Ile Val Lys Phe Ala Glu Ala Val
    130                 135                 140

Gly Thr Ser Ala Lys Asp Ile Asp Gly Lys Val Cys Lys Lys Asn Thr
145                 150                 155                 160

Asn Asn Ala Ala Asp Ser Trp Lys Cys Glu Gln Thr Gly Ser Gly Ser
                165                 170                 175

Asp Gly Lys Glu Phe Ser Lys Leu Phe Thr Lys Ala Gly Val Asp Ala
            180                 185                 190

Asn Glu Lys Gly Lys Ala Trp Pro Asn Gly His Thr Asp Ser Ala Ala
        195                 200                 205

Lys Ala Glu Asp Leu Ser Thr Ala Leu Asn Arg Glu Leu Thr Ser Ala
    210                 215                 220

Glu Lys Asn Lys Val Ala Gly Leu Leu Thr Arg Thr Ile Ser Gly Gly
225                 230                 235                 240

Glu Val Val Glu Ile Arg Ala Val Ser Thr Thr Ser Val Met Leu Asn
                245                 250                 255
```

Ala Cys Tyr Asp Leu Leu Ser
        260

<210> SEQ ID NO 204
<211> LENGTH: 280
<212> TYPE: PRT
<213> ORGANISM: Artificial Sequence
<220> FEATURE:
<223> OTHER INFORMATION: Synthetic construct

<400> SEQUENCE: 204

Met Lys Glu Arg Lys Leu Ala Leu Ser Gly Ala Val Ala Met Thr Val
1               5                   10                  15

Leu Val Ser Thr Ala Gly Thr Gly Thr Ala Ala Gly Ala Asp Val Asp
            20                  25                  30

Tyr Val Ser Lys Phe Gly Glu Gly Ser Phe Tyr Val Gly Leu Asn Tyr
        35                  40                  45

Ser Pro Ala Phe Ser Lys Ile Asn Gly Phe Glu Ile Arg Glu Ser Thr
    50                  55                  60

Gly Glu Thr Ala Ala Val Tyr Pro Tyr Met Lys Asp Gly Thr Arg Val
65                  70                  75                  80

Glu Trp Lys Ala Glu Lys Phe Asp Trp Asn Thr Pro Asp Pro Arg Ile
                85                  90                  95

Lys Phe Lys Asn Asn Pro Ile Val Ala Leu Glu Gly Ser Val Gly Tyr
            100                 105                 110

Ser Ile Gly Ile Ala Arg Val Glu Leu Glu Ile Gly Tyr Glu Gln Phe
        115                 120                 125

Lys Thr Lys Gly Ile Arg Asp Thr Gly Ser Lys Glu Glu Ala Asp
130                 135                 140

Ala Val Tyr Leu Leu Ala Lys Lys Leu Pro His Thr Leu Val Ser Asp
145                 150                 155                 160

Gln Ser Asp Lys Phe Leu Glu Glu Leu Lys Asn Thr Lys Ala Ala Glu
                165                 170                 175

Ile Val Lys Phe Ala Glu Ala Val Gly Thr Ser Ala Lys Asp Ile Asp
            180                 185                 190

Gly Lys Val Cys Lys Lys Thr Gly Asn Glu Ala Asp Ser Trp Lys Cys
        195                 200                 205

Thr Gln Thr Gly Asn Gly Ser Gly Asn Ala Thr Glu Phe Ser Lys Ile
    210                 215                 220

Phe Thr Lys Lys Asn Val Asp Ala Glu Gly Lys Gly Lys Ala Trp Pro
225                 230                 235                 240

Asn Gly His Thr Asp Ser Ala Ala Lys Ala Glu Asp Leu Ser Thr Ala
                245                 250                 255

Leu Asn Arg Glu Leu Thr Ser Ala Glu Lys Asn Lys Val Ala Gly Leu
            260                 265                 270

Leu Thr Arg Thr Ile Ser Gly Gly
        275                 280

<210> SEQ ID NO 205
<211> LENGTH: 431
<212> TYPE: PRT
<213> ORGANISM: Artificial Sequence
<220> FEATURE:
<223> OTHER INFORMATION: Synthetic construct

<400> SEQUENCE: 205

Met Arg Lys Gly Lys Ile Ile Leu Gly Ser Val Met Met Ser Met Ala
1               5                   10                  15

Ile Val Met Ala Gly Asn Asp Val Arg Ala His Asp Val Ser Ala
            20                  25                  30
Leu Glu Thr Gly Gly Ala Gly Tyr Phe Tyr Val Gly Leu Asp Tyr Ser
        35                  40                  45
Pro Ala Phe Ser Lys Ile Arg Asp Phe Ser Ile Arg Glu Ser Asn Gly
50                  55                  60
Glu Thr Lys Ala Val Tyr Pro Tyr Leu Lys Asp Gly Lys Ser Val Lys
65                  70                  75                  80
Leu Glu Ser His Lys Phe Asp Trp Asn Thr Pro Asp Pro Arg Ile Gly
                85                  90                  95
Phe Lys Asp Asn Met Leu Val Ala Met Glu Gly Ser Val Gly Tyr Gly
            100                 105                 110
Ile Gly Gly Ala Arg Val Glu Leu Glu Ile Gly Tyr Glu Arg Phe Lys
        115                 120                 125
Thr Lys Gly Ile Arg Asp Ser Gly Ser Lys Glu Asp Glu Ala Asp Thr
130                 135                 140
Val Tyr Leu Leu Ala Lys Glu Leu Ala Tyr Asp Val Val Thr Gly Gln
145                 150                 155                 160
Thr Asp Asn Leu Ala Ala Ala Leu Ala Lys Thr Ser Gly Lys Asp Ile
                165                 170                 175
Val Gln Phe Ala Lys Ala Val Glu Ile Ser Asn Ser Gly Ile Gly Lys
            180                 185                 190
Lys Val Cys Glu Thr Lys Arg Lys Asp Gly Asp Thr Thr Asn Arg Phe
        195                 200                 205
Ala Lys Tyr Ile Val Gly Ala Gly Asp Ser Ser Asn Ala Gly Thr Ser
210                 215                 220
Leu Cys Gly Gly Lys Asn Gln Lys Ser Ser Asp Thr Asp Thr Gly Val
225                 230                 235                 240
Glu Lys Ala Gln Ala Leu His Asp Phe Val Ser Asn Thr Leu Ser Asp
                245                 250                 255
Gly Thr Lys Asn Trp Pro Thr Ser Ser Glu Thr Ser Lys Ser Asn Asn
            260                 265                 270
Asp Asn Ala Lys Ala Val Ala Gly Asp Leu Thr Lys Lys Leu Thr Pro
        275                 280                 285
Glu Glu Lys Thr Ile Val Ala Gly Leu Leu Ala Lys Thr Ile Glu Gly
290                 295                 300
Gly Glu Val Val Glu Ile Arg Ala Val Ser Ser Thr Ser Val Met Val
305                 310                 315                 320
Asn Ala Cys Tyr Asp Leu Leu Ser Glu Gly Leu Gly Val Val Pro Tyr
                325                 330                 335
Ala Cys Val Gly Leu Gly Gly Asn Phe Val Gly Val Val Asp Gly His
            340                 345                 350
Ile Thr Pro Lys Leu Ala Tyr Arg Leu Lys Ala Gly Leu Ser Tyr Gln
        355                 360                 365
Leu Ser Pro Glu Ile Ser Ala Phe Ala Gly Gly Phe Tyr His Arg Val
370                 375                 380
Val Gly Asp Gly Val Tyr Asp Asp Leu Pro Ala Gln Arg Leu Val Asp
385                 390                 395                 400
Asp Thr Ser Pro Ala Gly Arg Thr Lys Asp Thr Ala Ile Ala Asn Phe
                405                 410                 415
Ser Met Ala Tyr Val Gly Gly Glu Phe Gly Val Arg Phe Ala Phe
            420                 425                 430

<210> SEQ ID NO 206
<211> LENGTH: 433
<212> TYPE: PRT
<213> ORGANISM: Artificial Sequence
<220> FEATURE:
<223> OTHER INFORMATION: Synthetic construct

<400> SEQUENCE: 206

```
Met Met Ser Met Ala Ile Val Met Ala Gly Ser Asp Val Arg Ala His
1               5                   10                  15

Asp Asp Val Ser Ala Leu Asp Thr Gly Gly Ala Gly Tyr Phe Tyr Val
                20                  25                  30

Gly Leu Asp Tyr Ser Pro Ala Phe Ser Lys Ile Arg Asp Phe Ser Ile
            35                  40                  45

Arg Glu Ser Asn Gly Glu Thr Lys Ala Val Tyr Pro Tyr Leu Lys Asp
        50                  55                  60

Gly Lys Ser Val Lys Leu Glu Ser His Lys Phe Asp Trp Asn Thr Pro
65                  70                  75                  80

Asp Pro Arg Ile Gly Phe Lys Asp Asn Met Leu Val Ala Met Glu Gly
                85                  90                  95

Ser Val Gly Tyr Gly Ile Gly Gly Ala Arg Val Glu Leu Glu Ile Gly
                100                 105                 110

Tyr Glu Arg Phe Lys Thr Lys Gly Ile Arg Asp Ser Gly Ser Lys Glu
            115                 120                 125

Asp Glu Ala Asp Thr Val Tyr Leu Leu Ala Lys Glu Leu Ala Tyr Asp
        130                 135                 140

Val Val Thr Gly Gln Thr Asp Lys Leu Thr Ala Ala Leu Ala Lys Thr
145                 150                 155                 160

Ser Gly Lys Asp Ile Val Gln Phe Ala Lys Thr Leu Gly Ile Ser His
                165                 170                 175

Ser Glu Ile Asp Lys Lys Val Cys Ser Gly Ser His Ala Lys Gly Asn
            180                 185                 190

Ser Glu Thr Thr Lys Asn Asn Thr Val Ala Ser Tyr Thr Glu Lys Pro
        195                 200                 205

Thr Ala Ala Thr Ala Thr Ala Gln Cys Ser Gly Phe Pro Asp Glu Ala
    210                 215                 220

Ala Gly Asn Lys Ala Gly Gly Leu Asn Arg Phe Val Ser Glu Thr Lys
225                 230                 235                 240

Val Glu Glu Gly Lys Asn Trp Pro Thr Gly Lys Ile His Ser Gly Ser
                245                 250                 255

Ser Thr Asn Asn Val Asp Gly Thr His Asn Gly Asn Ala Lys Ala Val
            260                 265                 270

Ala Thr Asp Leu Val Asn Leu Asn Arg Asp Glu Lys Thr Ile Val Ala
        275                 280                 285

Gly Leu Leu Ala Lys Thr Ile Glu Gly Gly Glu Val Val Glu Ile Arg
    290                 295                 300

Ala Val Ser Ser Thr Ser Val Met Val Asn Ala Cys Tyr Asp Leu Leu
305                 310                 315                 320

Ser Glu Gly Leu Gly Val Val Pro Tyr Ala Cys Val Gly Leu Gly Gly
                325                 330                 335

Asn Phe Val Gly Val Val Asp Gly His Ile Thr Pro Lys Leu Ala Tyr
            340                 345                 350

Arg Leu Lys Ala Gly Leu Ser Tyr Gln Leu Ser Pro Glu Ile Ser Ala
        355                 360                 365
```

```
Phe Ala Gly Gly Phe Tyr His Arg Val Val Gly Asp Gly Val Tyr Asp
        370                 375                 380

Asp Leu Pro Ala Gln Arg Leu Val Asp Asp Thr Ser Pro Ala Gly Arg
385                 390                 395                 400

Thr Lys Asp Thr Ala Ile Ala Asn Phe Ser Met Ala Tyr Val Gly Ala
                405                 410                 415

Ser Phe Gln Pro Tyr Tyr Ala Val Leu Leu Val Glu Leu Tyr Glu Tyr
                420                 425                 430

Arg

<210> SEQ ID NO 207
<211> LENGTH: 1230
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: a, c, g or t
<220> FEATURE:
<221> NAME/KEY: misc_feature
<222> LOCATION: (19)..(19)
<223> OTHER INFORMATION: a, c, g or t
<220> FEATURE:
<221> NAME/KEY: misc_feature
<222> LOCATION: (34)..(34)
<223> OTHER INFORMATION: a, c, g or t
<220> FEATURE:
<221> NAME/KEY: misc_feature
<222> LOCATION: (40)..(40)
<223> OTHER INFORMATION: a, c, g or t
<220> FEATURE:
<221> NAME/KEY: misc_feature
<222> LOCATION: (49)..(49)
<223> OTHER INFORMATION: a, c, g or t
<220> FEATURE:
<221> NAME/KEY: misc_feature
<222> LOCATION: (55)..(55)
<223> OTHER INFORMATION: a, c, g or t
<220> FEATURE:
<221> NAME/KEY: misc_feature
<222> LOCATION: (58)..(58)
<223> OTHER INFORMATION: a, c, g or t
<220> FEATURE:
<221> NAME/KEY: misc_feature
<222> LOCATION: (60)..(60)
<223> OTHER INFORMATION: a, c, g or t
<220> FEATURE:
<221> NAME/KEY: misc_feature
<222> LOCATION: (66)..(66)
<223> OTHER INFORMATION: a, c, g or t
<220> FEATURE:
<221> NAME/KEY: misc_feature
<222> LOCATION: (71)..(72)
<223> OTHER INFORMATION: a, c, g or t
<220> FEATURE:
<221> NAME/KEY: misc_feature
<222> LOCATION: (84)..(84)
<223> OTHER INFORMATION: a, c, g or t
<220> FEATURE:
<221> NAME/KEY: misc_feature
<222> LOCATION: (87)..(87)
<223> OTHER INFORMATION: a, c, g or t
<220> FEATURE:
<221> NAME/KEY: misc_feature
<222> LOCATION: (93)..(93)
<223> OTHER INFORMATION: a, c, g or t
<220> FEATURE:
<221> NAME/KEY: misc_feature
<222> LOCATION: (98)..(98)
<223> OTHER INFORMATION: a, c, g or t
<220> FEATURE:
<221> NAME/KEY: misc_feature
```

```
<222> LOCATION: (100)..(100)
<223> OTHER INFORMATION: a, c, g or t
<220> FEATURE:
<221> NAME/KEY: misc_feature
<222> LOCATION: (103)..(104)
<223> OTHER INFORMATION: a, c, g or t
<220> FEATURE:
<221> NAME/KEY: misc_feature
<222> LOCATION: (107)..(108)
<223> OTHER INFORMATION: a, c, g or t
<220> FEATURE:
<221> NAME/KEY: misc_feature
<222> LOCATION: (110)..(110)
<223> OTHER INFORMATION: a, c, g or t
<220> FEATURE:
<221> NAME/KEY: misc_feature
<222> LOCATION: (120)..(120)
<223> OTHER INFORMATION: a, c, g or t
<220> FEATURE:
<221> NAME/KEY: misc_feature
<222> LOCATION: (168)..(168)
<223> OTHER INFORMATION: a, c, g or t
<220> FEATURE:
<221> NAME/KEY: misc_feature
<222> LOCATION: (171)..(171)
<223> OTHER INFORMATION: a, c, g or t
<220> FEATURE:
<221> NAME/KEY: misc_feature
<222> LOCATION: (177)..(177)
<223> OTHER INFORMATION: a, c, g or t
<220> FEATURE:
<221> NAME/KEY: misc_feature
<222> LOCATION: (191)..(191)
<223> OTHER INFORMATION: a, c, g or t
<220> FEATURE:
<221> NAME/KEY: misc_feature
<222> LOCATION: (195)..(195)
<223> OTHER INFORMATION: a, c, g or t
<220> FEATURE:
<221> NAME/KEY: misc_feature
<222> LOCATION: (198)..(198)
<223> OTHER INFORMATION: a, c, g or t
<220> FEATURE:
<221> NAME/KEY: misc_feature
<222> LOCATION: (203)..(203)
<223> OTHER INFORMATION: a, c, g or t
<220> FEATURE:
<221> NAME/KEY: misc_feature
<222> LOCATION: (233)..(233)
<223> OTHER INFORMATION: a, c, g or t
<220> FEATURE:
<221> NAME/KEY: misc_feature
<222> LOCATION: (237)..(237)
<223> OTHER INFORMATION: a, c, g or t
<220> FEATURE:
<221> NAME/KEY: misc_feature
<222> LOCATION: (245)..(245)
<223> OTHER INFORMATION: a, c, g or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (252)..(252)
<223> OTHER INFORMATION: a, c, g or t
<220> FEATURE:
<221> NAME/KEY: misc_feature
<222> LOCATION: (282)..(282)
<223> OTHER INFORMATION: a, c, g or t
<220> FEATURE:
<221> NAME/KEY: misc_feature
<222> LOCATION: (315)..(316)
<223> OTHER INFORMATION: a, c, g or t
<220> FEATURE:
<221> NAME/KEY: misc_feature
<222> LOCATION: (324)..(324)
<223> OTHER INFORMATION: a, c, g or t
<220> FEATURE:
```

-continued

```
<221> NAME/KEY: misc_feature
<222> LOCATION: (345)..(345)
<223> OTHER INFORMATION: a, c, g or t
<220> FEATURE:
<221> NAME/KEY: misc_feature
<222> LOCATION: (363)..(363)
<223> OTHER INFORMATION: a, c, g or t
<220> FEATURE:
<221> NAME/KEY: misc_feature
<222> LOCATION: (369)..(369)
<223> OTHER INFORMATION: a, c, g or t
<220> FEATURE:
<221> NAME/KEY: misc_feature
<222> LOCATION: (372)..(372)
<223> OTHER INFORMATION: a, c, g or t
<220> FEATURE:
<221> NAME/KEY: misc_feature
<222> LOCATION: (390)..(390)
<223> OTHER INFORMATION: a, c, g or t
<220> FEATURE:
<221> NAME/KEY: misc_feature
<222> LOCATION: (396)..(396)
<223> OTHER INFORMATION: a, c, g or t
<220> FEATURE:
<221> NAME/KEY: misc_feature
<222> LOCATION: (399)..(399)
<223> OTHER INFORMATION: a, c, g or t
<220> FEATURE:
<221> NAME/KEY: misc_feature
<222> LOCATION: (407)..(407)
<223> OTHER INFORMATION: a, c, g or t
<220> FEATURE:
<221> NAME/KEY: misc_feature
<222> LOCATION: (411)..(411)
<223> OTHER INFORMATION: a, c, g or t
<220> FEATURE:
<221> NAME/KEY: misc_feature
<222> LOCATION: (429)..(429)
<223> OTHER INFORMATION: a, c, g or t
<220> FEATURE:
<221> NAME/KEY: misc_feature
<222> LOCATION: (433)..(433)
<223> OTHER INFORMATION: a, c, g or t
<220> FEATURE:
<221> NAME/KEY: misc_feature
<222> LOCATION: (462)..(462)
<223> OTHER INFORMATION: a, c, g or t
<220> FEATURE:
<221> NAME/KEY: misc_feature
<222> LOCATION: (469)..(469)
<223> OTHER INFORMATION: a, c, g or t
<220> FEATURE:
<221> NAME/KEY: misc_feature
<222> LOCATION: (471)..(471)
<223> OTHER INFORMATION: a, c, g or t
<220> FEATURE:
<221> NAME/KEY: misc_feature
<222> LOCATION: (474)..(474)
<223> OTHER INFORMATION: a, c, g or t
<220> FEATURE:
<221> NAME/KEY: misc_feature
<222> LOCATION: (480)..(480)
<223> OTHER INFORMATION: a, c, g or t
<220> FEATURE:
<221> NAME/KEY: misc_feature
<222> LOCATION: (485)..(486)
<223> OTHER INFORMATION: a, c, g or t
<220> FEATURE:
<221> NAME/KEY: misc_feature
<222> LOCATION: (492)..(492)
<223> OTHER INFORMATION: a, c, g or t
<220> FEATURE:
<221> NAME/KEY: misc_feature
<222> LOCATION: (507)..(507)
<223> OTHER INFORMATION: a, c, g or t
<220> FEATURE:
<221> NAME/KEY: misc_feature
<222> LOCATION: (509)..(510)
<223> OTHER INFORMATION: a, c, g or t
```

-continued

```
<220> FEATURE:
<221> NAME/KEY: misc_feature
<222> LOCATION: (513)..(513)
<223> OTHER INFORMATION: a, c, g or t
<220> FEATURE:
<221> NAME/KEY: misc_feature
<222> LOCATION: (521)..(521)
<223> OTHER INFORMATION: a, c, g or t
<220> FEATURE:
<221> NAME/KEY: misc_feature
<222> LOCATION: (524)..(524)
<223> OTHER INFORMATION: a, c, g or t
<220> FEATURE:
<221> NAME/KEY: misc_feature
<222> LOCATION: (528)..(528)
<223> OTHER INFORMATION: a, c, g or t
<220> FEATURE:
<221> NAME/KEY: misc_feature
<222> LOCATION: (549)..(549)
<223> OTHER INFORMATION: a, c, g or t
<220> FEATURE:
<221> NAME/KEY: misc_feature
<222> LOCATION: (552)..(552)
<223> OTHER INFORMATION: a, c, g or t
<220> FEATURE:
<221> NAME/KEY: misc_feature
<222> LOCATION: (557)..(557)
<223> OTHER INFORMATION: a, c, g or t
<220> FEATURE:
<221> NAME/KEY: misc_feature
<222> LOCATION: (561)..(561)
<223> OTHER INFORMATION: a, c, g or t
<220> FEATURE:
<221> NAME/KEY: misc_feature
<222> LOCATION: (567)..(567)
<223> OTHER INFORMATION: a, c, g or t
<220> FEATURE:
<221> NAME/KEY: misc_feature
<222> LOCATION: (569)..(569)
<223> OTHER INFORMATION: a, c, g or t
<220> FEATURE:
<221> NAME/KEY: misc_feature
<222> LOCATION: (579)..(579)
<223> OTHER INFORMATION: a, c, g or t
<220> FEATURE:
<221> NAME/KEY: misc_feature
<222> LOCATION: (589)..(589)
<223> OTHER INFORMATION: a, c, g or t
<220> FEATURE:
<221> NAME/KEY: misc_feature
<222> LOCATION: (593)..(593)
<223> OTHER INFORMATION: a, c, g or t
<220> FEATURE:
<221> NAME/KEY: misc_feature
<222> LOCATION: (596)..(596)
<223> OTHER INFORMATION: a, c, g or t
<220> FEATURE:
<221> NAME/KEY: misc_feature
<222> LOCATION: (605)..(605)
<223> OTHER INFORMATION: a, c, g or t
<220> FEATURE:
<221> NAME/KEY: misc_feature
<222> LOCATION: (624)..(625)
<223> OTHER INFORMATION: a, c, g or t
<220> FEATURE:
<221> NAME/KEY: misc_feature
<222> LOCATION: (632)..(632)
<223> OTHER INFORMATION: a, c, g or t
<220> FEATURE:
<221> NAME/KEY: misc_feature
<222> LOCATION: (641)..(642)
<223> OTHER INFORMATION: a, c, g or t
<220> FEATURE:
<221> NAME/KEY: misc_feature
<222> LOCATION: (645)..(645)
<223> OTHER INFORMATION: a, c, g or t
<220> FEATURE:
<221> NAME/KEY: misc_feature
<222> LOCATION: (665)..(665)
```

```
<223> OTHER INFORMATION: a, c, g or t
<220> FEATURE:
<221> NAME/KEY: misc_feature
<222> LOCATION: (668)..(668)
<223> OTHER INFORMATION: a, c, g or t
<220> FEATURE:
<221> NAME/KEY: misc_feature
<222> LOCATION: (678)..(678)
<223> OTHER INFORMATION: a, c, g or t
<220> FEATURE:
<221> NAME/KEY: misc_feature
<222> LOCATION: (688)..(688)
<223> OTHER INFORMATION: a, c, g or t
<220> FEATURE:
<221> NAME/KEY: misc_feature
<222> LOCATION: (694)..(694)
<223> OTHER INFORMATION: a, c, g or t
<220> FEATURE:
<221> NAME/KEY: misc_feature
<222> LOCATION: (698)..(699)
<223> OTHER INFORMATION: a, c, g or t
<220> FEATURE:
<221> NAME/KEY: misc_feature
<222> LOCATION: (701)..(701)
<223> OTHER INFORMATION: a, c, g or t
<220> FEATURE:
<221> NAME/KEY: misc_feature
<222> LOCATION: (706)..(706)
<223> OTHER INFORMATION: a, c, g or t
<220> FEATURE:
<221> NAME/KEY: misc_feature
<222> LOCATION: (713)..(713)
<223> OTHER INFORMATION: a, c, g or t
<220> FEATURE:
<221> NAME/KEY: misc_feature
<222> LOCATION: (720)..(721)
<223> OTHER INFORMATION: a, c, g or t
<220> FEATURE:
<221> NAME/KEY: misc_feature
<222> LOCATION: (727)..(727)
<223> OTHER INFORMATION: a, c, g or t
<220> FEATURE:
<221> NAME/KEY: misc_feature
<222> LOCATION: (735)..(735)
<223> OTHER INFORMATION: a, c, g or t
<220> FEATURE:
<221> NAME/KEY: misc_feature
<222> LOCATION: (744)..(744)
<223> OTHER INFORMATION: a, c, g or t
<220> FEATURE:
<221> NAME/KEY: misc_feature
<222> LOCATION: (750)..(750)
<223> OTHER INFORMATION: a, c, g or t
<220> FEATURE:
<221> NAME/KEY: misc_feature
<222> LOCATION: (764)..(764)
<223> OTHER INFORMATION: a, c, g or t
<220> FEATURE:
<221> NAME/KEY: misc_feature
<222> LOCATION: (769)..(769)
<223> OTHER INFORMATION: a, c, g or t
<220> FEATURE:
<221> NAME/KEY: misc_feature
<222> LOCATION: (780)..(780)
<223> OTHER INFORMATION: a, c, g or t
<220> FEATURE:
<221> NAME/KEY: misc_feature
<222> LOCATION: (782)..(782)
<223> OTHER INFORMATION: a, c, g or t
<220> FEATURE:
<221> NAME/KEY: misc_feature
<222> LOCATION: (786)..(786)
<223> OTHER INFORMATION: a, c, g or t
<220> FEATURE:
<221> NAME/KEY: misc_feature
<222> LOCATION: (789)..(789)
<223> OTHER INFORMATION: a, c, g or t
<220> FEATURE:
<221> NAME/KEY: misc_feature
```

<222> LOCATION: (792)..(792)
<223> OTHER INFORMATION: a, c, g or t
<220> FEATURE:
<221> NAME/KEY: misc_feature
<222> LOCATION: (797)..(798)
<223> OTHER INFORMATION: a, c, g or t
<220> FEATURE:
<221> NAME/KEY: misc_feature
<222> LOCATION: (801)..(801)
<223> OTHER INFORMATION: a, c, g or t
<220> FEATURE:
<221> NAME/KEY: misc_feature
<222> LOCATION: (823)..(823)
<223> OTHER INFORMATION: a, c, g or t
<220> FEATURE:
<221> NAME/KEY: misc_feature
<222> LOCATION: (855)..(855)
<223> OTHER INFORMATION: a, c, g or t
<220> FEATURE:
<221> NAME/KEY: misc_feature
<222> LOCATION: (858)..(858)
<223> OTHER INFORMATION: a, c, g or t
<220> FEATURE:
<221> NAME/KEY: misc_feature
<222> LOCATION: (873)..(873)
<223> OTHER INFORMATION: a, c, g or t
<220> FEATURE:
<221> NAME/KEY: misc_feature
<222> LOCATION: (892)..(892)
<223> OTHER INFORMATION: a, c, g or t
<220> FEATURE:
<221> NAME/KEY: misc_feature
<222> LOCATION: (894)..(894)
<223> OTHER INFORMATION: a, c, g or t
<220> FEATURE:
<221> NAME/KEY: misc_feature
<222> LOCATION: (924)..(924)
<223> OTHER INFORMATION: a, c, g or t
<220> FEATURE:
<221> NAME/KEY: misc_feature
<222> LOCATION: (933)..(933)
<223> OTHER INFORMATION: a, c, g or t
<220> FEATURE:
<221> NAME/KEY: misc_feature
<222> LOCATION: (955)..(955)
<223> OTHER INFORMATION: a, c, g or t
<220> FEATURE:
<221> NAME/KEY: misc_feature
<222> LOCATION: (957)..(957)
<223> OTHER INFORMATION: a, c, g or t
<220> FEATURE:
<221> NAME/KEY: misc_feature
<222> LOCATION: (972)..(972)
<223> OTHER INFORMATION: a, c, g or t
<220> FEATURE:
<221> NAME/KEY: misc_feature
<222> LOCATION: (987)..(987)
<223> OTHER INFORMATION: a, c, g or t
<220> FEATURE:
<221> NAME/KEY: misc_feature
<222> LOCATION: (1017)..(1017)
<223> OTHER INFORMATION: a, c, g or t
<220> FEATURE:
<221> NAME/KEY: misc_feature
<222> LOCATION: (1056)..(1056)
<223> OTHER INFORMATION: a, c, g or t
<220> FEATURE:
<221> NAME/KEY: misc_feature
<222> LOCATION: (1059)..(1059)
<223> OTHER INFORMATION: a, c, g or t
<220> FEATURE:
<221> NAME/KEY: misc_feature
<222> LOCATION: (1101)..(1101)
<223> OTHER INFORMATION: a, c, g or t
<220> FEATURE:
<221> NAME/KEY: misc_feature
<222> LOCATION: (1116)..(1116)
<223> OTHER INFORMATION: a, c, g or t
<220> FEATURE:

<221> NAME/KEY: misc_feature
<222> LOCATION: (1122)..(1122)
<223> OTHER INFORMATION: a, c, g or t
<220> FEATURE:
<221> NAME/KEY: misc_feature
<222> LOCATION: (1144)..(1144)
<223> OTHER INFORMATION: a, c, g or t
<220> FEATURE:
<221> NAME/KEY: misc_feature
<222> LOCATION: (1146)..(1146)
<223> OTHER INFORMATION: a, c, g or t
<220> FEATURE:
<221> NAME/KEY: misc_feature
<222> LOCATION: (1173)..(1173)
<223> OTHER INFORMATION: a, c, g or t
<220> FEATURE:
<221> NAME/KEY: misc_feature
<222> LOCATION: (1179)..(1179)
<223> OTHER INFORMATION: a, c, g or t
<220> FEATURE:
<221> NAME/KEY: misc_feature
<222> LOCATION: (1195)..(1195)
<223> OTHER INFORMATION: a, c, g or t
<220> FEATURE:
<221> NAME/KEY: misc_feature
<222> LOCATION: (1209)..(1209)
<223> OTHER INFORMATION: a, c, g or t
<220> FEATURE:
<221> NAME/KEY: misc_feature
<222> LOCATION: (1224)..(1224)
<223> OTHER INFORMATION: a, c, g or t

<400> SEQUENCE: 207

```
atgagnaaaa gaaagcttnc cctaggaggc gtgntgatgn cgatggttnt agtgntgncn    60
gctggnactg nngctggggc tggngcngac gtngacgntn tanntanngn cggtgcgggn   120
agtttctacg taggtctgga ctacagtcca gcgtttagca agataaanga ntttaanata   180
agagagagta ncggnganac tanggcagta tatccgtaca tgaaagatgg aantagngtg   240
gagttnaagg cncacaagtt cgactggaac acaccagatc naggattag gtttaaggac   300
aacatgctcg tagcnntaga aggnagtgtt gggtacagta ttggnggagc cagggttgaa   360
ctngagatng gntatgaacg gttcaagacn aagggnatna gagatanggg nagtaaggaa   420
gatgaagcng atncagtata cctattagct aaggagttag cntatgatnt ngtnagtggn   480
cagannngata ancttgccgc tgctctngnn aanacgacag nggngganat cgttaagttt   540
gctaaggcng tngaganttc ngctacngnt attggtgana aggtgtgtna ganagngcgg   600
aaggntggtg ataccacggg cagnntggca angtatgtag nntgncagca acagcgctgg   660
caccncanag tttagtgnaa tattcacnaa ggcngacnna natacngaca gcncaggcan   720
ngcatgncct aacangaaca atgncactan gaacagcgaa aggnctaant aataacgttn   780
antaanaanc tnaccannga ngaaaagacc atagtagctg ggntactagc taggactatt   840
gaaggtggtg aggtngtnga gatcagggcg gtntcgtcta cttctgtaat gntnaatgct   900
tgttatgatc ttctgagtga aggntttggt gtngttcctt atgcttgtgt tggtntnggt   960
ggtaacttcg tnggcgttgt tgatggncac atcactccta agcttgctta cagagtnaag   1020
gctgggttga gttatgagct gtctcctgaa atctcngcnt ttgctggggg tttctaccat   1080
cgggtgctgg gtgatggtga ntatgatgat ctgccngtgc ancgtcttgt agatgatact   1140
agtncngcgg gtaagactaa ggatactgct atngcttcnt tcaacatggc ttacnttggt   1200
ggtgaattng gtgttaggtt tgcnttctaa                                    1230
```

<210> SEQ ID NO 208
<211> LENGTH: 1224

```
<212> TYPE: DNA
<213> ORGANISM: Artificial Sequence
<220> FEATURE:
<223> OTHER INFORMATION: Synthetic construct

<400> SEQUENCE: 208
atgagtgctg taagtaatag gaagcttccc ctaggaggcg tgttgatggc tctggttgca      60
gcggttgcac caatccattc tttactggct gccctgcag ctggtgctgg cgcaggcggc     120
gagggtctat tttcaggcgc cggagccggg agtttttaca taggactgga ctacagccca     180
gcattcggca gcatcaagga ctttaaagtc caagaggctg gcggcactac tagaggtgtg     240
ttcccgtaca agcgagatgc tgcaggtcgg gtggatttca aggtccacaa cttcgactgg     300
agtgctccag aacccaagat tagcttcaag gatagcatgc tcacagccct agaggggagc     360
attgggtata gtattggagg agccagggtt gaagtagaag tagggtatga aaggtttgtc     420
attaagggag gtaagaagtc taatgaggat acagcttcag tattcttatt aggaaaggag     480
ttagcatatg atacagcaag aggtcaggta gaccgtcttg ccactgcttt aggtaagatg     540
actaagggtg aagccaagaa gtggggtaat gcagtagaga atgctactaa tggtgataag     600
gtgagccaga atgtgtgcaa gggtactggt agcactggca gcagtggcaa caaatgtggt     660
accaccgata gcactgccac caccaagatt agtgcggtgt tcactgagga tgcagcagcg     720
cagttatcta ctatggacaa taccaccatc aacacgacag gaatggcgaa taacattaat     780
agcctgacaa aagatgagaa ggccatagtt gctggggcat ttgctagagc tgttgaaggt     840
gctgaggtga tagaggtcag ggctataggg tctacttctg taatgctcaa tgcttgttat     900
gaccttctga ctgatggtat tggggttgtt ccttatgctt gtgctggtat cggtggtaac     960
tttgtcagtg ttgttgatgg tcacattaat cctaagtttg cttacagagt gaaggctggg    1020
ctgagttatg ctctgactcc tgaaatttct gcctttgctg gggctttcta ccataaggtg    1080
ctaggtgatg gtgactatga tgagctacct ttgagtcata tttctgatta tactggtact    1140
gctggtaaga ataaggatac tggtatcgct tcatttaact tcgcttactt tggtggtgag    1200
ttgggtgtta ggtttgcctt ctag                                           1224

<210> SEQ ID NO 209
<211> LENGTH: 1296
<212> TYPE: DNA
<213> ORGANISM: Artificial Sequence
<220> FEATURE:
<223> OTHER INFORMATION: Synthetic construct

<400> SEQUENCE: 209
atgagaaaag gaaagataat cttaggaagc gtaatgatgt cgatggctat agtcatggct      60
gggaatgatg tcagggctca tgatgacgtt agcgctttgg agactggtgg tgcgggatat     120
ttctatgttg gtttggatta cagtccagcg tttagcaaga taagagattt tagtataagg     180
gagagtaacg gagagactaa ggcagtatat ccatacttaa aggatggaaa gagtgtaaag     240
ctagagtcac acaagtttga ctggaacaca cctgatcctc ggattgggtt taaggacaac     300
atgcttgtag ctatggaagg cagtgttggg tacggtattg gtggtgccag ggttgagctt     360
gagattggtt acgagcgctt caagaccaag ggtattagag atagtggtag taaggaagat     420
gaagcagata cagtatatct actagctaag gagttagctt atgatgttgt tactgggcag     480
actgataacc ttgccgctgc tcttgccaaa acctcaggta aggacatcgt tcagtttgct     540
aaggccgtgg agatttctaa ttccggtatt ggtaagaagg tgtgtgagac aaagcggaag     600
```

| | |
|---|---|
| gatggtgata ctacgaacag gtttgcaaag tatatagttg gtgcgggtga tagtagcaat | 660 |
| gctggtacat cattgtgtgg tggtaagaac caaaagagtt cggacacaga caccggggtg | 720 |
| gagaaggctc aggctctgca tgactttgtt tctaacacat tgagtgatgg tactaagaac | 780 |
| tggcctacgt cgagtgaaac gtctaaatcg aataacgaca acgccaaagc tgtagcggga | 840 |
| gacttaacta agaagctcac ccctgaagaa aaaccatag tagcagggtt actagctaag | 900 |
| actattgaag gtggtgaggt tgttgaaatt agggcggttt cttctacttc tgtgatggtt | 960 |
| aatgcttgtt atgatcttct tagtgaaggc ttaggtgtcg ttccttatgc ttgcgtcggt | 1020 |
| cttggtggta acttcgtggg cgttgttgat gggcatatca ctcctaagct tgcttataga | 1080 |
| ttaaaggctg ggttgagtta tcagctctct cctgaaatct cggcttttgc tgggggtttc | 1140 |
| taccatcgtg ttgtgggaga tggtgtttat gatgatctgc cggctcaacg tcttgtagat | 1200 |
| gatactagtc cggcgggtcg tactaaggat actgctattg ctaacttctc catggcttat | 1260 |
| gtcggtgggg aatttggtgt taggtttgct tttaa | 1296 |

<210> SEQ ID NO 210
<211> LENGTH: 3954
<212> TYPE: DNA
<213> ORGANISM: Artificial Sequence
<220> FEATURE:
<223> OTHER INFORMATION: Synthetic construct

<400> SEQUENCE: 210

| | |
|---|---|
| taacacatgg gataatgttt atgacttctc aagcacaaaa ccaaagttca atccctataa | 60 |
| cagtggaggg aaaggtgagg cccccaccag ttgatgagta tgtgggaaga gagataaaga | 120 |
| agcagcgtat catgaaggga atgagccaga atcagctggc tagtagattg ggaattactt | 180 |
| tccaacaggt acaaaagtac gaaaagggaa caaatcgtat agttattagc agattgtatg | 240 |
| aattggccag ggttttgggt attgaaatca acgatttaat atctaaactt caaaatgacc | 300 |
| tgcgctcgat aaccgaagga actgatacat caggaacatc attcttaaaa gacggtgatg | 360 |
| agacatcctt agaggagttc aaccacaact acaacgacgg taaggaagtt ctgatgcttg | 420 |
| tgagagcata tcgtaaaatt aagagcgaaa aaatgcgtgg tgcaatacac acattagtaa | 480 |
| aggtaatgtg tgctgagcaa tctagcaatg atgattatga gaattcctat gtagattcag | 540 |
| attacgaatc tgggacaggc acggaagatt agttaacatg cgataagttc gccaggaccc | 600 |
| tgttcctgcg tatcggaagt gctggtatgc gggtggcttt tctttatggt ttgcgctgcc | 660 |
| cgcatagtac ggttaccttt tggtgcgctt agtaccagtg aaagttgccc tactctccaa | 720 |
| aaaacaccac gtaaatcggt gcttcactca aattatttaa gaactccttt atgttagacc | 780 |
| tatagagaga aaaatcgtgt ctatgttctt tgacacatga tcacggtgct tctatgctac | 840 |
| gaacttggaa tatgtaaggt gtcggtgtat aagtgatgaa gaagagaatc cgggttttcg | 900 |
| cgtttgcagt gttcatgctt gggttgccct ccgtatcatt tgcttctcca caacccgtgg | 960 |
| attttcgta ccacgagggt gcatccggct ttttccagc gttcagtata agtacggtgc | 1020 |
| accctatttc ggaagcctta cactggaaag cggcgggaag acgctgaatc ttgtgagcgc | 1080 |
| ggtgcaggaa aagaaacccc cggaagcccc cgcagctgac gaagctgctg aacctgccac | 1140 |
| ccctgctccc tcaagccctg aagggtttgg ttcatctacc gatgattttc aaggtaggta | 1200 |
| ctcgccaacc tatttaaagg acgcaggagc cttttcaata acagcgggtt ataccaccgg | 1260 |
| tattatgaga tttgaagcag aggctatgcg ttcgcgtttc caggtaaatg gcagtaaatg | 1320 |
| gaatcctgta gagaacgctt atatatttgc cgctgctaaa cccagtgaga atatatcgta | 1380 |

```
ccctgctcag atactggagg cacaaaagta cttcgtcacc ttggaaaaca gggatgttgc    1440
catcacttcg ctggtggcaa atgcctgcta cgacatgatg ccagcaacct ctagcatcgc    1500
acctagtgcg tgcgtgggtg tagggggttag cttttgccaaa ctgttaggtg ttctggaaca   1560
aaggctaacc tatcaattca aaggtggatt gcaatatttt gtcggcaaaa agaccgtcat    1620
cttcctatct ggatacgtat ccacaatagg tggaaggaaa atcactcagg taaaagtgaa    1680
acatcgtttg tccacgcctc agaccgcgtc agttggtgca gaaggcagtg gagcaggtgc    1740
tgctgcaaca tcttctgctc ccccagcccc cattcacctg ttgtacccag atgcaaattt    1800
atcgctagcg tactacgggt ttgagcttgg ggtgcgtctt gttttctaag gcagaggctc    1860
tatagcggct gcgcacacag ggatatcggc gttgataggg aatattacag acagctgttg    1920
ctgcggcgat gttctggctc ttgatctggt gcaccttgag gttgcggacc atagattact    1980
aatcaatcgt taagctacgc catcaaattg caaaatatat cttctgttct cctgacttaa    2040
ttctttttta gtataactta gtcagtgagc tggttgcatg cccgcccctg tctgtgtaca    2100
aaatggggtg aaggtattgg gatcgggggt gttttttgtat tggtggtcaa ggagtggcgt   2160
gttgcttgtg ggagttgttg gggtttggta gcggcttgtg taggggggta tagcattggt    2220
agctgcagga gccgggtttg tgttgctggt gattggagga ttttgagcca cggtggaagg    2280
tgagttttga ttaagtggaa agtttagttt ttggctgagg atggtagctg gttagatgct    2340
gtgcttgctc gtggttgagc tgtggaatgt gaagctggtg tcggttggtg agagtacggg    2400
ggagtcgagg aacactgtgg aggtgtgctg cgcgcgagaa aaaggtgtgc ggcgaaggga    2460
agctattgta aaaggaagtg aggtaaaagg aatgaaggaa agaaaacttg cgctaagtgg    2520
agcggtggcg atgacagttt tggtgtcgac tgctggtacc gggactgcgg cagggtcgga    2580
cgtggactat gtaagtaagt tcggtgaggg cagcttctac gtaggtctaa actatagtcc    2640
ggcgtttagt aagataaatg ggtttgagat aagagagagt accggggaaa ctgcggcagt    2700
atatccgtac atgaaagatg gaactagagt ggagtggaaa gctgagaagt tcgactggaa    2760
cacaccagat ccgaggatta agtttaaaaa caatcctatc gtggcgttag aaggaagtgt    2820
gggctacagt atcggggtag cgagagtaga actggagatc ggctatgaac agttcaagac    2880
gaaaggaata agagatacgg gaagtaagga agaagaagct gatgccgtgt acctgttggc    2940
taagaagcta ccgcataccc tggtgagtga ccagagcgat aaattcctgg aggagctgaa    3000
gaatacgaaa gcggcggaga tcgttaaatt tgctgaggct gttggcacat cggcaaagga    3060
tattgatgga aaggtttgta agaagggcgg cagcggcaat gccgcgggca gctggaagtg    3120
tacgcagact ggcagcaacg gcgtcagcac cgcagagttc agtaaaatat ttacgaaggc    3180
agacgtaaat actgacaaca aaggcaaagc atggcctaac gggaacaacg acgctgcgaa    3240
agcggaagac ctaagtattg cgttgaatag agaactaacc agcgccgaaa agaacaaggt    3300
agctggccta ctaaccagga ctatatccgg tggtgaggta gtggagatcc gtgcggtgtc    3360
gacaacgtca gtaatgttga atggttgtta tgatctgcag agtgaagggt ttagtatagt    3420
accttatgca tgtcttggtg taggtgctaa cttcgttggc attgttgacg gacacgtcac    3480
tcctaaactg gcttacaagg tcaaggctgg tttgagttat gagttgtcgc cggaaatctc    3540
aatgttcgct ggtgggttct atcatcgggt gctgggtgaa ggtgagtacg atgatctgcc    3600
agtgcagagg cttgtagacg atgcgactac gaacaagact aaagagttcg ctaaagcgtc    3660
gttcaagatg gcgtacactg gtgctgaaat cggtgttagg tctgcgttct aatgcgcagt    3720
```

```
gcatggcggg cttaggcccg ccatgattta accctgactg tagaaagcta actagaagga    3780
aagagatgaa gcgagtttgt gttgtgacaa gtttgatgtt agtggcgctg actagtacaa    3840
cgcaaactaa tgctcggagt actaaagtac aacctacgag ccaagatctg tatgtcgggt    3900
taagttacag tccggcatgg caaagataac tgacttcaac atcggagcga acga          3954
```

```
<210> SEQ ID NO 211
<211> LENGTH: 324
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (239)..(239)
<223> OTHER INFORMATION: any amino acid
<220> FEATURE:
<221> NAME/KEY: MISC_FEATURE
<222> LOCATION: (264)..(264)
<223> OTHER INFORMATION: any amino acid
<220> FEATURE:
<221> NAME/KEY: MISC_FEATURE
<222> LOCATION: (287)..(287)
<223> OTHER INFORMATION: any amino acid
<220> FEATURE:
<221> NAME/KEY: MISC_FEATURE
<222> LOCATION: (299)..(299)
<223> OTHER INFORMATION: any amino acid

<400> SEQUENCE: 211

Met Lys Lys Arg Ile Arg Val Phe Ala Phe Ala Val Phe Met Leu Gly
1               5                   10                  15

Leu Pro Ser Val Ser Phe Ala Ser Pro Gln Pro Val Asp Phe Ser Tyr
            20                  25                  30

His Glu Gly Ala Ser Gly Phe Phe Ala Ser Val Gln Tyr Lys Tyr Gly
        35                  40                  45

Ala Pro Tyr Phe Gly Ser Leu Thr Leu Glu Ser Gly Gly Lys Thr Leu
    50                  55                  60

Asn Leu Val Ser Ala Val Gln Glu Lys Lys Pro Glu Ala Pro Ala
65                  70                  75                  80

Ala Asp Glu Ala Ala Gly Pro Ala Thr Pro Ala Pro Ser Ser Pro Glu
                85                  90                  95

Gly Phe Gly Ser Ser Thr Asp Asp Phe Gln Gly Arg Tyr Ser Pro Thr
            100                 105                 110

Tyr Leu Lys Asp Ala Gly Ala Phe Ser Ile Thr Ala Gly Tyr Thr Thr
        115                 120                 125

Gly Ile Met Arg Phe Glu Ala Glu Ala Met Arg Ser Arg Phe Gln Val
    130                 135                 140

Asn Gly Ser Lys Trp Asn Pro Val Glu Asn Ala Tyr Ile Phe Ala Ala
145                 150                 155                 160

Ala Lys Pro Ser Glu Asn Ile Ser Tyr Pro Ala Gln Ile Leu Glu Ala
                165                 170                 175

Gln Lys Tyr Phe Val Thr Leu Glu Asn Arg Asp Val Ala Ile Thr Ser
            180                 185                 190

Leu Val Ala Asn Ala Cys Tyr Asp Met Met Pro Ala Thr Ser Ser Ile
        195                 200                 205

Ala Pro Ser Ala Cys Val Gly Val Gly Val Ser Phe Ala Lys Leu Leu
    210                 215                 220

Gly Val Leu Glu Gln Arg Leu Thr Tyr Gln Phe Lys Gly Gly Xaa Gln
225                 230                 235                 240
```

```
Tyr Phe Val Gly Lys Lys Thr Val Ile Phe Leu Ser Gly Tyr Val Ser
                245                 250                 255

Thr Ile Gly Gly Arg Lys Ile Xaa Gln Val Lys Val Lys His Arg Leu
            260                 265                 270

Pro Thr Pro Gln Thr Ala Ser Val Gly Ala Glu Gly Ser Gly Xaa Gly
        275                 280                 285

Ala Ala Ala Thr Ser Ser Ala Pro Pro Ala Xaa Ile His Leu Leu Tyr
        290                 295                 300

Pro Asp Ala Asn Leu Ser Leu Ala Tyr Tyr Gly Phe Glu Leu Gly Val
305                 310                 315                 320

Arg Leu Val Phe

<210> SEQ ID NO 212
<211> LENGTH: 324
<212> TYPE: PRT
<213> ORGANISM: Artificial Sequence
<220> FEATURE:
<223> OTHER INFORMATION: Synthetic construct

<400> SEQUENCE: 212

Met Lys Lys Arg Ile Arg Val Phe Ala Phe Ala Val Phe Met Leu Gly
1               5                   10                  15

Leu Pro Ser Val Ser Phe Ala Ser Pro Gln Pro Val Asp Phe Ser Tyr
            20                  25                  30

His Glu Gly Ala Ser Gly Phe Phe Ala Ser Val Gln Lys Tyr Lys Gly
        35                  40                  45

Ala Pro Tyr Phe Gly Ser Leu Thr Leu Glu Ser Gly Gly Lys Ile Leu
    50                  55                  60

Asn Leu Val Ser Ala Val Gln Glu Lys Lys Pro Pro Glu Ala Pro Ala
65                  70                  75                  80

Ala Asp Glu Ala Ala Gly Pro Ala Thr His Ala Pro Ser Ser Pro Glu
                85                  90                  95

Gly Phe Gly Ser Ser Thr Asp Asp Phe Gln Gly Arg Tyr Ser Pro Thr
            100                 105                 110

Tyr Leu Lys Asp Ala Gly Ala Phe Ser Ile Thr Ala Gly Tyr Thr Thr
        115                 120                 125

Gly Ile Met Arg Phe Glu Ala Glu Ala Met Arg Ser Arg Phe Gln Val
    130                 135                 140

Asn Gly Ser Lys Trp Asn Pro Val Glu Asn Ala Tyr Ile Phe Ala Ala
145                 150                 155                 160

Ala Lys Pro Ser Glu Asn Ile Ser Tyr Pro Ala Gln Ile Leu Glu Thr
                165                 170                 175

Gln Lys Tyr Phe Val Thr Leu Glu Asn Arg Asp Val Ala Ile Thr Ser
            180                 185                 190

Leu Val Ala Ser Ala Cys Tyr Asp Met Met Pro Ala Thr Ser Ser Ile
        195                 200                 205

Ala Pro Ser Ala Cys Val Gly Val Gly Val Ser Phe Ala Lys Leu Leu
    210                 215                 220

Gly Val Leu Glu Gln Arg Leu Thr Tyr Gln Phe Lys Gly Gly Leu Gln
225                 230                 235                 240

Tyr Phe Val Gly Lys Lys Thr Val Ile Phe Leu Ser Gly Tyr Val Ser
                245                 250                 255

Thr Ile Gly Gly Arg Lys Ile Ser Gln Val Lys Val Lys His Arg Leu
            260                 265                 270

Pro Thr Pro Gln Thr Ala Ser Val Gly Ala Glu Gly Ser Gly Ser Gly
```

-continued

```
              275                 280                 285
Ala Ala Ala Thr Ser Ser Ala Pro Pro Ala Leu Ile His Leu Leu Tyr
        290                 295                 300

Pro Asp Ala Asn Leu Ser Leu Ala Tyr Tyr Gly Phe Glu Leu Gly Val
305                 310                 315                 320

Arg Leu Val Phe
```